United States Patent
Hawley et al.

(10) Patent No.: US 12,029,744 B2
(45) Date of Patent: Jul. 9, 2024

(54) BICYCLIC HETEROARYL DERIVATIVES AS ECTONUCLEOTIDE PYROPHOSPHATASE PHOSPHODIESTERASE 1 INHIBITORS

(71) Applicant: Riboscience LLC, Palo Alto, CA (US)

(72) Inventors: Ronald Hawley, Palo Alto, CA (US); Klaus Klumpp, Palo Alto, CA (US)

(73) Assignee: Riboscience LLC, Palo Alto, CA (US)

( * ) Notice: Subject to any disclaimer, the term of this patent is extended or adjusted under 35 U.S.C. 154(b) by 273 days.

(21) Appl. No.: 17/264,684

(22) PCT Filed: Apr. 10, 2020

(86) PCT No.: PCT/US2020/027700
§ 371 (c)(1),
(2) Date: Jan. 29, 2021

(87) PCT Pub. No.: WO2020/210649
PCT Pub. Date: Oct. 15, 2020

(65) Prior Publication Data
US 2022/0362266 A1   Nov. 17, 2022

Related U.S. Application Data

(60) Provisional application No. 62/833,455, filed on Apr. 12, 2019, provisional application No. 62/881,111, filed on Jul. 31, 2019.

(51) Int. Cl.
| | |
|---|---|
| *C07F 5/02* | (2006.01) |
| *A61K 31/675* | (2006.01) |
| *A61K 31/683* | (2006.01) |
| *A61K 31/69* | (2006.01) |
| *A61K 45/06* | (2006.01) |
| *C07F 9/6503* | (2006.01) |
| *C07F 9/6506* | (2006.01) |

(52) U.S. Cl.
CPC ............ *A61K 31/69* (2013.01); *A61K 31/675* (2013.01); *A61K 31/683* (2013.01); *A61K 45/06* (2013.01); *C07F 5/027* (2013.01); *C07F 9/65038* (2013.01); *C07F 9/65068* (2013.01)

(58) Field of Classification Search
CPC .... A61K 31/69; A61K 31/675; A61K 31/683; A61K 45/06; C07F 5/027; C07F 9/65038; C07F 9/65068; C07F 5/025; C07F 9/6561; A61P 31/00; A61P 35/00
See application file for complete search history.

(56) References Cited

U.S. PATENT DOCUMENTS

| | | | |
|---|---|---|---|
| 5,240,938 A | 8/1993 | Greenlee et al. | |
| 5,245,035 A | 9/1993 | Andrew et al. | |
| 5,294,716 A | 3/1994 | Andrew et al. | |
| 5,360,809 A | 11/1994 | Axelsson et al. | |
| 5,468,757 A | 11/1995 | Jakubowski et al. | |
| 8,592,396 B2 | 11/2013 | Meng et al. | |
| 2002/0132819 A1 | 9/2002 | Metcalf, III et al. | |
| 2003/0114467 A1 | 6/2003 | Shakespeare et al. | |
| 2006/0264644 A1 | 11/2006 | Allegrini et al. | |
| 2008/0008682 A1 | 1/2008 | Chong et al. | |
| 2008/0114045 A1 | 5/2008 | Wang et al. | |
| 2009/0149521 A1 | 6/2009 | Choi et al. | |
| 2009/0156596 A1 | 6/2009 | Wang et al. | |
| 2009/0176849 A1 | 7/2009 | Selic | |
| 2009/0264384 A1 | 10/2009 | Didsbury et al. | |
| 2017/0057968 A1 | 3/2017 | Li et al. | |
| 2017/0305893 A1 | 10/2017 | Llona-Minguez et al. | |
| 2019/0055246 A1 | 2/2019 | He et al. | |
| 2022/0056052 A1 | 2/2022 | Hawley et al. | |

FOREIGN PATENT DOCUMENTS

| CN | 1752087 A | 3/2006 |
|---|---|---|
| CN | 108409767 | 8/2008 |

(Continued)

OTHER PUBLICATIONS

International Search Report and Written Opinion from PCT/US19/68669 mailed May 5, 2020 (10 pages).
Carozza et al., Nature Cancer | vol. 1 | Feb. 2020 | 184-196.
Carozza et al Cell Chemical Biology, vol. 27, Issue 11, Nov. 19, 2020, pp. 1347-1358.e5.
Kumar, A. Sanjeev et al. "alternative synthesis of telmisartan via suzuki coupling". Archives of Applied Science Research. (2010): 135-141.

(Continued)

*Primary Examiner* — Clinton A Brooks
*Assistant Examiner* — Kyle Nottingham
(74) *Attorney, Agent, or Firm* — Mintz, Levin, Cohn, Ferris, Glovsky and Popeo, P.C.

(57) ABSTRACT

The present disclosure provides certain bicyclic heteroaryl compounds that inhibit ectonucleotide pyrophosphatase/phosphodiesterase 1 (ENPP1) enzymatic activity and are therefore useful for the treatment of diseases and conditions modulated at least in part by ENPP1. In some embodiments, the bicyclic heteroaryl compounds includes those of Formula (I). Also provided herein are pharmaceutical compositions containing such compounds and processes for preparing such compounds.

40 Claims, No Drawings

(56) References Cited

FOREIGN PATENT DOCUMENTS

| | | | |
|---|---|---|---|
| JP | 2005089334 A | | 4/2005 |
| WO | 1992005180 A1 | | 4/1992 |
| WO | 2002076986 | | 10/2002 |
| WO | 2006125592 | | 1/2006 |
| WO | 2006067215 A1 | | 6/2006 |
| WO | 2007081755 A1 | | 7/2007 |
| WO | 2007134169 A1 | | 11/2007 |
| WO | 2008015794 | | 2/2008 |
| WO | 2008063300 | | 5/2008 |
| WO | 2008153857 A1 | | 12/2008 |
| WO | 2009139373 | | 11/2009 |
| WO | 2010009029 A2 | | 1/2010 |
| WO | 2010036357 A1 | | 4/2010 |
| WO | 2011127933 | | 4/2011 |
| WO | 2011053247 A1 | | 5/2011 |
| WO | 2012106343 | | 8/2012 |
| WO | 2013068438 A1 | | 5/2013 |
| WO | 2013132253 | | 9/2013 |
| WO | 2016036887 | | 3/2016 |
| WO | WO-2016055582 A1 * | 4/2016 | ......... A61K 31/4184 |
| WO | 20160200840 | | 12/2016 |
| WO | 2018005591 | | 1/2018 |
| WO | 2018119325 | | 6/2018 |
| WO | 2018119328 | | 6/2018 |
| WO | 2019051269 | | 3/2019 |
| WO | 2019046778 | | 7/2019 |
| WO | 2020/160333 | | 8/2020 |
| WO | 2020191501 | | 10/2020 |
| WO | 2021061803 | | 1/2021 |
| WO | 2021133915 | | 1/2021 |
| WO | 2021053507 | | 3/2021 |
| WO | 2021203772 | | 10/2021 |
| WO | 2021158829 | | 12/2021 |

OTHER PUBLICATIONS

Patel, Snahel D et al. "Quinazolin-4-piperidin-4-methyl sulfamide PC-1 inhibitors: alleviating hERG interactions through structure based design." *Bioorganic & medicinal chemistry letters* vol. 19,12 (2009): 3339-43.

Stanford 1: Nat Cancer. Feb. 2020; 1(2): 184-196 Extracellular cGAMP is a cancer cell-produced immunotransmitter involved in radiation-induced anti-cancer immunity.

Forcellini, Elsa et al. "Synthesis and biological evaluation of novel quinazoline-4-piperidinesulfamide derivatives as inhibitors of NPP1." *European journal of medicinal chemistry* vol. 147 (2018): 130-149.

Lefebvre, Carole-Anne et al. "Synthesis of novel substituted pyrimidine derivatives bearing a sulfamide group and their in vitro cancer growth inhibition activity." Bioorganic & Medicinal Chemistry letters vol. 27,2 (2017): 299-302.

British Journal of Pharmacology (2015) 172 4189-4199 4189 Quinazoline-4-piperidine sulfamides are specific inhibitors of human NPP1 and prevent pathological mineralization of valve interstitial cells.

Llona-Minguez S., et al. Discovery of the First Potent and Selective Inhibitors of Human dCTP Pyrophosphatase 1. J Med Chem. Feb. 11, 2016;59(3):1140-1148. Epub Jan. 27, 2016.

Yu X-J, et al. Microwave assisted Synthesis and Biological activities of 9- boronobenzyladenine derivatives. Journal of Chemical Research. 2007. pp. 347-349.

CAS Registry No. 1334047-95-8, CAS SciFinder® entry for registry No., Dec. 8, 2022, 1 page (Year: 2022).

CAS Registry No. 1312936-65-4, CAS SciFinder® entry for registry No., Dec. 8, 2022, 1 page (Year: 2022).

CAS Registry No. 1313742-77-6, CAS SciFinder® entry for registry No., Dec. 8, 2022, 1 page (Year: 2022).

CAS Registry No. 1332718-43-0, CAS SciFinder® entry for registry No., Dec. 8, 2022, 1 page (Year: 2022).

CAS Registry No. 1333121-22-4, CAS SciFinder® entry for registry No., Dec. 8, 2022, 1 page (Year: 2022).

CAS Registry No. 1333478-08-2, CAS SciFinder® entry for registry No., Dec. 8, 2022, 1 page (Year: 2022).

CAS Registry No. 1333997-56-0, CAS SciFinder® entry for registry No., Dec. 8, 2022, 1 page (Year: 2022).

CAS Registry No. 1333997-61-7, CAS SciFinder® entry for registry No., Dec. 8, 2022, 1 page (Year: 2022).

CAS Registry No. 1333997-70-8, CAS SciFinder® entry for registry No., Dec. 8, 2022, 1 page (Year: 2022).

CAS Registry No. 1334047-99-2, CAS SciFinder® entry for registry No., Dec. 8, 2022, 1 page (Year: 2022).

CAS Registry No. 1334241-18-7, CAS SciFinder® entry for registry No., Dec. 8, 2022, 1 page (Year: 2022).

CAS Registry No. 1334241-20-1, CAS SciFinder® entry for registry No., Dec. 8, 2022, 1 page (Year: 2022).

CAS Registry No. 1334241-41-6, CAS SciFinder® entry for registry No., Dec. 8, 2022, 1 page (Year: 2022).

CAS Registry No. 1334334-16-5, CAS SciFinder® entry for registry No., Dec. 8, 2022, 1 page (Year: 2022).

CAS Registry No. 1334752-34-9, CAS SciFinder® entry for registry No., Dec. 8, 2022, 1 page (Year: 2022).

CAS Registry No. 2246839-39-2, CAS SciFinder® entry for registry No., Dec. 8, 2022, 1 page (Year: 2022).

CAS Registry No. 2246866-59-9, CAS SciFinder® entry for registry No., Dec. 8, 2022, 1 page (Year: 2022).

International Search Report and Written opinion from corresponding International Appl. PCT/US20/27700, mailed on Aug. 19, 2020 (21 pages).

REAXYS Database Accession Nos. 33750111 and 33502876.

* cited by examiner

BICYCLIC HETEROARYL DERIVATIVES AS ECTONUCLEOTIDE PYROPHOSPHATASE PHOSPHODIESTERASE 1 INHIBITORS

CROSS-REFERENCES TO RELATED APPLICATIONS

This application is a U.S. National Phase Application of PCT International Application No. PCT/US2020/027700, filed Apr. 10, 2020, which is an international application of and claims the benefit of priority under 35 U.S.C. § 119(e) to U.S. Provisional Application No. 62/833,455 filed Apr. 12, 2019 and U.S. Provisional Application No. 62/881,111 filed Jul. 31, 2019, the contents of each are herein incorporated by reference in their entirety for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

FIELD OF THE DISCLOSURE

The present disclosure provides certain bicyclic heteroaryl phosphonate and boronate compounds that inhibit ectonucleotide pyrophosphatase/phosphodiesterase 1 (ENPP1) enzymatic activity and are therefore useful for the treatment of diseases treatable by inhibition of ENPP1. Also provided are pharmaceutical compositions containing such compounds and processes for preparing such compounds.

BACKGROUND

ENPP1 enzyme is present in a wide range of tissues and cell types, such as lymphocytes, macrophages, liver, brain, heart, kidney, vascular smooth muscle cells, and chondrocytes. ENPP1 hydrolyzes ATP and other nucleoside triphosphates and releases AMP or other nucleoside monophosphates as well as pyrophosphate (PPi) (Kato K et al. 2012 PNAS 109:16876-16881; Hessle L et al. 2002 PNAS 99:9445-9449). The enzyme can also hydrolyze other nucleoside monophosphate esters (Kato K et al. 2012 PNAS 109:16876-16881). ENPP1 has been identified as the dominant 2'-3'-cGAMP hydrolase in cultured cells, tissue extracts and blood (Li L et al. 2014 Nat Chem Biol 10:1043-1048). Tissues and blood from ENPP1 knockout mice lack 2'-3'-cGAMP hydrolase activity. Elevated levels of ENPP1 have been associated with calcific aortic valve disease (CAVD) and calcium pyrophosphate dihydrate (CPPD) disease, an inflammatory disease resulting from CPPD crystal deposits in the joint and surrounding tissues (Cote N et al. 2012 Eur J Pharmacol 689:139-146; Johnson K et al. 2001 Arthritis Rheum 44:1071). ENPP1 expression is upregulated in certain hepatocellular carcinomas, glioblastomas, melanomas, testicular, pancreatic and thyroid and breast cancers and has been associated with resistance to chemotherapy (see Lau W M et al. 2013 PLoS One 8:5; Bageritz J et al. 2014 Mol Cell Oncology 1:3; Bageritz J et al. 2014 Cell Death, Differentiation 21:929-940; Umar A et al. 2009 Mol Cell Proteomics 8:1278-1294). ENPP1 upregulation and variants of ENPP1 are also associated with insulin resistance and type 2 diabetes (Meyre D et al. 2005 Nat Genet 37:863-867; Maddux B A et al. 1995 Nature 373:448-451; Rey D et al. 2012 Mol Biol Rep 39:7687-7693) and enzyme activity of ENPP1 was reported to be required for the inhibition of insulin receptor signaling (Chin C N et al. 2009 Eur J Pharmacol 606:17-24).

Cyclic GMP-AMP synthase (cGAS) is a pattern recognition receptor that synthesizes the endogenous messenger molecule cGAMP from ATP and GTP in response to the presence of DNA derived from viruses, bacteria, damaged mitochondria or cancer cells. The cGAMP molecule then binds to the stimulator of interferon genes (STING) protein, which initiates a signaling response that activates innate immunity and results in the production of type I interferon, antiviral and immune-stimulatory cytokines (Sun L et al. 2013 Science 339:786-791; Wu J et al. 2013 Science 339:826-830; Gao D et al. 2013 Science 341:903-906; Li X et al. 2013 Science 341:1390-1394; Schoggins J W et al. 2014 Nature 505:691-695; Wassermann R et al. 2015 Cell Host Microbe 17:799-810; Watson R O et al. 2015 Cell Host Microbe 17:811-819; Collins A et al. 2015 Cell Host Microbe 17:820-828; West A et al. 2015 Nature 520:533-557; Woo S R et al. 2014 Immunity 41:830-842; Deng L et al. 2014 Immunity 41:843-852; Chen Q et al. 2016 Nat Immunol 17:1142-1148). The cGAS enzyme, cGAMP messenger and STING are is also involved in host defense against RNA viruses and the immune control of tumor development (Aguirre S et al. 2012 PLoS Pathog 8:e1002934; Barber G N 2015 Nat Rev Immunol 15:760-770). ENPP1 has been identified as the enzyme that naturally hydrolyzes cGAMP and therefore counteracts the innate immune response against infectious agents, damaged cells and cancer cells (Li L et al. 2014 Nat Chem Biol 10:1043-1048). The efficacy of non-hydrolyzable cGAMP analogs in inducing functional immune responses is higher than that of natural, hydrolysable cGAMP (Li L et al. 2014 Nat Chem Biol 10:1043-1048; Corrales L et al. 2015 Cell Rep 11:1018-1030). Virus infection has been demonstrated to be facilitated by ENPP1 overexpression and is attenuated by silencing of ENPP1 (Wang J et al. 2018 Mol Immunol 95:56-63).

Inhibitors of cGAMP hydrolysis may therefore be used to increase the effectiveness of immune responses against cancer cells and tumors and against infections by RNA or DNA viruses or bacteria. Inhibitors of ENPP1 and of cGAMP or nucleoside triphosphate hydrolysis may also be used for the treatment of inflammatory diseases that are associated with elevated nucleotidase levels, reduced nucleoside triphosphate, reduced cGAMP or reduced nucleoside monophosphate ester levels or diseases associated with elevated nucleoside or nucleoside monophosphate levels. For these reasons, ENPP1 is an attractive therapeutic target for the treatment of diseases.

The present disclosure addresses these needs and provides related advantages as well.

SUMMARY

In a first aspect, provided is a compound of Formula (I):

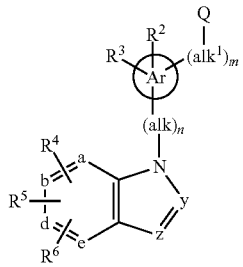

wherein:
- a, b, d, and e are CH; or one or two of a, b, d, and e are N and remaining of a, b, d, and e are CH;
- one of y and z is N and the other y and z is $CR^7$; or both y and z are $CR^7$ wherein each $R^7$ is independently hydrogen, alkyl, hydroxy, or halo;
- alk is alkylene optionally substituted with one, two, or three halo;
- $alk^1$ is alkylene wherein one carbon atom in the alkylene chain can be replaced by oxygen and the alkylene chain is optionally substituted with one, two, or three halo;
- m and n are independently 0 or 1; provided that at least one of m and n is 1;
- Ar is aryl or heteroaryl;
- Q is —P(O)($R^a$)($R^b$) or —B($R^w$)($R^x$), wherein $R^a$ and $R^b$ are independently selected from hydroxy, alkoxy, —Oaryl (where aryl is optionally substituted with one to three substituents independently selected from alkyl, alkenyl, alkoxy, halo, haloalkyl, amino, alkylamino, dialkylamino, cyano, or nitro), —O—($CH_2$)$OCOR^c$ (where $R^c$ is alkyl), —O—($CH_2$)$OCOOR^c$ (where $R^c$ is alkyl), —O-($alk^2$)$OR^d$ (where $alk^2$ is alkylene and $R^d$ is alkyl), —S—($CH_2$)$_2SCOR^e$ (where $R^e$ is alkyl), or —$NR^g$—(CHR)$OCOR^f$ (where R is hydrogen, alkyl, hydroxymethyl, thiomethyl, methylthiomethyl, amidinopropyl, indol-3-ylmethyl, indol-4-ylmethyl, carboxymethyl, carboxyethyl, aminocarbonylmethyl, aminocarbonylethyl, phenyl or phenylalkyl (wherein phenyl either alone or as part of phenylalkyl is optionally substituted with one to three substituents independently selected from alkyl, alkoxy, halo, hydroxy, cyano or nitro), $R^f$ is alkyl or benzyl and $R^g$ is hydrogen or together with R forms —($CH_2$)$_3$—); or $R^a$ and $R^b$ together with the phosphorus atom to which they are attached form a ring of formula (a):

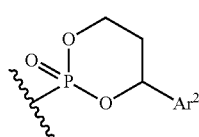

wherein $Ar^2$ is phenyl or six membered heteroaryl optionally substituted with one to three halo; and
$R^w$ and $R^x$ are independently selected from hydroxy, alkoxy, —Oaryl (where aryl is optionally substituted with one to three substituents independently selected from alkyl, alkenyl, alkoxy, halo, haloalkyl, amino, alkylamino, dialkylamino, cyano, or nitro), —O—($CH_2$)$OCOR^c$ (where $R^c$ is alkyl), —O-($alk^2$)$OR^d$ (where $alk^2$ is alkylene and $R^d$ is alkyl), —S—($CH_2$)$_2SCOR^e$ (where $R^e$ is alkyl), or —$NR^g$—(CHR)$OCOR^f$ (where R is hydrogen, alkyl, hydroxymethyl, thiomethyl, methylthiomethyl, amidinopropyl, indol-3-ylmethyl, indol-4-ylmethyl, carboxymethyl, carboxyethyl, aminocarbonylmethyl, aminocarbonylethyl, phenyl or phenylalkyl (wherein phenyl either alone or as part of phenylalkyl is optionally substituted with one to three substituents independently selected from alkyl, alkoxy, halo, hydroxy, cyano or nitro), $R^f$ is alkyl or benzyl and $R^g$ is hydrogen or together with R forms —($CH_2$)$_3$—); or
$R^w$ and $R^x$ together with the boron atom to which they are attached can form —O(CRR')$_2$O— or —O(CRR')$_3$O— wherein each R and R' is independently hydrogen or methyl;
$R^2$ and $R^3$ are independently hydrogen, alkyl, alkoxy, halo, haloalkyl, haloalkoxy, or cyano;
$R^4$ is hydrogen, alkyl, alkoxy, alkylthio, alkylsulfonyl, halo, haloalkyl, haloalkoxy, cyano, carboxy, alkoxycarbonyl, aminocarbonyl, alkylaminocarbonyl, dialkylaminocarbonyl, aminosulfonyl, alkylaminosulfonyl, or dialkylaminosulfonyl; and
$R^5$ and $R^6$ are independently hydrogen, alkyl, alkoxy, hydroxy, halo, haloalkyl, haloalkoxy, hydroxyalkyl, alkoxyalkyl, hydroxyalkoxy, alkoxyalkoxy, hydroxyalkylamino, alkoxyalkylamino, amino, aminoalkyl, aminoalkoxy, aminoalkylamino, heterocyclyl, heterocyclyloxy, heterocyclylamino (wherein heterocyclyl either alone or part of heterocyclyloxy and heterocyclylamino is optionally substituted with $R^h$, $R^i$, or $R^k$ independently selected from alkyl, halo, hydroxy, alkoxy, hydroxyalkyl, alkoxyalkyl, and aminoalkyl), heterocyclylalkyl, heterocyclylalkyloxy, heterocyclylalkylamino (wherein the heterocyclyl ring in heterocyclylalkyl, heterocyclylalkyloxy, and heterocyclylalkylamino is optionally substituted with one, two, or three substituents independently selected from alkyl, halo, hydroxy, alkoxy, hydroxyalkyl, alkoxyalkyl, and aminoalkyl), cycloalkyloxy, phenyloxy, or heteroaryloxy (where phenyl in phenyloxy and heteroaryl in heteroaryloxy are optionally substituted with one, two, or three substituents where two of the optional substituents are independently selected from alkyl, hydroxy, alkoxy, halo, haloalkyl, haloalkoxy, and cyano); or a pharmaceutically acceptable salt thereof;
provided that:
1. when Formula (I) has the structure

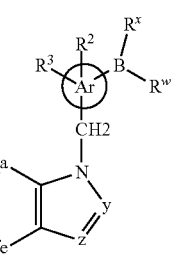

and:

(i) $R^w$ and $R^x$ are each —OH, then

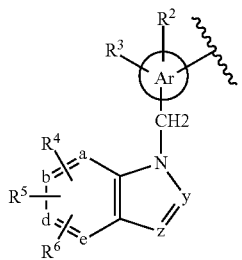

is not 4-((6-amino-2-butoxy-8-methoxy-9H-purin-9-yl)methyl)phenyl; 4-((5,6-dichloro-2-methyl-1H-benzimidazol-1-yl)methyl)phenyl; 4-((2-methyl-1H-benzimidazol-1-yl)methyl)phenyl; 5-fluoro-2-((2-methyl-1H-benzimidazol-1-yl)methyl)phenyl; 3-fluoro-4-((2-methyl-1H-benzimidazol-1-yl)methyl)phenyl; 3-((5,6-dimethyl-1H-benzimidazol-1-yl)methyl)phenyl; 4-((5,6-dimethyl-1H-benzimidazol-1-yl)methyl)phenyl; 2-((2-methyl-1H-benzimidazol-1-yl)methyl)phenyl; 2-((5,6-dimethyl-1H-benzimidazol-1-yl)methyl)phenyl; 2-fluoro-5-((2-methyl-1H-benzimidazol-1-yl)methyl)phenyl; 3-((2-methyl-1H-benzimidazol-1-yl)methyl)phenyl; 3-(1H-benzimidazol-1-ylmethyl)phenyl; 3-(1H-indazol-1-ylmethyl)phenyl; 2-(1H-benzimidazol-1-ylmethyl)phenyl; 4-(1H-benzimidazol-1-ylmethyl)phenyl; 4-(1H-indol-1-ylmethyl)phenyl; 4-((6-amino-9H-purin-9-yl)methyl)phenyl; 3-((6-amino-9H-purin-9-yl)methyl)phenyl; 2-((6-amino-9H-purin-9-yl)methyl)phenyl; 4-(1H-benzimidazol-1-ylmethyl)-3-fluorophenyl; 4-((2-ethyl-5,7-dimethyl-3H-imidazo[4,5-b]pyridin-3-yl)methyl)-3-fluorophenyl; 5-(1H-benzimidazol-1-ylmethyl)-2-fluorophenyl; 4-((2-ethyl-5,7-dimethyl-3H-imidazo[4,5-b]pyridin-3-yl)methyl)-3-fluorophenyl; 2-(1H-benzimidazol-1-ylmethyl)-5-fluorophenyl; 5-(1H-benzimidazol-1-ylmethyl)-2-methoxyphenyl; 3-(1H-benzimidazol-1-ylmethyl)-4-methoxyphenyl; 2-((2-ethyl-5,7-dimethyl-3H-imidazo[4,5-b]pyridin-3-yl)methyl)-5-pyrimidinyl; 6-((2-ethyl-5,7-dimethyl-3H-imidazo[4,5-b]pyridin-3-yl)methyl)-3-pyridinyl, or 4-(2-ethoxy-7-carboxy-1H-benzimidazol-1-ylmethyl)phenyl;

(ii) —B($R^w$)($R^x$) is

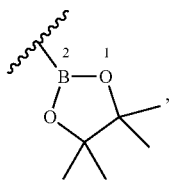 [SMILES: *B1OC(C)(C)C(C)(C)O1]

then

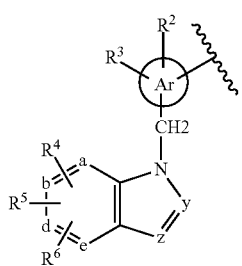

is not 2-(1H-benzo[d]imidazol-1-ylmethyl)phenyl, 2-(1H-indol-1-ylmethyl)phenyl, 3-(1H-indazol-1-ylmethyl)phenyl-, 4-(2-ethyl-5,7-dimethyl-3H-imidazo[4,5-b]pyridin-3-yl)methylphenyl, 4-(2-methyl-1H-benzimidazol-1-ylmethyl)phenyl; 4-(6-amino-8-methoxy-2-(tetrahydro-2H-pyran-4-yl)methoxy-9H-purin-9-ylmethyl)phenyl, 3-fluoro-4-(6-amino-8-methoxy-2-(2-methoxyethoxy)-9H-purin-9-ylmethyl)phenyl, 4-(6-amino-8-methoxy-2-(2-methoxyethoxy)-9H-purin-9-ylmethyl)phenyl, 4-(6-amino-2-butoxy-8-methoxy-9H-purin-9-ylmethyl)phenyl, 4-(1H-Indol-1-ylmethyl)phenyl, 4-(1H-benimidazol-1-ylmethyl)phenyl, 3-(7-methoxycarbonyl-1H-indol-1-ylmethyl)phenyl, 4-(7-methoxycarbonyl-1H-indol-1-ylmethyl)phenyl, 4-(2-ethoxy-7-methoxycarbonyl-1H-benzimidazol-1-ylmethyl)phenyl, or 4-(2-ethoxy-7-ethoxycarbonyl-1H-benzimidazol-1-ylmethyl)phenyl; and (iii) —B($R^w$)($R^x$) is

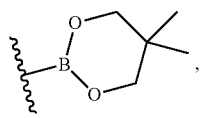 [SMILES: *B1OCC(C)(C)CO1]

then

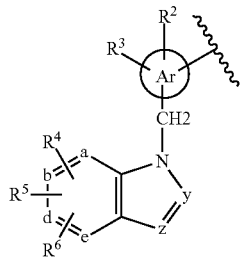

is not 4-(2-ethoxy-7-ethoxycarbonyl-1H-benzimidazol-1-ylmethyl)phenyl; and 2. when Q is —P(O)($R^a$)($R^b$), then one of m and n is 1 and the other of m and n is 0;

or a pharmaceutically acceptable salt thereof.

In a second aspect, provided is a compound of Formula (IA):

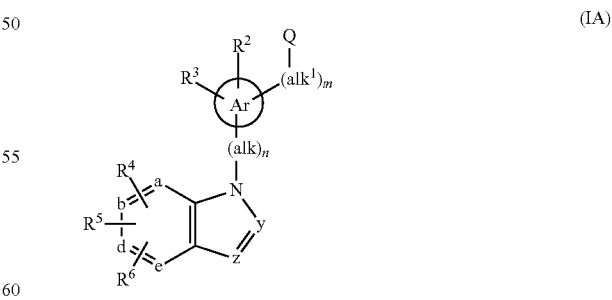

(IA)

wherein:
a, b, d, and e are CH; or one or two of a, b, d, and e are N and remaining of a, b, d, and e are CH;
one of y and z is N and the other y and z is $CR^7$; or both y and z are $CR^7$ wherein each $R^7$ is independently hydrogen, alkyl, hydroxy, or halo;

alk is alkylene optionally substituted with one, two, or three halo;

alk$^1$ is alkylene wherein one carbon atom in the alkylene chain can be replaced by oxygen and the alkylene chain is optionally substituted with one, two, or three halo;

m and n are independently 0 or 1; provided that at least one of m and n is 1;

Ar is aryl, heteroaryl, cycloalkyl, or heterocyclyl;

Q is —P(O)(R$^a$)(R$^b$) or —B(R$^w$)(R$^x$) wherein R$^a$, R$^b$, R$^w$ and R$^x$ are independently selected from hydroxy, alkoxy, —Oaryl (where aryl is optionally substituted with one to three substituents independently selected from alkyl, alkenyl, alkoxy, halo, haloalkyl, amino, alkylamino, dialkylamino, cyano, or nitro), —O—(CH$_2$)OCOR$^c$ (where R$^c$ is alkyl), —O-(alk$^2$)OR$^d$ (where alk$^2$ is alkylene and R$^d$ is alkyl), —S—(CH$_2$)$_2$SCOR$^e$ (where R$^e$ is alkyl), or —NR$^g$—(CHR)OCOR$^f$ (where R is hydrogen, alkyl, hydroxymethyl, thiomethyl, methylthiomethyl, amidinopropyl, indol-3-ylmethyl, indol-4-ylmethyl, carboxymethyl, carboxyethyl, aminocarbonylmethyl, aminocarbonylethyl, phenyl or phenylalkyl (wherein phenyl either alone or as part of phenylalkyl is optionally substituted with one to three substituents independently selected from alkyl, alkoxy, halo, hydroxy, cyano or nitro), R$^f$ is alkyl or benzyl and R$^g$ is hydrogen or together with R forms —(CH$_2$)$_3$—); or R$^a$ and R$^b$ together with the phosphorus atom to which they are attached form a ring of formula (a):

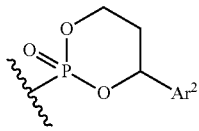

(a)

wherein Ar$^2$ is phenyl or six membered heteroaryl optionally substituted with one to three halo; or R$^w$ and R$^x$ together with the boron atom to which they are attached can form —O(CRR')$_2$O— or —O(CRR')$_3$O— wherein each R and R' is independently hydrogen or methyl;

R$^2$ and R$^3$ are independently hydrogen, alkyl, alkoxy, halo, haloalkyl, haloalkoxy, or cyano;

R$^4$ is hydrogen, alkyl, alkoxy, alkylthio, alkylsulfonyl, halo, haloalkyl, haloalkoxy, cyano, carboxy, alkoxycarbonyl, aminocarbonyl, alkylaminocarbonyl, dialkylaminocarbonyl, aminosulfonyl, alkylaminosulfonyl, or dialkylaminosulfonyl; and R$^5$ and R$^6$ are independently hydrogen, alkyl, alkoxy, hydroxy, halo, haloalkyl, haloalkoxy, hydroxyalkyl, alkoxyalkyl, hydroxyalkoxy, alkoxyalkoxy, hydroxyalkylamino, alkoxyalkylamino, amino, aminoalkyl, aminoalkoxy, aminoalkylamino, heterocyclyl, heterocyclyloxy, heterocyclylamino (wherein heterocyclyl either alone or part of heterocyclyloxy and heterocyclylamino is optionally substituted with R$^h$, R$^i$, or R$^k$ independently selected from alkyl, halo, hydroxy, alkoxy, hydroxyalkyl, alkoxyalkyl, and aminoalkyl), heterocyclylalkyl, heterocyclylalkyloxy, heterocyclylalkylamino (wherein the heterocyclyl ring in heterocyclylalkyl, heterocyclylalkyloxy, and heterocyclylalkylamino is optionally substituted with one, two, or three substituents independently selected from alkyl, halo, hydroxy, alkoxy, hydroxyalkyl, alkoxyalkyl, and aminoalkyl), cycloalkyloxy, phenyloxy, or heteroaryloxy (where phenyl in phenyloxy and heteroaryl in heteroaryloxy are optionally substituted with one, two, or three substituents where two of the optional substituents are independently selected from alkyl, hydroxy, alkoxy, halo, haloalkyl, haloalkoxy, and cyano); or a pharmaceutically acceptable salt thereof;

provided that:

1. when the compound of Formula (IA) has the structure

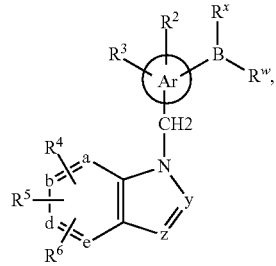

where Ar is aryl or heteroaryl and:

(i) R$^w$ and R$^x$ are each —OH, then

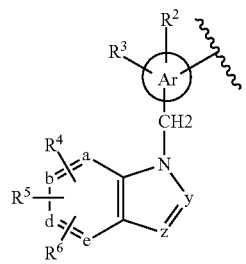

is not 4-((6-amino-2-butoxy-8-methoxy-9H-purin-9-yl)methyl)phenyl; 4-((5,6-dichloro-2-methyl-1H-benzimidazol-1-yl)methyl)phenyl; 4-((2-methyl-1H-benzimidazol-1-yl)methyl)phenyl; 5-fluoro-2-((2-methyl-1H-benzimidazol-1-yl)methyl)phenyl; 3-fluoro-4-((2-methyl-1H-benzimidazol-1-yl)methyl)phenyl; 3-((5,6-dimethyl-1H-benzimidazol-1-yl)methyl)phenyl; 4-((5,6-dimethyl-1H-benzimidazol-1-yl)methyl)phenyl; 2-((2-methyl-1H-benzimidazol-1-yl)methyl)phenyl; 2-((5,6-dimethyl-1H-benzimidazol-1-yl)methyl)phenyl; 2-fluoro-5-((2-methyl-1H-benzimidazol-1-yl)methyl)phenyl; 3-((2-methyl-1H-benzimidazol-1-yl)methyl)phenyl; 3-(1H-benzimidazol-1-ylmethyl)phenyl; 3-(1H-indazol-1-ylmethyl)phenyl; 2-(1H-benzimidazol-1-ylmethyl)phenyl; 4-(1H-benzimidazol-1-ylmethyl)phenyl; 4-(1H-indol-1-ylmethyl)phenyl; 4-((6-amino-9H-purin-9-yl)methyl)phenyl; 3-((6-amino-9H-purin-9-yl)methyl)phenyl; 2-((6-amino-9H-purin-9-yl)methyl)phenyl; 4-(1H-benzimidazol-1-ylmethyl)-3-fluorophenyl; 4-((2-ethyl-5,7-dimethyl-3H-imidazo[4,5-b]pyridin-3-yl)methyl)-3-fluorophenyl; 5-(1H-benzimidazol-1-ylmethyl)-2-fluorophenyl; 4-((2-ethyl-5,7-dimethyl-3H-imidazo[4,5-b]pyridin-3-yl)methyl)-3-fluorophenyl; 2-(1H-benzimidazol-1-ylmethyl)-5-fluorophenyl; 5-(1H-benzimidazol-1-ylmethyl)-2-methoxyphenyl; 3-(1H-benzimidazol-1-ylmethyl)-4-methoxyphenyl; 2-((2-ethyl-5,7-dimethyl-3H-imidazo[4,5-b]pyridin-3-yl)methyl)-5-pyrimidinyl; 6-((2-ethyl-5,7-dimethyl-3H-imidazo[4,5-b]

pyridin-3-yl)methyl)-3-pyridinyl, or 4-(2-ethoxy-7-carboxy-1H-benzimidazol-1-ylmethyl)phenyl;

(ii) —B($R^w$)($R^x$) is

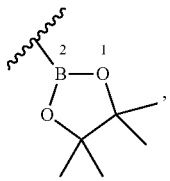 [SMILES: *B1OC(C)(C)C(C)(C)O1]

then

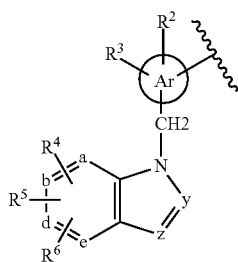

is not 2-(1H-benzo[d]imidazol-1-ylmethyl)phenyl, 2-(1H-indol-1-ylmethyl)phenyl, 3-(1H-indazol-1-ylmethyl)phenyl-, 4-(2-ethyl-5,7-dimethyl-3H-imidazo[4,5-b]pyridin-3-yl)methylphenyl, 4-(2-methyl-1H-benzimidazol-1-ylmethyl)phenyl; 4-(6-amino-8-methoxy-2-(tetrahydro-2H-pyran-4-yl)methoxy-9H-purin-9-ylmethyl)phenyl, 3-fluoro-4-(6-amino-8-methoxy-2-(2-methoxyethoxy)-9H-purin-9-ylmethyl)phenyl, 4-(6-amino-8-methoxy-2-(2-methoxyethoxy)-9H-purin-9-ylmethyl)phenyl, 4-(6-amino-2-butoxy-8-methoxy-9H-purin-9-ylmethyl)phenyl, 4-(1H-Indol-1-ylmethyl)phenyl, 4-(1H-benimidazol-1-ylmethyl)phenyl, 3-(7-methoxycarbonyl-1H-indol-1-ylmethyl)phenyl, 4-(7-methoxycarbonyl-1H-indol-1-ylmethyl)phenyl, 4-(2-ethoxy-7-methoxycarbonyl-1H-benzimidazol-1-ylmethyl)phenyl, or 4-(2-ethoxy-7-ethoxycarbonyl-1H-benzimidazol-1-ylmethyl)phenyl; and (iii) —B($R^w$)($R^x$) is

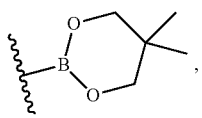

then

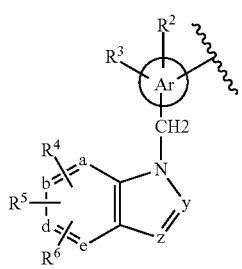

is not 4-(2-ethoxy-7-ethoxycarbonyl-1H-benzimidazol-1-ylmethyl)phenyl; and 2. when Q is —P(O)($R^a$)($R^b$), then one of m and n is 1 and the other of m and n is 0;

or a pharmaceutically acceptable salt thereof.

In a second aspect, provided is a pharmaceutical composition comprising a compound of the present disclosure, e.g., Formula (I) or (IA) (or any of the embodiments thereof described herein) or a pharmaceutically acceptable salt thereof and a pharmaceutically acceptable excipient.

In a third aspect, provided are methods of treating a disease or mediated by ENPP1 in a patient, preferably in a patient recognized as needing such a treatment, comprising administering to the patient a compound of Formula (I) or (IA) (or any of the embodiments thereof described herein) or a pharmaceutically acceptable salt thereof in a therapeutically effective amount. In one embodiment, the disease is cancer such as hepatocellular carcinomas, glioblastomas, melanomas, testicular, pancreatic, thyroid and breast cancer. In another embodiment, the disease is an inflammatory disease e.g., calcific aortic valve disease and calcium pyrophosphate dihydrate. In yet another embodiment the disease metabolic disease e.g., type 2 diabetes or a viral infection.

In a fourth aspect, provided is a compound of Formula (I) or (IA) (or any embodiments thereof described herein) or a pharmaceutically acceptable salt thereof for use as a medicament. In one embodiment, the medicament is for use in the treatment of cancer such as bepatocellular carcinomas, glioblastomas, melanomas, testicular, pancreatic, thyroid and breast cancer. In another embodiment, the medicament is for use in the treatment of an inflammatory disease e.g., calcific aortic valve disease and calcium pyrophosphate dihydrate. In yet another embodiment, the medicament is for use in the treatment of a metabolic disease e.g., type 2 diabetes or a viral infection.

In a fifth aspect provided is the use of a compound of Formula (I) or (IA) or a pharmaceutically acceptable salt thereof (and any embodiments thereof disclosed herein) in the manufacture of a medicament for treating a disease in a patient in which the activity of ENPP1 contributes to the pathology and/or symptoms of the disease. In one embodiment, the disease is cancer such as hepatocellular carcinomas, glioblastomas, melanomas, testicular, pancreatic, thyroid and breast cancer. In another embodiment, the disease is an inflammatory disease e.g., calcific aortic valve disease and calcium pyrophosphate dihydrate. In yet another embodiment, the disease metabolic disease e.g., type 2 diabetes or a viral disease.

In any of the aforementioned aspects involving the treatment of cancer, are further embodiments comprising administering the compound of Formula (I) or (IA) or a pharmaceutically acceptable salt thereof (or any embodiments thereof disclosed herein) in combination with at least one additional anticancer. When combination therapy is used, the agents can be administered simultaneously or sequentially.

DETAILED DESCRIPTION

Definitions

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl, pentyl, and the like.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkenyl" means a linear or branched monovalent hydrocarbon radical of two to six carbon atoms containing a double bond, e.g., ethenyl, propenyl, 2-propenyl, and the like.

"Alkylthio" means —SR radical where R is alkyl as defined above, e.g., methylthio, ethylthio, and the like.

"Alkylsulfonyl" means —SO$_2$R radical where R is alkyl as defined above, e.g., methylsulfonyl, ethylsulfonyl, and the like.

"Amino" means a —NH$_2$.

"Aminocarbonyl" means —CONH$_2$.

"Alkylaminocarbonyl" means —CONHR radical where R is alkyl as defined above, e.g., methylaminocarbonyl, ethylaminocarbonyl, and the like.

"Aminosulfonyl" means —SO$_2$NH$_2$.

"Alkylaminosulfonyl" means —SO$_2$NHR radical where R is alkyl as defined above, e.g., methylaminosulfonyl, ethylaminosulfonyl, and the like.

"Alkylamino" means a —NHR radical where R is alkyl as defined above, e.g., methylamino, ethylamino, propylamino, or 2-propylamino, and the like.

"Aminoalkyl" means a linear monovalent hydrocarbon radical of one to six carbon atoms or a branched monovalent hydrocarbon radical of three to six carbons substituted with —NR'R" where R' and R" are independently hydrogen or alkyl as defined above, e.g., aminomethyl, aminoethyl, methylaminomethyl, and the like.

"Aminoalkylamino" means a —NR$^a$R$^b$ radical where R$^a$ is hydrogen or alkyl and R$^b$ is aminoalkyl as defined above, e.g., aminoethylamino, dimethylaminoethylamino, diethylaminoethylamino, dimethylaminopropylamino, diethylaminopropylamino, and the like.

"Aminoalkyloxy" means a —OR$^a$ radical where R$^a$ is aminoalkyl as defined above, e.g., aminoethyloxy, dimethylaminoethyloxy, diethylaminoethyloxy, dimethylaminopropyloxy, diethylaminopropyloxy, and the like.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to six carbon atoms or a branched monovalent hydrocarbon radical of three to six carbons substituted with at least one alkoxy group, such as one or two alkoxy groups, as defined above, e.g., 2-methoxyethyl, 1-, 2-, or 3-methoxypropyl, 2-ethoxyethyl, and the like.

"Alkoxyalkylamino" means a —NRR' radical where R is hydrogen or alkyl and R' is alkoxyalkyl as defined above, e.g., methoxyethylamino, ethoxyethylamino, propoxypropylamino, ethoxypropylamino, and the like.

"Alkoxyalkyloxy" or "alkoxyalkoxy" means a —(O)R radical where R is alkoxyalkyl as defined above, e.g., methoxyethoxy, ethoxyethoxy, and the like.

"Aryl" means a monovalent monocyclic or bicyclic aromatic hydrocarbon radical of 6 to 10 ring atoms e.g., phenyl or naphthyl.

"Phenyloxy" means a —OR radical where R is phenyl.

"Cycloalkyl" means a cyclic saturated monovalent hydrocarbon radical of three to ten carbon atoms, e.g., cyclopropyl, cyclobutyl, cyclopentyl, or cyclohexyl, and the like.

"Cycloalkyloxy" means a —OR radical where R is cycloalkyl (including specific heterocyclyl rings) as defined above e.g., cyclopropyloxy, and the like.

"Carboxy" means —COOH.

"Dialkylaminocarbonyl" means —CONHRR' where R and R' are independently alkyl as defined above, e.g., dimethylaminocarbonyl, methylethylaminocarbonyl, and the like.

"Dialkylaminosulfonyl" means —SO$_2$NHRR' where R and R' are independently alkyl as defined above, e.g., dimethylaminosulfonyl, methylethylaminosulfonyl, and the like.

"Dialkylamino" means a —NRR' radical where R and R' are alkyl as defined above, e.g., dimethylamino, methylethylamino, and the like.

"Halo" means fluoro, chloro, bromo, or iodo, preferably fluoro or chloro.

"Haloalkyl" means alkyl radical as defined above, which is substituted with one or more halogen atoms, such as one to five halogen atoms, such as fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it can be referred to in this Application as fluoroalkyl.

"Haloalkoxy" means a —OR radical where R is haloalkyl as defined above e.g., —OCF$_3$, —OCHF$_2$, and the like. When R is haloalkyl where the alkyl is substituted with only fluoro, it is referred to in this Application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxy-ethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Hydroxyalkylamino" means a —NR$^a$R$^b$ radical where R$^a$ is hydrogen or alkyl and R$^b$ is hydroxyalkyl as defined above, e.g., hydroxyethylamino, hydroxypropylamino, and the like.

"Hydroxyalkyloxy" means a —OR$^a$ radical where R$^a$ is aminhydroxyalkyl as defined above, e.g., hydroxyethyloxy, hydroxypropyloxy, and the like.

"Heterocyclyl" means a saturated or unsaturated monovalent monocyclic group of 4 to 8 ring atoms in which one or two ring atoms are heteroatom selected from N, O, or S(O)$_n$, where n is an integer from 0 to 2, the remaining ring atoms being C. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydro-pyranyl, thiomorpholino, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group.

"Heterocyclylalkyl" or "heterocycloalkyl" means a -(alkylene)-R radical where R is heterocyclyl ring (including specific heterocyclyl rings) as defined above e.g., tetraydrofuranylmethyl, piperazinylmethyl, morpholinylethyl, and the like.

"Heterocyclylamino" means a —NRR' radical where R is hydrogen or alkyl and R' is heterocyclyl (including specific heterocyclyl rings) as defined above.

"Heterocyclylalkylamino" or "heterocycloalkylamino" means a —NRR' radical where R is hydrogen or alkyl and R' is heterocyclylalkyl ring (including specific heterocyclyl rings) as defined above e.g., tetraydrofuranylmethylamino, piperazinylethylamino, morpholinylethylamino, piperidinylmethylamino, and the like.

"Heterocyclyloxy" means a —OR radical where R is heterocyclyl (including specific heterocyclyl rings) as defined above.

"Heterocyclylalkyloxy" or "heterocycloalkyloxy" means a —OR radical where R is heterocyclylalkyl ring (including specific heterocyclyl rings) as defined above e.g., tetraydrofuranylmethyloxy, piperazinylethyloxy, morpholinylethyloxy, piperidinylmethyloxy, and the like.

"Heteroaryl" means a monovalent monocyclic or bicyclic aromatic radical of 5 to 10 ring atoms, unless otherwise stated, where one or more, (in one embodiment, one, two, or three), ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like. As defined herein, the terms "heteroaryl" and "aryl" are mutually exclusive. When the heteroaryl ring contains 5- or 6 ring atoms it is also referred to herein as 5- or 6-membered heteroaryl.

"Heteroaryloxy" means a —OR radical where R is heteroaryl (including specific heteroaryl rings) as defined above.

The present disclosure also includes protected derivatives of compounds of the present disclosure (I). For example, when compounds of the present disclosure contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of the present disclosure can be prepared by methods well known in the art.

The present disclosure also includes polymorphic forms and deuterated forms of the compound of the present disclosure and/or a pharmaceutically acceptable salt thereof.

A "pharmaceutically acceptable salt" of a compound means a salt that is pharmaceutically acceptable and that possesses the desired pharmacological activity of the parent compound. Such salts include: acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, PA, 1985, which is incorporated herein by reference in its entirety.

The compounds of the present disclosure may have asymmetric centers. Compounds of the present disclosure containing an asymmetrically substituted atom may be isolated in optically active or racemic forms. It is well known in the art how to prepare optically active forms, such as by resolution of materials. All chiral, diastereomeric, all mixtures of chiral or diasteromeric forms, and racemic forms are within the scope of this disclosure, unless the specific stereochemistry or isomeric form is specifically indicated. It will also be understood by a person of ordinary skill in the art that when a compound is denoted as (R) stereoisomer, it may contain the corresponding (S) stereoisomer as an impurity i.e., the (S) stereoisomer in less than about 5%, preferably 2% by wt and then it is denoted as a mixture of R and S isomers, the amounts of R or S isomer in the mixture is greater than about 5%, preferably 2% w/w.

Certain compounds of the present disclosure can exist as tautomers and/or geometric isomers. All possible tautomers and cis and trans isomers, as individual forms and mixtures thereof are within the scope of this disclosure. For example, hydroxy substituted compound of Formula (I) can exist as a tautomer as shown below:

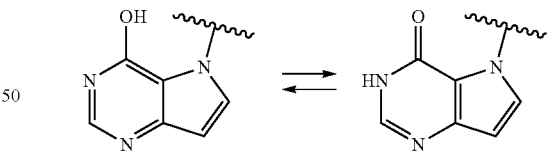

Additionally, as used herein the term alkyl includes all the possible isomeric forms of said alkyl group. Furthermore, when the cyclic groups such as aryl, heteroaryl, heterocyclyl are substituted, they include all the positional isomers. Furthermore, all hydrates of a compound of the present disclosure are within the scope of this disclosure.

Certain structures provided herein are drawn with one or more floating substituents. Unless provided otherwise or otherwise clear from the context, the substituent(s) may be present on any atom of the ring through which the substituent is drawn, where chemically feasible and valency rules permitting. For example, in the structure:

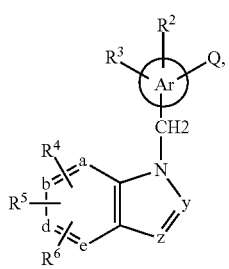

the R⁴ substituent can replace any hydrogen on the six membered aromatic ring portion of the bicyclic ring system, including the hydrogen of CH when a is CH.

The compounds of the present disclosure may also contain unnatural amounts of isotopes at one or more of the atoms that constitute such compounds. Unnatural amounts of an isotope may be defined as ranging from the amount found in nature to an amount 100% of the atom in question. that differ only in the presence of one or more isotopically enriched atoms. Exemplary isotopes that can be incorporated into compounds of the present invention, such as a compound of Formula (I) (and any embodiment thereof disclosed herein including specific compounds) include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Isotopically-labeled compounds (e.g., those labeled with .sup.3H and .sup.14C) can be useful in compound or substrate tissue distribution assays. Tritiated (i.e., .sup.3H) and carbon-14 (i.e., .sup.14C) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, in compounds disclosed herein, including in Table 1 below one or more hydrogen atoms are replaced by $^{2}H$ or $^{3}H$, or one or more carbon atoms are replaced by $^{13}C$- or $^{14}C$-enriched carbon. Positron emitting isotopes such as $^{15}O$, $^{13}N$, $^{11}C$, and $^{15}F$ are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

"Oxo" or "carbonyl" means =(O) group.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass ±10%, preferably ±5%, the recited value and the range is included.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "patient" is generally synonymous with the term "subject" and includes all mammals including humans. Examples of patients include humans, livestock such as cows, goats, sheep, pigs, and rabbits, and companion animals such as dogs, cats, and horses. Preferably, the patient is a human.

The terms "inhibiting" and "reducing," or any variation of these terms in relation of EPPI, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of EPPI activity compared to normal.

"Treating" or "treatment" of a disease includes:
(1) preventing the disease, i.e. causing the clinical symptoms of the disease not to develop in a mammal that may be exposed to or predisposed to the disease but does not yet experience or display symptoms of the disease;
(2) inhibiting the disease, i.e., arresting or reducing the development of the disease or its clinical symptoms; or
(3) relieving the disease, i.e., causing regression of the disease or its clinical symptoms.

A "therapeutically effective amount" means the amount of a compound of the present disclosure and/or a pharmaceutically acceptable salt thereof that, when administered to a patient for treating a disease, is sufficient to effect such treatment for the disease. The "therapeutically effective amount" will vary depending on the compound, the disease and its severity and the age, weight, etc., of the mammal to be treated.

Representative compound of Formula (I) are disclosed in Table 1 below:

| Cmpd | Structure | Name |
|---|---|---|
| 1 | 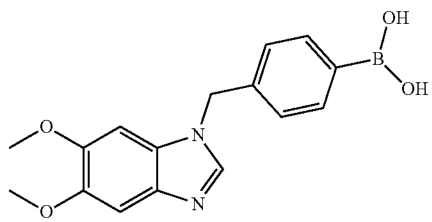 [SMILES: COc1cc2ncn(Cc3ccc(B(O)O)cc3)c2cc1OC] | 4-((5,6-dimethoxy-1,3-benzodiazol-1-yl)methyl)phenylboronic acid |
| 2 | 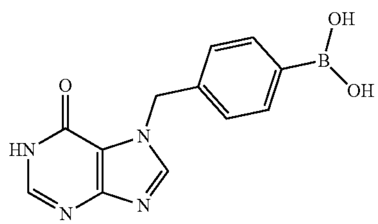 [SMILES: O=c1[nH]cnc2ncn(Cc3ccc(B(O)O)cc3)c12] | 4-((6-Oxo-1H-purin-7-yl)methyl)phenylboronic acid |
| 3 | 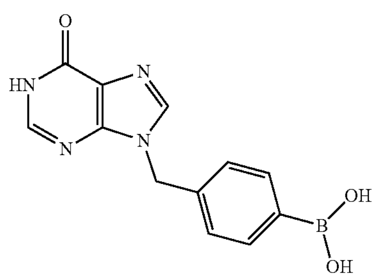 [SMILES: O=c1[nH]cnc2c1ncn2Cc1ccc(B(O)O)cc1] | 4-((6-oxo-1H-purin-9-yl)methyl)phenylboronic acid |
| 4 | 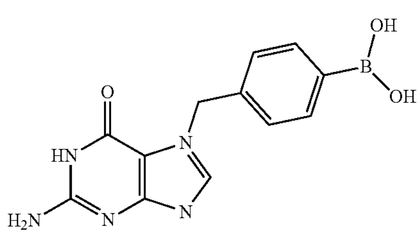 | 4-((2-amino-6-oxo-1H-purin-7-yl)methyl)phenylboronic acid |
| 5 | 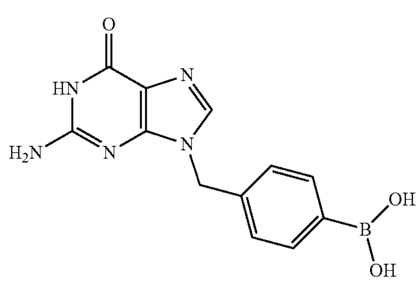 [SMILES: Nc1nc2c(ncn2Cc2ccc(B(O)O)cc2)c(=O)[nH]1] | 4-((2-amino-6-oxo-1H-purin-9-yl)methyl)phenylboronic acid |
| 6 | 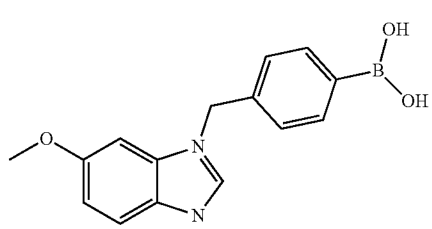 | 4-((6-methoxy-1,3-benzodiazol-1-yl)methyl)phenylboronic acid |

-continued

| Cmpd | Structure | Name |
|---|---|---|
| 7 | 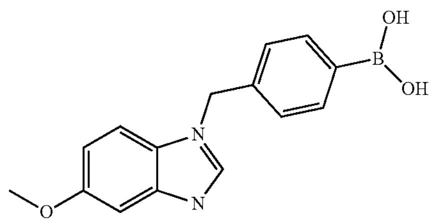 | 4-((5-methoxy-1,3-benzodiazol-1-yl)methyl)phenylboronic acid |
| 8 | 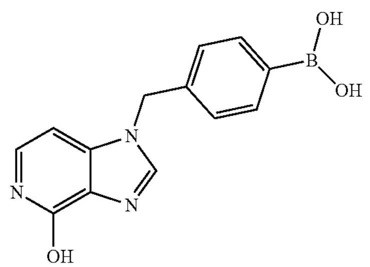 [SMILES: OB(O)c1ccc(Cn2cnc3c(O)nccc32)cc1] | 4-((4-hydroxyimidazo[4,5-c]pyridin-1-yl)methyl)phenylboronic acid |
| 9 | 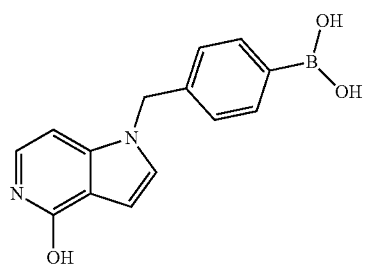 [SMILES: OB(O)c1ccc(Cn2ccc3c(O)nccc32)cc1] | (4-((4-hydroxy-1H-pyrrolo[3,2-c]pyridin-1-yl)methyl)phenyl)boronic acid |
| 10 | 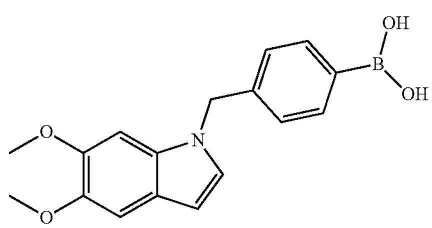 [SMILES: COc1cc2ccn(Cc3ccc(B(O)O)cc3)c2cc1OC] | 4-((5,6-dimethoxyindol-1-yl)methyl)phenylboronic acid |
| 11 | 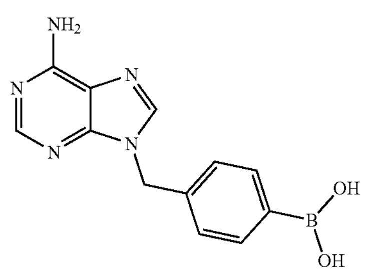 [SMILES: Nc1ncnc2c1ncn2Cc1ccc(B(O)O)cc1] | 4-((6-aminopurin-9-yl)methyl)phenylboronic acid |
| 12 | 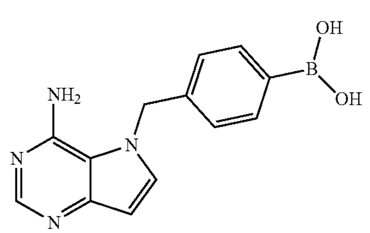 [SMILES: Nc1ncnc2ccn(Cc3ccc(B(O)O)cc3)c12] | (4-((6-amino-7H-purin-7-yl)methyl)phenyl)boronic acid |

-continued

| Cmpd | Structure | Name |
|---|---|---|
| 13 | 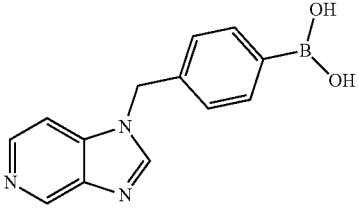 [SMILES: OB(O)c1ccc(Cn2cnc3cnccc32)cc1] | (4-((1H-imidazo[4,5-c]pyridin-1-yl)methyl)phenyl)boronic acid |
| 14 | 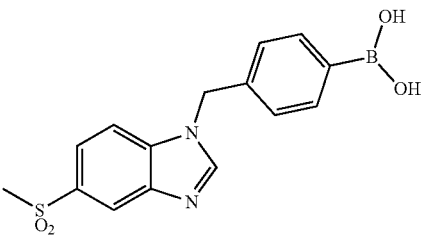 [SMILES: CS(=O)(=O)c1ccc2c(c1)ncn2Cc1ccc(B(O)O)cc1] | (4-((5-(methylsulfonyl)-1H-benzo[d]imidazol-1-yl)methyl)phenyl)boronic acid |
| 15 | 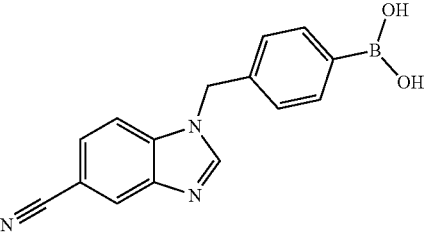 [SMILES: N#Cc1ccc2c(c1)ncn2Cc1ccc(B(O)O)cc1] | 4-((5-cyano-1,3-benzodiazol-1-yl)methyl)phenylboronic acid |
| 16 | 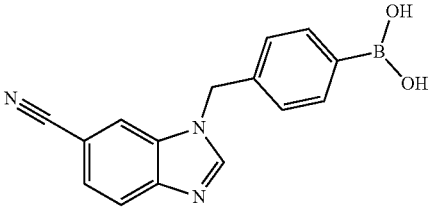 [SMILES: N#Cc1ccc2ncn(Cc3ccc(B(O)O)cc3)c2c1] | 4-((6-cyano-1,3-benzodiazol-1-yl)methyl)phenylboronic |
| 17 | 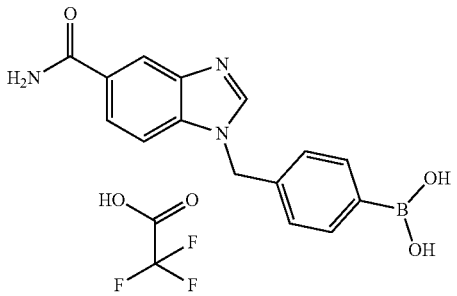 | 4-((5-carbamoyl-1,3-benzodiazol-1-yl)methyl)phenylboronic acid trifluoroacetic acid salt |
| 18 | 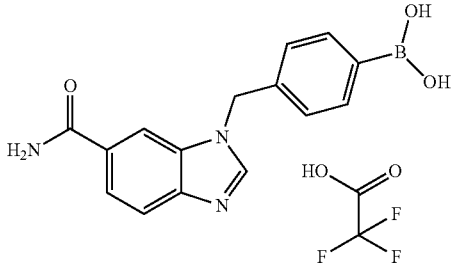 | 4-((6-carbamoyl-1,3-benzodiazol-1-yl)methyl)phenylboronic acid trifluoroacetic acid salt |

-continued

| Cmpd | Structure | Name |
|---|---|---|
| 19 | 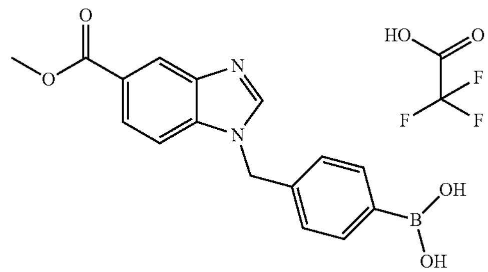 [SMILES: COC(=O)c1ccc2c(c1)ncn2Cc1ccc(B(O)O)cc1 ; O=C(O)C(F)(F)F] | 4-((5-(methoxycarbonyl)-1,3-benzodiazol-1-yl)methyl)-phenylboronic acid trifluoroacetic acid salt |
| 20 | 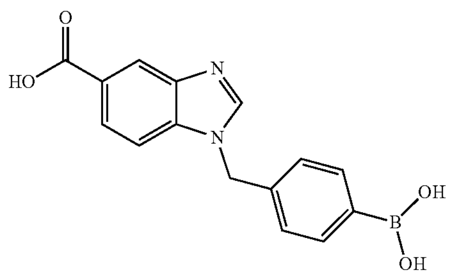 [SMILES: O=C(O)c1ccc2c(c1)ncn2Cc1ccc(B(O)O)cc1] | 1-((4-(dihydroxyboranyl)phenyl)methyl)-1,3-benzodiazole-5-carboxylic acid |
| 21 | 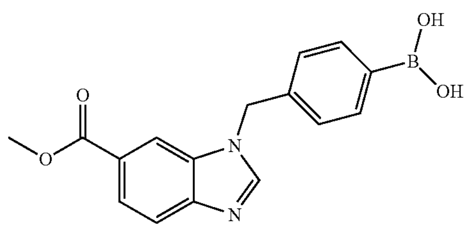 [SMILES: COC(=O)c1ccc2ncn(Cc3ccc(B(O)O)cc3)c2c1] | 4-((6-(methoxycarbonyl)-1,3-benzodiazol-1-yl)methyl)phenylboronic acid |
| 22 | 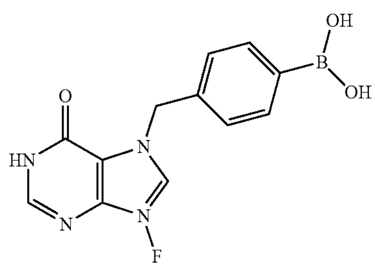 | (4-((7-fluoro-4-oxo-3,4-dihydro-5H-pyrrolo[3,2-d]pyrimidin-5-yl)methyl)phenyl)boronic acid |
| 23 | 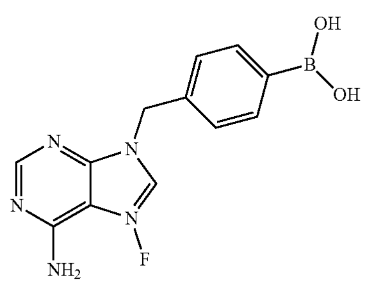 | (4-((4-amino-5-fluoro-7H-pyrrolo[2,3-d]pyrimidin-7-yl)methyl)phenyl)boronic acid |
| 24 | 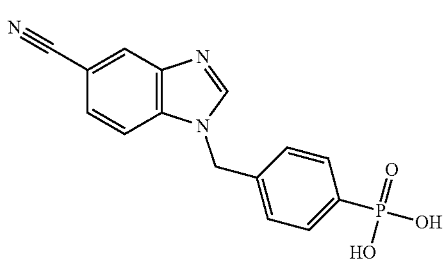 [SMILES: N#Cc1ccc2c(c1)ncn2Cc1ccc(P(=O)(O)O)cc1] | (4-((5-cyano-1H-benzo[d]imidazol-1-yl)methyl)phenyl)phosphonic acid |

-continued

| Cmpd | Structure | Name |
|---|---|---|
| 25 | 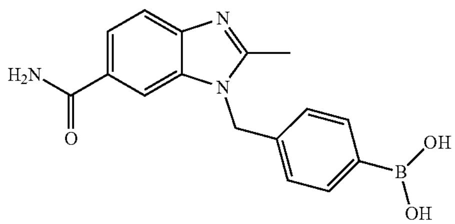 [SMILES: Cc1nc2ccc(C(N)=O)cc2n1Cc1ccc(B(O)O)cc1] | (4-((6-carbamoyl-2-methyl-1H-benzo[d]imidazol-1-yl)methyl)phenyl) boronic acid |
| 26 | 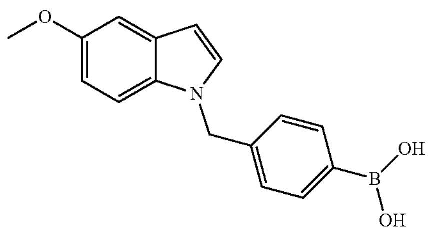 [SMILES: COc1ccc2c(ccn2Cc2ccc(B(O)O)cc2)c1] | 4-((5-methoxyindol-1-yl)methyl) phenylboronic acid |
| 27 | 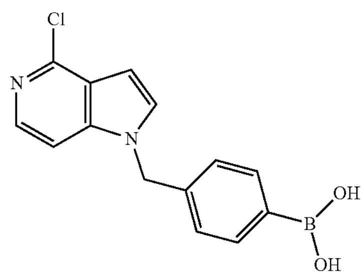 [SMILES: OB(O)c1ccc(Cn2ccc3c(Cl)nccc32)cc1] | 4-((4-chloropyrrolo[3,2-c]pyridin-1-yl)methyl) phenylboronic acid |
| 28 | 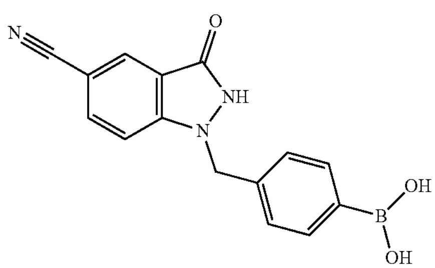 [SMILES: N#Cc1ccc2c(c1)c(=O)[nH]n2Cc1ccc(B(O)O)cc1] | 4-((5-cyano-3-oxo-2H-indazol-1-yl)methyl) phenylboronic acid |
| 29 | 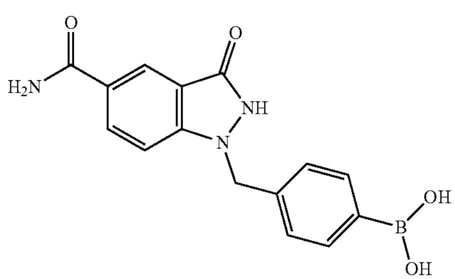 [SMILES: NC(=O)c1ccc2c(c1)c(=O)[nH]n2Cc1ccc(B(O)O)cc1] | 4-((5-carbamoyl-3-oxo-2H-indazol-1-yl)methyl) phenylboronic acid |
| 30 | 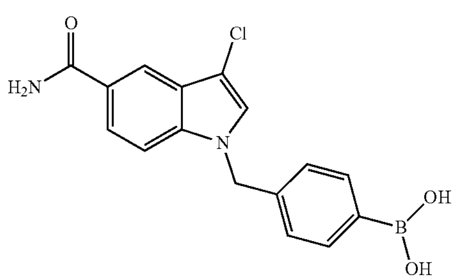 [SMILES: Cc1cn(Cc2ccc(B(O)O)cc2)c2ccc(C(N)=O)cc12] | 4-((5-carbamoyl-3-chloroindol-1-yl)methyl) phenylboronic acid |

| Cmpd | Structure | Name |
|---|---|---|
| 31 | 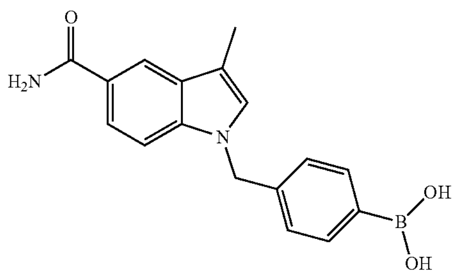 | 4-((5-carbamoyl-3-methylindol-1-yl)methyl)phenylboronic acid |
| 32 | 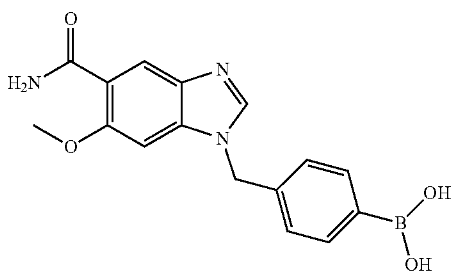 [SMILES: COc1cc2c(cc1C(N)=O)ncn2Cc1ccc(B(O)O)cc1] | 4-((5-carbamoyl-6-methoxy-1,3-benzodiazol-1-yl)methyl) phenylboronic acid |
| 33 | 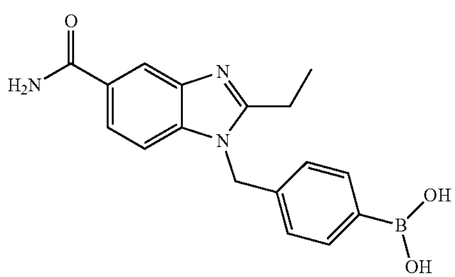 [SMILES: CCc1nc2cc(C(N)=O)ccc2n1Cc1ccc(B(O)O)cc1] | 4-((5-carbamoyl-2-ethyl-1,3-benzodiazol-1-yl)methyl) phenylboronic acid |
| 34 | 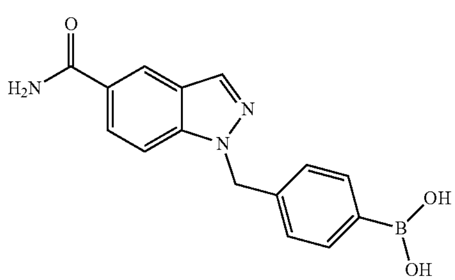 [SMILES: NC(=O)c1ccc2c(cnn2Cc2ccc(B(O)O)cc2)c1] | 4-((5-carbamoylindazol-1-yl)methyl) phenylboronic acid |
| 35 | 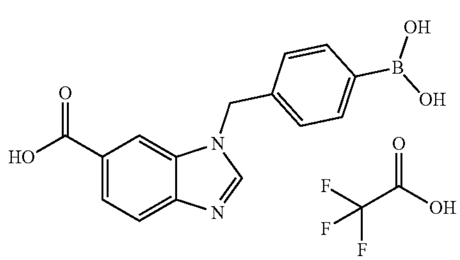 | 3-((4-(dihydroxyboranyl) phenyl)methyl)-1,3-benzodiazol-5-carboxylic acid trifluoroacetic acid salt |

| Cmpd | Structure | Name |
|---|---|---|
| 36 | 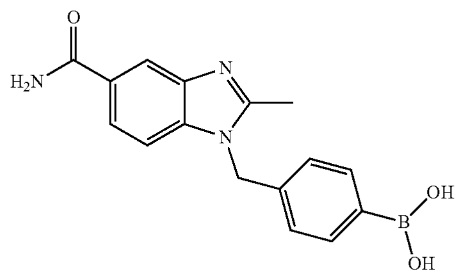 [SMILES: Cc1nc2cc(C(N)=O)ccc2n1Cc1ccc(B(O)O)cc1] | (4-((5-carbamoyl-2-methyl-1H-benzo[d]imidazol-1-yl)methyl)phenyl) boronic acid |
| 37 | 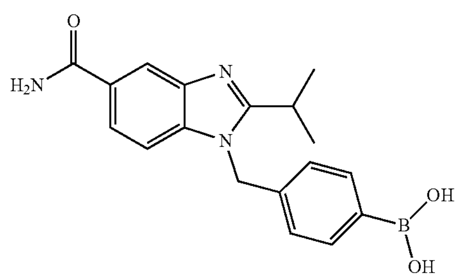 [SMILES: CC(C)c1nc2cc(C(N)=O)ccc2n1Cc1ccc(B(O)O)cc1] | 4-((5-carbamoyl-2-isopropyl-1,3-benzodiazol-1-yl)methyl) phenylboronic acid |
| 38 | 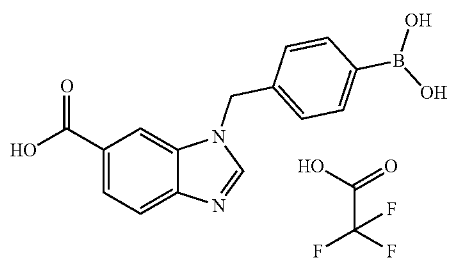 | 3-((4-(dihydroxyboranyl) phenyl)methyl)-1,3-benzodiazole-5-carboxylic acid trifluoroacetic acid salt |
| 39 | 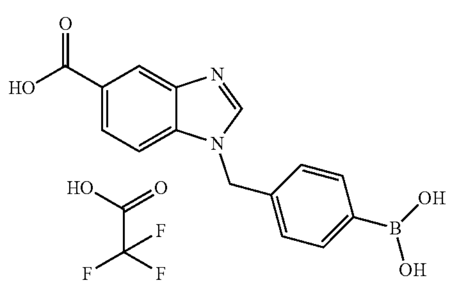 | 1-(4-boronobenzyl)-1H-benzo[d]imidazole-5-carboxylic acid--2,2,2-trifluoroacetic acid (1/1) |
| 40 | 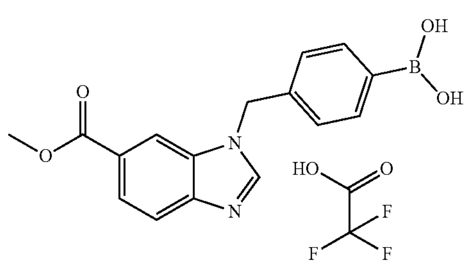 | 2,2,2-trifluoroacetic acid--(4-((6-(methoxycarbonyl)-1H-benzo[d]imidazol-1-yl)methyl)phenyl) boronic acid (1/1) |

-continued

| Cmpd | Structure | Name |
|---|---|---|
| 41 | 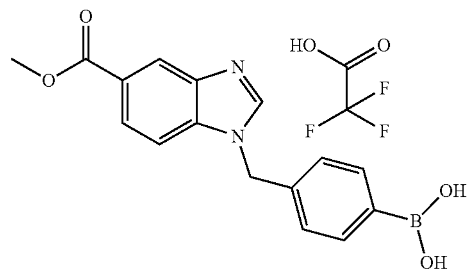 | 2,2,2-trifluoroacetic acid--(4-((5-(methoxycarbonyl)-1H-benzo[d]imidazol-1-yl)methyl)phenyl) boronic acid (1/1) |
| 42 | 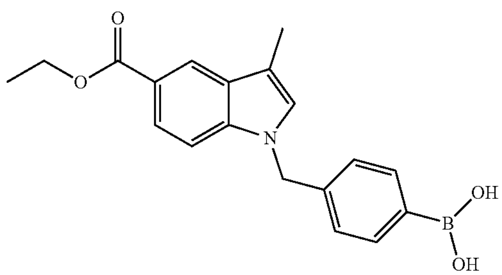 [SMILES: CCOC(=O)c1ccc2c(c1)c(C)cn2Cc1ccc(B(O)O)cc1] | 4-((5-(ethoxycarbonyl)-3-methylindol-1-yl)methyl) phenylboronic acid |
| 43 | 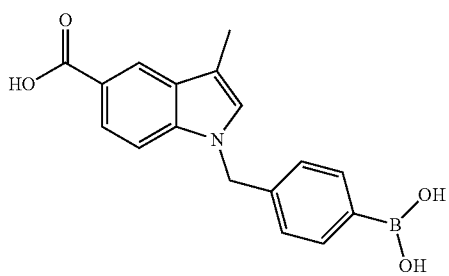 [SMILES: Cc1cn(Cc2ccc(B(O)O)cc2)c2ccc(C(=O)O)cc12] | 1-((4-(dihydroxyboranyl) phenyl)methyl)-3-methylindole-5-carboxylic acid |
| 44 | 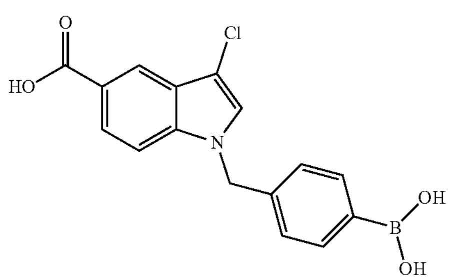 [SMILES: O=C(O)c1ccc2c(c1)c(Cl)cn2Cc1ccc(B(O)O)cc1] | 1-(4-boronobenzyl)-3-chloro-1H-indole-5-carboxylic acid |
| 45 | 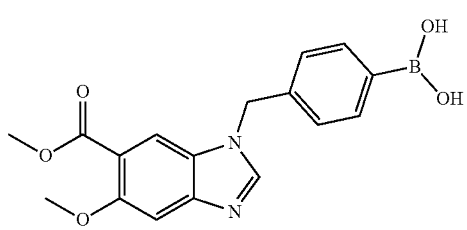 [SMILES: COC(=O)c1cc2c(cc1OC)ncn2Cc1ccc(B(O)O)cc1] | 4-((5-methoxy-6-(methoxycarbonyl)-1,3-benzodiazol-1-yl)methyl)-phenyl-boronic acid |
| 46 | 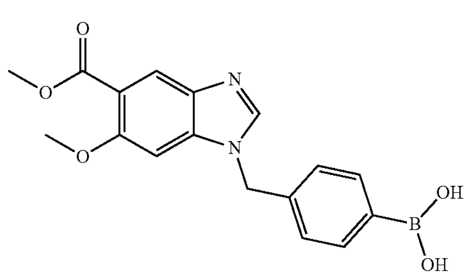 [SMILES: COC(=O)c1cc2ncn(Cc3ccc(B(O)O)cc3)c2cc1OC] | 4-((6-methoxy-5-(methoxycarbonyl)-1,3-benzodiazol-1-yl)methyl) phenyl-boronic acid |

-continued

| Cmpd | Structure | Name |
|---|---|---|
| 47 | 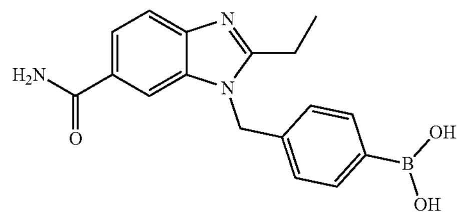 [SMILES: CCc1nc2ccc(C(N)=O)cc2n1Cc1ccc(B(O)O)cc1] | (4-((6-carbamoyl-2-ethyl-1H-benzo[d]imidazol-1-yl)methyl)phenyl) boronic acid |
| 48 | 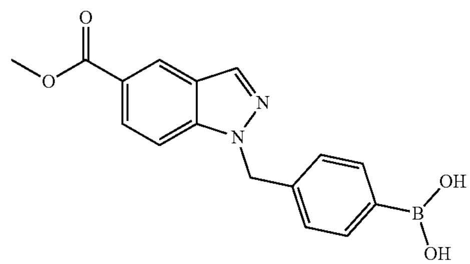 [SMILES: COC(=O)c1ccc2c(cnn2Cc2ccc(B(O)O)cc2)c1] | 4-((5-(methoxycarbonyl) indazol-1-yl)methyl) phenylboronic acid |
| 49 | 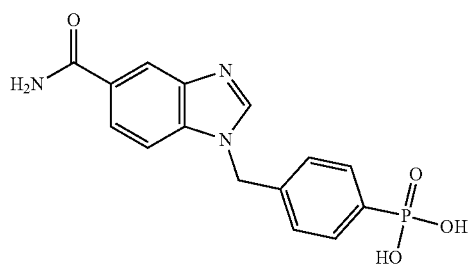 [SMILES: NC(=O)c1ccc2c(c1)ncn2Cc1ccc(P(=O)(O)O)cc1] | 4-((5-carbamoyl-1,3-benzodiazol-1-yl)methyl) phenylphosphonic acid |
| 50 | 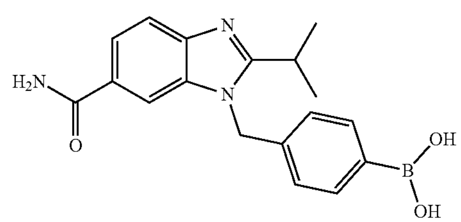 [SMILES: CC(C)c1nc2ccc(C(N)=O)cc2n1Cc1ccc(B(O)O)cc1] | 4-((6-carbamoyl-2-isopropyl-1,3-benzodiazol-1-yl)methyl) phenylboronic acid |
| 51 | 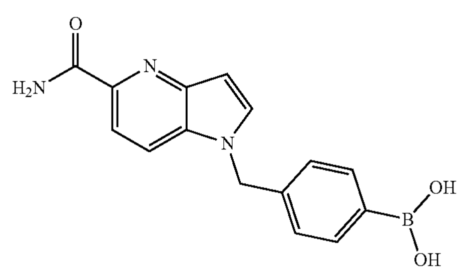 [SMILES: NC(=O)c1ccc2c(ccn2Cc2ccc(B(O)O)cc2)n1] | (4-((5-carbamoyl-1H-pyrrolo[1,3-b]pyridin-1-yl)methyl)phenyl) boronic acid |
| 52 | 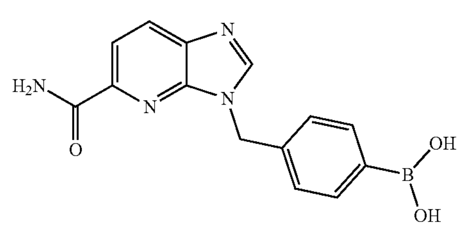 [SMILES: NC(=O)c1ccc2ncn(Cc3ccc(B(O)O)cc3)c2n1] | 4-((5-carbamoylimidazo[4,5-b]pyridin-3-yl)methyl) phenylboronic acid |

-continued

| Cmpd | Structure | Name |
|---|---|---|
| 53 | 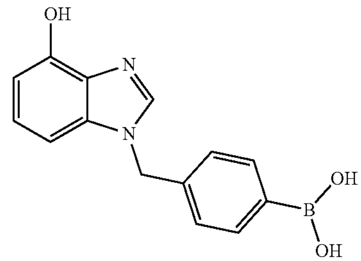 [SMILES: OB(O)c1ccc(Cn2cnc3c(O)cccc32)cc1] | 4-((4-hydroxy-1,3-benzodiazol-1-yl)methyl)phenylboronic acid |
| 54 | 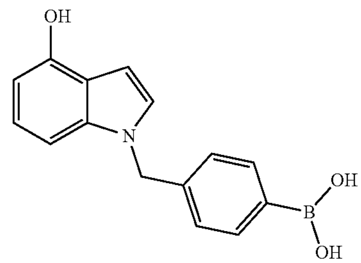 [SMILES: OB(O)c1ccc(Cn2ccc3c(O)cccc32)cc1] | 4-((4-hydroxyindol-1-yl)methyl)phenylboronic acid |
| 55 | 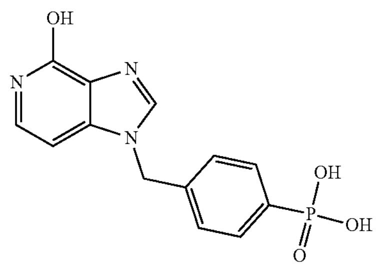 [SMILES: O=P(O)(O)c1ccc(Cn2cnc3c(O)nccc32)cc1] | (4-((4-hydroxy-1H-imidazo[4,5-c]pyridin-1-yl)methyl)phenyl)phenylboronic acid |
| 56 | 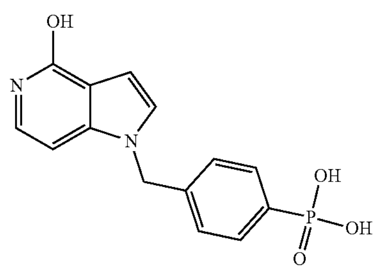 [SMILES: O=P(O)(O)c1ccc(Cn2ccc3c(O)nccc32)cc1] | (4-((4-hydroxy-1H-pyrrolo[3,2-c]pyridin-1-yl)methyl)phenyl)phosphonic acid |
| 57 | 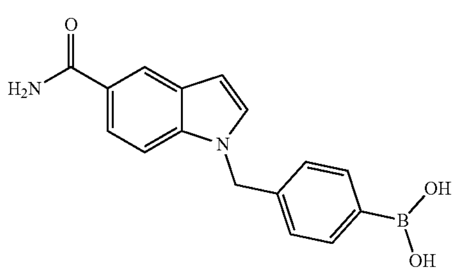 [SMILES: NC(=O)c1ccc2c(ccn2Cc2ccc(B(O)O)cc2)c1] | (4-((5-carbamoyl-1H-indol-1-yl)methyl)phenyl)boronic acid |
| 58 | 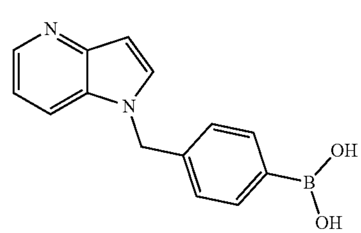 [SMILES: OB(O)c1ccc(Cn2ccc3ncccc32)cc1] | (4-((1H-pyrrolo[3,2-b]pyridin-1-yl)methyl)phenyl)boronic acid |

-continued

| Cmpd | Structure | Name |
|---|---|---|
| 59 | 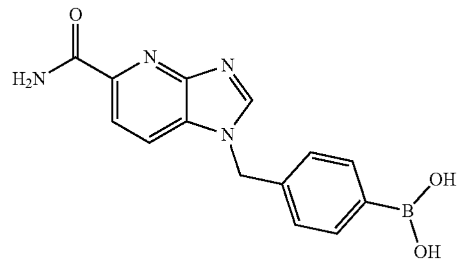 [SMILES: NC(=O)c1ccc2c(ncn2Cc2ccc(B(O)O)cc2)n1] | 4-((5-carbamoylimidazo[4,5-b]pyridin-1-yl)methyl)phenylboronic acid |
| 60 | 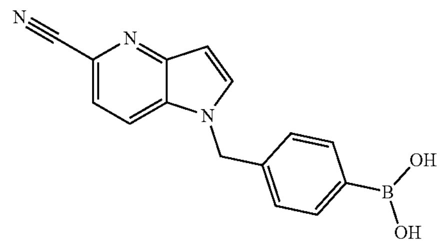 [SMILES: N#Cc1ccc2c(ccn2Cc2ccc(B(O)O)cc2)n1] | (4-((5-cyano-1H-pyrrolo[3,2-b]pyridin-1-yl)methyl)phenyl)boronic acid |
| 61 | 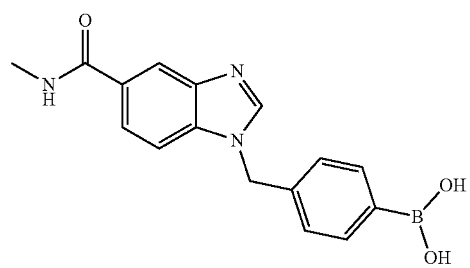 [SMILES: CNC(=O)c1ccc2c(c1)ncn2Cc1ccc(B(O)O)cc1] | 4-((5-(methylcarbamoyl)-1,3-benzodiazol-1-yl)methyl)phenylboronic acid |
| 62 | 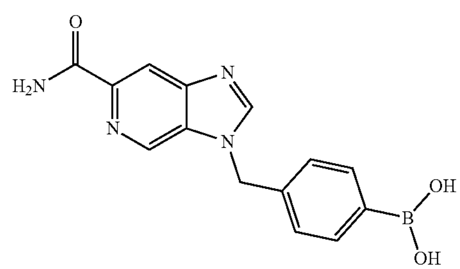 [SMILES: NC(=O)c1cc2ncn(Cc3ccc(B(O)O)cc3)c2cn1] | 4-((6-carbamoylimidazo[4,5-c]pyridin-3-yl)methyl)phenylboronic acid |
| 63 | 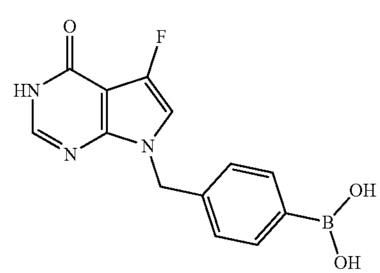 [SMILES: O=c1[nH]cnc2c1c(F)cn2Cc1ccc(B(O)O)cc1] | (4-((5-fluoro-4-oxo-3,4-dihydro-7H-pyrrolo[2,3-d]pyrimidin-7-yl)methyl)phenyl)boronic acid |
| 64 | 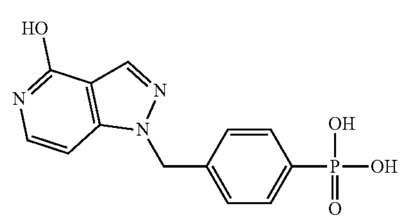 [SMILES: O=P(O)(O)c1ccc(Cn2ncc3c(O)nccc32)cc1] | 4-((4-hydroxypyrazolo[4,3-c]pyridin-1-yl)methyl)phenylphosphonic acid |

-continued

| Cmpd | Structure | Name |
|---|---|---|
| 65 | 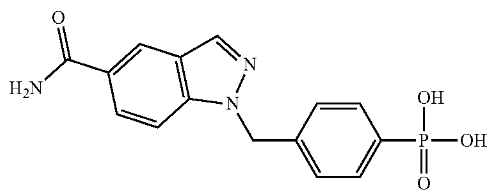 [SMILES: NC(=O)c1ccc2c(cnn2Cc2ccc(P(=O)(O)O)cc2)c1] | 4-((5-carbamoylindazol-1-yl)methyl)phenylphosphonic acid |
| 67 | 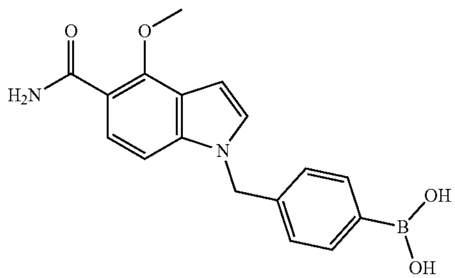 | 4-((5-carbamoyl-4-methoxyindol-1-yl)methyl)phenylboronic acid |
| 68 | 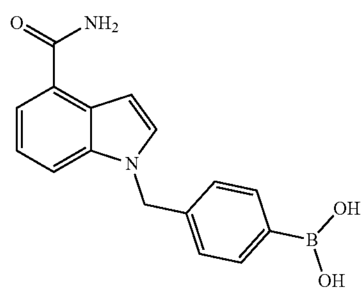 | 4-((4-carbamoylinol-1-yl)methyl)phenylboronic acid |
| 69 | 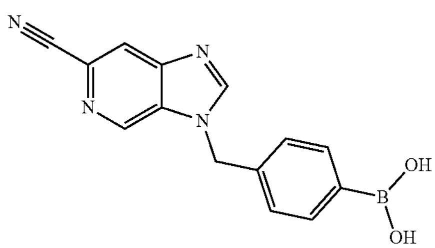 [SMILES: N#Cc1cc2ncn(Cc3ccc(B(O)O)cc3)c2cn1] | 4-((6-cyanoimidazo[4,5-c]pyridin-3-yl)methyl)phenylboronic acid |
| 70 | 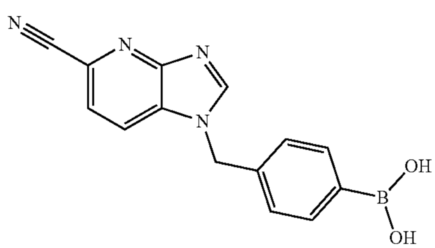 [SMILES: N#Cc1ccc2c(ncn2Cc2ccc(B(O)O)cc2)n1] | 4-((5-cyanoimidazo[4,5-b]pyridin-1-yl)methyl)phenylboronic acid |
| 71 | 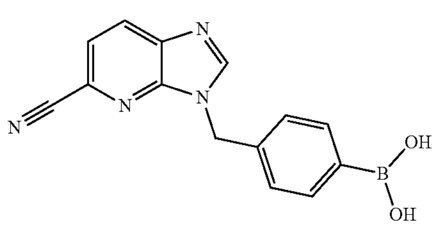 [SMILES: N#Cc1ccc2ncn(Cc3ccc(B(O)O)cc3)c2n1] | 4-((5-cyanoimidazo[4,5-b]pyridin-3-yl)methyl)phenylboronic acid |

-continued

| Cmpd | Structure | Name |
|------|-----------|------|
| 72 | 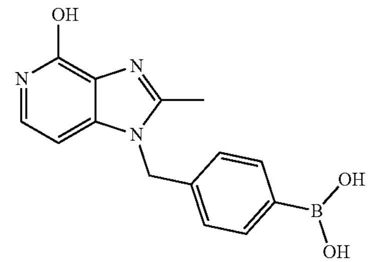 [SMILES: Cc1nc2c(O)nccc2n1Cc1ccc(B(O)O)cc1] | 4-((4-hydroxy-2-methylimidazo[4,5-c]pyridin-1-yl)methyl)phenylboronic acid |
| 73 | 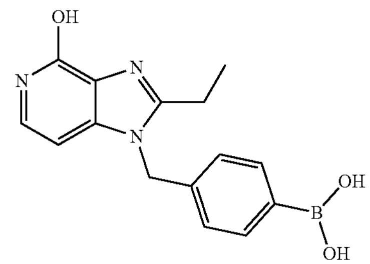 [SMILES: CCc1nc2c(O)nccc2n1Cc1ccc(B(O)O)cc1] | 4-((2-ethyl-4-hydroxyimidazo[4,5-c]pyridin-1-yl)methyl)phenylboronic acid |
| 74 | 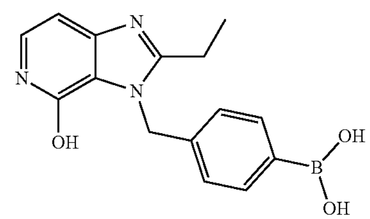 [SMILES: CCc1nc2ccnc(O)c2n1Cc1ccc(B(O)O)cc1] | 4-((2-ethyl-4-hydroxyimidazo[4,5-c]pyridin-3-yl)methyl)phenylboronic acid |
| 75 | 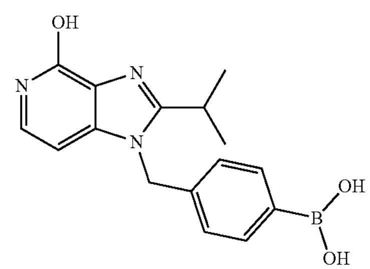 [SMILES: CC(C)c1nc2c(O)nccc2n1Cc1ccc(B(O)O)cc1] | 4-((4-hydroxy-2-isopropylimidazo[4,5-c]pyridin-1-yl)methyl)phenylboronic acid |
| 76 | 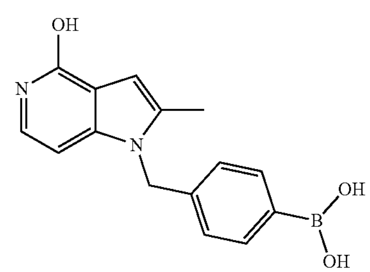 [SMILES: Cc1cc2c(O)nccc2n1Cc1ccc(B(O)O)cc1] | 4-((4-hydroxy-2-methylpyrrolo[3,2-c]pyridin-1-yl)methyl)phenylboronic acid |
| 77 | 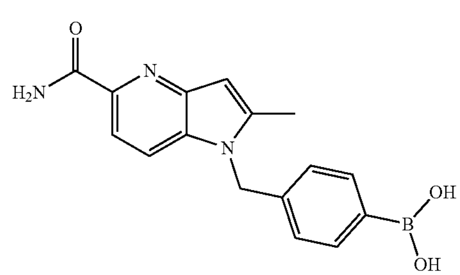 [SMILES: Cc1cc2nc(C(N)=O)ccc2n1Cc1ccc(B(O)O)cc1] | 4-((5-carbamoyl-2-methylpyrrolo[3,2-b]pyridin-1-yl)methyl)phenylboronic acid |

-continued

| Cmpd | Structure | Name |
|---|---|---|
| 78 | 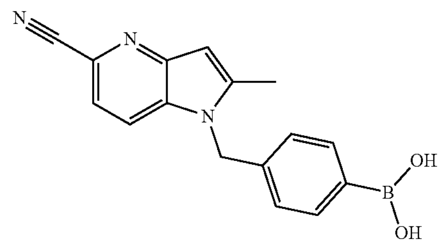 [SMILES: Cc1cc2nc(C#N)ccc2n1Cc1ccc(B(O)O)cc1] | 4-((5-cyano-2-methylpyrrolo[3,2-b]pyridin-1-yl)methyl)phenylboronic acid |
| 79 | 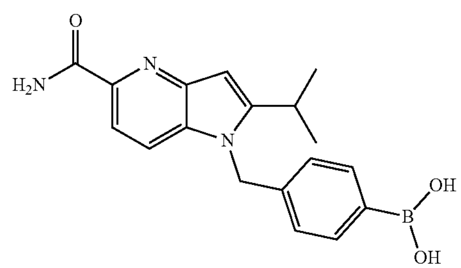 [SMILES: CC(C)c1cc2nc(C(N)=O)ccc2n1Cc1ccc(B(O)O)cc1] | 4-((5-carbamoyl-2-isopropylpyrrolo[3,2-b]pyridin-1-yl)methyl)phenylboronic acid |
| 80 | 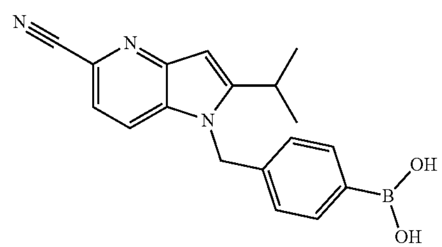 [SMILES: CC(C)c1cc2nc(C#N)ccc2n1Cc1ccc(B(O)O)cc1] | 4-((5-cyano-2-isopropylpyrrolo[3,2-b]pyridin-1-yl)methyl)phenylboronic acid |
| 81 | 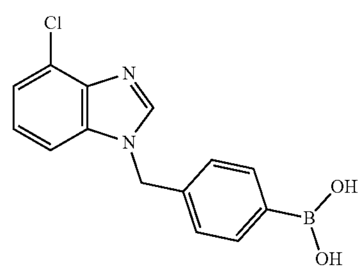 [SMILES: OB(O)c1ccc(Cn2cnc3c(Cl)cccc32)cc1] | 4-((4-chloro-1,3-benzodiazol-1-yl)methyl)phenylboronic acid |
| 82 | 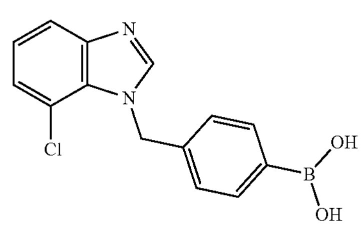 [SMILES: OB(O)c1ccc(Cn2cnc3cccc(Cl)c32)cc1] | 4-((7-chloro-1,3-benzodiazol-1-yl)methyl)phenylboronic acid |
| 83 | 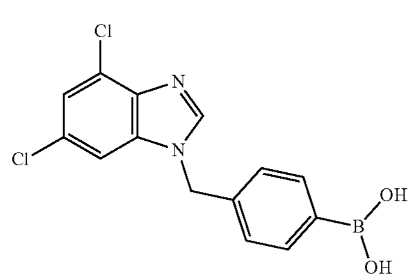 [SMILES: OB(O)c1ccc(Cn2cnc3c(Cl)cc(Cl)cc32)cc1] | 4-((4,6-dichloro-1,3-benzodiazol-1-yl)methyl)phenylboronic acid |

| Cmpd | Structure | Name |
|---|---|---|
| 84 | 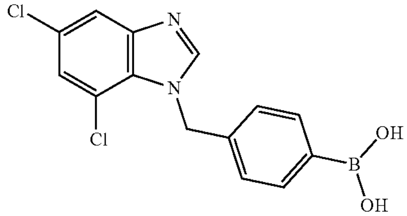 [SMILES: OB(O)c1ccc(Cn2cnc3cc(Cl)cc(Cl)c32)cc1] | 4-((5,7-dichloro-1,3-benzodiazol-1-yl)methyl)phenylboronic acid |
| 85 | 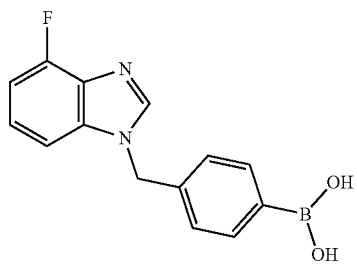 [SMILES: OB(O)c1ccc(Cn2cnc3c(F)cccc32)cc1] | 4-((4-fluoro-1,3-benzodiazol-1-yl)methyl)phenylboronic acid |
| 86 | 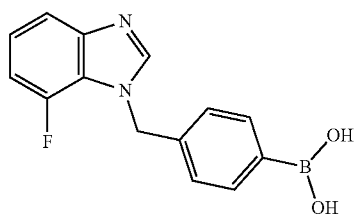 [SMILES: OB(O)c1ccc(Cn2cnc3cccc(F)c32)cc1] | 4-((7-fluoro-1,3-benzodiazol-1-yl)methyl)phenylboronic acid |
| 87 | 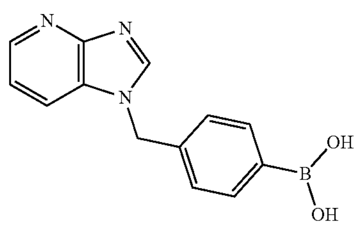 [SMILES: OB(O)c1ccc(Cn2cnc3ncccc32)cc1] | 4-(imidazo[4,5-b]pyridin-1-yl)methyl)phenylboronic acid |
| 88 | 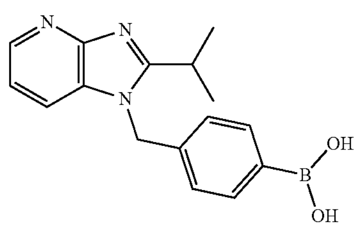 [SMILES: CC(C)c1nc2ncccc2n1Cc1ccc(B(O)O)cc1] | 4-((2-isopropylimidazo[4,5-b]pyridin-1-yl)methyl)phenylboronic acid |
| 89 | 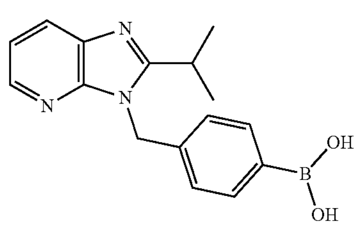 [SMILES: CC(C)c1nc2cccnc2n1Cc1ccc(B(O)O)cc1] | 4-((2-isopropylimidazo[4,5-b]pyridin-3-yl)methyl)phenylboronic acid |

-continued

| Cmpd | Structure | Name |
|---|---|---|
| 90 | 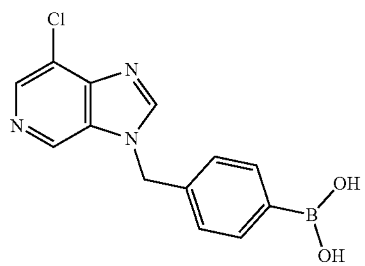 [SMILES: OB(O)c1ccc(Cn2cnc3c(Cl)cncc32)cc1] | 4-((7-chloroimidazo[4,5-c]pyridin-3-yl)methyl)phenylboronic acid |
| 91 | 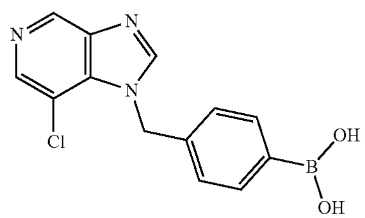 [SMILES: OB(O)c1ccc(Cn2cnc3cncc(Cl)c32)cc1] | 4-((7-chloroimidazo[4,5-c]pyridin-1-yl)methyl)phenylboronic acid |
| 92 | 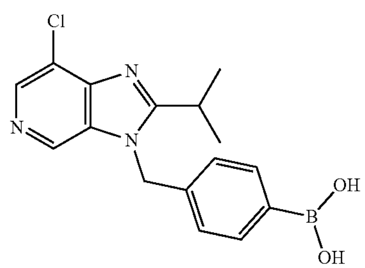 [SMILES: CC(C)c1nc2c(Cl)cncc2n1Cc1ccc(B(O)O)cc1] | 4-((7-chloro-2-isopropylimidazo[4,5-c]pyridin-3-yl)methyl)phenylboronic acid |
| 93 | 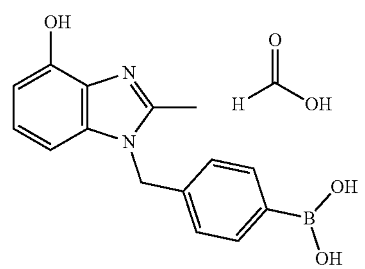 | 4-((4-hydroxy-2-methyl-1,3-benzodiazol-1-yl)methyl)phenylboronic acid formic acid salt |
| 94 | 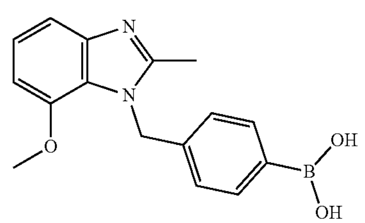 [SMILES: COc1cccc2nc(C)n(Cc3ccc(B(O)O)cc3)c12] | 4-((7-methoxy-2-methyl-1,3-benzodiazol-1-yl)methyl)phenylboronic acid |
| 95 | 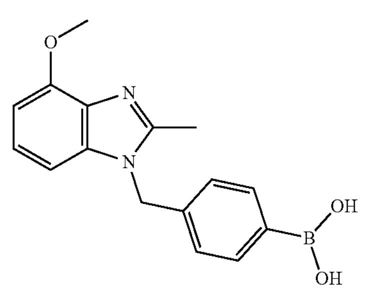 [SMILES: COc1cccc2c1nc(C)n2Cc1ccc(B(O)O)cc1] | 4-((4-methoxy-2-methyl-1,3-benzodiazol-1-yl)methyl)phenylboronic acid |

-continued

| Cmpd | Structure | Name |
|---|---|---|
| 96 | 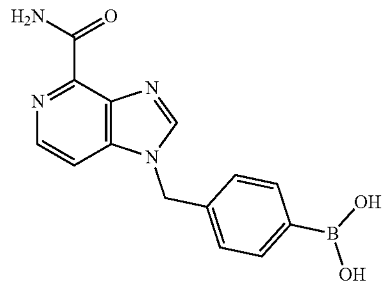 | 4-((4-carbamoylimidazo[4,5-c]pyridin-1-yl)methyl)phenylboronic acid |
| 97 | 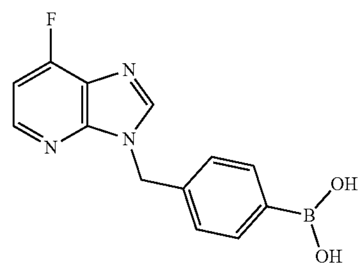 [SMILES: OB(O)c1ccc(Cn2cnc3c(F)ccnc32)cc1] | 4-((4-fluoropyrrolo[2,3-b]pyridin-1-yl)methyl)phenylboronic acid |
| 98 | 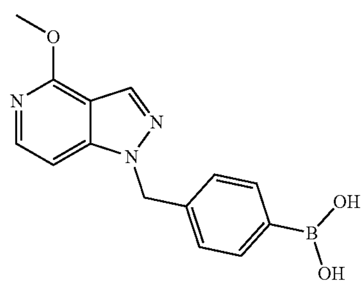 [SMILES: COc1nccc2c1cnn2Cc1ccc(B(O)O)cc1] | 4-((4-methoxypyrazolo[4,3-c]pyridin-1-yl)methyl)phenylboronic acid |
| 99 | 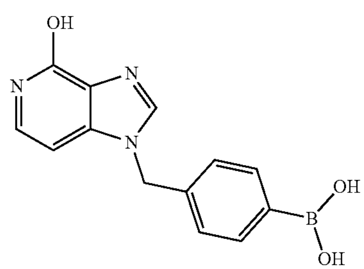 [SMILES: OB(O)c1ccc(Cn2cnc3c(O)nccc32)cc1] | 4-((4-hydroxypyrazolo[4,3-c]pyridin-1-yl)methyl)phenylboronic acid |
| 100 | 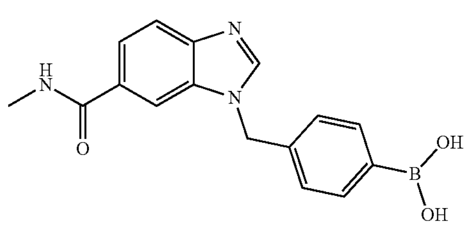 [SMILES: CNC(=O)c1ccc2ncn(Cc3ccc(B(O)O)cc3)c2c1] | 4-((6-(methylcarbamoyl)-1,3-benzodiazol-1-yl)methyl)phenylboronic acid |
| 101 | 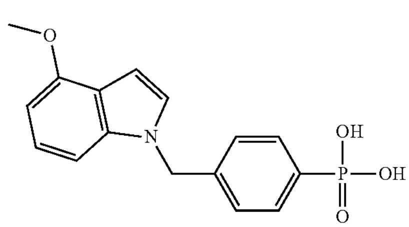 [SMILES: COc1cccc2c1ccn2Cc1ccc(P(=O)(O)O)cc1] | 4-((4-methoxyindol-1-yl)methyl)phenylphosphonic acid |

| Cmpd | Structure | Name |
|---|---|---|
| 102 | 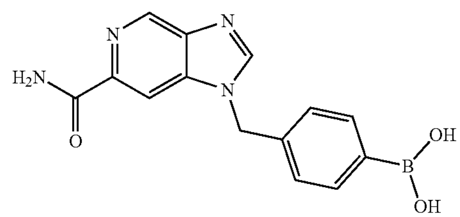 [SMILES: NC(=O)c1cc2c(cn1)ncn2Cc1ccc(B(O)O)cc1] | 4-((6-carbamoylimidazo[4,5-c]pyridin-1-yl)methyl)phenylboronic acid |
| 103 | 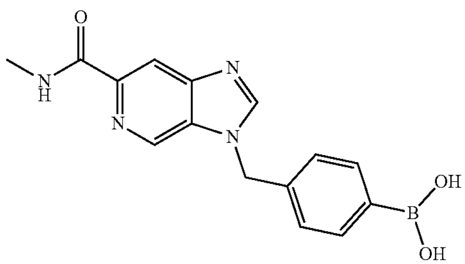 [SMILES: CNC(=O)c1cc2ncn(Cc3ccc(B(O)O)cc3)c2cn1] | 4-((6-(methylcarbamoyl)imidazo[4,5-c]pyridin-3-yl)methyl)phenylboronic acid |
| 104 | 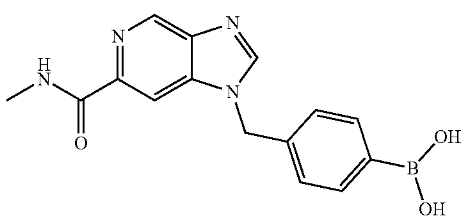 [SMILES: CNC(=O)c1cc2c(cn1)ncn2Cc1ccc(B(O)O)cc1] | 4-((6-(methylcarbamoyl)imidazo[4,5-c]pyridin-1-yl)methyl)phenylboronic acid |
| 105 | 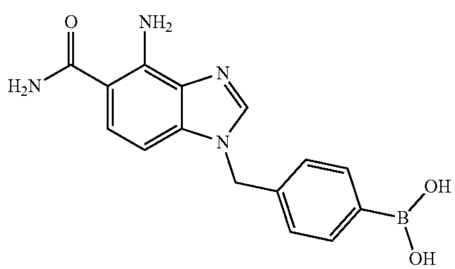 [SMILES: NC(=O)c1ccc2c(ncn2Cc2ccc(B(O)O)cc2)c1N] | 4-((4-amino-5-carbamoyl-1,3-benzodiazol-1-yl)methyl)phenylboronic acid |
| 106 | 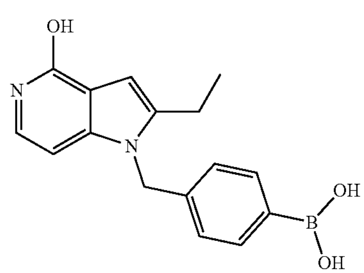 [SMILES: CCc1cc2c(O)nccc2n1Cc1ccc(B(O)O)cc1] | 4-((2-ethyl-4-hydroxypyrrolo[3,2-c]pyridin-1-yl)methyl)phenylboronic acid |
| 107 | 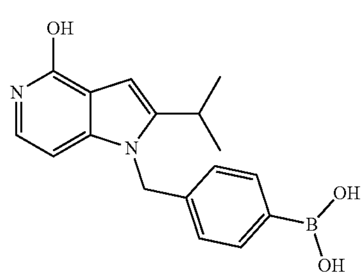 [SMILES: CC(C)c1cc2c(O)nccc2n1Cc1ccc(B(O)O)cc1] | 4-((4-hydroxy-2-isopropylpyrrolo[3,2-c]pyridin-1-yl)methyl)phenylboronic acid |

| Cmpd | Structure | Name |
|---|---|---|
| 108 | 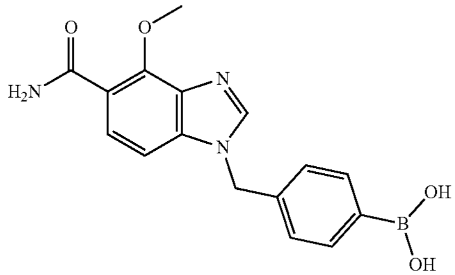 [SMILES: COc1c(C(N)=O)ccc2c1ncn2Cc1ccc(B(O)O)cc1] | 4-((5-carbamoyl-4-methoxy-1,3-benzodiazol-1-yl)methyl)phenylboronic acid |
| 109 | 0.5 p-TsOH | 4-((5-carbamoyl-4-hydroxy-1,3-benzodiazol-1-yl)methyl)phenylboronic acid |
| 110 | 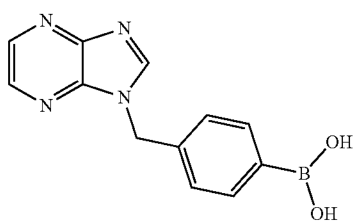 [SMILES: OB(O)c1ccc(Cn2cnc3nccnc32)cc1] | 4-(imidazo[4,5-b]pyrazin-1-ylmethyl)phenylboronic acid |
| 111 | 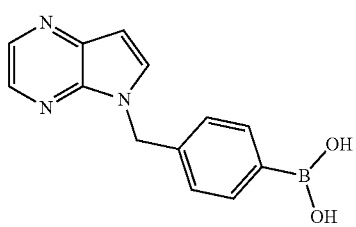 [SMILES: OB(O)c1ccc(Cn2ccc3nccnc32)cc1] | 4-(pyrrolo[2,3-b]pyrazin-5-ylmethyl)phenylboronic acid |
| 112 | 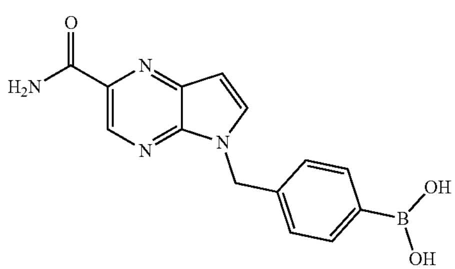 [SMILES: NC(=O)c1cnc2c(ccn2Cc2ccc(B(O)O)cc2)n1] | 4-((2-carbamoylpyrrolo[2,3-b]pyrazin-5-yl)methyl)phenylboronic acid |
| 113 | 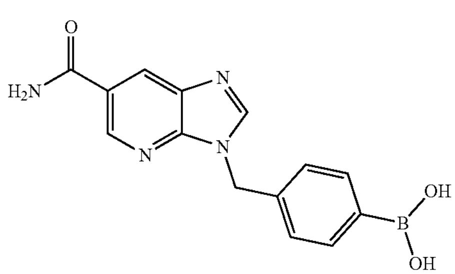 [SMILES: NC(=O)c1cnc2c(c1)ncn2Cc1ccc(B(O)O)cc1] | 4-((6-carbamoylimidazo[4,5-b]pyridin-3-yl)methyl)phenylboronic acid |

| Cmpd | Structure | Name |
|---|---|---|
| 114 | 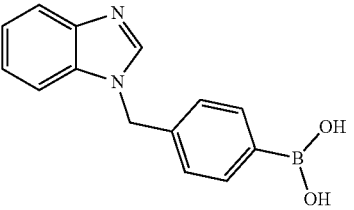 [SMILES: OB(O)c1ccc(Cn2cnc3ccccc32)cc1] | (4-((1H-benzo[d]imidazol-1-yl)methyl)phenyl)phenylboronic acid |
| 115 | 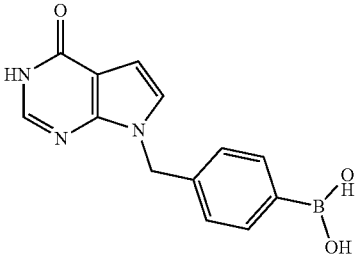 [SMILES: O=c1[nH]cnc2c1ccn2Cc1ccc(B(O)O)cc1] | (4-((4-oxo-3,4-dihydro-7H-pyrrolo[2,3-d]pyrimidin-7-yl)methyl)phenyl)boronic acid |
| 116 | 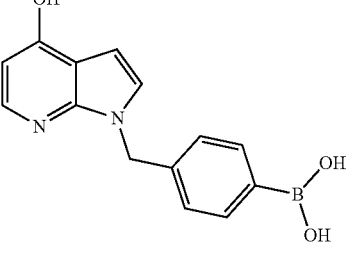 | 4-((4-hydroxypyrrolo[2,3-b]pyridin-1-yl)methyl)phenylboronic acid |
| 117 | 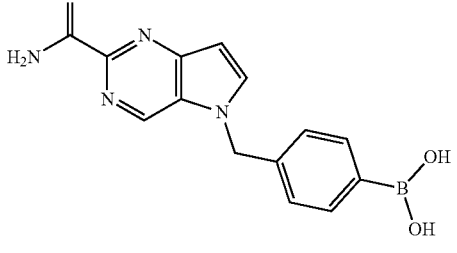 | 4-((2-carbamoylpyrrolo[2,3-b]pyrimidin-5-yl)methyl)phenylboronic acid |
| 118 | 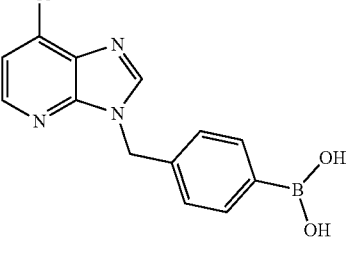 | 4-((7-chloroimidazo[4,5-b]pyridin-3-yl)methyl)phenylboronic acid |
| 119 | 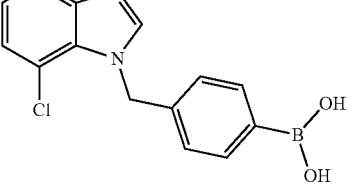 | 4-((7-chloroimidazo[4,5-b]pyridin-1-yl)methyl)phenylboronic acid |

-continued

| Cmpd | Structure | Name |
|---|---|---|
| 120 | | 4-((5-chloro-1,3-benzodiazol-1-yl)methyl)phenylboronic acid and 4-((6-chloro-1,3-benzodiazol-1-yl)methyl)phenylboronic acid (1:1 mixture) |
| 121 | 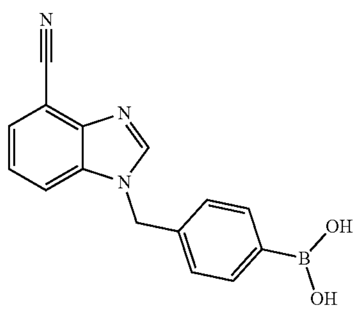 [SMILES: N#Cc1cccc2c1ncn2Cc1ccc(B(O)O)cc1] | 4-((4-cyano-1,3-benzodiazol-1-yl)methyl)phenylboronic acid |
| 122 | 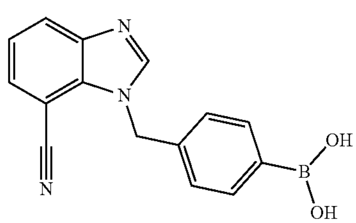 [SMILES: N#Cc1cccc2ncn(Cc3ccc(B(O)O)cc3)c12] | 4-((7-cyano-1,3-benzodiazol-1-yl)methyl)phenylboronic acid |
| 123 | 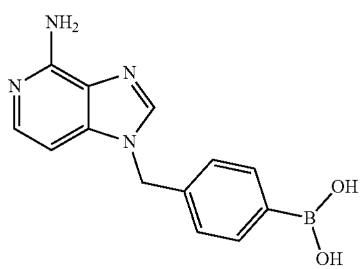 [SMILES: Nc1nccc2c1ncn2Cc1ccc(B(O)O)cc1] | 4-((4-aminoimidazo[4,5-c]pyridin-1-yl)methyl)phenylboronic acid |
| 124 | 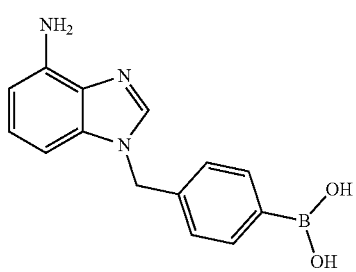 [SMILES: Nc1cccc2c1ncn2Cc1ccc(B(O)O)cc1] | 4-((4-amino-1,3-benzodiazol-1-yl)methyl)phenylboronic acid |

-continued

| Cmpd | Structure | Name |
|---|---|---|
| 125 | 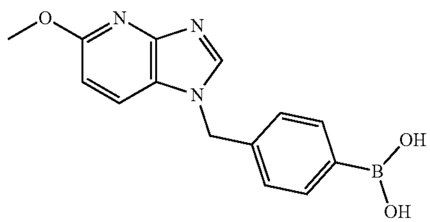 [SMILES: COc1ccc2c(ncn2Cc2ccc(B(O)O)cc2)n1] | 4-((5-methoxyimidazo[4,5-b]pyridin-1-yl)methyl)phenylboronic acid |
| 126 | 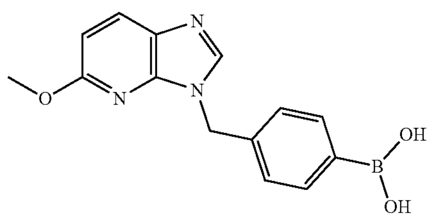 [SMILES: COc1ccc2ncn(Cc3ccc(B(O)O)cc3)c2n1] | 4-((5-methoxyimidazo[4,5-b]pyridin-3-yl)methyl)phenylboronic acid |
| 127 | 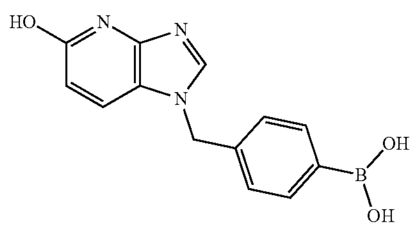 [SMILES: OB(O)c1ccc(Cn2cnc3nc(O)ccc32)cc1] | 4-((5-hydroxy-1H-imidazo[4,5-b]pyridin-1-yl)methyl)phenyl)boronic acid |
| 128 | 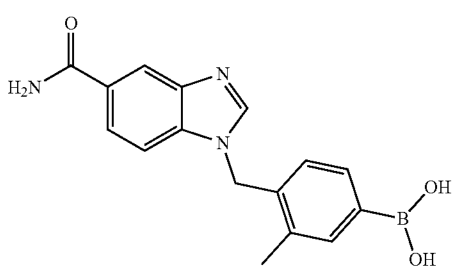 [SMILES: Cc1cc(B(O)O)ccc1Cn1cnc2cc(C(N)=O)ccc21] | (4-((5-carbamoyl-1H-benzo[d]imidazol-1-yl)methyl)-3-methylphenyl)boronic acid |
| 129 | 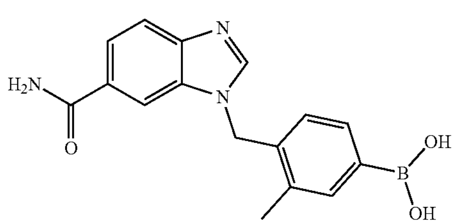 [SMILES: Cc1cc(B(O)O)ccc1Cn1cnc2ccc(C(N)=O)cc21] | (4-((6-carbamoyl-1H-benzo[d]imidazol-1-yl)methyl)-3-methylphenyl)boronic acid |
| 130 | 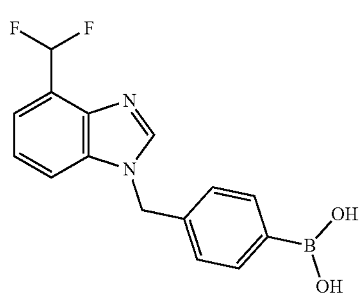 [SMILES: OB(O)c1ccc(Cn2cnc3c(C(F)F)cccc32)cc1] | 4-((4-(difluoromethyl)-1,3-benzodiazol-1-yl)methyl)phenylboronic acid |

-continued

| Cmpd | Structure | Name |
|---|---|---|
| 131 | 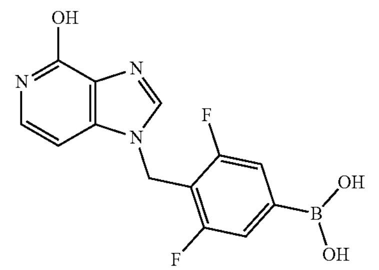 [SMILES: OB(O)c1cc(F)c(Cn2cnc3c(O)nccc32)c(F)c1] | 3,5-difluoro-4-((4-hydroxyimidazo[4,5-c]pyridin-1-yl)methyl)phenylboronic acid |
| 132 | 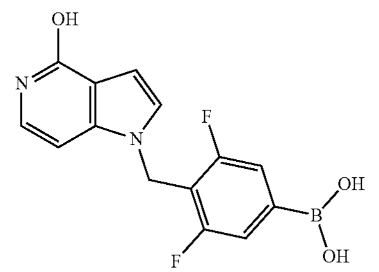 [SMILES: OB(O)c1cc(F)c(Cn2ccc3c(O)nccc32)c(F)c1] | 3,5-difluoro-4-((4-hydroxypyrrolo[3,2-c]pyridin-1-yl)methyl)phenylboronic acid |
| 133 | 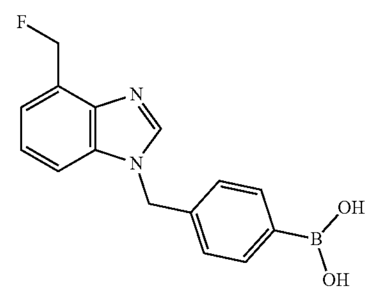 [SMILES: OB(O)c1ccc(Cn2cnc3c(CF)cccc32)cc1] | 4-((4-(fluoromethyl)-1,3-benzodiazol-1-yl)methyl)phenylboronic acid |
| 134 | 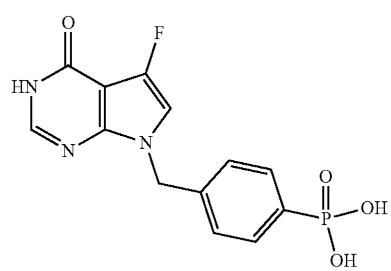 [SMILES: O=c1[nH]cnc2c1c(F)cn2Cc1ccc(P(=O)(O)O)cc1] | 4-((5-fluoro-4-oxo-3H-pyrrolo[2,3-d]pyrimidin-7-yl)methyl)phenylphosphonic acid |
| 135 | 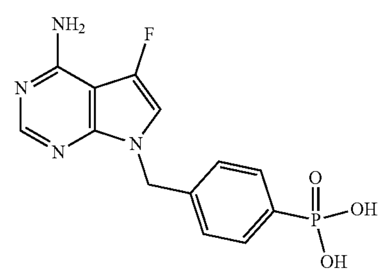 [SMILES: Nc1ncnc2c1c(F)cn2Cc1ccc(P(=O)(O)O)cc1] | 4-((4-amino-5-fluoropyrrolo[2,3-d]pyrimidin-7-yl)methyl)phenylphosphonic acid |
| 136 | 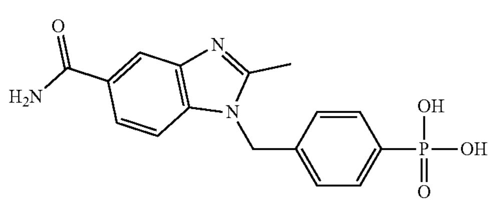 [SMILES: Cc1nc2cc(C(N)=O)ccc2n1Cc1ccc(P(=O)(O)O)cc1] | 4-((5-carbamoyl-2-methyl-1,3-benzodiazol-1-yl)methyl)phenylphosphonic acid |

| Cmpd | Structure | Name |
|---|---|---|
| 137 | 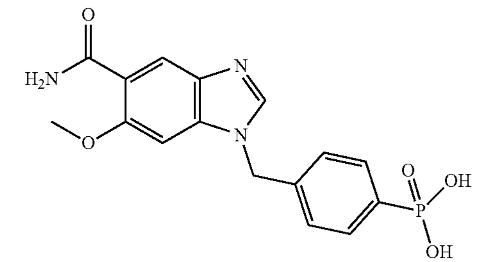 [SMILES: COc1cc2c(cc1C(N)=O)ncn2Cc1ccc(P(=O)(O)O)cc1] | 4-((5-carbamoyl-6-methoxy-1,3-benzodiazol-1-yl)methyl)phenylphosphonic acid |
| 138 | 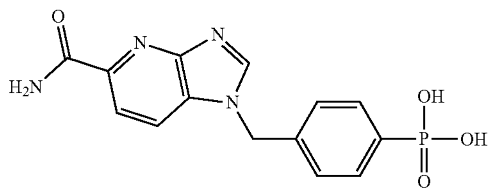 [SMILES: NC(=O)c1ccc2c(ncn2Cc2ccc(P(=O)(O)O)cc2)n1] | 4-((5-carbamoylimidazo[4,5-b]pyridin-1-yl)methyl)phenylphosphonic acid |
| 139 | 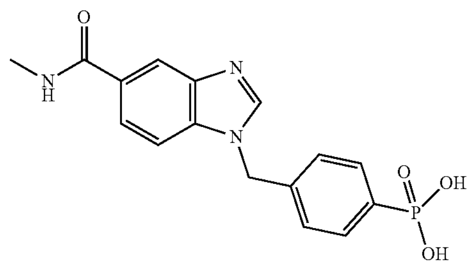 [SMILES: CNC(=O)c1ccc2c(c1)ncn2Cc1ccc(P(=O)(O)O)cc1] | 4-((5-(methylcarbamoyl)-1,3-benzodiazol-1-yl)methyl)phenylphosphonic acid |
| 140 | 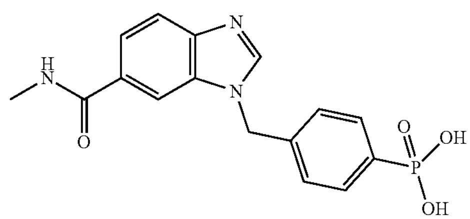 [SMILES: CNC(=O)c1ccc2ncn(Cc3ccc(P(=O)(O)O)cc3)c2c1] | 4-((6-(methylcarbamoyl)-1,3-benzodiazol-1-yl)methyl)phenylphosphonic acid |
| 141 | 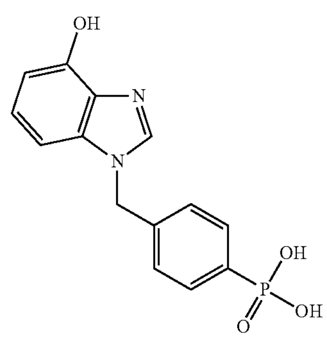 [SMILES: O=P(O)(O)c1ccc(Cn2cnc3c(O)cccc32)cc1] | (4-((4-hydroxy-1H-benzo[d]imidazol-1-yl)methyl)phenyl)phosphonic acid |
| 142 | 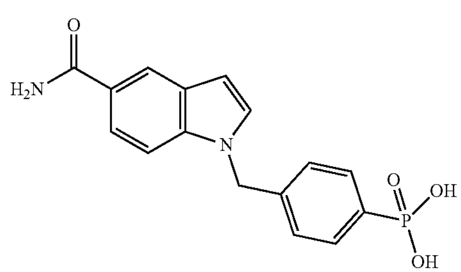 [SMILES: NC(=O)c1ccc2c(ccn2Cc2ccc(P(=O)(O)O)cc2)c1] | 4-((5-carbamoylindol-1-yl)methyl)phenylphosphonic acid |

| Cmpd | Structure | Name |
|---|---|---|
| 143 | 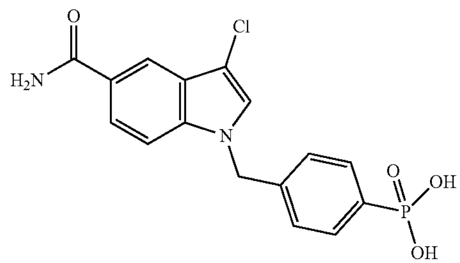 [SMILES: NC(=O)c1ccc2c(c1)c(Cl)cn2Cc1ccc(P(=O)(O)O)cc1] | 4-((5-carbamoyl-3-chloroindol-1-yl)methyl) phenylphosphonic acid |
| 144 | 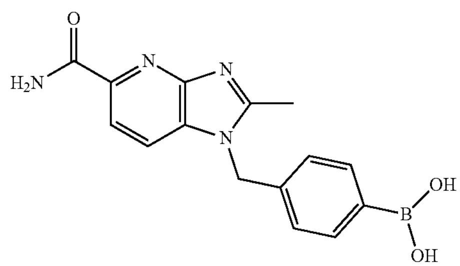 [SMILES: Cc1nc2nc(C(N)=O)ccc2n1Cc1ccc(B(O)O)cc1] | (4-((5-carbamoyl-2-methyl-1H-imidazo[4,5-b]pyridin-1-yl)methyl) phenyl)boronic acid |
| 145 | 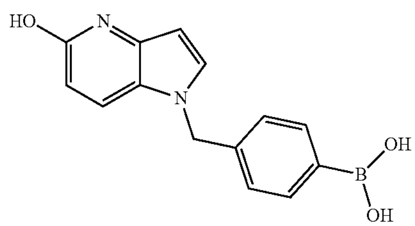 [SMILES: OB(O)c1ccc(Cn2ccc3nc(O)ccc32)cc1] | 4-((5-hydroxypyrrolo[3,2-b]pyridin-1-yl)methyl) phenylboronic acid |
| 146 | 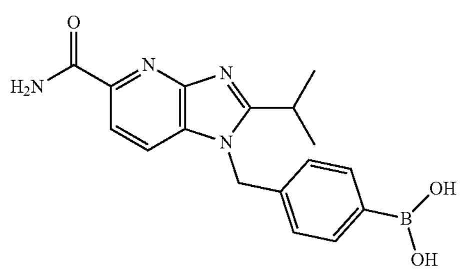 [SMILES: CC(C)c1nc2nc(C(N)=O)ccc2n1Cc1ccc(B(O)O)cc1] | 4-((5-carbamoyl-2-isopropylimidazo[4,5-b]pyridin-1-yl)methyl) phenylboronic acid |
| 147 | 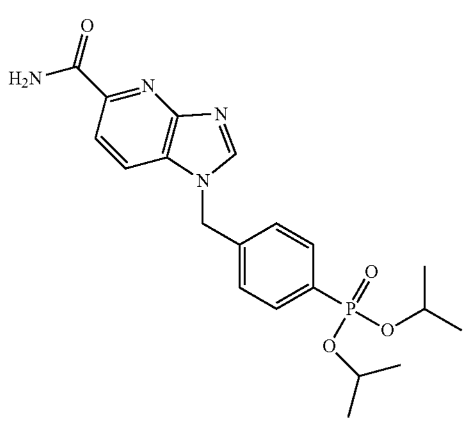 [SMILES: CC(C)OP(=O)(OC(C)C)c1ccc(Cn2cnc3nc(C(N)=O)ccc32)cc1] | diisopropyl 4-((5-carbamoylimidazo[4,5-b]pyridin-1-yl)methyl) phenylphosphonate |

| Cmpd | Structure | Name |
|---|---|---|
| 148 | 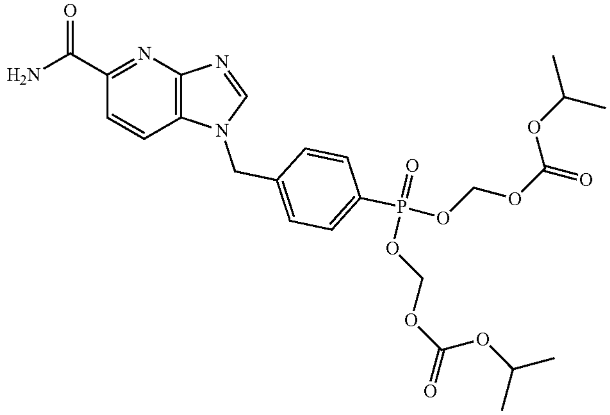 [SMILES: CC(C)OC(=O)OCOP(=O)(OCOC(=O)OC(C)C)c1ccc(Cn2cnc3nc(C(N)=O)ccc32)cc1] | 1-((4-(di((isopropoxycarbonyl)oxy)methoxyphosphoryl)phenyl)methyl)imidazo[4,5-b]pyridine-5-carboxamide |
| 149 | 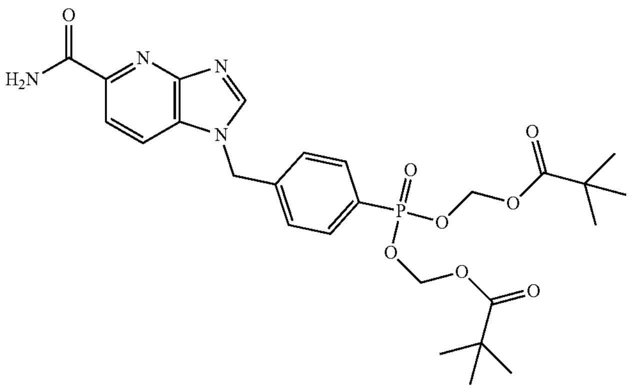 [SMILES: CC(C)(C)C(=O)OCOP(=O)(OCOC(=O)C(C)(C)C)c1ccc(Cn2cnc3nc(C(N)=O)ccc32)cc1] | ((4-((5-carbamoylimidazo[4,5-b]pyridin-1-yl)methyl)phenyl(((2,2-dimethylpropanoyl)oxy)methoxy)phosphoryl)oxy)methyl 2,2-dimethylpropanoate |
| 150 | 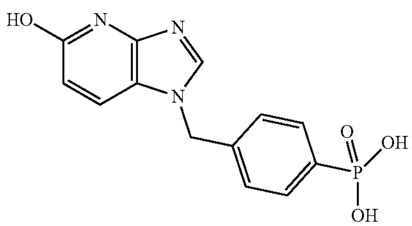 [SMILES: O=P(O)(O)c1ccc(Cn2cnc3nc(O)ccc32)cc1] | 4-((5-hydroxyimidazo[4,5-b]pyridin-1-yl)methyl)phenylphosphonic acid |
| 151 | 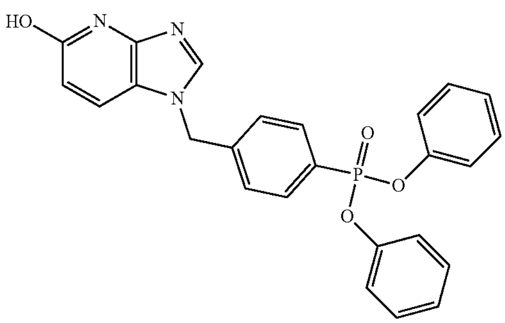 [SMILES: O=P(Oc1ccccc1)(Oc1ccccc1)c1ccc(Cn2cnc3nc(O)ccc32)cc1] | diphenyl 4-((5-hydroxyimidazo[4,5-b]pyridin-1-yl)methyl)phenylphosphonate |
| 152 | 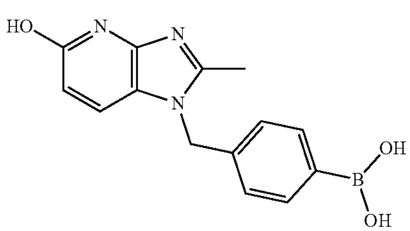 [SMILES: Cc1nc2nc(O)ccc2n1Cc1ccc(B(O)O)cc1] | (4-((5-hydroxy-2-methyl-1H-imidazo[4,5-b]pyridin-1-yl)methyl)phenyl)boronic acid |

-continued

| Cmpd | Structure | Name |
|---|---|---|
| 153 | 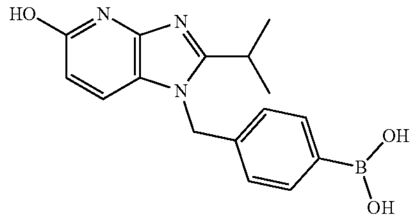 [SMILES: CC(C)c1nc2nc(O)ccc2n1Cc1ccc(B(O)O)cc1] | (4-((5-hydroxy-2-isopropyl-1H-imidazo[4,5-b]pyridin-1-yl)methyl)phenyl)boronic acid |
| 154 | 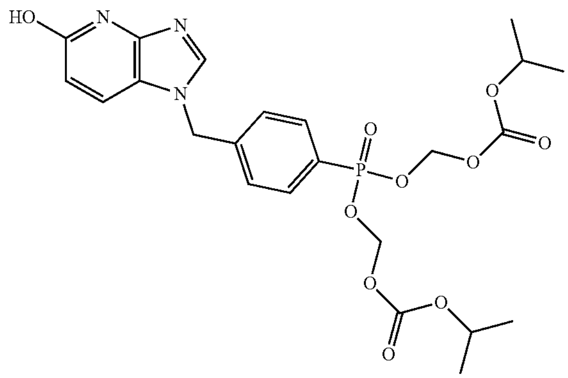 [SMILES: CC(C)OC(=O)OCOP(=O)(OCOC(=O)OC(C)C)c1ccc(Cn2cnc3nc(O)ccc32)cc1] | (((4-((5-hydroxy-1H-imidazo[4,5-b]pyridin-1-yl)methyl)phenyl)phosphoryl)bis(oxy))bis(methylene) diisopropyl bis(carbonate) |
| 155 | 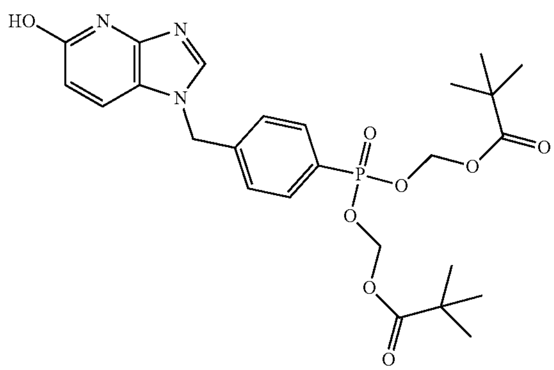 [SMILES: CC(C)(C)C(=O)OCOP(=O)(OCOC(=O)C(C)(C)C)c1ccc(Cn2cnc3nc(O)ccc32)cc1] | (((4-((5-hydroxy-1H-imidazo[4,5-b]pyridin-1-yl)methyl)phenyl)phosphoryl)bis(oxy))bis(methylene) bis(2,2-dimethylpropanoate) |

EMBODIMENTS

Embodiment A

In embodiment A, the compounds of Formula (I) or (IA) or a pharmaceutically acceptable salt thereof as defined in the Summary above.

In a first subembodiment A, the compounds are of Formula (I) or a pharmaceutically acceptable salt thereof as defined in the Summary above. Within first subembodiment A, the compounds of Formula (I) or a pharmaceutically acceptable salt thereof are those wherein Q is —P(O)(R$^a$)(R$^b$) or —B(R$^w$)(R$^x$) wherein R$^a$, R$^b$, R$^w$ and R$^x$ are independently selected from hydroxy, alkoxy, —Oaryl (where aryl is optionally substituted with one to three substituents independently selected from alkyl, alkenyl, alkoxy, halo, haloalkyl, amino, alkylamino, dialkylamino, cyano, or nitro), —O—(CH$_2$)OCOR$^c$ (where R$^c$ is alkyl), —O-(alk$^2$)OR$^d$ (where alk$^2$ is alkylene and R$^d$ is alkyl), —S—(CH$_2$)$_2$SCOR$^e$ (where R$^e$ is alkyl), or —NR$^g$—(CHR)OCOR$^f$ (where R is hydrogen, alkyl, hydroxymethyl, thiomethyl, methylthiomethyl, amidinopropyl, indol-3-ylmethyl, indol-4-ylmethyl, carboxymethyl, carboxyethyl, aminocarbonylmethyl, aminocarbonylethyl, phenyl or phenylalkyl (wherein phenyl either alone or as part of phenylalkyl is optionally substituted with one to three substituents independently selected from alkyl, alkoxy, halo, hydroxy, cyano or nitro), R$^f$ is alkyl or benzyl and R$^g$ is hydrogen or together with R forms —(CH$_2$)$_3$—); or R$^a$ and R$^b$ together with the phosphorus atom to which they are attached form a ring of formula (a):

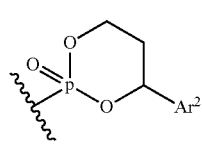

(a)

wherein Ar$^2$ is phenyl or six membered heteroaryl optionally substituted with one to three halo; and R$^w$ and R$^x$ together with the boron atom to which they are attached can form —O(CRR')$_2$O— or —O(CRR')$_3$O— wherein each R and R' is independently hydrogen or methyl.

In a second subembodiment A, the compounds are of Formula (IA) or a pharmaceutically acceptable salt thereof as defined in the Summary above.

Embodiment B

In embodiment B, the compounds of any one of embodiment A and subembodiments contained therein, or a pharmaceutically acceptable salt thereof has a structure of formula (Ia) or (Ib):

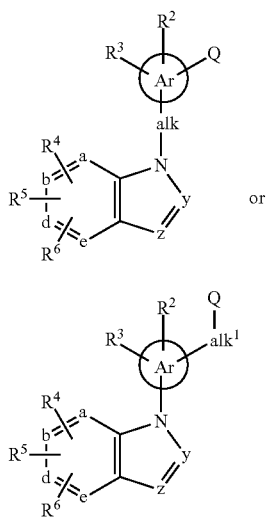

(Bi) In subembodiment (Bi) of embodiment B, the compound or a pharmaceutically acceptable salt thereof has structure (Ia).

(Bii) In subembodiment (Bii) of embodiment B, the compound or a pharmaceutically acceptable salt thereof has structure (Ib).

(Biii) In subembodiment (Biii) of embodiment B, the compound of formula (Ia) and (Ib) or a pharmaceutically acceptable salt thereof are wherein y is N and z is $CR^7$.

Embodiment C

In embodiment C, the compounds of any one of embodiment A and subembodiments contained therein, or a pharmaceutically acceptable salt thereof has a structure of formula (Ic) or (Id):

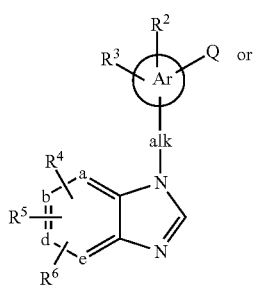

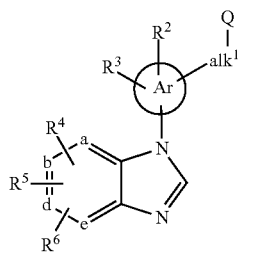

(Ci) In subembodiment (Ci) of embodiment C, the compound or a pharmaceutically acceptable salt thereof has structure (Ic).

(Cii) In subembodiment (Cii) of embodiment C, the compound or a pharmaceutically acceptable salt thereof has structure (Id).

Embodiment D

In embodiment D, the compounds of any one of embodiment A and subembodiments contained therein, or a pharmaceutically acceptable salt thereof has a structure of formula (Ie) or (If):

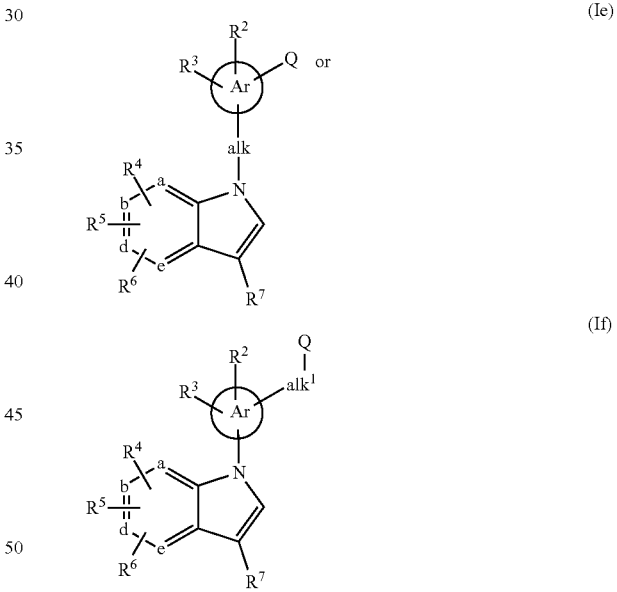

(Di) In subembodiment (Di) of embodiment D, the compound or a pharmaceutically acceptable salt thereof has structure (Ie).

(Dii) In subembodiment (Dii) of embodiment D, the compound or a pharmaceutically acceptable salt thereof has structure (If).

Embodiment D1

In embodiment D, the compounds of any one of embodiment A and subembodiments contained therein, or a pharmaceutically acceptable salt thereof has a structure of formula (Ig) or (Ih):

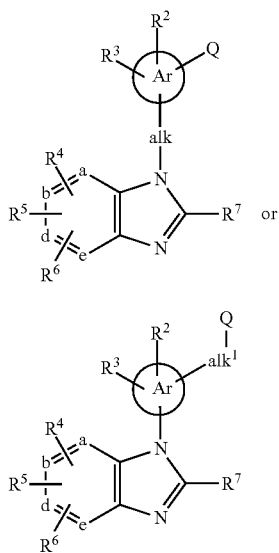

where R[7] is alkyl, halo, or hydroxy.

(D1i) In subembodiment (D1i) of embodiment D, the compound or a pharmaceutically acceptable salt thereof has structure (Ig).

(D1ii) In subembodiment (Dii) of embodiment D, the compound or a pharmaceutically acceptable salt thereof has structure (Ih).

(D1iii) In subembodiment (Dii) of embodiment D, the compound of structure (Ig) and (Ih) or a pharmaceutically acceptable salt are those wherein R[7] is alkyl.

Embodiment E

In embodiment E, the compounds of any one of embodiments A, B, C, D, and D1 and subembodiments contained therein or a pharmaceutically acceptable salt thereof, are wherein a, b, d, and e are CH or C when attached to any one of R[4], R[5], and R[6].

Embodiment F

In embodiment F, the compounds of any one of embodiments A, B, C, D, and D1 and subembodiments contained therein or a pharmaceutically acceptable salt thereof, are wherein a is N and b, d, and e are CH or C when attached to any one of R[4], R[5], and R[6].

Embodiment G

In embodiment G, the compounds of any one of embodiments A, B, C, D, and D1 and subembodiment contained therein or a pharmaceutically acceptable salt thereof, are wherein a and d are N and b, and e are CH or C when attached to any one of R[4], R[5], and R[6].

Embodiment H

In embodiment H, the compounds of any one of embodiments A, B, C, D, and D1 and subembodiments contained therein or a pharmaceutically acceptable salt thereof, are wherein b is N and a, c, and e are CH or C when attached to any one of R[4], R[5], and R[6].

Embodiment I

In embodiment I, the compounds of any one of embodiments A, B, C, D, and D1 and subembodiments contained therein or a pharmaceutically acceptable salt thereof, are wherein b and e are N and a and d are CH or C when attached to any one of R[4], R[5], and R[6].

In subembodiment Ii, the compounds of any one of embodiments A, B, C, D, and D1 and subembodiments contained therein or a pharmaceutically acceptable salt thereof, are wherein b and e are N, a is C—R[5] and d is C—R[6], and R[5] is hydroxyl. As described above, subembodiment Ii, where R[5] is hydroxyl, can exist in the tautomeric forms shown below:

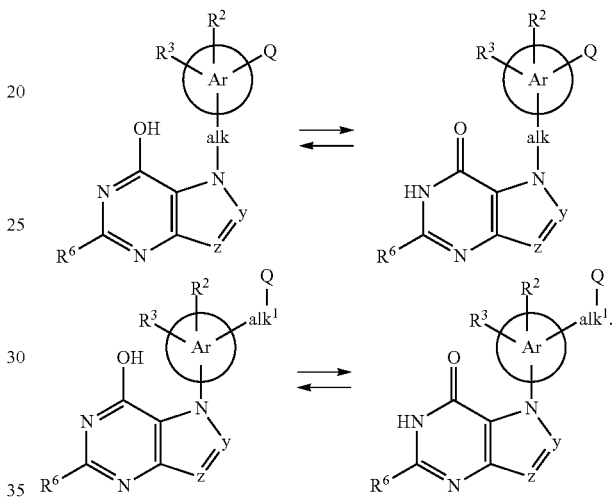

Embodiment J

In embodiment J, the compounds of any one of embodiments A, B, C, D, and D1 and subembodiment contained therein or a pharmaceutically acceptable salt thereof, are wherein b and e are N and a and d are CH or C when attached to any one of R[4], R[5], and R[6].

Embodiment K

In embodiment K, the compounds of any one of embodiments A, B, C, D, and D1 and subembodiments contained therein or a pharmaceutically acceptable salt thereof, are wherein d is N and a, b and e are CH or C when attached to any one of R[4], R[5], and R[6].

Embodiment L (Li). In subembodiment Li, the compounds of any one of embodiments A, B, C, D1, E, F, G, H, I, J, and K, and subembodiment contained therein or a pharmaceutically acceptable salt thereof, are wherein Q is —P(O)(OH)$_2$ (Lii). Within subembodiment Lii, the compounds of any one of embodiments A, B, C, D, D1, E, F, G, H, I, J, and K, and subembodiment contained therein or a pharmaceutically acceptable salt thereof, are wherein Q is —B(OH)$_2$.

(Liii). In subembodiment Liii, the compounds of any one of embodiments A, B, C, D1, E, F, G, H, I, J, and K, and subembodiments contained therein or a pharmaceutically acceptable salt thereof, are wherein Q is —P(O)(R$^a$)(R$^b$).

Within subembodiment (Liii), in a first group of compounds, Q is $R^a$ and $R^b$ are independently selected from hydroxy, alkoxy, —Oaryl (where aryl is optionally substituted with one to three substituents independently selected from alkyl, halo, haloalkyl, cyano, or nitro), —O—(CH$_2$)OCOR$^c$ (where R$^c$ is alkyl), —O—(CH$_2$)OCOOR$^c$ (where R$^c$ is alkyl), —O-(alk$^2$)OR$^d$ (where alk$^2$ is alkylene and R$^d$ is alkyl), and —S—(CH$_2$)$_2$SCOR$^e$(where R$^e$ is alkyl). Preferably, R$^a$ and R$^b$ are independently selected from alkoxy, —Oaryl (where aryl is optionally substituted with one to three substituents independently selected from alkyl, halo, haloalkyl, cyano, or nitro), —O—(CH$_2$)OCOR$^c$ (where R$^c$ is alkyl), and —O-(alk$^2$)OR$^d$ (where alk$^2$ is alkylene and R$^d$ is alkyl, such as methyl, isopropyl, n-propyl, isobutyl, or n-butyl). Preferably, R$^a$ and R$^b$ are independently hydroxy, alkoxy, —Ophenyl (where phenyl is optionally substituted with one to three substituents independently selected from alkoxy, halo, haloalkyl, cyano, or nitro), —O—(CH$_2$)OCOR$^c$ (where R$^c$ is alkyl), or —NH—(CHR)OCOR$^f$ (where R is alkyl, R$^f$ is alkyl such as methyl, isopropyl, n-propyl, isobutyl, n-butyl or benzyl), preferably hydroxy or alkoxy.

Within subembodiment (Liii), in a second group of compounds, Q is R$^a$ is selected from hydroxy, alkoxy, —Oaryl (where aryl is optionally substituted with one to three substituents independently selected from alkyl, alkenyl, alkoxy, halo, haloalkyl, amino, alkylamino, dialkylamino, cyano, or nitro), —O—(CH$_2$)OCOR$^c$ (where R$^c$ is alkyl), —O-(alk$^2$)OR$^d$ (where alk$^2$ is alkylene and R$^d$ is alkyl), and —S—(CH$_2$)$_2$SCOR$^e$ (where R$^e$ is alkyl), and R$^b$ is selected from —NR$^g$—(CHR)OCOR$^f$ (where R is hydrogen, alkyl, hydroxymethyl, thiomethyl, methylthiomethyl, amidinopropyl, indol-3-ylmethyl, indol-4-ylmethyl, carboxymethyl, carboxyethyl, aminocarbonylmethyl, aminocarbonylethyl, phenyl or phenylalkyl (wherein phenyl either alone or as part of phenylalkyl is optionally substituted with one to three substituents independently selected from alkyl, alkoxy, halo, hydroxy, cyano or nitro), R$^f$ is alkyl or benzyl, and R$^g$ is hydrogen or together with R forms —(CH$_2$)$_3$—). Preferably, R$^a$ is selected from alkoxy and —Oaryl (where aryl is optionally substituted with one to three substituents independently selected from halo, cyano, or nitro) and R$^b$ selected from —NR$^g$—(CHR)OCOR$^f$ (where R is alkyl such as methyl, isopropyl, n-propyl, isobutyl, n-butyl).

Within subembodiment (Liii), in a third group of compounds, Q is where R$^a$ and R$^b$ together with the phosphorus atom to which they are attached form a ring of formula (a):

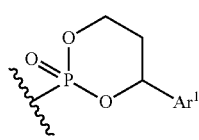

(a)

wherein Ar$^1$ is phenyl or six membered heteroaryl optionally substituted with one to three halo. Preferably, Ar$^1$ is phenyl substituted one to three halo or pyridinyl.

(Liv). In subembodiment Liv, the compounds of any one of embodiments A, B, C, D, D1, E, F, G, H, I, J, and K, and subembodiments contained therein or a pharmaceutically acceptable salt thereof, are wherein Q is —B(R$^w$)(R$^x$). Within subembodiment (Liv), in a first group of compounds, R$^w$ and R$^x$ are independently selected from hydroxy, alkoxy, —Oaryl (where aryl is optionally substituted with one to three substituents independently selected from alkyl, halo, haloalkyl, cyano, or nitro), —O—(CH$_2$)OCOR$^c$ (where R$^c$ is alkyl), or —O-(alk$^2$)OR$^d$ (where alk$^2$ is alkylene and R$^d$ is alkyl). Preferably, R$^w$ and R$^x$ are independently selected from alkoxy, —Oaryl (where aryl is optionally substituted with one to three substituents independently selected from alkyl, halo, haloalkyl, cyano, or nitro), —O—(CH$_2$)OCOR$^c$ (where R$^c$ is alkyl), and —O-(alk$^2$)OR$^d$ (where alk$^2$ is alkylene and R$^d$ is alkyl, such as methyl, isopropyl, n-propyl, isobutyl, or n-butyl). Preferably, R$^w$ and R$^x$ are independently hydroxy, alkoxy, or —Ophenyl (where phenyl is optionally substituted with one to three substituents independently selected from alkoxy, halo, haloalkyl, cyano, or nitro).

Within subembodiment (Liv), in a second group of compounds, R$^w$ and R$^x$ are independently selected from hydroxy and alkoxy.

Within subembodiment (Liii), in a third group of compounds, R$^w$ and R$^x$ together with the boron atom to which they are attached form a ring of formula (b) or (c):

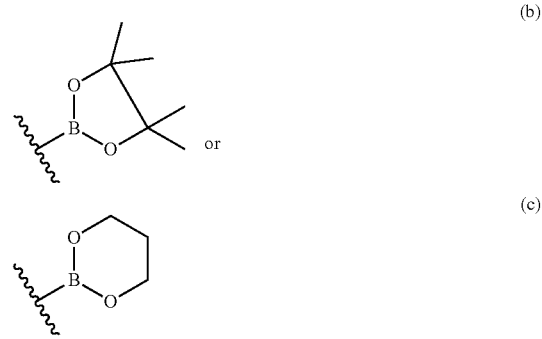

Embodiment M

In embodiment M, the compounds of any one of embodiments A, B, C, D, D1, E, F, G, H, I, J, K, and L, and subembodiments contained therein or a pharmaceutically acceptable salt thereof, are wherein Ar is aryl or heteroaryl.

(Mi). In subembodiment Mi of embodiment M, the compounds of embodiment M or a pharmaceutically acceptable salt thereof are those wherein Ar is phenyl. In one subembodiment of subembodiment Mi, the compounds of subembodiment Mi or a pharmaceutically acceptable salt thereof is wherein Q is attached to carbon of the phenyl ring that is meta to the carbon attaching the phenyl ring to remaining compound of Formula (I). In another subembodiment of subembodiment Mi, the compounds of subembodiment Mi or a pharmaceutically acceptable salt thereof is wherein Q is attached to carbon on the phenyl ring that is para to the carbon attaching the phenyl ring to remaining compound of Formula (I) and (Ia) to (Ih), respectively.

(Mii). In subembodiment Mii of embodiment M, the compounds of embodiment M are those wherein Ar is heteroaryl. In one subembodiment of subembodiment Mii, the compounds of subembodiment Mii or a pharmaceutically acceptable salt thereof is wherein Ar is pyridinyl, pyrimidinyl, pyridazinyl, thienyl, furanyl, thiazolyl, oxazolyl, isoxazolyl, pyrazolyl, triazolyl, oxadiazolyl, or imidazolyl. In another subembodiment of embodiment Mii, the compounds of subembodiment Mii or a pharmaceutically acceptable salt thereof is wherein Ar is a six-membered ring such as pyridinyl, pyrimidinyl, or pyridazinyl wherein Q is attached to carbon on the pyridinyl, pyrimidinyl, or pyridazinyl ring that is meta to the carbon attaching the pyridinyl, pyrimidinyl, or pyridazinyl ring to remaining compound of Formula (I) and (Ia) to (Ih), respectively.

With subembodiment Mii, in yet another group of compounds Ar is benzofuranyl, quinolinyl, quinazolinyl, benzimidazolyl, indazolyl, benzotriazolyl, or benzoxazolyl.

Embodiment N

In embodiment N, the compounds of any one of embodiments A, B, C, D, D1, E, F, G, H, I, J, K, and L, and subembodiments contained therein or a pharmaceutically acceptable salt thereof, are wherein Ar is heterocyclyl.

(Ni). In subembodiment Ni of embodiment N, the compounds of subembodiment Ni or a pharmaceutically acceptable salt thereof is wherein Ar is pyrrolidinyl, piperidinyl, or homopiperidinyl, preferably Ar is piperidin-4-yl wherein Q is attached to the to the nitrogen atom of the piperidinyl ring via alk$^1$.

Embodiment O

In embodiment O, the compounds of any one of embodiments A, B, C, D, D1, E, F, G, H, I, J, K, L, M and N, and subembodiments contained therein or a pharmaceutically acceptable salt thereof, are wherein alk and alk$^1$ are independently methylene, ethylene, or propylene. In a first subembodiment, alk and alk$^1$ are methylene, preferably alk and alk$^1$ are methylene when Ar is a six membered ring. In a second subembodiment, alk is methylene and alk$^1$ is absent (i.e., m is 0).

Embodiment P

In embodiment P, the compounds of any one of embodiments A, B, D, D1, E, F, G, H, J, K, L, M, and O, and subembodiments contained therein or a pharmaceutically acceptable thereof are wherein R$^7$ is hydrogen, methyl, isopropyl, or fluoro. In a first subembodiment of embodiment P, the compounds are those wherein R$^7$ is hydrogen, methyl, or fluoro. In a second subembodiment of embodiment P, the compounds are those wherein R$^7$ is hydrogen. In a second subembodiment of embodiment P, the compounds are those wherein R$^7$ is methyl or isopropyl.

Embodiment Q

In embodiment Q, the compounds of any one of embodiments A, B, C, D, D1, E, F, G, H, I, J, K, L, M, N, O, and P, and subembodiments contained therein or a pharmaceutically acceptable thereof, are wherein R$^2$ and R$^3$ are independently hydrogen, methyl, ethyl, methoxy, fluoro, trifluoromethyl, trifluoromethoxy, or cyano. In a first subembodiment of embodiment Q, the compounds are those wherein R$^2$ and R$^3$ are hydrogen.

Embodiment R

In embodiment R, the compounds of any one of embodiments A, B, C, D, D1, E, F, G, H, I, J, K, L, M, N, O, P, and Q, and subembodiments contained therein or a pharmaceutically acceptable thereof, are wherein R$^4$ is hydrogen, alkyl, alkoxy, alkylsulfonyl, halo, haloalkyl, haloalkoxy, cyano, carboxy, alkoxycarbonyl, aminocarbonyl, alkylaminocarbonyl, dialkylaminocarbonyl, aminosulfonyl, alkylaminosulfonyl, or dialkylaminosulfonyl.

(Ri) In subembodiment (Ri) of embodiment R, the compounds are wherein R$^4$ is hydrogen, methyl, methoxy, ethoxy, fluoro, chloro, trifluoromethyl, cyano, or trifluoromethyloxy In a first subembodiment of (Ri), the compounds are wherein R$^4$ is hydrogen, methoxy or ethoxy. In a second subembodiment of (Ri), the compounds are wherein R$^4$ is hydrogen.

(Rii) In subembodiment (Rii) of embodiment R, R$^4$ is cyano, carboxy, alkoxycarbonyl, alkylsulfonyl, aminocarbonyl, alkylaminocarbonyl, dialkylaminocarbonyl, aminosulfonyl, alkylaminosulfonyl, or dialkylaminosulfonyl. Within (Rii), in one group of compounds, R$^4$ is cyano, carboxy, methoxycarbonyl, methylsulfonyl, aminocarbonyl, methylaminocarbonyl, dimethylaminocarbonyl, aminosulfonyl, methylaminosulfonyl, or dimethylaminosulfonyl. Within (Rii), in another group of compounds, R$^4$ is cyano, carboxy, methoxycarbonyl, aminocarbonyl, methylsulfonyl, methylaminocarbonyl, dimethylaminocarbonyl, aminosulfonyl, methylaminosulfonyl, or dimethylaminosulfonyl. Within (Rii), in yet another group of compounds, R$^4$ is aminocarbonyl, methylaminocarbonyl, or dimethylaminocarbonyl. Within R(ii) and groups contained therein, in another group of compounds, R$^4$ is attached to the six membered ring comprising a, b, d, and e of Formula (I) as shown below

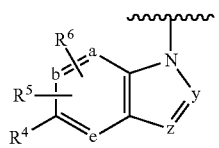

wherein the wavy line denotes the attachment point to the remainder of the molecule (for sake of clarity, the six membered ring comprising a, b, d, and e of Formula (I) has been shown as an example. It will be apparent to a person skilled in the art, that in embodiments covering one or more of compounds of formulae (Ia) to (Ih), R$^4$ will be attached to the same carbon of the six membered ring comprising a, b, d, and e as depicted above).

(Riii) In subembodiment (Riii) of embodiment R, the compounds are wherein R$^4$ is alkylsulfonyl, preferably methylsulfonyl and R$^4$ is attached to the six membered ring comprising a, b, d, and e of Formula I as shown below

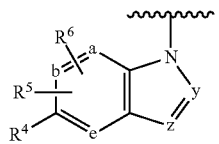

wherein the wavy line denotes the attachment point to the remainder of the molecule.

Embodiment S (Si) In embodiment Si, the compounds of any one of embodiments A, B, C, D, D1, E, F, G, H, I, J, K, L, M, N, O, P, Q and R, and subembodiments (or groups) contained therein or a pharmaceutically acceptable thereof, are wherein R$^5$ and R$^6$ are independently hydrogen, alkyl, alkoxy, hydroxy, amino, halo, haloalkyl, or haloalkoxy. In a first subembodiment of embodiment (Si) the compounds are wherein $R^5$ and $R^6$ are independently hydrogen, alkoxy, amino, or hydroxy. In a second subembodiment of embodiment (Si) the compounds are wherein $R^5$ and $R^6$ are independently alkoxy such as methoxy, ethoxy, or propoxy and are attached to the six membered ring comprising a, b, d, and e of Formula I as shown below

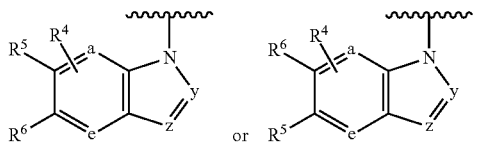

wherein the wavy line denotes the attachment point to the remainder of the molecule. In a third subembodiment of embodiment (Si) the compounds are wherein $R^5$ and $R^6$ are independently hydrogen. In a fourth subembodiment of embodiment (Si) the compounds are wherein $R^5$ is attached to the six membered ring comprising a, b, d, and e of Formula I as shown below

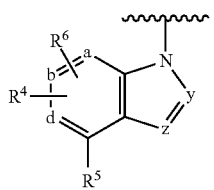

wherein the wavy line denotes the attachment point to the remainder of the molecule. Within the fourth subembodiment, in one group of compounds $R^5$ is hydroxy and $R^4$ and $R^6$ are hydrogen.

(Mii) In embodiment Mii, the compounds of any one of embodiments A, B, C, D, D1, E, F, G, H, I, J, K, L, M, N, O, P, Q and R, and subembodiments contained therein or a pharmaceutically acceptable thereof are those wherein:

$R^5$ is hydrogen, alkyl, alkoxy, hydroxy, halo, haloalkyl, or haloalkoxy; and $R^6$ is hydroxyalkyl, alkoxyalkyl, hydroxyalkoxy, alkoxyalkoxy, hydroxyalkylamino, alkoxyalkylamino, aminoalkyl, aminoalkoxy, aminoalkylamino, heterocyclyl, heterocyclyloxy, heterocyclylamino (wherein heterocyclyl either alone or part of heterocyclyloxy and heterocyclylamino is optionally substituted with one, two, or three substituents independently selected from alkyl, halo, hydroxy, alkoxy, hydroxyalkyl, alkoxyalkyl, and aminoalkyl), heterocyclylalkyl, heterocyclylalkyloxy, heterocyclylalkylamino (wherein the heterocyclyl ring in heterocyclylalkyl, heterocyclylalkyloxy, and heterocyclylalkylamino is optionally substituted with one, two, or three substituents independently selected from alkyl, halo, hydroxy, alkoxy, hydroxyalkyl, alkoxyalkyl, and aminoalkyl), cycloalkyloxy, phenyloxy, or heteroaryloxy (where phenyl in phenyloxy and heteroaryl in heteroaryloxy are optionally substituted with one, two, or three substituents where two of the optional substituents are independently selected from alkyl, hydroxy, alkoxy, halo, haloalkyl, haloalkoxy, and cyano).

In a first subembodiment of embodiment Mii, $R^5$ is hydrogen, methoxy, ethoxy, or hydroxy, preferably $R^5$ is methoxy or ethoxy; and $R^6$ is 2-hydroxyethyloxy, 3-hydroxypropyloxy, 2-methoxyethyloxy, 2-ethoxyethyloxy, 3-methoxypropyloxy, 3-ethoxypropyloxy, 2-aminoethyloxy, 2-methylaminoethyloxy, 2-dimethylaminoethyloxy, 2-diethylaminoethyloxy, 3-aminopropyloxy, 3-methylaminopropyloxy, 3-dimethylaminopropyloxy, 3-diethylaminopropyloxy, pyrrolidinyloxy, piperidinyloxy, pyrrolidinylmethyloxy, piperidinylmethyloxy, pyrrolidinylethyloxy, piperidinylethyloxy, 2-hydroxyethylamino, 3-hydroxypropylamino, 2-methoxyethylamino, 2-ethoxyethylamino, 3-methoxypropylamino, 3-ethoxypropylamino, 2-aminoethylamino, 2-methylaminoethylamino, 2-dimethylaminoethylamino, 2-diethylaminoethylamino, 3-aminopropylamino, 3-methylaminopropylamino, 3-dimethylaminopropylamino, 3-diethylaminopropylamino, pyrrolidinylamino, piperidinylamino, pyrrolidinylmethylamino, piperidinylmethylamino, pyrrolidinylethylamino, or piperidinylethylamino (wherein pyrrolidinyl and piperidinyl in each of aforementioned groups, alone or part of another group is optionally substituted with one or two substituents independently selected from methyl, fluoro, hydroxy, or methoxy). Preferably, $R^5$ and $R^6$ are attached to the six membered ring comprising a, b, d, and e of Formula I as shown below

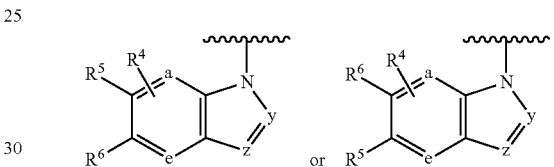

wherein the wavy line denotes the attachment point to the remainder of the molecule.

(Miii) In embodiment Mi, the compounds of any one of embodiments A, B, C, D, D1, E, F, G, H, I, J, K, L, M, N, O, P, Q and R, and subembodiments contained therein or a pharmaceutically acceptable thereof are those wherein $R^5$ and $R^6$ are independently hydroxyalkyl, alkoxyalkyl, hydroxyalkoxy, alkoxyalkoxy, hydroxyalkylamino, alkoxyalkylamino, aminoalkyl, aminoalkoxy, aminoalkylamino, heterocyclyl, heterocyclyloxy, heterocyclylamino (wherein heterocyclyl either alone or part of heterocyclyloxy and heterocyclylamino is optionally substituted with one, two, or three substituents independently selected from alkyl, halo, hydroxy, alkoxy, hydroxyalkyl, alkoxyalkyl, and aminoalkyl), heterocyclylalkyl, heterocyclylalkyloxy, heterocyclylalkylamino (wherein the heterocyclyl ring in heterocyclylalkyl, heterocyclylalkyloxy, and heterocyclylalkylamino is optionally substituted with one, two, or three substituents independently selected from alkyl, halo, hydroxy, alkoxy, hydroxyalkyl, alkoxyalkyl, and aminoalkyl), cycloalkyloxy, phenyloxy, or heteroaryloxy (where phenyl of phenyloxy and heteroaryl of heteroaryloxy are optionally substituted with one, two, or three substituents where two of the optional substituents are independently selected from alkyl, hydroxy, alkoxy, halo, haloalkyl, haloalkoxy, and cyano).

In a first subembodiment of embodiment Miii, $R^5$ and $R^6$ are independently 2-hydroxyethyloxy, 3-hydroxypropyloxy, 2-methoxyethyloxy, 2-ethoxyethyloxy, 3-methoxypropyloxy, 3-ethoxypropyloxy, 2-aminoethyloxy, 2-methylaminoethyloxy, 2-dimethylaminoethyloxy, 2-diethylaminoethyloxy, 3-aminopropyloxy, 3-methylaminopropyloxy, 3-dimethylaminopropyloxy, 3-diethylaminopropyloxy, pyrrolidinyloxy, piperidinyloxy, pyrrolidinylmethyloxy, piperidinylmethyloxy, pyrrolidinylethyloxy, piperidinylethyloxy, 2-hydroxyethylamino, 3-hydroxypropylamino, 2-methoxyethylamino, 2-ethoxyethylamino, 3-methoxypropylamino, 3-ethoxypropylamino, 2-aminoethylamino, 2-methylaminoethylamino, 2-dimethylaminoethylamino, 2-diethylaminoethylamino, 3-aminopropylamino, 3-methylaminopropylamino, 3-dimethylaminopropylamino, 3-diethylaminopropylamino, pyrrolidinylamino, piperidinylamino, pyrrolidinylmethylamino, piperidinylmethylamino, pyrrolidinylethylamino, or piperidinylethylamino (wherein pyrrolidinyl and piperidinyl in each of aforementioned groups, alone or part of another group is optionally substituted with one or two substituents independently selected from methyl, fluoro, hydroxy, or methoxy). Preferably, $R^5$ and $R^6$ are attached to the six membered ring comprising a, b, d, and e of Formula I as shown below

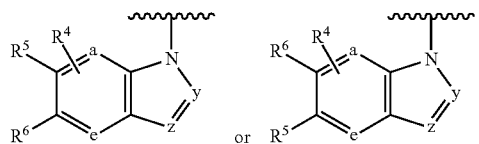

wherein the wavy line denotes the attachment point to the remainder of the molecule.

Additional embodiments of the disclosure include embodiments 1 to 58 below:

1. In embodiment 1, provided is a compound of Formula (I):

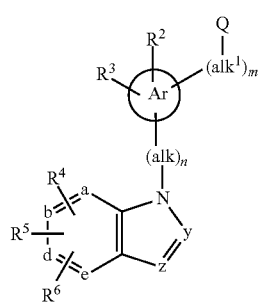

wherein:
- a, b, d, and e are CH; or one or two of a, b, d, and e are N and remaining of a, b, d, and e are CH;
- one of y and z is N and the other y and z is $CR^7$; or both y and z are $CR^7$ wherein each $R^7$ is independently hydrogen, alkyl, hydroxy, or halo;
- alk is alkylene optionally substituted with one, two, or three halo;
- $alk^1$ is alkylene wherein one carbon atom in the alkylene chain can be replaced by oxygen and the alkylene chain is optionally substituted with one, two, or three halo;
- m and n are independently 0 or 1; provided that at least one of m and n is 1;
- Ar is aryl or heteroaryl;
- Q is —B($R^w$)($R^x$), wherein $R^w$ and $R^x$ are independently selected from hydroxy, alkoxy, —Oaryl (where aryl is optionally substituted with one to three substituents independently selected from alkyl, alkenyl, alkoxy, halo, haloalkyl, amino, alkylamino, dialkylamino, cyano, or nitro), —O—(CH$_2$)OCOR$^c$ (where R$^c$ is alkyl), —O-(alk$^2$)OR$^d$ (where alk$^2$ is alkylene and R$^d$ is alkyl); or $R^w$ and $R^x$ together with the boron atom to which they are attached can form —O(CRR')$_2$O— or —O(CRR')$_3$O— wherein each R and R' is independently hydrogen or methyl;
- $R^2$ and $R^3$ are independently hydrogen, alkyl, alkoxy, halo, haloalkyl, haloalkoxy, or cyano;
- $R^4$ is hydrogen, alkyl, alkoxy, alkylthio, alkylsulfonyl, halo, haloalkyl, haloalkoxy, cyano, carboxy, alkoxycarbonyl, aminocarbonyl, alkylaminocarbonyl, dialkylaminocarbonyl, aminosulfonyl, alkylaminosulfonyl, or dialkylaminosulfonyl; and
- $R^5$ and $R^6$ are independently hydrogen, alkyl, alkoxy, hydroxy, halo, haloalkyl, haloalkoxy, hydroxyalkyl, alkoxyalkyl, hydroxyalkoxy, alkoxyalkoxy, hydroxyalkylamino, alkoxyalkylamino, amino, aminoalkyl, aminoalkoxy, aminoalkylamino, heterocyclyl, heterocyclyloxy, heterocyclylamino (wherein heterocyclyl either alone or part of heterocyclyloxy and heterocyclylamino is optionally substituted with $R^h$, $R^i$, or $R^k$ independently selected from alkyl, halo, hydroxy, alkoxy, hydroxyalkyl, alkoxyalkyl, and aminoalkyl), heterocyclylalkyl, heterocyclylalkyloxy, heterocyclylalkylamino (wherein the heterocyclyl ring in heterocyclylalkyl, heterocyclylalkyloxy, and heterocyclylalkylamino is optionally substituted with one, two, or three substituents independently selected from alkyl, halo, hydroxy, alkoxy, hydroxyalkyl, alkoxyalkyl, and aminoalkyl), cycloalkyloxy, phenyloxy, or heteroaryloxy (where phenyl in phenyloxy and heteroaryl in heteroaryloxy are optionally substituted with one, two, or three substituents where two of the optional substituents are independently selected from alkyl, hydroxy, alkoxy, halo, haloalkyl, haloalkoxy, and cyano); or a pharmaceutically acceptable salt thereof;

provided that when Formula (I) has the structure

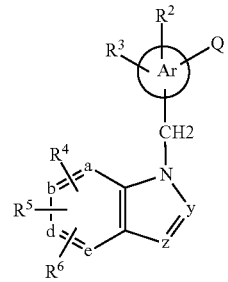

and:
(i) Q is —B(OH)$_2$, then

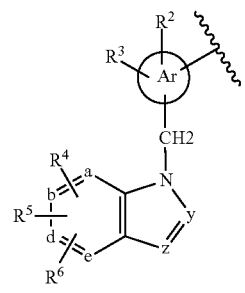

is not 4-((6-amino-2-butoxy-8-methoxy-9H-purin-9-yl)methyl)phenyl; 4-((5,6-dichloro-2-methyl-1H-benzimidazol-1-yl)methyl)phenyl; 4-((2-methyl-1H-benzimidazol-1-yl)methyl)phenyl; 5-fluoro-2-((2-methyl-1H-benzimidazol-1-yl)methyl)phenyl; 3-fluoro-4-((2-methyl-1H-benzimidazol-1-yl)methyl)phenyl; 3-((5,6-dimethyl-1H-benzimidazol-1-yl)methyl)phenyl; 4-((5,6-dimethyl-1H-benzimidazol-1-yl)methyl)phenyl; 2-((2-methyl-1H-benzimidazol-1-yl)methyl)phenyl; 2-((5,6-dimethyl-1H-benzimidazol-1-yl)methyl)phenyl; 2-fluoro-5-((2-methyl-1H-benzimidazol-1-yl)methyl)phenyl; 3-((2-methyl-1H-benzimidazol-1-yl)methyl)phenyl; 3-(1H-benzimidazol-1-ylmethyl)phenyl; 3-(1H-indazol-1-ylmethyl)phenyl; 2-(1H-benzimidazol-1-ylmethyl)phenyl; 4-(1H-benzimidazol-1-ylmethyl)phenyl; 4-(1H-indol-1-ylmethyl)phenyl; 4-((6-amino-9H-purin-9-yl)methyl)phenyl; 3-((6-amino-9H-purin-9-yl)methyl)phenyl; 2-((6-amino-9H-purin-9-yl)methyl)phenyl; 4-(1H-benzimidazol-1-ylmethyl)-3-fluorophenyl; 4-((2-ethyl-5,7-dimethyl-3H-imidazo[4,5-b]pyridin-3-yl)methyl)-3-fluorophenyl; 5-(1H-benzimidazol-1-ylmethyl)-2-fluorophenyl; 4-((2-ethyl-5,7-dimethyl-3H-imidazo[4,5-b]pyridin-3-yl)methyl)-3-fluorophenyl; 2-(1H-benzimidazol-1-ylmethyl)-5-fluorophenyl; 5-(1H-benzimidazol-1-ylmethyl)-2-methoxyphenyl; 3-(1H-benzimidazol-1-ylmethyl)-4-methoxyphenyl; 2-((2-ethyl-5,7-dimethyl-3H-imidazo[4,5-b]pyridin-3-yl)methyl)-5-pyrimidinyl, 6-((2-ethyl-5,7-dimethyl-3H-imidazo[4,5-b]pyridin-3-yl)methyl)-3-pyridinyl, or 4-(2-ethoxy-7-carboxy-1H-benzimidazol-1-ylmethyl)phenyl;

(ii) Q is

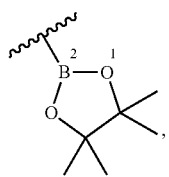 [SMILES: *B1OC(C)(C)C(C)(C)O1]

then

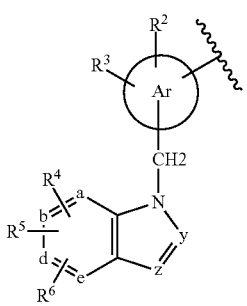

is not 2-(1H-benzo[d]imidazol-1-ylmethyl)phenyl, 2-(1H-indol-1-ylmethyl)phenyl, 3-(1H-indazol-1-ylmethyl)phenyl-, 4-(2-ethyl-5,7-dimethyl-3H-imidazo[4,5-b]pyridin-3-yl)methylphenyl, 4-(2-methyl-1H-benzimidazol-1-ylmethyl)phenyl; 4-(6-amino-8-methoxy-2-(tetrahydro-2H-pyran-4-yl)methoxy-9H-purin-9-ylmethyl)phenyl, 3-fluoro-4-(6-amino-8-methoxy-2-(2-methoxyethoxy)-9H-purin-9-ylmethyl)phenyl, 4-(6-amino-8-methoxy-2-(2-methoxyethoxy)-9H-purin-9-ylmethyl)phenyl, 4-(6-amino-2-butoxy-8-methoxy-9H-purin-9-ylmethyl)phenyl, 4-(1H-Indol-1-ylmethyl)phenyl, 4-(1H-benimidazol-1-ylmethyl) phenyl, 3-(7-methoxycarbonyl-1H-indol-1-ylmethyl) phenyl, 4-(7-methoxycarbonyl-1H-indol-1-ylmethyl) phenyl, 4-(2-ethoxy-7-methoxycarbonyl-1H-benzimidazol-1-ylmethyl)phenyl, or 4-(2-ethoxy-7-ethoxycarbonyl-1H-benzimidazol-1-ylmethyl)phenyl; and (iii) Q is

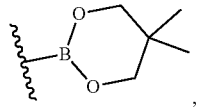

then

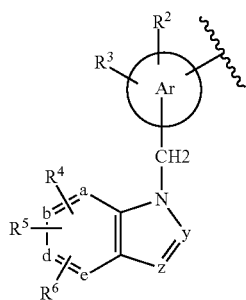

is not 4-(2-ethoxy-7-ethoxycarbonyl-1H-benzimidazol-1-ylmethyl)phenyl.

2. In embodiment 2, the compound of embodiment 1, or a pharmaceutically acceptable salt thereof has a structure of formula (Ia) or (Ib):

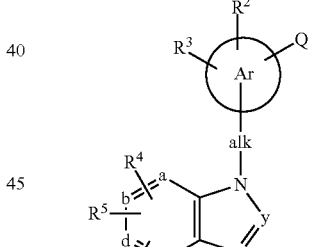

(Ia)

or

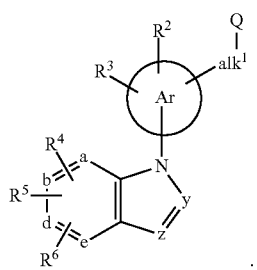

(Ib)

3. In embodiment 3, the compound of embodiment 2, or a pharmaceutically acceptable salt thereof has structure of formula (Ia).

4. In embodiment 4, the compound of embodiment 2, or a pharmaceutically acceptable salt thereof has structure of formula (Ib).

5. In embodiment 5, the compound of embodiment 1, or a pharmaceutically acceptable salt thereof has structure of formula (Ic) or (Id):

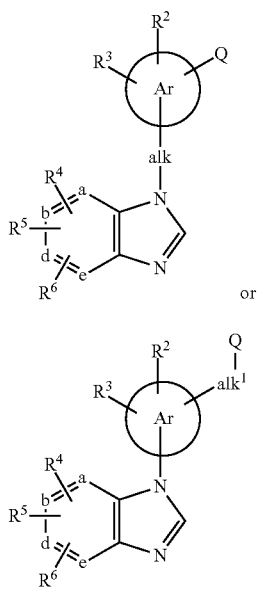

(Ic)

or (Id)

6. In embodiment 6, the compound of embodiment 5, or a pharmaceutically acceptable salt thereof has a structure of formula (Ic).
7. In embodiment 7, the compound of embodiment 5, or a pharmaceutically acceptable salt thereof has a structure of formula (Id).
8. In embodiment 8, the compound of embodiment 1, or a pharmaceutically acceptable salt thereof has a structure of formula (Ie) or (If):

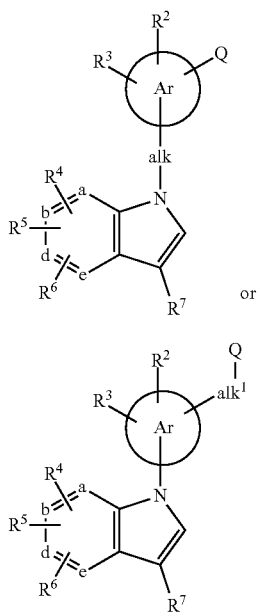

(Ie)

or (If)

9. In embodiment 9, the compound of embodiment 8, or a pharmaceutically acceptable salt thereof has a structure of formula (Ie).
10. In embodiment 18, the compound of embodiment 8, or a pharmaceutically acceptable salt thereof has a structure of formula (If).
11. In embodiment 11, the compound of embodiment 1, or a pharmaceutically acceptable salt thereof has structure of formula (Ig) or (Ih):

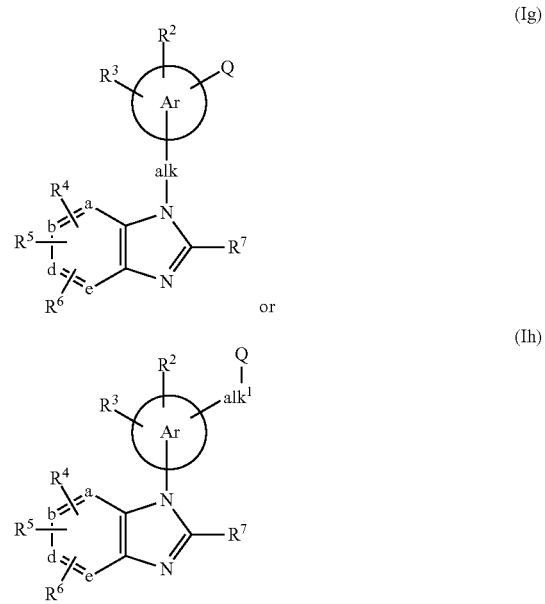

(Ig)

or (Ih)

where $R^7$ is alkyl, halo, or hydroxy.

12. In embodiment 12, the compound of embodiment 11, or a pharmaceutically acceptable salt thereof has a structure of formula (Ig).
13. In embodiment 13, the compound of embodiment 11, or a pharmaceutically acceptable salt thereof has a structure of formula (Ih).
14. In embodiment 14, the compound of embodiment 12 or 13, or a pharmaceutically acceptable salt thereof is wherein $R^7$ is alkyl.
15. In embodiment 15, the compound of any one of embodiments 1 to 14, or a pharmaceutically acceptable salt thereof is wherein a, b, d, and e are CH.
16. In embodiment 16, the compound of any one of embodiments 1 to 14, or a pharmaceutically acceptable salt thereof is wherein a is N and b, d, and e are CH.
17. In embodiment 17, the compound of any one of embodiments 1 to 14, or a pharmaceutically acceptable salt thereof is wherein a and d are N and b, and e are CH.
18. In embodiment 18, the compound of any one of embodiments 1 to 14, or a pharmaceutically acceptable salt thereof is wherein b is N and a, c, and e are CH.
19. In embodiment 19, the compound of any one of embodiments 1 to 14, or a pharmaceutically acceptable salt thereof is wherein b and e are N and a and d are CH.
20. In embodiment 20, the compound of any one of embodiments 1 to 14, or a pharmaceutically acceptable salt thereof is wherein d is N and a, b, and e are CH.
21. In embodiment 21, the compound of any one of embodiments 1 to 14, or a pharmaceutically acceptable salt thereof is wherein one of d and e is N and the remaining of a, b, d and e are CH.

21a. In embodiment 21a, the compound of any one of embodiments 1 to 14, or a pharmaceutically acceptable salt thereof is wherein a and e are N and b and d are CH.

21b. In embodiment 21b, the compound of embodiment 21, or a pharmaceutically acceptable salt thereof has a structure of formula (Ii):

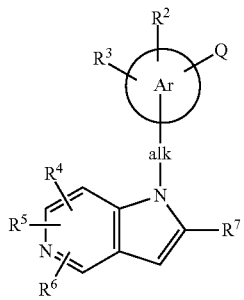
(Ii)

21c. In embodiment 21c, the compound of embodiment 21, or a pharmaceutically acceptable salt thereof has a structure of formula (Ij):

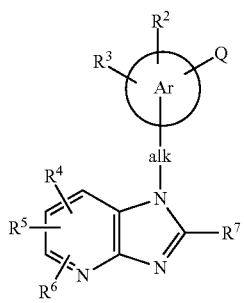
(Ij)

where $R^7$ is alkyl, halo, or hydroxy.

21d. In embodiment 21d, the compound of embodiment 21b and 21c, or a pharmaceutically acceptable salt thereof is wherein $R^7$ is alkyl.

21e. In embodiment 21d, the compound of embodiment 21b and 21c, or a pharmaceutically acceptable salt thereof is wherein $R^7$ is methyl or isopropyl.

22. In embodiment 22, the compound of any one of embodiments 1 to 21e, or a pharmaceutically acceptable salt thereof is wherein Q is —B(OH)$_2$.

23. In embodiment 23, the compound of any one of embodiments 1 to 21e, or a pharmaceutically acceptable salt thereof is wherein Q is —B(R$^w$)(R$^x$) wherein R$^w$ and R$^x$ are independently selected from hydroxy and alkoxy.

24. In embodiment 24, the compound of any one of embodiments 1 to 21e, or a pharmaceutically acceptable salt thereof is wherein Q is —B(R$^w$)(R$^x$) wherein R$^w$ and R$^x$ together with the boron atom to which they are attached form a ring of formula (b) or (c):

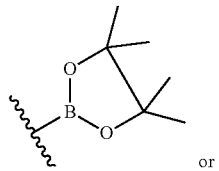
(b)

or

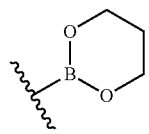
(c)

25. In embodiment 25, the compound of any one of embodiments 1 to 24, or a pharmaceutically acceptable salt thereof is wherein Ar is phenyl.

26. In embodiment 26, the compound of embodiment 25, or a pharmaceutically acceptable salt thereof is wherein Q is attached to carbon on the phenyl ring that is para to the carbon attaching the phenyl ring to the remainder of the compound of Formula (I), (Ia), (Ib), (Ic), (Id), (Ie), (If), (If), and (Ig).

27. In embodiment 27, the compound of any one of embodiments 1 to 24, or a pharmaceutically acceptable salt thereof wherein Ar is heteroaryl.

28. In embodiment 28, the compound of embodiment 27, or a pharmaceutically acceptable salt thereof is wherein Ar is pyridinyl, pyrimidinyl, pyridazinyl, thienyl, furanyl, thiazolyl, oxazolyl, isoxazolyl, pyrazolyl, triazolyl, oxadiazolyl, or imidazolyl.

29. In embodiment 29, the compound of any one of embodiments 1 to 28, or a pharmaceutically acceptable salt thereof is wherein alk and alk$^1$ are independently methylene, ethylene, or propylene.

30. In embodiment 30, the compound of any one of embodiments 1 to 28, or a pharmaceutically acceptable salt thereof is wherein alk and alk$^1$ are methylene.

31. In embodiment 31, the compound of any one of embodiments 1 to 4 and 8 to 20, 21a, and 22 to 30, or a pharmaceutically acceptable salt thereof is wherein $R^7$ is hydrogen, methyl, isopropyl, or fluoro.

32. In embodiment 32, the compound of any one of embodiments 1 to 4 and 8 to 20, 21a, and 22 to 30, or a pharmaceutically acceptable salt thereof is wherein $R^7$ is hydrogen, methyl, or fluoro.

33. In embodiment 33, the compound of any one of embodiments 1 to 32, or a pharmaceutically acceptable salt thereof is wherein $R^2$ and $R^3$ are independently hydrogen, methyl, ethyl, methoxy, fluoro, trifluoromethyl, trifluoromethoxy, or cyano.

34. In embodiment 34, the compound of any one of embodiments 1 to 32, or a pharmaceutically acceptable salt thereof is wherein $R^2$ and $R^3$ are hydrogen.

35. In embodiment 35, the compound of any one of embodiments 1 to 34, or a pharmaceutically acceptable salt thereof is wherein $R^4$ is hydrogen, alkyl, alkoxy, alkylsulfonyl, halo, haloalkyl, haloalkoxy, cyano, carboxy, alkoxycarbonyl, aminocarbonyl, alkylaminocarbonyl, dialkylaminocarbonyl, aminosulfonyl, alkylaminosulfonyl, or dialkylaminosulfonyl.

36. In embodiment 36, the compound of embodiment 35, or a pharmaceutically acceptable salt thereof is wherein $R^4$ is hydrogen, methyl, methoxy, ethoxy, fluoro, chloro, trifluoromethyl, cyano, or trifluoromethyloxy.

37. In embodiment 27, the compound of any one of embodiments 1 to 35, or a pharmaceutically acceptable salt thereof is wherein $R^4$ is cyano, carboxy, alkoxycarbonyl, alkylsulfonyl, aminocarbonyl, alkylaminocarbonyl, dialkylaminocarbonyl, aminosulfonyl, alkylaminosulfonyl, or dialkylaminosulfonyl.

38. In embodiment 38, the compound of embodiment 37, or a pharmaceutically acceptable thereof is wherein $R^4$ is cyano, carboxy, methoxycarbonyl, aminocarbonyl, methylsulfonyl, methylaminocarbonyl, dimethylaminocarbonyl, aminosulfonyl, methylaminosulfonyl, or dimethylaminosulfonyl.

39. In embodiment 39, the compound of embodiment 37, or a pharmaceutically acceptable salt thereof is wherein $R^4$ is attached to the six membered ring comprising a, b, d, and e of Formula I as shown below

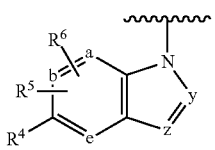

wherein the wavy line denotes the attachment point to the remainder of the molecule.

40. In embodiment 40, the compound of any one of embodiments 1 to 39, or a pharmaceutically acceptable salt thereof is wherein $R^5$ and $R^6$ are hydrogen.

41. In embodiment 41, the compound of any one of embodiments 1 to 36, or a pharmaceutically acceptable salt thereof is wherein $R^5$ and $R^6$ are independently hydrogen, alkyl, alkoxy, hydroxy, amino, halo, haloalkyl, or haloalkoxy.

42. In embodiment 42, the compound of embodiment 41, or a pharmaceutically acceptable salt thereof is wherein $R^5$ is attached to the six membered ring comprising a, b, d, and e of Formula I as shown below

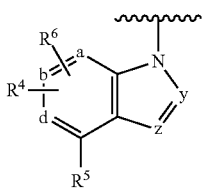

wherein the wavy line denotes the attachment point to the remainder of the molecule.

43. In embodiment 43, the compound of embodiment 42, or a pharmaceutically acceptable salt thereof is wherein $R^5$ is hydroxy and $R^4$ and $R^6$ are hydrogen.

44. In embodiment 44, the compound of embodiment 41, or a pharmaceutically acceptable salt thereof is wherein $R^5$ and $R^6$ are attached to the six membered ring comprising a, b, d, and e of Formula I as shown below

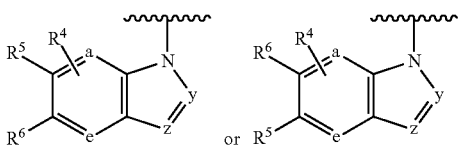

wherein the wavy line denotes the attachment point to the remainder of the molecule.

45. In embodiment 45, the compound of any one of embodiments 1 to 36, or a pharmaceutically acceptable salt thereof is wherein $R^5$ is hydrogen, alkyl, alkoxy, hydroxy, halo, haloalkyl, or haloalkoxy; and $R^6$ is hydroxyalkyl, alkoxyalkyl, hydroxyalkoxy, alkoxyalkoxy, hydroxyalkylamino, alkoxyalkylamino, aminoalkyl, aminoalkoxy, aminoalkylamino, heterocyclyl, heterocyclyloxy, heterocyclylamino (wherein heterocyclyl either alone or part of heterocyclyloxy and heterocyclylamino is optionally substituted with one, two, or three substituents independently selected from alkyl, halo, hydroxy, alkoxy, hydroxyalkyl, alkoxyalkyl, and aminoalkyl), heterocyclylalkyl, heterocyclylalkyloxy, heterocyclylalkylamino (wherein the heterocyclyl ring in heterocyclylalkyl, heterocyclylalkyloxy, and heterocyclylalkylamino is optionally substituted with one, two, or three substituents independently selected from alkyl, halo, hydroxy, alkoxy, hydroxyalkyl, alkoxyalkyl, and aminoalkyl), cycloalkyloxy, phenyloxy, or heteroaryloxy (where phenyl in phenyloxy and heteroaryl in heteroaryloxy are optionally substituted with one, two, or three substituents where two of the optional substituents are independently selected from alkyl, hydroxy, alkoxy, halo, haloalkyl, haloalkoxy, and cyano).

46. In embodiment 46, the compound of embodiment 45, or a pharmaceutically acceptable salt thereof is wherein $R^5$ is hydrogen, methoxy, ethoxy, or hydroxy and $R^6$ is 2-hydroxyethyloxy, 3-hydroxypropyloxy, 2-methoxyethyloxy, 2-ethoxyethyloxy, 3-methoxypropyloxy, 3-ethoxypropyloxy, 2-aminoethyloxy, 2-methylaminoethyloxy, 2-dimethylaminoethyloxy, 2-diethylaminoethyloxy, 3-aminopropyloxy, 3-methylaminopropyloxy, 3-dimethylaminopropyloxy, 3-diethylaminopropyloxy, pyrrolidinyloxy, piperidinyloxy, pyrrolidinylmethyloxy, piperidinylmethyloxy, pyrrolidinylethyloxy, piperidinylethyloxy, 2-hydroxyethylamino, 3-hydroxypropylamino, 2-methoxyethylamino, 2-ethoxyethylamino, 3-methoxypropylamino, 3-ethoxypropylamino, 2-aminoethylamino, 2-methylaminoethylamino, 2-dimethylaminoethylamino, 2-diethylaminoethylamino, 3-aminopropylamino, 3-methylaminopropylamino, 3-dimethylaminopropylamino, 3-diethylaminopropylamino, pyrrolidinylamino, piperidinylamino, pyrrolidinylmethylamino, piperidinylmethylamino, pyrrolidinylethylamino, or piperidinylethylamino (wherein pyrrolidinyl and piperidinyl in each of aforementioned groups, alone or part of another group is optionally substituted with one or two substituents independently selected from methyl, fluoro, hydroxy, or methoxy).

47. In embodiment 47, the compound of embodiment 45 or 46, or a pharmaceutically acceptable salt thereof is wherein $R^5$ and $R^6$ are attached to the six membered ring comprising a, b, d, and e of Formula I as shown below

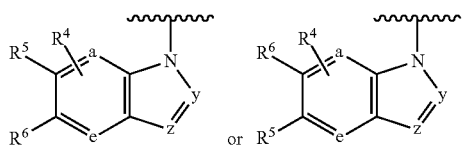

wherein the wavy line denotes the attachment point to the remainder of the molecule.

48. In embodiment 48, the compound of any one of embodiments 1 to 36, or a pharmaceutically acceptable salt thereof is wherein R⁵ and R⁶ are independently hydroxyalkyl, alkoxyalkyl, hydroxyalkoxy, alkoxyalkoxy, hydroxyalkylamino, alkoxyalkylamino, aminoalkyl, aminoalkoxy, aminoalkylamino, heterocyclyl, heterocyclyloxy, heterocyclylamino (wherein heterocyclyl either alone or part of heterocyclyloxy and heterocyclylamino is optionally substituted with one, two, or three substituents independently selected from alkyl, halo, hydroxy, alkoxy, hydroxyalkyl, alkoxyalkyl, and aminoalkyl), heterocyclylalkyl, heterocyclylalkyloxy, heterocyclylalkylamino (wherein the heterocyclyl ring in heterocyclylalkyl, heterocyclylalkyloxy, and heterocyclylalkylamino is optionally substituted with one, two, or three substituents independently selected from alkyl, halo, hydroxy, alkoxy, hydroxyalkyl, alkoxyalkyl, and aminoalkyl), cycloalkyloxy, phenyloxy, or heteroaryloxy (where phenyl of phenyloxy and heteroaryl of heteroaryloxy are optionally substituted with one, two, or three substituents where two of the optional substituents are independently selected from alkyl, hydroxy, alkoxy, halo, haloalkyl, haloalkoxy, and cyano).

49. In embodiment 49, the compound of embodiment 48, or a pharmaceutically acceptable salt thereof is wherein R⁵ and R⁶ are independently 2-hydroxyethyloxy, 3-hydroxypropyloxy, 2-methoxyethyloxy, 2-ethoxyethyloxy, 3-methoxypropyloxy, 3-ethoxypropyloxy, 2-aminoethyloxy, 2-methylaminoethyloxy, 2-dimethylaminoethyloxy, 2-diethylaminoethyloxy, 3-aminopropyloxy, 3-methylaminopropyloxy, 3-dimethylaminopropyloxy, 3-diethylaminopropyloxy, pyrrolidinyloxy, piperidinyloxy, pyrrolidinylmethyloxy, piperidinylmethyloxy, pyrrolidinylethyloxy, piperidinylethyloxy, 2-hydroxyethylamino, 3-hydroxypropylamino, 2-methoxyethylamino, 2-ethoxyethylamino, 3-methoxypropylamino, 3-ethoxypropylamino, 2-aminoethylamino, 2-methylaminoethylamino, 2-dimethylaminoethylamino, 2-diethylaminoethylamino, 3-aminopropylamino, 3-methylaminopropylamino, 3-dimethylaminopropylamino, 3-diethylaminopropylamino, pyrrolidinylamino, piperidinylamino, pyrrolidinylmethylamino, piperidinylmethylamino, pyrrolidinylethylamino, or piperidinylethylamino (wherein pyrrolidinyl and piperidinyl in each of aforementioned groups, alone or part of another group is optionally substituted with one or two substituents independently selected from methyl, fluoro, hydroxy, or methoxy).

50. In embodiment 50, the compound of embodiment 48 or 49, or a pharmaceutically acceptable salt thereof is wherein R⁵ and R⁶ are attached to the six membered ring comprising a, b, d, and e of Formula I as shown below

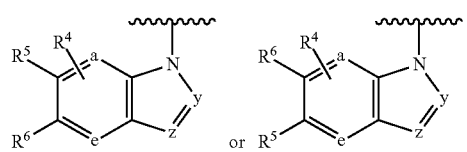

wherein the wavy line denotes the attachment point to the remainder of the molecule.

51. In embodiment 51, provided is a pharmaceutical composition comprising a compound any one of claims 1 to 50, or a pharmaceutically acceptable salt thereof and a pharmaceutically acceptable excipient.

52. In embodiment 52, provided is a method of treating a disease or condition mediated by ENPP1 in a patient comprising administering to the patient a compound of any one of claims 1 to 50, or a pharmaceutically acceptable salt thereof.

53. In embodiment 53, the method of embodiment 52 is wherein the disease or condition is a cancer, an inflammatory disease, a metabolic disease, or a viral disease.

54. In embodiment 54, the method of embodiment 52 is wherein the disease or condition is a cancer.

55. In embodiment 55, the method of embodiment 52 is wherein the disease or condition is a cancer wherein the cancer is hepatocellular carcinomas, glioblastomas, melanomas, testicular, pancreatic, thyroid or breast cancer.

56. In embodiment 56, the method of claim 54 or 55 is wherein the compound of any one of claims 1 to 50 is administered with an anticancer agent.

General Synthetic Scheme

Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art reading this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., such as from about 0° C. to about 125° C. and further such as at about room (or ambient) temperature, e.g., about 20° C.

Compounds of Formula (I) where Ar is aryl or heteroaryl, n is 1, m is 0, and other groups are as defined in the Summary can be prepared as illustrated and described in Scheme 1 below.

Scheme 1

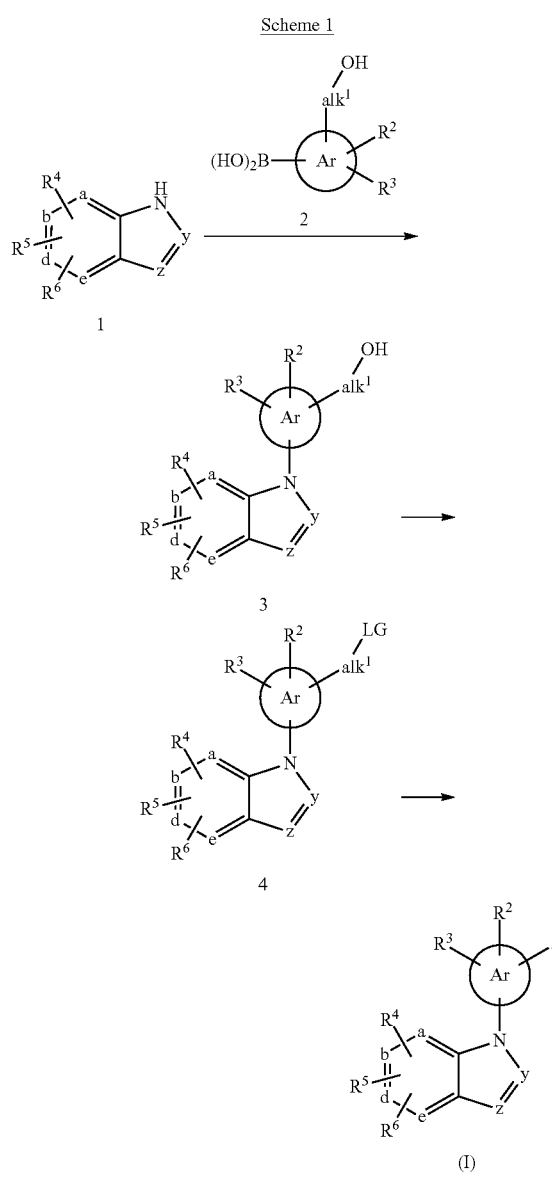

Arylation of a compound of formula 1 where a, b, d, e, y and z are as defined in the Summary and $R^4$, $R^5$, and $R^6$ are as defined in the Summary or a precursor group thereof (e.g., hydroxy is a precursor group of alkoxy etc.), a boronic acid of the formula 2 where Ar is aryl or heteroaryl under Suzuki reaction (Suzuki, A Journal of Organometallic Chemistry. 576: 147-168, and references cited therein) conditions provides an alcohol compound of formula 3. The reaction is carried out under palladium or nickel catalyzed conditions using a base such as lithium, sodium, potassium or cesium carbonate; lithium, sodium or potassium tert-butoxide; lithium, sodium or potassium hydroxide; phosphate bases such as tripotassium phosphate; or any other organic or inorganic base, in solvents comprised of a mixture of water and organic solvents such as 1,4-dioxane, tetrahydrofuran (THF), diethyl ether, toluene, ethanol or methanol, dimethylformamide (DMF) and the like, either at room temperature or heating. Compounds of formula 1 such as 5,6-dimethoxy-1H-benzo[d]imidazole, 6-methoxy-1H-benzo[d]imidazole, 6-chloro-9H-purin-2-amine, 6-chloro-9H-purin, 5-methoxy-1H-indol, 5,6-dimethoxy-1H-indol, 9H-purin-6-amine, 1H-benzo[d]imidazole-5-carbonitrile, methyl 1H-benzo[d]imidazole-5-carboxylate, 1H-benzo[d]imidazole-5-carboxamide, 1H-benzo[d]imidazole-5-carboxylic acid, 1H-pyrrolo[3,2-c]pyridin-4-ol, 1H-imidazo[4,5-c]pyridine, are commercially available.

Conversion of the hydroxyl in a compound of formula 3 to a leaving group in compounds of formula 4 that is halide may be accomplished by means of the Appel reaction (Appel, R Angewandte Chemie International Edition in English. 14:801-811) by treatment of compound 3 with a halogenating agent such as N-bromosuccinimide, carbon tetrachloride, carbon tetrabromide, bromine, methyl iodide or iodine, in the presence of triphenylphosphine. The halo group in compounds of the formula 4 can be displaced by a variety of boronate or phosphite nucleophiles to provide a compound of Formula (I). For example, treatment of compound 4 with triethyl phosphite via heating in the absence or presence of aprotic organic solvents such as DMF or THF, followed by hydrolysis of the resulting triethylphosphonate provides a compound of Formula (I) where Q is —P(O)(OH)$_2$. Triethylphosphonate may be hydrolyzed in the presence of bromo- or chloro-trimethylsilane in dichloromethane, or hydrogen chloride in water, or trimethylsilyl iodide in dichloromethane either at room temperature or with heating. Compounds of Formula (I) where Q is —B(OH)$_2$ can be prepared by treatment of compound 4 with 4,4,5,5-tetramethyl-2-(4,4,5,5-tetramethyl-1,3,2-dioxaborolan-2-yl)-1,3,2-dioxaborolane, followed by hydrolysis of resulting 4-(4-((4,4,5,5-tetramethyl-1,3,2-dioxaborolanyl group by methods well known in the art. Compounds of Formula (I) can be converted to other compounds of Formula (I) by method well known in the art. For example, diethyl (4-((5-cyano-1H-benzo[d]imidazol-1-yl)methyl)phenyl)phosphonate is converted to (4-((5-cyano-1H-benzo[d]imidazol-1-yl)methyl)phenyl)phosphonic acid by treatment with bromotrimethylsilane in dichloromethane at room temperature.

Compounds of Formula (I) where Ar is aryl or heteroaryl, n is 1, m is 0, and other groups are as defined in the Summary can be prepared as illustrated and described in Scheme 2 below.

Scheme 2

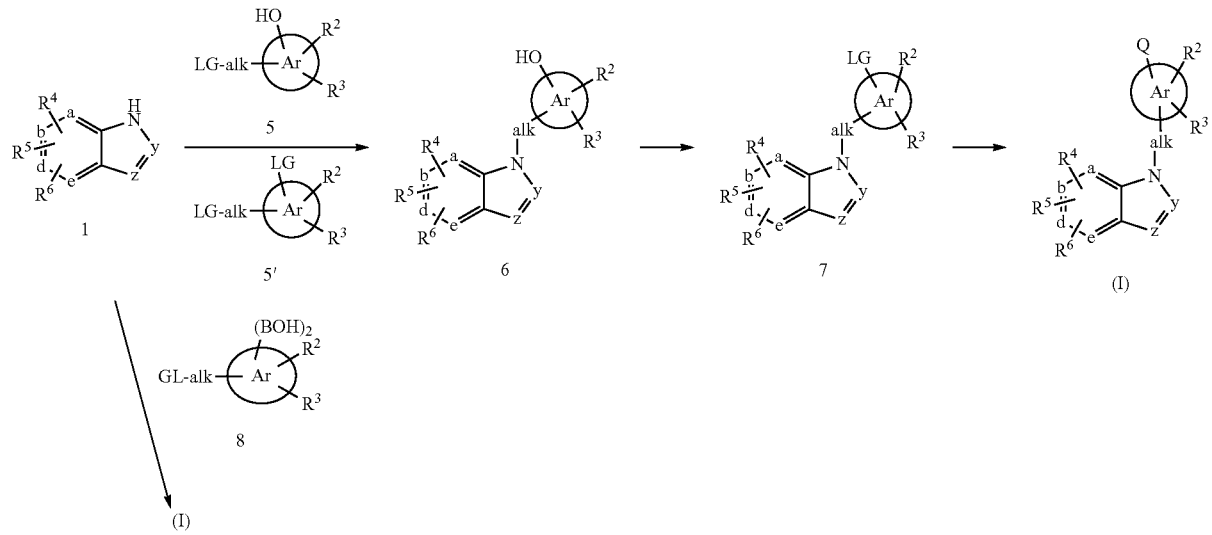

Treatment of a compound of formula 1 with a compound of formula 5 or 5' wherein Ar, alk are as defined in the Summary and $R^2$ and $R^3$ are as defined in the Summary or a precursor group thereof and LG is a suitable leaving group such as halo, in the presence of carbonate, hydroxide, or alkoxide (e.g. tert-butoxide) bases, either with heating or at room temperature, provides a compound of formula 6 or 7 respectively. Compound of formula 6 can be converted to compound 7 where LG is halo by methods well known in the art. Compounds of the formula 5 are either commercially available or may be prepared by methods well known in the art. Compounds of formula 7 can then be coverted to compounds of Formula (I) as described in Scheme 1 above.

Alternatively, compounds of the Formula (I) where Q is boronic acid may be prepared by displacement of the leaving group in compounds of the formula 8 by compounds of the formula 1. The reaction is carried out by treating a mixture of compounds of the formulas 1 and 8 with carbonate, hydroxide, or alkoxide (e.g. tert-butoxide) bases, or other organic or inorganic bases, in solvents such as acetonitrile, DMF, or THF and the like, either at room temperature or with heating. Compounds of the formula 8 are either commercially available or can be readily prepared by methods well known in the art. Compounds of formula 1 such as 5,6-dimethoxy-1H-benzo[d]imidazole, 6-methoxy-1H-bezno[d]imidazole, 6-chloro-9H-purin-2-amine, 6-chloro-9H-purin, 5-methoxy-1H-indol, 5,6-dimethoxy-1H-indol, 9H-purin-6-amine, 1H-benzo[d]imidazole-5-carbonitrile, methyl 1H-benzo[d]imidazole-5-carboxylate, 1H-benzo[d]imidazole-5-carboxamide, 1H-benzo[d]imidazole-5-carboxylic acid, 1H-pyrrolo[3,2-c]pyridin-4-ol, 1H-imidazo[4,5-c]pyridine, 5-methanesulfonyl-1H-1,3-benzodiazole are commercially available. Compounds of formula 8 such as (4-(bromomethyl)phenyl)boronic acid, are commercially available. Compounds of formula 5, such as 1-bromo-4-(bromomethyl)benzene, 5-Bromo-2-(bromomethyl)pyridine, are commercially available.

Testing

The ENPP1 inhibitory activity of the compounds of the present disclosure can be tested using the in vitro assays described in Biological Examples 1 and 2 below.

Administration and Pharmaceutical Composition

In general, the compounds of this disclosure will be administered in a therapeutically effective amount by any of the accepted modes of administration for agents that serve similar utilities. Therapeutically effective amounts of compounds this disclosure may range from about 0.01 to about 500 mg per kg patient body weight per day, which can be administered in single or multiple doses. A suitable dosage level may be from about 0.1 to about 250 mg/kg per day; about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount of the compound of this disclosure, i.e., the active ingredient, will depend upon numerous factors such as the severity of the disease to be treated, the age and relative health of the patient, the potency of the compound being utilized, the route and form of administration, and other factors.

In general, compounds of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of this disclosure in combination with at least one pharmaceutically acceptable excipient. Acceptable excipients are non-toxic, aid administration, and do not adversely affect the therapeutic benefit of the compound of this disclosure. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this disclosure in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt. %) basis, from about 0.01-99.99 wt. % of a compound of this disclosure based on the total formulation, with the balance being one or more suitable pharmaceutical excipients. For example, the compound is present at a level of about 1-80 wt. %.

The compounds of this disclosure may be used in combination with one or more other drugs in the treatment of diseases or conditions for which compounds of this disclosure or the other drugs may have utility. Such other drug(s) may be administered, by a route and in an amount commonly used therefore, contemporaneously or sequentially with a compound of the present disclosure. When a compound of this disclosure is used contemporaneously with one or more other drugs, a pharmaceutical composition in unit dosage form containing such other drugs and the compound of the present disclosure is preferred. However, the combination therapy may also include therapies in which the compound of this disclosure and one or more other drugs are administered on different overlapping schedules. It is also contemplated that when used in combination with one or more other active ingredients, the compounds of the present disclosure and the other active ingredients may be used in lower doses than when each is used singly. Accordingly, the pharmaceutical compositions of the present disclosure also include those that contain one or more other drugs, in addition to a compound of the present disclosure.

The above combinations include combinations of a compound of this disclosure not only with one other drug, but also with two or more other active drugs. Likewise, a compound of this disclosure may be used in combination with other drugs that are used in the prevention, treatment, control, amelioration, or reduction of risk of the diseases or conditions for which a compound of this disclosure is useful. Such other drugs may be administered, by a route and in an amount commonly used therefore, contemporaneously or sequentially with a compound of the present disclosure. When a compound of this disclosure is used contemporaneously with one or more other drugs, a pharmaceutical composition containing such other drugs in addition to the compound of this disclosure can be used. Accordingly, the pharmaceutical compositions of the present disclosure also include those that also contain one or more other active ingredients, in addition to a compound of this disclosure. The weight ratio of the compound of this disclosure to the second active ingredient may be varied and will depend upon the effective dose of each ingredient. Generally, an effective dose of each will be used.

Where the subject in need is suffering from or at risk of suffering from cancer, the subject can be treated with a compound of this disclosure in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a compound of this disclosure include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; antibodies (e.g., rituxan); MET inhibitor such as foretinib, carbozantinib, or crizotinib; VEGFR inhibitor such as sunitinib, sorafenib, regorafinib, lenvatinib, vandetanib, carbozantinib, axitinib; EGFR inhibitor such as afatinib, brivanib, carbozantinib, erlotinib, gefitinib, neratinib, lapatinib; PI3K inhibitor such as XL147, XL765, BKM120 (buparlisib), GDC-0941, BYL719, IPI145, BAY80-6946. BEX235 (dactolisib), CAL101 (idelalisib), GSK2636771, TG100-115; MTOR inhibitor such as rapamycin (sirolimus), temsirolimus, everolimus, XL388, XL765, AZD2013, PF04691502, PKI-587, BEZ235, GDC0349; MEK inhibitor such as AZD6244, trametinib, PD184352, pimasertinib, GDC-0973, AZD8330; and proteasome inhibitor such as carfilzomib, MLN9708, delanzomib, or bortezomib.

Other anti-cancer agents that can be employed in combination with a compound of this disclosure include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or Ril2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a compound of the disclosure such as 8-(3-(4-acryloylpiperazin-1-yl)propyl)-6-(2,6-dichloro-3,5-dimethoxyphenyl)-2-(methylamino)pyrido[2,3-d]pyrimidin-7(8H)-one used to determine the anti-tumor activity in HGS and RT4 tumor models (Example 4 below: In HGS model, vehicle dosed group reached tumor size 645 dosing at day 42 after inoculation whereas for animals treated with 20/kg of compound, the tumor size was 55 mm3 showing significant antitumor activity and induced tumor regression), include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; Bfgf inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+-72-iethylstilbe cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; R.sub.11 retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of this disclosure include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., cytarabine), purine analogs (e.g., mercaptopurine, thioguanine, pentostatin).

Examples of natural products useful in combination with a compound of this disclosure include but are not limited to vinca alkaloids (e.g., vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a compound of this disclosure) include, but are not limited to, nitrogen mustards (e.g., mechloroethamine, cyclophosphamide, chlorambucil, melphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, cytarabine), purine analogs (e.g., mercaptopurine, thioguanine, pentostatin.

Examples of hormones and antagonists useful in combination a compound of this disclosure include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with an irreversible Btk inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Further examples of anti-cancer agents for use in combination with a compound of this disclosure include immune checkpoint inhibitors. Exemplary immune checkpoint inhibitors include inhibitors (smack molecules or biologics) against immune checkpoint molecules such as CD27, CD28, CD40, CD122, CD96, CD73, CD39, CD47, OX40, GITR, CSF1R, JAK, PI3K delta, PI3K gamma, TAM kinase, arginase, CD137 (also known as 4-1BB), ICOS, A2AR, A2BR, HIF-2a, B7-H3, B7-H4, BTLA, CTLA-4, LAG3, TIM3, VISTA, CD96, TIGIT, PD-1, PD-L1 and PD-L2. In some embodiments, the immune checkpoint molecule is a stimulatory checkpoint molecule selected from CD27, CD28, CD40, ICOS, OX40, GITR, CD137 and STING. In some embodiments, the immune checkpoint molecule is an inhibitory checkpoint molecule selected from B7-H3, B7-H4, BTLA, CTLA-4, IDO, TDO, Arginase, KIR, LAG3, PD-1, TIM3, CD96, TIGIT and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab, or pembrolizumab or PDR001. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A (atezolizumab) or MEDI4736 (durvalumab).

In some embodiments, the inhibitor of an immune checkpoint molecule is an inhibitor of CTLA-4, e.g., an anti-CTLA-4 antibody. In some embodiments, the anti-CTLA-4 antibody is ipilimumab or tremelimumab. In some embodiments, the inhibitor of an immune checkpoint molecule is an inhibitor of LAG3, e.g., an anti-LAG3 antibody. In some embodiments, the anti-LAG3 antibody is BMS-986016 or LAG525. In some embodiments, the inhibitor of an immune checkpoint molecule is an inhibitor of GITR, e.g., an anti-GITR antibody. In some embodiments, the anti-GITR antibody is TRX518 or, MK-4166, INCAGN01876 or MK-1248. In some embodiments, the inhibitor of an immune checkpoint molecule is an inhibitor of OX40, e.g., an anti-OX40 antibody or OX40L fusion protein. In some embodiments, the anti-OX40 antibody is MED10562 or, INCAGN01949, GSK2831781, GSK-3174998, MOXR-0916, PF-04518600 or LAG525. In some embodiments, the OX40L fusion protein is MEDI6383

EXAMPLES

The following preparations of compounds of Formula (I) are given to enable those skilled in the art to more clearly understand and to practice the present disclosure. They should not be considered as limiting the scope of the disclosure, but merely as being illustrative and representative thereof.

All solvents used were commercially available and were used without further purification. Reactions were typically run using anhydrous solvents under an inert atmosphere of nitrogen.

$^1$H spectra were recorded at 400 MHz or 300 MHz for proton on a Bruker 400 NMR Spectrometer equipped with a Bruker 400 BBO probe or Bruker BBFO ULTRASHIELD™300 AVANCE III, respectively. All deuterated solvents contained typically 0.03% to 0.05% v/v tetramethylsilane, which was used as the reference signal (set at δ 0.00 for both $^1$H and $^{13}$C).

LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 3.0 s.

HPLC analyses were performed on a SHIMADZU UFLC with two LC20 AD pump and a SPD-M20A Photodiiode Array Detector. The column used was an XBridge C18, 3.5 µm, 4.6×100 mm. A linear gradient was applied, starting at 90% A (A: 0.05% TFA in water) and ending at 95% B (B: 0.05% TFA in MeCN) over 10 min with a total run time of

105

15 min. The column temperature was at 40° C. with the flow rate of 1.5 m/min. The Diode Array Detector was scanned from 200-400 nm.

Thin layer chromatography (TLC) was performed on Alugram® (Silica gel 60 F254) from Mancherey-Nagel and UV was typically used to visualize the spots. Additional visualization methods were also employed in some cases. In these cases the TLC plate was developed with iodine (generated by adding approximately 1 g of $I_2$ to 10 g silica gel and thoroughly mixing), ninhydrin (available commercially from Aldrich), or Magic Stain (generated by thoroughly mixing 25 g $(NH_4)_6Mo_7O_{24}.4H_2O$, 5 g $(NH_4)_2Ce(IV)(NO_3)_6$ in 450 mL water and 50 mL concentrated $H_2SO_4$) to visualize the compound. Flash chromatography was performed using 40-63 μm (230-400 mesh) silica gel from Silicycle following analogous techniques to those disclosed in Still, W. C.; Kahn, M.; and Mitra, M. Journal of Organic Chemistry, 1978, 43, 2923. Typical solvents used for flash chromatography or thin layer chromatography were mixtures of chloroform/methanol, dichloromethane/methanol, ethyl acetate/methanol and hexanes/ethyl acetate.

Synthetic Examples

Example 1

Synthesis of 4-((5,6-dimethoxy-1,3-benzodiazol-1-yl)methyl)phenylboronic acid

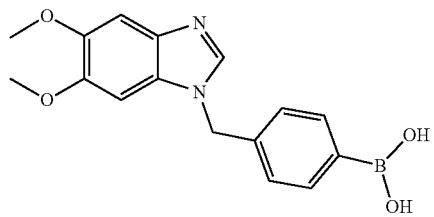

To a stirred solution of 5,6-dimethoxy-1H-1,3-benzodiazole (50 mg, 0.281 mmol, 1.00 equiv) in N,N-dimethylformamide (3.00 mL) was added cesium carbonate (183 mg, 0.562 mmol, 2.00 equiv). After stirring for 1 h at room temperature, 4-(bromomethyl)phenylboronic acid (91 mg, 0.421 mmol, 1.50 equiv) was added. The mixture was stirred overnight at room temperature and the solids were filtered off and washed with methanol. The filtrate was concentrated under reduced pressure. The crude product was purified by prep-HPLC with the following conditions Column: XBridge Prep C18 OBD Column 19×150 mm, 5 um; Mobile Phase A: Water (0.1% FA), Mobile Phase B: acetonitrile; Flow rate: 20 m/min; Gradient: 10% B to 25% B in 7 min, 220 & 254 nm. The fractions containing the desired product were combined and lyophilized to give 48.4 mg (54%) of the title compound as an off-white solid. MS (ESI, pos. ion) m/z: 313.2 (M+1). $^1$H-NMR: (300 MHz, DMSO-$d_6$, ppm) δ 8.18-8.14 (m, 1H), 8.03 (s, 2H), 7.75-7.72 (m, 2H), 7.25-7.20 (m, 3H), 7.11 (s, 1H), 5.45 (s, 2H), 3.74 (s, 3H), 3.72 (s, 3H).

106

Example 2

Syntheses of 4-((6-oxo-1H-purin-7-yl)methyl)phenylboronic acid (2a) and 4-((6-oxo-1H-purin-9-yl)methyl)phenylboronic acid (2b)

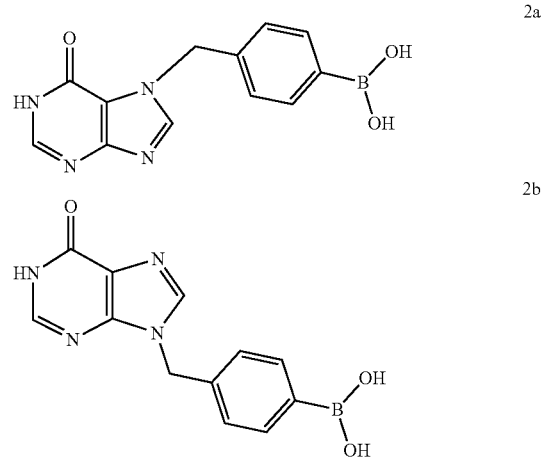

Step 1: 4-((6-chloro-7H-purin-7-yl)methyl)phenylboronic acid and 4-((6-chloropurin-9-yl)methyl)phenylboronic acid

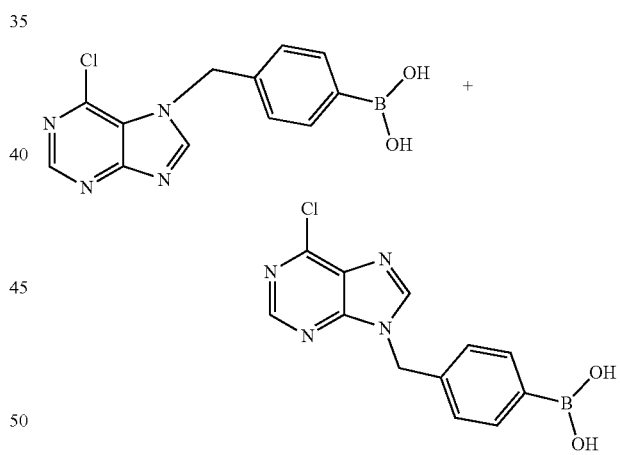

To a solution of 6-chloro-9H-purine (300 mg, 1.941 mmol, 1.00 equiv) in N,N-dimethylformamide (10 mL) were added 4-(bromomethyl)phenylboronic acid (625 mg, 2.909 mmol, 1.50 equiv) and potassium carbonate (537 mg, 3.882 mmol, 2.00 equiv) at room temperature. After stirring overnight, the reaction mixture was concentrated under reduced pressure. The residue was dissolved in methanol and the solids were filtered off. The filtrate was concentrated under reduced pressure and the residue was treated with dichloromethane. The precipitates were collected by filtration, washed with dichloromethane and dried in vacuo to afford 450 mg (80%) of a mixture of 4-((6-chloro-7H-purin-7-yl)methyl)phenylboronic acid and 4-((6-chloropurin-9-yl)methyl)phenylboronic acid as a yellow solid.

Step 2: 4-((6-oxo-1H-purin-7-yl)methyl)phenylboronic acid and 4-((6-oxo-1H-purin-9-yl)methyl)phenylboronic acid

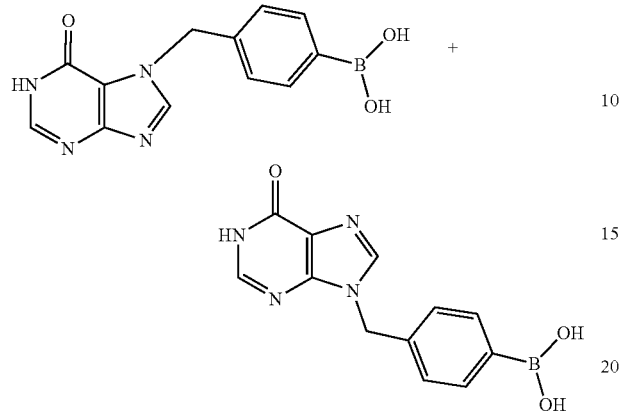

To a mixture of 4-((6-chloro-7H-purin-7-yl)methyl)phenylboronic acid and 4-((6-chloropurin-9-yl)methyl)phenylboronic acid (200 mg, 0.694 mmol, 1.00 equiv) in tetrahydrofuran (5 mL) was added 6 N hydrochloric acid (4 mL) dropwise at room temperature. After reflux for 2 h, the reaction mixture was concentrated under reduced pressure. The residue was dissolved in N,N-dimethylformamide and filtered. The filtrate was purified by prep-HPLC with the following conditions Column: XBridge Prep Phenyl OBD Column, 19×150 mm, 5 um; Mobile Phase A: Water (0.05% FA), Mobile Phase B: acetonitrile; Flow rate: 25 mL/min; Gradient: 8% B to 15% B in 10 min, 220 & 254 nm. The fractions containing the desired products were combined and lyophilized to give two fractions.

Fraction 1: Rt: 8.02 min. 8.2 mg (4% yield) of 4-((6-oxo-1H-purin-7-yl)methyl)phenylboronic acid (2a) as a white solid. MS (ESI, pos. ion) m/z: 271.2 (M+1). $^1$H-NMR (300 MHz, DMSO-d$_6$, ppm) δ 12.14 (brs, 1H), 8.39 (s, 1H), 8.08 (brs, 2H), 7.96 (s, 1H), 7.74 (d, J=7.8 Hz, 2H), 7.27 (d, J=8.1 Hz, 2H), 5.57 (s, 2H).

Fraction 2: Rt: 9.35 min. 11.2 mg (6% yield) of 4-((6-oxo-1H-purin-9-yl)methyl)phenylboronic acid (2b) as a white solid. MS (ESI, pos. ion) m/z: 271.2 (M+1). $^1$H-NMR (300 MHz, DMSO-d$_6$, ppm) δ 11.98 (brs, 1H), 8.25-8.02 (m, 4H), 7.74 (d, J=8.1 Hz, 2H), 7.24 (d, J=7.8 Hz, 2H), 5.38 (s, 2H).

Example 3

Syntheses of 4-((2-amino-6-oxo-1H-purin-7-yl)methyl)phenylboronic acid (3a) and 4-((2-amino-6-oxo-1H-purin-9-yl)methyl)phenylboronic acid (3b

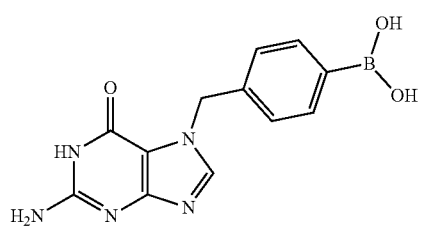

3a

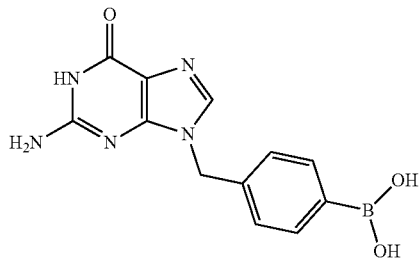

3b

Step 1: 4-((2-amino-6-chloropurin-7-yl)methyl)phenylboronic acid and 4-((2-amino-6-chloropurin-9-yl)methyl)phenylboronic acid

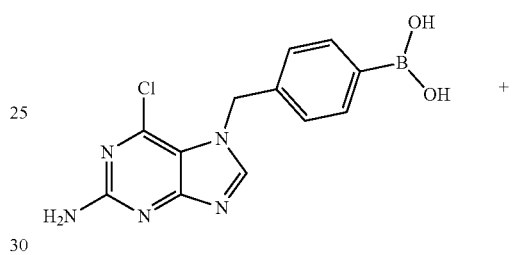

To a solution of 6-chloro-9H-purin-2-amine (100 mg, 0.590 mmol, 1.00 equiv) in N,N-dimethylformamide (3 mL) were added 4-(bromomethyl)phenylboronic acid (127 mg, 0.590 mmol, 1.00 equiv) and potassium carbonate (204 mg, 1.474 mmol, 2.50 equiv) at room temperature. After stirring overnight, the reaction mixture was concentrated under reduced pressure. The residue was dissolved in methanol and the solids were filtered off. The filtrate was concentrated under reduced pressure and the residue was treated with dichloromethane. The precipitates were collected by filtration, washed with dichloromethane and dried in vacuo to afford 200 mg (86% yield, 77% purity) mixture of 4-((2-amino-6-chloropurin-7-yl)methyl)phenylboronic acid and 4-((2-amino-6-chloropurin-9-yl)methyl)phenylboronic acid as a yellow solid.

Step 2: 4-((2-amino-6-oxo-1H-purin-7-yl)methyl)phenylboronic acid and 4-((2-amino-6-oxo-1H-purin-9-yl)methyl)phenylboronic acid

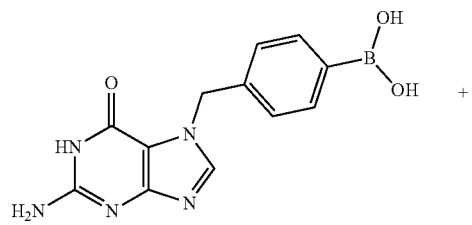

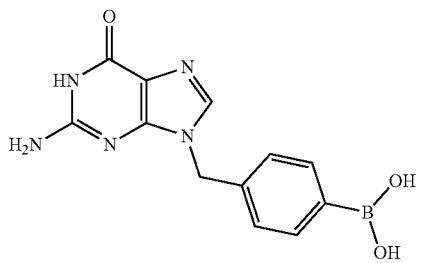

To a mixture of 4-((6-chloro-7H-purin-7-yl)methyl)phenylboronic acid and 4-((6-chloropurin-9-yl)methyl)phenylboronic acid (200 mg, 0.507 mmol, 1.00 equiv, 77% purity) in tetrahydrofuran (2 mL) was added 6 N hydrochloric acid (4 mL) dropwise at room temperature. After reflux for 2 h, the reaction mixture was concentrated under reduced pressure. The residue was dissolved in N,N-dimethylformamide and filtered to give 3.7 mL clear solution, which was purified by prep-HPLC with the following conditions Column: XBridge Shield RP18 OBD Column, 19×250 mm, 10 um; Mobile Phase A: Water (0.1% FA), Mobile Phase B: acetonitrile; Flow rate: 25 mL/min; Gradient: 10% B to 20% B in 7 min, 220 & 254 nm. The fractions containing the desired products were combined and lyophilized to give two fractions.

Fraction 1: Rt: 5.17 min. 17.5 mg (12% yield) of 4-((2-amino-6-oxo-1H-purin-7-yl)methyl)phenylboronic acid (3a) as an off-white solid. MS (ESI, pos. ion) m/z: 286.2 (M+1). $^1$H-NMR (400 MHz, DMSO-$d_6$, ppm) δ 10.73 (brs, 1H), 8.15-8.04 (m, 3H), 7.78-7.72 (m, 2H), 7.25-7.18 (m, 2H), 6.14 (s, 2H), 5.42 (s, 2H).

Fraction 2: Rt: 6.45 min. 13.0 mg (9% yield) of 4-((2-amino-6-oxo-1H-purin-9-yl)methyl)phenylboronic acid (3b) as a white solid. MS (ESI, pos. ion) m/z: 286.2 (M+1). $^1$H-NMR (300 MHz, DMSO-$d_6$, ppm) δ 10.60 (brs, 1H), 8.04 (s, 2H), 7.76-7.72 (m, 3H), 7.17-7.14 (m, 2H), 6.46 (s, 2H), 5.18 (s, 2H).

Example 4

Syntheses of 4-((6-methoxy-1,3-benzodiazol-1-yl)methyl)phenylboronic acid (4a) and 4-((5-methoxy-1,3-benzodiazol-1-yl)methyl)phenylboronic acid (4b

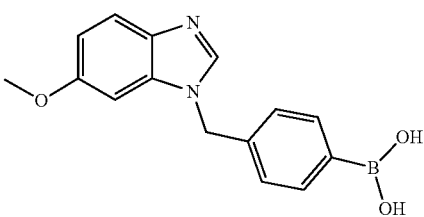

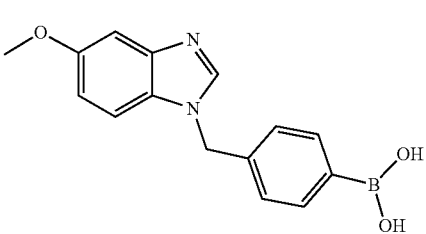

A mixture of 5-methoxybenzimidazole (100 mg, 0.675 mmol, 1.00 equiv) and cesium carbonate (449 mg, 1.350 mmol, 2.00 equiv) in N,N-dimethylformamide (3 mL) was stirred at room temperature for 20 min. 4-(Bromomethyl)phenylboronic acid (174 mg, 0.810 mmol, 1.20 equiv) was added. After stirring for 2 h, the reaction mixture was filtered through a Celite. The filtrate was purified by prep-HPLC with the following conditions: Column: XBridge Prep Phenyl OBD Column, 19×150 mm, 5 um; Mobile Phase A: Water (0.05% TFA), Mobile Phase B: Acetonitrile; Flow rate: 25 mL/min; Gradient: 30% B to 35% B in 10 min, 220 & 254 nm. Two fractions were obtained.

Fraction 1: RT: 8.02 min. 47.8 mg (25%) of 4-((6-methoxy-1,3-benzodiazol-1-yl)methyl)phenylboronic acid as a white solid (4a). MS (ESI, pos. ion) m/z: 283.2 (M+1). $^1$H-NMR (400 MHz, DMSO-$d_6$, ppm): δ 9.31-9.17 (m, 1H), 8.18 (brs, 2H), 7.87-7.72 (m, 3H), 7.54-7.25 (m, 3H), 7.18-7.05 (m, 1H), 5.66-5.60 (m, 2H), 3.80-3.62 (m, 3H).

Fraction 2: RT: 9.35 min. 36.3 mg (17%) of 4-((5-methoxy-1,3-benzodiazol-1-yl)methyl)phenylboronic acid (4b) as a white solid. MS (ESI, pos. ion) m/z: 283.2 (M+1). $^1$H-NMR (400 MHz, DMSO-$d_6$, ppm): δ 9.44-9.31 (m, 1H), 8.22 (brs, 2H), 7.88-7.65 (m, 3H), 7.39-7.22 (m, 3H), 7.17-7.05 (m, 1H), 5.68-5.60 (m, 2H), 3.82-3.76 (m, 3H).

Example 5

Synthesis of 4-((5,6-dimethoxyindol-1-yl)methyl)phenylboronic acid

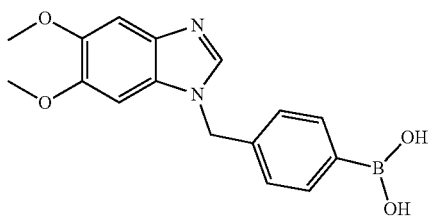

To a stirred solution of 5,6-dimethoxy-1H-indole (150 mg, 0.847 mmol, 1.00 equiv) in N,N-dimethylformamide (5 mL) was added sodium hydride (51 mg, 1.271 mmol, 60% in mineral oil, 1.50 equiv) at 0° C. After stirring for 30 minutes, 4-(bromomethyl)phenylboronic acid (218 mg, 1.016 mmol, 1.20 equiv) was added. The resulting mixture was stirred for 2 h at room temperature. The reaction mixture was quenched with water and filtered. The filtrate was purified prep-HPLC with the following conditions: Column: XBridge Prep OBD C18 Column, 19×250 mm, 5 um; Mobile Phase A: Water (0.1% FA), Mobile Phase B: acetonitrile; Flow rate: 25 mL/min; Gradient: 45% B to 45% B in 7 min, 220 & 254 nm. The fractions containing the desired product were combined and lyophilized to give 63.7 mg (24%) of 4-((5,6-dimethoxyindol-1-yl)methyl)phenylboronic acid. MS (ESI, pos. ion) m/z: 312.0 (M+1). $^1$H-NMR (300 MHz, DMSO-$d_6$, ppm): δ 7.99 (s, 2H), 7.71 (d, J=5.7 Hz, 2H), 7.42-7.03 (m, 5H), 6.34 (s, 1H), 5.36 (s, 2H), 3.74 (s, 6H).

Example 6

Syntheses of 4-((6-aminopurin-7-yl)methyl)phenylboronic (6a) and 4-((6-aminopurin-9-yl)methyl)phenylboronic acid (6b

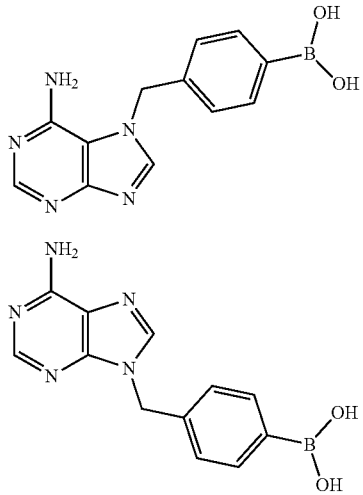

To a mixture of 9H-purin-6-amine (150 mg, 1.110 mmol, 1.00 equiv) and cesium carbonate (724 mg, 2.222 mmol, 2.00 equiv) in N,N-dimethylformamide (8 mL) was added 4-(bromomethyl)phenylboronic acid (286 mg, 1.333 mmol, 1.20 equiv) at room temperature. After stirring at 80° C. for 3 h, the reaction mixture was treated with 2N HCl (2 mL) and filtered. The filtrate was purified by prep-HPLC with the following conditions: Column: XBridge Shield RP18 OBD Column, 19×250 mm, 10 um; Mobile Phase A: Water (0.05% TFA), Mobile Phase B: methanol; Flow rate: 25 mL/min; Gradient: 19% B to 27% B in 7 min, 220 & 254 nm. Two fractions were obtained.

Fraction 1: Rt=4.22 min. 79.6 mg (23%) of 4-((6-aminopurin-7-yl)methyl)phenylboronic acid hydrochloride (6a) as a white solid. MS (ESI, pos. ion) m/z: 270.3 (M+1). $^1$H-NMR (400 MHz, DMSO-$d_6$, ppm): δ 14.52 (brs, 1H), 9.38 (s, 1H), 9.16 (s, 1H), 9.02 (s, 1H), 8.64 (s, 1H), 8.21 (brs, 2H), 7.77 (d, J=7.6 Hz, 2H), 7.41 (d, J=7.6 Hz, 2H), 5.63 (s, 2H).

Fraction 2: Rt=5.53 min. 34.8 mg (11%) of 4-((6-aminopurin-9-yl)methyl)phenylboronic acid (76b) as a white solid. MS (ESI, pos. ion) m/z: 270.2 (M+1). $^1$H-NMR (400 MHz, DMSO-$d_6$, ppm): δ 8.71 (brs, 2H), 8.52 (s, 1H), 8.40 (s, 1H), 8.14 (brs, 2H), 7.76 (d, J=8.0 Hz, 2H), 7.28 (d, J=8.0 Hz, 2H), 5.45 (s, 2H).

Example 7

Syntheses of 4-((6-cyano-1,3-benzodiazol-1-yl)methyl)phenylboronic (7a) and 4-((5-cyano-1,3-benzodiazol-1-yl)methyl)phenylboronic acid (7b

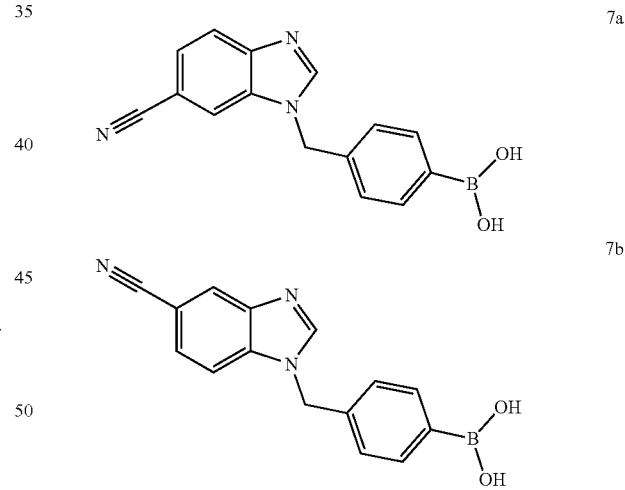

To a suspension of sodium hydride (112 mg, 2.79 mmol, 60% in mineral oil, 2.00 equiv.) in N,N-dimethylformamide (4 mL) was added a solution of 1H-1,3-benzodiazole-5-carbonitrile (200 mg, 1.40 mmol, 1.00 equiv.) in N,N-dimethylformamide (1 mL) at 0° C. under nitrogen atmosphere. After stirring for 30 minutes at this temperature, 4-(bromomethyl)phenylboronic acid (360 mg, 1.68 mmol, 1.20 equiv.) was added. The resulting mixture was stirred at room temperature for 2 h, quenched with 1 N hydrochloride acid (2 mL) and concentrated under reduced pressure. The residue was purified by prep-HPLC with the following conditions Column: XBridge Prep C18 OBD Column, 19×250 mm, 5 um; Mobile Phase A: Water (0.1% FA), Mobile Phase B: acetonitrile; Flow rate: 25 mL/min; Gradient: 21% B to 21% B in 10 min; 220 & 254 nm. Two fractions were obtained.

Fraction 1: Rt=8.77 min. 42.4 mg (11% yield) of 4-((6-cyano-1,3-benzodiazol-1-yl)methyl)phenylboronic acid (7a) as a white solid. MS (ESI, pos. ion) m/z: 278.3 (M+1). $^1$H-NMR (400 MHz, DMSO-$d_6$, ppm): δ 8.72 (s, 1H), 8.21 (s, 1H), 8.05 (s, 2H), 7.85-7.82 (m, 1H), 7.75 (d, J=8.0 Hz, 2H), 7.60-7.58 (m, 1H), 7.32 (d, J=8.0 Hz, 2H), 5.57 (s, 2H).

Fraction 2: Rt=10.18 min. 79.1 mg (20% yield) of 4-((5-cyano-1,3-benzodiazol-1-yl)methyl)phenylboronic acid (7b) as a white solid. MS (ESI, pos. ion) m/z: 278.3 (M+1). $^1$H-NMR (400 MHz, DMSO-$d_6$, ppm): δ 8.68 (s, 1H), 8.24 (s, 1H), 8.05 (s, 2H), 7.80-7.71 (m, 3H), 7.63-7.59 (m, 1H), 7.27 (d, J=8.0 Hz, 2H), 5.58 (s, 2H).

Example 8

Synthesis of (4-((5-fluoro-4-oxo-3,4-dihydro-7H-pyrrolo[2,3-d]pyrimidin-7-yl)methyl)phenyl)boronic acid

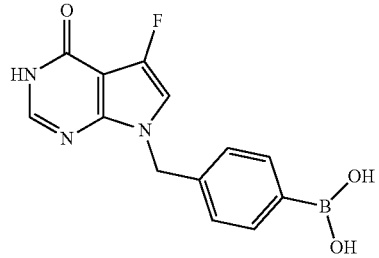

Step 1: 4-((4-chloro-5-fluoropyrrolo[2,3-d]pyrimidin-7-yl)methyl)phenyl-boronic acid

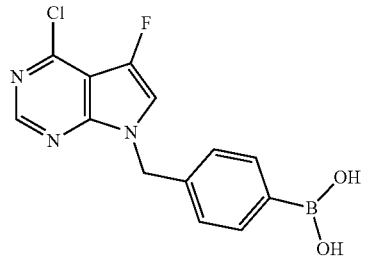

The title compound was synthesized by the same method described in example 7 except 4-chloro-5-fluoro-7H-pyrrolo[2,3-d]pyrimidine (300 mg, 1.75 mmol, 1.00 equiv.) was used in place of 1H-1,3-benzodiazole-5-carbonitrile. Yield: 0.45 g (69%). MS (ESI, pos. ion) m/z: 306.2 (M+1).

Step 2: (4-((5-fluoro-4-oxo-3,4-dihydro-7H-pyrrolo[2,3-d]pyrimidin-7-yl)methyl)phenyl)boronic acid

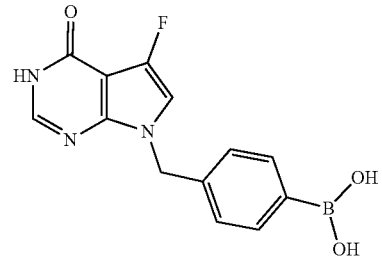

4-((4-Chloro-5-fluoropyrrolo[2,3-d]pyrimidin-7-yl)methyl)phenylboronic acid (150 mg, 0.49 mmol, 82% purity, 1.00 equiv.) was dissolved in mixed solvents of hydrochloric acid (4 mL) and tetrahydrofuran (20 mL) at room temperature and stirred for 48 hours at 80° C. The mixture was cooled to room temperature and concentrated under reduced pressure. The residue was purified by prep-HPLC with the following conditions Column: XBridge Shield RP18 OBD Column, 19×250 mm, 10 um; Mobile Phase A: Water (0.1% FA), Mobile Phase B: acetonitrile; Flow rate: 25 mL/min; Gradient: 23% B to 23% B in 6 min; 220 & 254 nm. The fraction containing the desired product were combined and lyophilized to give 6.1 mg (4%) of (4-((5-fluoro-4-oxo-3,4-dihydro-7H-pyrrolo[2,3-d]pyrimidin-7-yl)methyl)phenyl)boronic acid as a white solid. MS (ESI, pos. ion) m/z: 288.2 (M+1). $^1$H-NMR: (400 MHz, DMSO-$d_6$, ppm) δ 12.03 (s, 1H), 8.02 (s, 2H), 7.90 (d, J=4.0 Hz, 1H), 7.72 (d, J=8.0 Hz, 2H), 7.19-7.13 (m, 3H), 5.27 (s, 2H). $^{19}$F-NMR: (376 MHz, DMSO-$d_6$, ppm) 6-166.3 (1F).

Example 9

Synthesis of (4-((4-amino-5-fluoro-7H-pyrrolo[2,3-d]pyrimidin-7-yl)methyl)phenyl)boronic acid

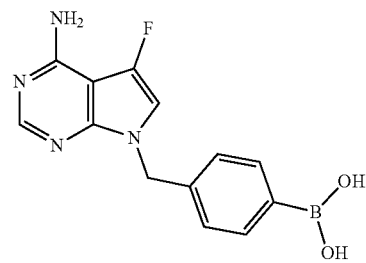

To a sealed tube were added 4-((4-chloro-5-fluoropyrrolo[2,3-d]pyrimidin-7-yl)-methyl)phenylboronic acid (product of example 8 step 1) 150 mg, 0.49 mmol, 1.00 equiv.), ethanol (10 mL) and ammonia (4 mL) at room temperature, respectively. After stirring at 90° C. for 48 h, the mixture was cooled to room temperature and concentrated under reduced pressure. The residue was purified by prep-HPLC with following conditions Column: XBridge Prep OBD C18 Column, 19×250 mm, 5 um; Mobile Phase A: Water (0.1% FA), Mobile Phase B: acetonitrile; Flow rate: 25 mL/min; Gradient: 16% B to 16% B in 7 min; 220 & 254 nm. The fraction containing the desired product were combined and lyophilized to give 41 mg (29%) of (4-((4-amino-5-fluoro- 7H-pyrrolo[2,3-d]pyrimidin-7-yl)methyl)phenyl)boronic acid as a white solid. MS (ESI, pos. ion) m/z: 287.3 (M+1). $^1$H-NMR: (400 MHz, DMSO-d$_6$, ppm) δ 8.07 (s, 1H), 8.02 (s, 2H), 7.71 (d, J=8.0 Hz, 2H), 7.20 (d, J=2.0 Hz, 1H), 7.14 (d, J=8.0 Hz, 2H), 6.97 (s, 2H), 5.27 (s, 2H). $^{19}$F-NMR: (376 MHz, DMSO-d$_6$, ppm) 6-168.2 (1F).

Example 10

Synthesis of 4-((5-methoxyindol-1-yl)methyl)phenylboronic acid

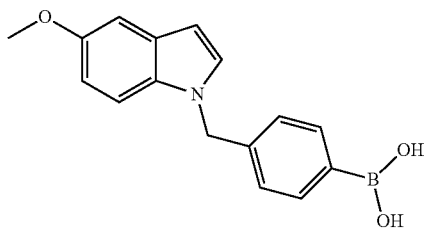 [SMILES: COc1ccc2c(ccn2Cc2ccc(B(O)O)cc2)c1]

The title compound was synthesized as described in example 7 except 5-methoxyindole (100 mg, 0.679 mmol, 1.00 equiv) was used in place of 1H-1,3-benzodiazole-5-carbonitrile. Yield: 61.8 mg (32%). MS (ESI, pos. ion) m/z: 282.3 (M+1). $^1$H-NMR (300 MHz, DMSO-d$_6$, ppm): δ 8.00 (s, 2H), 7.75-7.68 (m, 2H), 7.45-7.43 (m, 1H), 7.29 (d, J=8.7 Hz, 1H), 7.15-7.05 (m, 3H), 6.74-6.70 (m, 1H), 6.40-6.37 (m, 1H), 5.37 (s, 2H), 3.74 (s, 3H).

Example 11

Synthesis of (4-((4-hydroxy-1H-pyrrolo[3,2-c]pyridin-1-yl)methyl)phenyl)boronic acid

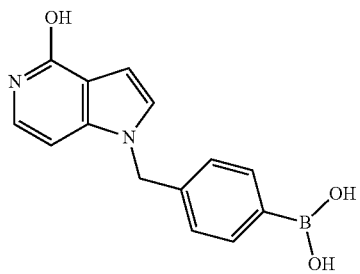

Step 1: 4-methoxy-1H-pyrrolo[3,2-c]pyridine

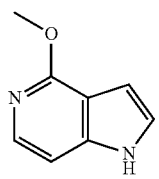

To a solution of NaOMe in methanol (20 mL, 30%) was added 4-chloro-1H-pyrrolo[3,2-c]pyridine (1.00 g, 6.554 mmol, 1.00 equiv.). The resulting mixture was stirred for 16 hours at 120° C. in a sealed tube. After cooling to room temperature, the reaction mixture was diluted with ethyl acetate (80 mL), washed with water, brine, dried over anhydrous sodium sulfate and filtered, and the solvent was evaporated to dryness to give 0.7 g (58%) of 4-methoxy-1H-pyrrolo[3,2-c]pyridine as a light yellow solid. $^1$H-NMR: (400 MHz, DMSO-d$_6$, ppm) δ 11.48 (s, 1H), 7.70 (d, J=5.8 Hz, 1H), 7.32-7.25 (m, 1H), 7.02 (dd, J=5.9, 1.0 Hz, 1H), 6.48-6.44 (m, 1H), 3.94 (s, 3H)

Step 2: 4-((4-methoxypyrrolo[3,2-c]pyridin-1-yl)methyl)-phenylboronic acid

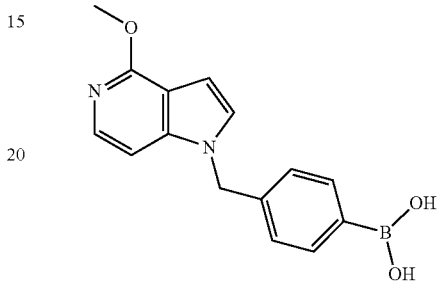

To a solution of 4-methoxy-1H-pyrrolo[3,2-c]pyridine (400.0 mg, 2.16 mmol, 80% purity, 1.00 equiv.) in DMF (4 mL) was added NaH (207.3 mg, 8.64 mol, 4.00 equiv) at 0° C. under argon atmosphere. After stirring for 30 minutes at this temperature, a solution of 4-(bromomethyl)phenylboronic acid (640.4 mg, 2.98 mmol, 1.38 equiv.) in DMF (1 mL) was added. The reaction mixture was stirred for 2 hours at room temperature, quenched with 2 N hydrochloric acid and concentrated under reduced pressure. The residue was suspended in ACN and stirred for 30 minutes. The solid was removed by filtration and the filtrate was evaporated to dryness to give 0.45 g (63%) of 4-((4-methoxypyrrolo[3,2-c]pyridin-1-yl)methyl)phenylboronic acid as a light yellow solid. 0.25 g of this material was further purified by prep-HPLC with the following conditions Column: Sunfire prep C18 column, 30×150, 5 um; Mobile Phase A: Water (0.1% FA), Mobile Phase B: acetonitrile; Flow rate: 60 mL/min; Gradient: 7% B to 25% B in 7 min; 220 & 254 nm. The fractions containing the desired product were combined and lyophilized to give 88.7 mg of 4-((4-methoxypyrrolo[3,2-c]pyridin-1-yl)methyl)phenylboronic acid as a white solid. MS (ESI, pos. ion) m/z: 283.3 (M+1). $^1$H-NMR: (400 MHz, DMSO-d$_6$, ppm) δ 8.00 (s, 2H), 7.77-7.61 (m, 3H), 7.44 (d, J=3.2 Hz, 1H), 7.20-7.04 (m, 3H), 6.53 (dd, J=3.2, 0.9 Hz, 1H), 5.41 (s, 2H), 3.95 (s, 3H).

Step 3: (4-((4-hydroxy-1H-pyrrolo[3,2-c]pyridin-1-yl)methyl)phenyl)boronic acid

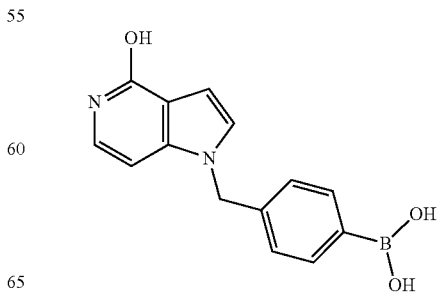

To a suspension of 4-((4-methoxypyrrolo[3,2-c]pyridin-1-yl)methyl)phenylboronic acid (0.20 g, 0.709 mmol, 1.00 equiv) in DCM (10.00 mL) was added BBr$_3$ (3.55 g, 14.18 mmol, 20.00 equiv) at room temperature. After stirring for overnight at room temperature, the mixture was quenched with methanol (10 mL) at −20° C., allowed to warm to room temperature, and concentrated under reduced pressure. The residue was purified by prep-HPLC with following conditions Column: XBridge Shield RP18 OBD Column, 19*250 mm, 10 um; Mobile Phase A: Water (10 mMol/L NH$_4$HCO$_3$), Mobile Phase B: ACN; Flow rate: 25 mL/min; Gradient: 10 B to 30 B in 10 min; 254/220 nm. The fraction containing the desired product were combined and lyophilized to give 59.8 mg (31%) of 4-((4-hydroxypyrrolo[3,2-c]pyridin-1-yl)methyl)-phenylboronic acid as a white solid. MS (ESI, pos. ion) m/z: 269.2 (M+1). $^1$H NMR (400 MHz, DMSO-d$_6$, ppm) δ 10.78 (d, J=5.6 Hz, 1H), 8.01 (s, 2H), 7.80-7.63 (m, 2H), 7.20 (d, J=3.1 Hz, 1H), 7.12 (d, J=7.7 Hz, 2H), 6.98 (dd, J=7.2, 5.8 Hz, 1H), 6.53 (d, J=3.0 Hz, 1H), 6.48 (d, J=7.2 Hz, 1H), 5.32 (s, 2H).

Example 12

Synthesis of (4-((4-hydroxy-3H-imidazo[4,5-c]pyridin-3-yl)methyl)phenyl)boronic acid (12a) and 4-((4-hydroxyimidazo[4,5-c]pyridin-1-yl)methyl)phenylboronic acid (12b

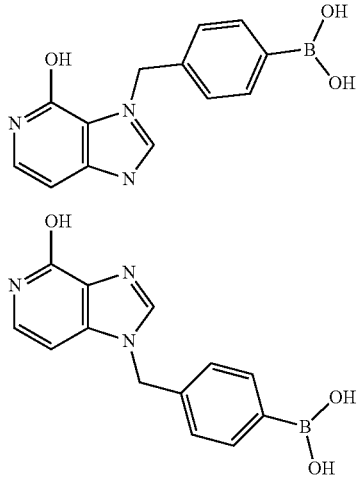

Step 1: 4-((4-chloro-3H-imidazo[4,5-c]pyridin-3-yl)methyl)phenylboronic acid and 4-((4-chloroimidazo[4,5-c]pyridin-1-yl)methyl)phenylboronic acid

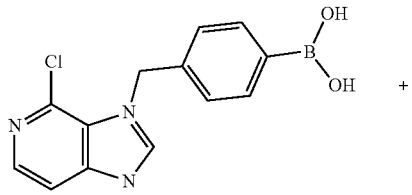 +

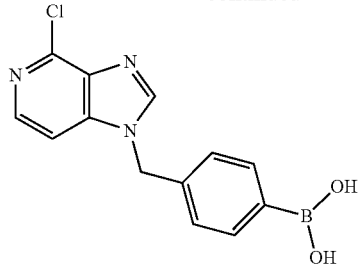 [SMILES: OB(O)c1ccc(Cn2ccc3c(Cl)nccc32)cc1]

To a solution of 4-chloro-1H-imidazo[4,5-c]pyridine (150 mg, 0.977 mmol, 1.00 equiv) in N,N-dimethylformamide (5 mL) were added 4-(bromomethyl)phenylboronic acid (252 mg, 1.172 mmol, 1.20 equiv) and cesium carbonate (636 mg, 1.954 mmol, 2.00 equiv) at room temperature. After stirring overnight, the reaction mixture was concentrated under reduced pressure. The residue was dissolved in methanol (10 mL) and the solids were filtered off. The filtrate was concentrated under reduced pressure. The residue was treated with dichloromethane (10 mL). The precipitate was collected by filtration, washed with dichloromethane (10 mL×3) and dried in vacuo to afford 200 mg (71%) of a mixture of 4-((4-chloro-3H-imidazo[4,5-c]pyridin-3-yl)methyl)phenylboronic acid and 4-((4-chloroimidazo[4,5-c]pyridin-1-yl)methyl)phenylboronic acid as a yellow solid. MS (ESI, pos. ion) m/z: 288.2 (M+1).

Step 2: 4-((4-hydroxyimidazo[4,5-c]pyridin-3-yl)methyl)phenylboronic acid and 4-((4-hydroxyimidazo[4,5-c]pyridin-1-yl)methyl)phenylboronic acid

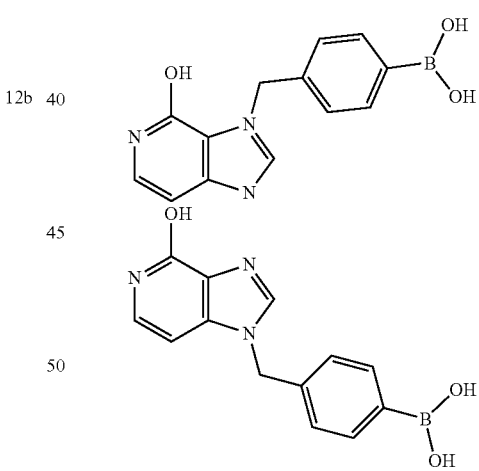

To a mixture of 4-((4-chloro-3H-imidazo[4,5-c]pyridin-3-yl)methyl)phenylboronic acid and 4-((4-chloroimidazo[4,5-c]pyridin-1-yl)methyl)phenylboronic acid (180 mg, 0.62 mmol, 1.00 equiv) in tetrahydrofuran (5 mL) was added 6 N hydrochloric acid (5 mL) dropwise at room temperature. After refluxing overnight, the reaction mixture was concentrated under reduced pressure. The residue was dissolved in N,N-dimethylformamide and filtered. The filtrate was purified by prep-HPLC with the following conditions Column: XBridge Prep Phenyl OBD Column, 19×150 mm, 5 um; Mobile Phase A: Water (0.05% FA), Mobile Phase B: acetonitrile; Flow rate: 25 mL/min; Gradient: 8% B to 15%

B in 10 min, 220 & 254 nm. The fractions containing the desired products were combined and lyophilized to give two fractions.

Fraction 1: Rt: 8.02 min. 80.2 mg (44% yield) of 4-((4-hydroxyimidazo[4,5-c]pyridin-3-yl)methyl)phenylboronic acid (13a) as a white solid. MS (ESI, pos. ion) m/z: 270.3 (M+1). $^1$H-NMR (300 MHz, DMSO-$d_6$, ppm) δ 11.26-11.24 (m, 1H), 8.30 (s, 1H), 8.00 (s, 2H), 7.72 (d, J=8.1 Hz, 2H), 7.26 (d, J=8.1 Hz, 2H), 7.10-7.06 (m, 1H), 6.54 (d, J=7.2 Hz, 1H), 5.65 (s, 2H).

Fraction 2: Rt: 9.35 min. 17.2 mg (10% yield) of 4-((4-hydroxyimidazo[4,5-c]pyridin-1-yl)methyl)phenylboronic acid (13b) as a white solid. MS (ESI, pos. ion) m/z: 270.3 (M+1). $^1$H-NMR (300 MHz, DMSO-$d_6$, ppm) δ 11.90 (s, 1H), 9.21 (s, 1H), 7.80-7.74 (m, 2H), 7.47-7.10 (m, 5H), 6.78-6.66 (m, 1H), 5.58 (s, 2H).

Example 13

Synthesis of 4-((4-chloropyrrolo[3,2-c]pyridin-1-yl)methyl)phenylboronic acid

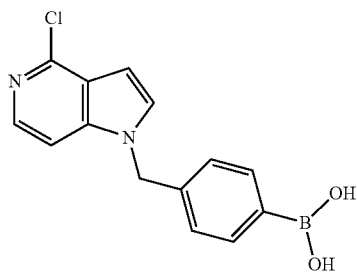

To a solution of 4-chloro-1H-pyrrolo[3,2-c]pyridine (150 mg, 0.98 mmol, 1.00 equiv) in N,N-dimethylformamide (8 mL) was added sodium hydride (47 mg, 1.97 mmol, 2.00 equiv, 60% purity) at 0° C. After stirring for 30 minutes at 0° C., 4-(bromomethyl)phenylboronic acid (253 mg, 1.18 mmol, 1.20 equiv) was added. The mixture was stirred for 3 h at room temperature and the mixture was quenched with 2 N hydrogen chloride and concentrated under reduced pressure. The residue was dissolved in methanol and the solids filtered off. The filtrate was concentrated under reduced pressure. The residue was treated with dichloromethane. The precipitated was collected by filtration, washed with dichloromethane and dried in vacuo to afford 250 mg (85% purity) of 4-((4-chloropyrrolo[3,2-c]pyridin-1-yl)methyl)-phenylboronic acid as a yellow solid. The crude product (50 mg) was purified by prep-HPLC with following conditions: Column: XBridge Shield RP18 OBD Column, 19×250 mm, 10 um; Mobile Phase A: water (0.1% FA), Mobile Phase B: acetonitrile; Flow rate: 25 mL/min; Gradient: 46% B to 46% B in 5 min, 220 & 254 nm. The fractions containing the desired product were combined and lyophilized to give 3.6 mg (6%) of 4-((4-chloropyrrolo[3,2-c]pyridin-1-yl)methyl)phenylboronic acid as a white solid. MS (ESI, pos. ion) m/z: 287.2 (M+1). $^1$H-NMR (300 MHz, DMSO-$d_6$, ppm) δ 7.99 (d, J=5.7 Hz, 1H), 7.74-7.71 (m, 3H), 7.60-7.57 (m, 1H), 7.18 (d, J=8.1 Hz, 2H), 6.64-6.63 (m, 1H), 5.50 (s, 2H).

Example 14

Synthesis of 4-((6-(methoxycarbonyl)-1,3-benzodiazol-1-yl)methyl)phenylboronic acid trifluoroacetic acid salt (14a), 4-((5-(methoxycarbonyl)-1,3-benzodiazol-1-yl)methyl)-phenylboronic acid trifluoroacetic acid salt (14b), 3-((4-(dihydroxyboranyl)phenyl)methyl)-1,3-benzodiazole-5-carboxylic acid trifluoroacetic acid salt (14c), 1-((4-(dihydroxyboranyl)phenyl)methyl)-1,3-benzodiazole-6-carboxylic acid trifluoroacetic acid salt (14d), 4-((5-carbamoyl-1,3-benzodiazol-1-yl)methyl)phenylboronic acid trifluoroacetic acid salt (14e), and 4-((6-carbamoyl-1,3-benzodiazol-1-yl)methyl)phenylboronic acid trifluoroacetic acid salt

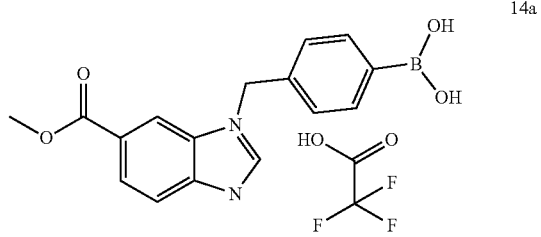

14a

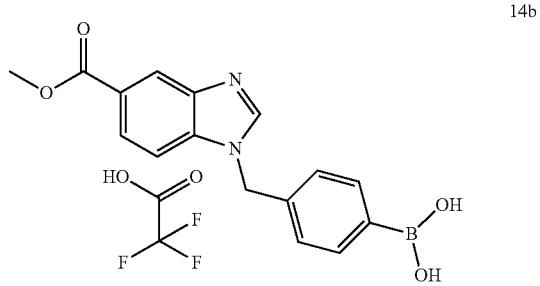

14b

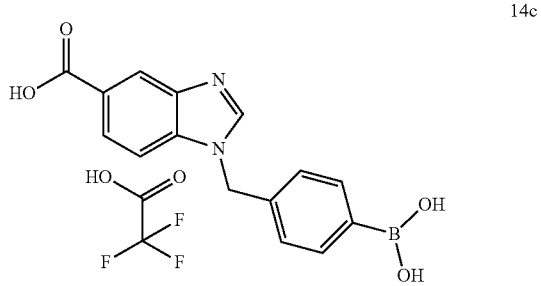

14c

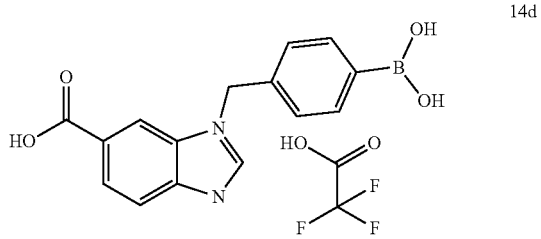

14d

-continued

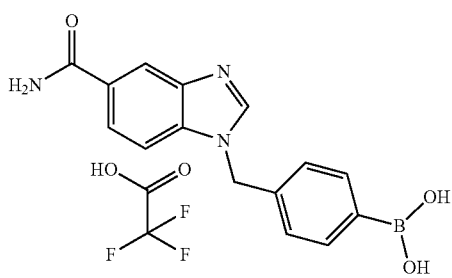
14e

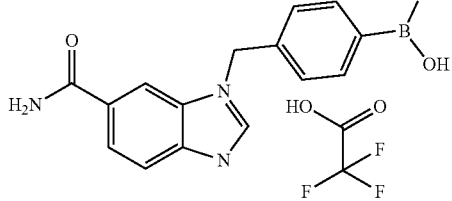
14f

Step 1: 4-((6-(methoxycarbonyl)-1,3-benzodiazol-1-yl)methyl)phenylboronic acid trifluoroacetic acid salt (14a) and 4-((5-(methoxycarbonyl)-1,3-benzodiazol-1-yl)methyl)phenylboronic acid trifluoroacetic acid salt (14b

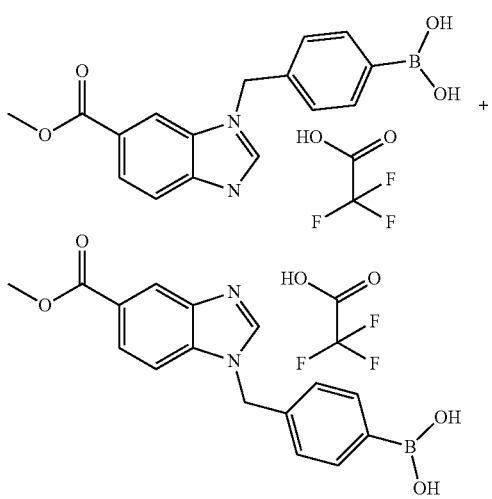

To a solution of methyl 1H-1,3-benzodiazole-5-carboxylate (500 mg, 2.838 mmol, 1.00 equiv) in DMF (5 mL) was added sodium hydride (170 mg, 4.257 mmol, 1.50 equiv, 60% purity) at 0° C. After stirred for 20 minutes, 4-(bromomethyl)phenylboronic acid (732 mg, 3.406 mmol, 1.20 equiv) was added. The resulting mixture was stirred for 2 h at room temperature. The reaction mixture was diluted with water and extracted with ethyl acetate. The combined organic layers were washed with water and brine, dried over anhydrous sodium sulfate and filtered. The filtrate was concentrated under reduced pressure to give 500 mg of a mixture of 4-((6-(methoxycarbonyl)-1,3-benzodiazol-1-yl)methyl)phenylboronic acid trifluoroacetic acid salt (14a) and 4-((5-(methoxycarbonyl)-1,3-benzodiazol-1-yl)methyl)-phenylboronic acid trifluoroacetic acid salt (14b). 250 mg of the mixture was purified by prep-HPLC with the following conditions Column: XSelect CSH Prep C18 OBD Column, 19×250 mm, 5 um; Mobile Phase A: Water (0.05% TFA), Mobile Phase B: acetonitrile; Flow rate: 25 mL/mi; Gradient: 12% B to 18% B in 17 min, 220 & 254 nm. The fractions containing the desired products were combined and lyophilized to give two fractions.

Fraction 1: Rt: 12.77 min. 70.3 mg (6% yield) of 4-((6-(methoxycarbonyl)-1,3-benzodiazol-1-yl)methyl)phenylboronic acid trifluoroacetic acid salt (14a) as a white solid. MS (ESI, pos. ion) m/z: 311.2 (M+1). $^1$H-NMR: (400 MHz, DMSO-$d_6$, ppm) δ 9.05-9.01 (m, 1H), 8.43-8.10 (m, 3H), 7.94-7.76 (m, 5H), 7.29 (d, J=7.6 Hz, 2H), 5.71-5.69 (m, 2H), 3.86-3.82 (m, 3H).

Fraction 2: Rt: 14.7 min. 80.8 mg (6% yield) of 4-((5-(methoxycarbonyl)-1,3-benzodiazol-1-yl)methyl)phenylboronic acid trifluoroacetic acid salt as a white solid (14b). MS (ESI, pos. ion) m/z: 311.2 (M+1). $^1$H-NMR: (400 MHz, DMSO-$d_6$, ppm) δ 9.05-9.01 (m, 1H), 8.34 (s, 1H), 7.96-7.85 (m, 2H), 7.77-7.50 (m, 5H), 7.36-7.32 (m, 2H), 5.60 (s, 2H), 3.87 (s, 3H).

Step 2: 3-((4-(dihydroxyboranyl)phenyl)methyl)-1,3-benzodiazole-5-carboxylic acid trifluoroacetic acid salt (14c), 1-((4-(dihydroxy-boranyl)phenyl)methyl)-1,3-benzodiazole-6-carboxylic acid trifluoroacetic acid salt (14d), 4-((5-carbamoyl-1,3-benzodiazol-1-yl)methyl)phenylboronic acid trifluoroacetic acid salt (14e) and 4-((6-carbamoyl-1,3-benzodiazol-1-yl)methyl)phenylboronic acid trifluoroacetic acid salt (14f

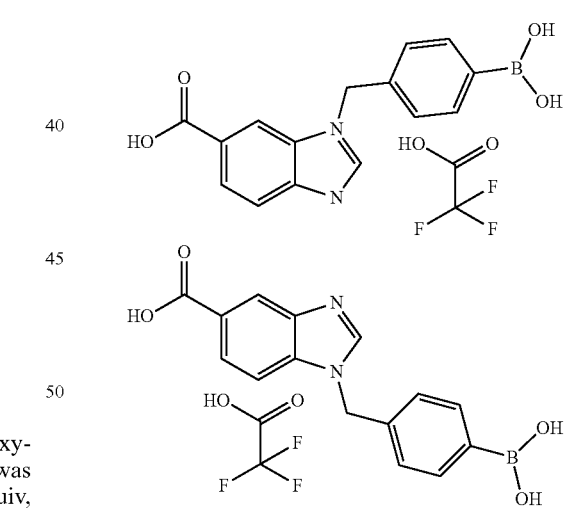

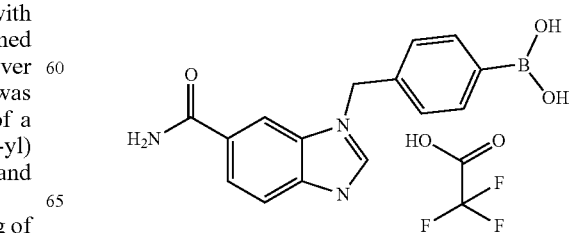

-continued

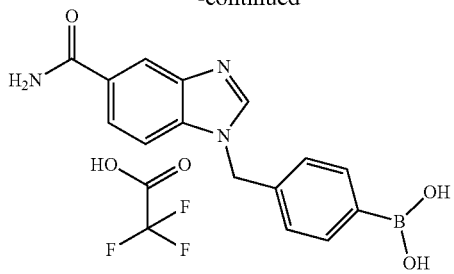

A mixture of 4-((6-(methoxycarbonyl)-1,3-benzodiazol-1-yl)methyl)phenylboronic acid) and 4-((5-(methoxycarbonyl)-1,3-benzodiazol-1-yl)methyl)phenylboronic acid trifluoroacetic acid salt (14a and 14b) (250 mg, 1 equiv) was dissolved in aqueous ammonia (10 mL). After stirring at 80° C. for 12 h in a sealed tube, the reaction mixture was concentrated under reduced pressure. The residue was purified by prep-HPLC with the following conditions Column: XSelect CSH Prep C18 OBD Column, 19×250 mm, 5 um; Mobile Phase A: Water (0.05% TFA), Mobile Phase B: acetonitrile; Flow rate: 25 mL/min; Gradient: 5% B to 15% B in 14 min, 220 & 254 nm. The fractions containing the desired products were combined and lyophilized to give four fractions.

Fraction 1: Rt: 7.25 min. 16.8 mg (5% yield) of 3-((4-(dihydroxyboranyl)phenyl)methyl)-1,3-benzodiazole-5-carboxylic acid trifluoroacetic acid salt (14c) as a white solid. MS (ESI, pos. ion) m/z: 297.2 (M+1). $^1$H-NMR: (400 MHz, DMSO-$d_6$, ppm) δ 9.07 (s, 1H), 8.20 (s, 1H), 7.94-7.75 (m, 4H), 7.30 (d, J=8.0 Hz, 2H), 5.65 (s, 2H).

Fraction 2: Rt: 8.92 min. 20.6 mg (6% yield) of 1-((4-(dihydroxy-boranyl)phenyl)methyl)-1,3-benzodiazole-5-carboxylic acid trifluoroacetic acid salt (14d) as a white solid. MS (ESI, pos. ion) m/z: 297.3 (M+1). $^1$H-NMR: (400 MHz, DMSO-$d_6$, ppm) δ 12.81 (brs, 1H), 8.68 (s, 1H), 8.26-7.85 (m, 4H), 7.76-7.61 (m, 3H), 7.35-7.28 (m, 2H), 5.57 (s, 2H).

Fraction 3: Rt: 10.22 min. 42.8 mg (13% yield) of 4-((6-carbamoyl-1,3-benzodiazol-1-yl)methyl)phenylboronic acid trifluoroacetic acid salt (14e) as a white solid. MS (ESI, pos. ion) m/z: 296.2 (M+1). $^1$H-NMR: (400 MHz, DMSO-$d_6$, ppm) δ 9.27 (s, 1H), 8.28 (s, 1H), 8.11 (s, 1H), 7.97-7.73 (m, 5H), 7.50-7.20 (m, 5H), 5.68 (s, 2H).

Fraction 4: Rt: 11.84 min. 53.0 mg (16% yield) of 4-((5-carbamoyl-1,3-benzodiazol-1-yl)methyl)phenylboronic acid trifluoroacetic acid salt (14f) as a white solid. MS (ESI, pos. ion) m/z: 296.2 (M+1). $^1$H-NMR: (400 MHz, DMSO-$d_6$, ppm) δ 9.20 (s, 1H), 8.31 (s, 1H), 8.11 (s, 1H), 7.94-7.88 (m, 1H), 7.79-7.73 (m, 3H), 7.43 (s, 1H), 7.44-7.29 (m, 3H), 5.66 (s, 2H).

Example 15

Synthesis of 4-((5-cyano-3-oxo-2H-indazol-1-yl)methyl)phenylboronic acid

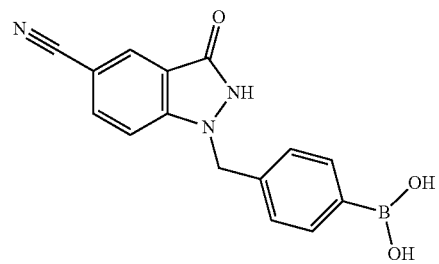 [SMILES: N#Cc1ccc2c(c1)c(=O)[nH]n2Cc1ccc(B(O)O)cc1]

Step 1: 3-oxo-1,2-dihydroindazole-5-carbonitrile

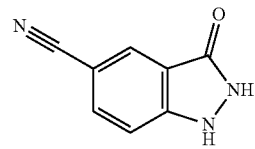 [SMILES: N#Cc1ccc2[nH][nH]c(=O)c2c1]

Methyl 5-cyano-2-fluorobenzoate (500 mg, 2.79 mmol, 1.00 equiv.) was dissolved in hydrazine monohydrate (50 mL) and stirred for 24 h at room temperature. The reaction mixture was diluted with ethyl acetate, washed with water, and brine. The organic layer was dried with over sodium sulfate, filtered and concentrated under reduced pressure. The residue was purified by silica gel column chromatography (eluent: petroleum ether/ethyl acetate=1:2) to give 310 mg (68% yield) of 3-oxo-1,2-dihydroindazole-5-carbonitrile as a light-yellow solid.

Step 2: 4-((5-cyano-3-oxo-2H-indazol-1-yl)methyl)phenylboronic acid

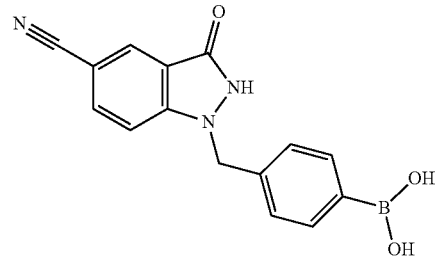

To a solution of 3-oxo-1,2-dihydroindazole-5-carbonitrile (100 mg, 0.63 mmol, 1.00 equiv.) in N,N-dimethylformamide (5 mL) were added potassium carbonate (127 mg, 1.26 mmol, 2.00 equiv.) and 4-(bromomethyl)phenylboronic acid (162 mg, 0.75 mmol, 1.20 equiv.) at room temperature. After stirring for 12 hour at 80° C., the reaction mixture was cooled to room temperature and filtered. The filtrate was concentrated under reduced pressure. The residue was purified by prep-HPLC with following conditions Column: Sunfire Prep C18 column, 30×150 mm, 5 um; Mobile Phase A: Water (0.1% FA), Mobile Phase B: acetonitrile; Flow rate: 60 mL/min; Gradient: 7% B to 52% B in 7 min; 220 & 254 nm. The fractions containing the desired product were combined and lyophilized to give 50 mg (27%) of 4-((5-cyano-3-oxo-2H-indazol-1-yl)methyl)phenylboronic acid as a white solid. MS (ESI, pos. ion) m/z: 294.3 (M+1). ¹H-NMR: (400 MHz, DMSO-$d_6$, ppm) δ 11.32 (s, 1H), 8.19 (s, 1H), 8.01 (s, 2H), 7.77-7.62 (m, 4H), 7.15 (d, J=8.0 Hz, 2H), 5.45 (s, 2H).

Example 16

Synthesis of 4-((5-carbamoyl-3-oxo-2H-indazol-1-yl)methyl)phenylboronic acid

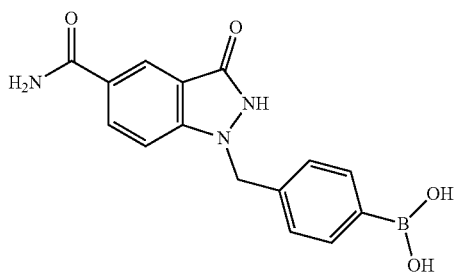 [SMILES: NC(=O)c1ccc2c(c1)c(=O)[nH]n2Cc1ccc(B(O)O)cc1]

Step 1: 3-oxo-1,2-dihydroindazole-5-carboxamide

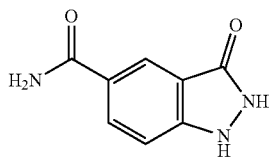

3-Oxo-1,2-dihydroindazole-5-carbonitrile (400 mg, 2.51 mmol, 1.00 equiv.) was dissolved in water (0.4 mL, 22.20 mmol) and concentrated sulfuric acid (2.4 mL, 45.03 mmol, 17.91 equiv.) at room temperature. After stirring at 100° C. for 1 h, the mixture was cooled to room temperature, diluted with ethyl acetate (150 mL), washed with water (50 mL) and a saturated aqueous solution of sodium bicarbonate (50 mL×2). The organic layer was dried with sodium sulfate, filtered and concentrated under reduced pressure. The residue was purified by prep-TLC (eluent: petroleum ether/ethyl acetate 1:2) to give 120 mg (22%) of 3-oxo-1,2-dihydroindazole-5-carboxamide as a light-yellow solid.

Step 2: 4-((5-carbamoyl-3-oxo-2H-indazol-1-yl)methyl)phenylboronic acid

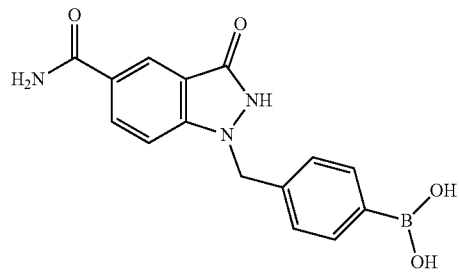 [SMILES: NC(=O)c1ccc2c(c1)c(=O)[nH]n2Cc1ccc(B(O)O)cc1]

To a solution of 3-oxo-1,2-dihydroindazole-5-carboxamide (120 mg, 0.68 mmol, 80%, 1.00 equiv.) in N,N-dimethylformamide (5 mL) was added sodium hydride (24 mg, 1.02 mmol, 1.50 equiv.) at 0° C. under argon atmosphere. Stirring for 30 minutes at this temperature, a solution of 4-(bromomethyl)phenylboronic acid (175 mg, 0.81 mmol, 1.20 equiv.) in N,N-dimethylformamide (2 mL) was added. After stirred for 1 h at room temperature, the reaction mixture was quenched with 2 N hydrochloric acid (5 mL) and concentrated under reduced pressure. The residue was purified by prep-HPLC with following conditions Column: Sunfire Prep C18 column, 30×150 mm, 5 um; Mobile Phase A: Water (0.1% FA), Mobile Phase B: acetonitrile; Flow rate: 60 mL/min; Gradient: 5% B to 35% B in 7 min; 220 & 254 nm. The fractions containing the desired product were combined and lyophilized to give 33.5 mg (16%) of 4-((5-carbamoyl-3-oxo-2H-indazol-1-yl)methyl)phenylboronic acid as a white solid. MS (ESI, pos. ion) m/z: 312.3 (M+1). ¹H-NMR: (300 MHz, DMSO-$d_6$, ppm) δ 10.97 (s, 1H), 8.23 (s, 1H), 7.97 (s, 2H), 7.96-7.78 (m, 2H), 7.69 (d, J=7.8 Hz, 2H), 7.55 (d, J=8.7 Hz, 1H), 7.17-7.11 (m, 3H), 5.39 (s, 2H).

Example 17

Synthesis of 1-(4-boronobenzyl)-3-chloro-1H-indole-5-carboxylic acid (17a) 4-((5-carbamoyl-3-chloroindol-1-yl)methyl)phenylboronic acid (17b 17a

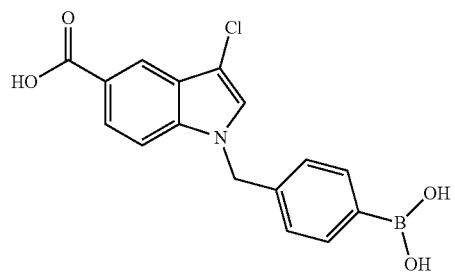

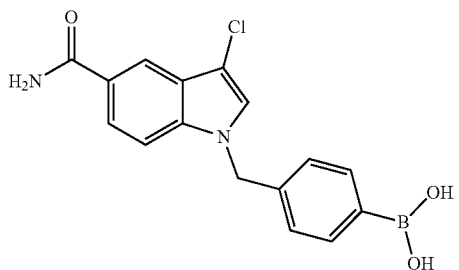

17b

Step 1: methyl 3-chloro-1H-indole-5-carboxylate

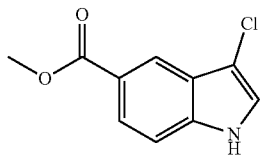

Methyl 1H-indole-5-carboxylate (240 mg, 1.370 mmol, 1.00 equiv) and N-chlorosuccinimide (366 mg, 2.740 mmol, 2.00 equiv) was dissolved in methanol (5 mL). After stirring for 1 h at room temperature, the reaction mixture was concentrated under reduced pressure. The residue was purified by silica gel column chromatography (eluent: dichloromethane/methanol 99:1) to give 170 mg (57%) of methyl 3-chloro-1H-indole-5-carboxylate as a yellow solid. MS (ESI, pos. ion) m/z: 210.1 (M+1).

Step 2: 4-((3-chloro-5-(methoxycarbonyl)indol-1-yl)methyl)phenylboronic acid

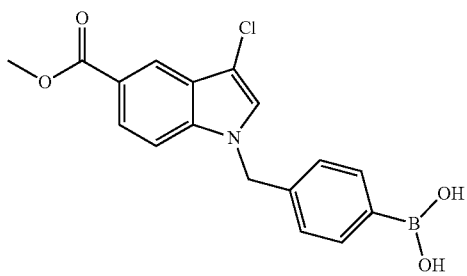 [SMILES: COC(=O)c1ccc2c(c1)c(Cl)cn2Cc1ccc(B(O)O)cc1]

To a stirred mixture of methyl 3-chloro-1H-indole-5-carboxylate (160 mg, 0.740 mmol, 1.00 equiv, 97% purity) and potassium carbonate (205 mg, 1.481 mmol, 2.00 equiv) in N,N-dimethylformamide (5 mL) was added 4-(bromomethyl)phenylboronic acid (175 mg, 0.814 mmol, 1.10 equiv) at room temperature. After stirring at room temperature for 2 h, the reaction mixture was diluted with water (30 mL) and extracted with ethyl acetate. The combined organic layers were washed with water and brine, dried over anhydrous sodium sulfate and filtered. The filtrate was concentrated under reduced pressure to give 210 mg (81%) of 4-((3-chloro-5-(methoxycarbonyl)indol-1-yl)methyl)phenylboronic acid as a yellow solid. MS (ESI, pos. ion) m/z: 344.2 (M+1).

Step 3: 1-(4-boronobenzyl)-3-chloro-1H-indole-5-carboxylic acid (17a) and 4-((5-carbamoyl-3-chloroindol-1-yl)methyl)phenylboronicacid (17b

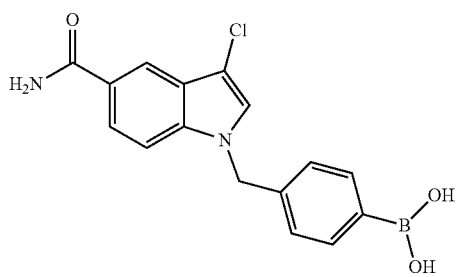

4-((3-Chloro-5-(methoxycarbonyl)indol-1-yl)methyl)phenylboronic acid (210 mg, 1.00 equiv, 98% purity) was dissolved in dioxane (3 mL) and aqueous ammonia (12 mL). After stirring at 80° C. for 48 h, the reaction mixture was cooled to room temperature and concentrated under reduced pressure. The residue was purified by prep-HPLC with following conditions Column: Sunfire Prep C18 column, 30×150 mm, 5 um; Mobile Phase A: Water (0.1% FA), Mobile Phase B: acetonitrile; Flow rate: 60 mL/min; Gradient: 31% B to 48% B in 8 min; 220 & 254 nm. The fractions containing the desired product were combined and lyophilized to give two fractions.

Fraction 1: Rt: 4.5 min. 55.1 mg (27% yield) of 1-(4-boronobenzyl)-3-chloro-1H-indole-5-carboxylic acid (17a) as an off-white solid. MS (ESI, pos. ion) m/z: 330.2 (M+1). $^1$H-NMR (300 MHz, DMSO-$d_6$, ppm) δ 12.70 (s, 1H), 8.14 (s, 1H), 8.02 (s, 2H), 7.86 (s, 1H), 7.81-7.61 (m, 4H), 7.21-7.18 (m, 2H), 5.46 (s, 2H).

Fraction 2: Rt: 6.62 min. 58.4 mg (29% yield) of 4-((5-carbamoyl-3-chloroindol-1-yl)methyl)phenylboronic acid (17b) as a light yellow solid. MS (ESI, pos. ion) m/z: 329.3 (M+1). $^1$H-NMR (300 MHz, DMSO-$d_6$, ppm) δ 8.13 (s, 1H), 8.01-7.90 (m, 3H), 7.81-7.71 (m, 4H), 7.58 (d, J=8.7 Hz, 1H), 7.21-7.18 (m, 3H), 5.45 (s, 2H).

Example 18

Synthesis of 4-((5-carbamoyl-3-methylindol-1-yl)methyl)phenylboronic acid (18a), 4-((5-(ethoxycarbonyl)-3-methylindol-1-yl)methyl)phenylboronic acid (18b), and 1-((4-(dihydroxyboranyl)phenyl)methyl)-3-methylindole-5-carboxylic acid (18c

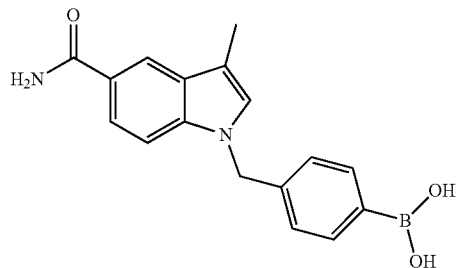 [SMILES: Cc1cn(Cc2ccc(B(O)O)cc2)c2ccc(C(N)=O)cc12]

18a

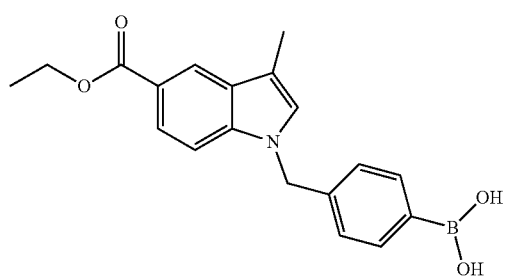

18b

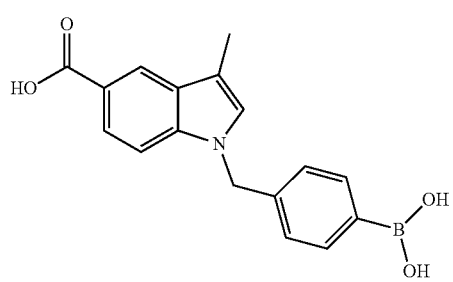

18c

Step 1: 4-((5-(ethoxycarbonyl)-3-methylindol-1-yl)methyl)-phenylboronic acid (18b) and 1-((4-(dihydroxyboranyl)phenyl)methyl)-3-methylindole-5-carboxylic acid (18c

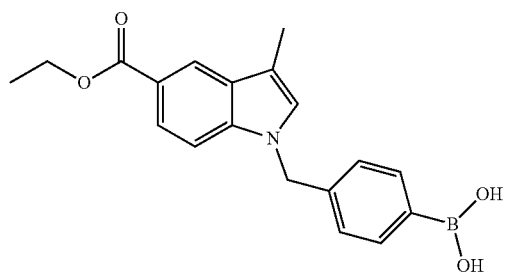

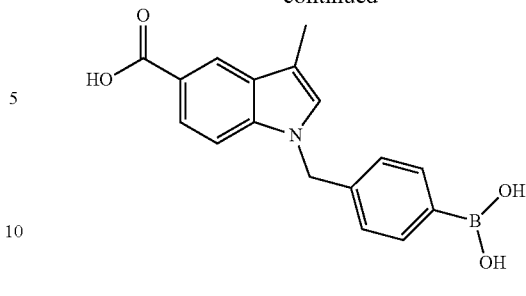

The title compounds were synthesized by the method described in example 7 except ethyl 3-methyl-1H-indole-5-carboxylate (100 mg, 0.49 mmol, 1.00 equiv) was used in place of 1H-1,3-benzodiazole-5-carbonitrile. The crude product was purified by silica gel column chromatography (dichloromethane/methanol (20:1)) to afford two fractions:

Fraction 1: 50 mg (26%) of 4-((5-(ethoxycarbonyl)-3-methylindol-1-yl)methyl)phenylboronic acid (18b) as an off-white solid. MS (ESI, pos. ion) m/z: 338.3 (M+1).

Fraction 2: 100 mg (85% purity) of 1-((4-(dihydroxyboranyl)phenyl)methyl)-3-methylindole-5-carboxylic acid (18c) as an off-white solid, which was further purified by prep-HPLC with following conditions Column: XBridge Prep OBD C18 Column, 19×250 mm, 5 um; Mobile Phase A: Water (0.10% FA), Mobile Phase B: acetonitrile; Flow rate: 25 mL/min; Gradient: 28% B to 64% B in 7 min; 220 & 254 nm. The fractions containing the desired product were combined and lyophilized to give 43.2 mg (27%) of 1-((4-(dihydroxyboranyl)phenyl)methyl)-3-methylindole-5-carboxylic acid (18c) as a white solid. MS (ESI, pos. ion) m/z: 310.3 (M+1). $^1$H-NMR (400 MHz, DMSO-$d_6$, ppm) δ 12.42 (s, 1H), 8.17 (s, 1H), 7.99 (s, 2H), 7.71-7.66 (m, 3H), 7.46 (d, J=8.4 Hz, 1H), 7.34 (s, 1H), 7.14 (d, J=8.0 Hz, 2H), 5.38 (s, 2H), 2.29 (s, 3H).

Step 2: 4-((5-carbamoyl-3-methylindol-1-yl)methyl)phenylboronic acid (18a

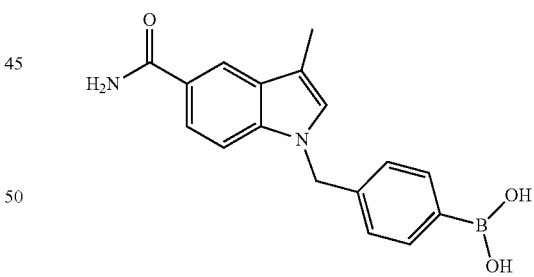

To a mixture of 4-((5-(ethoxycarbonyl)-3-methylindol-1-yl)methyl)phenylboronic acid (18b) (50 mg, 0.13 mmol, 1.00 equiv, 87% purity) in dioxane (3 mL) was added aqueous ammonia (3 mL). After stirring overnight at 80° C., the reaction mixture was cooled to room temperature and concentrated under reduced pressure. The crude product was purified by prep-HPLC with following conditions Column: XBridge Prep OBD C18 Column, 19×250 mm, 5 um; Mobile Phase A: Water (0.1% FA), Mobile Phase B: acetonitrile; Flow rate: 25 mL/min; Gradient: 28% B to 64% B in 7 min; 220 & 254 nm. The fractions containing the desired product were combined and lyophilized to give 4.9 mg (12%) of 4-((5-carbamoyl-3-methylindol-1-yl)methyl)phenylboronic acid (18a) as a white solid. MS (ESI, pos. ion) m/z: 309.2 (M+1). $^1$H-NMR (300 MHz, DMSO-$d_6$, ppm) δ 9.18 (s, 1H), 8.45 (s, 1H), 8.13 (s, 1H), 7.86 (s, 1H), 7.68-7.62 (m, 3H), 7.43-7.39 (m, 1H), 7.31-7.27 (m, 1H), 7.14-7.10 (m, 3H), 5.37 (s, 2H), 2.30 (s, 3H).

Example 19

Synthesis of 4-((6-methoxy-5-(methoxycarbonyl)-1, 3-benzodiazol-1-yl)methyl)phenyl-boronic acid (19a), 4-((5-methoxy-6-(methoxycarbonyl)-1,3-benzodiazol-1-yl)methyl)-phenyl-boronic acid (19b), 4-((6-carbamoyl-5-methoxy-1,3-benzodiazol-1-yl) methyl)-phenylboronic acid (19c), and 4-((5-carbamoyl-6-methoxy-1,3-benzodiazol-1-yl)methyl) phenylboronic acid (19d 19a 19b 19c 19d Step 1: methyl 4,5-diamino-2-methoxybenzoate

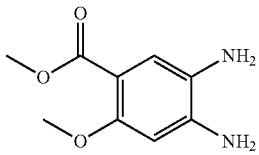

To a solution of methyl 4-amino-2-methoxy-5-nitrobenzoate (1.00 g, 4.421 mmol, 1.00 equiv) in methanol (10 mL) was added 10% Pd/C (200 mg, 0.20 equiv). The resulting mixture was stirred at room temperature for 12 hours under hydrogen atmosphere (2-3 atm). The reaction mixture was filtered through a Celite. The filtrate was concentrated under reduced pressure to give 760 mg (85%) of methyl 4,5-diamino-2-methoxybenzoate as a yellow oil.

Step 2: methyl 6-methoxy-11H-1,3-benzodiazole-5-carboxylate

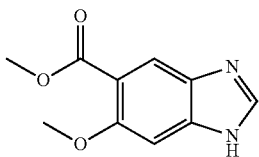

Into a solution of methyl 4,5-diamino-2-methoxybenzoate (710 mg, 3.535 mmol, 1.00 equiv, 97%) in DMF (10 mL) was dissolved imidazole hydrochloride (37 mg, 0.354 mmol, 0.10 equiv). The resulting mixture was stirred for 24 h at 150° C. After cooling down to room temperature, the reaction mixture was diluted with water and extracted with ethyl acetate. The 15 combined organic layers were washed with water and brine, and dried over anhydrous sodium sulfate and filtered. The filtrate was concentrated under reduced pressure to give methyl 6-methoxy-1H-1,3-benzodiazole-5-carboxylate (510 mg, 59%) as a yellow oil.

Step 3: a mixture of 4-((6-methoxy-5-(methoxycarbonyl)-1,3-benzodiazol-1-yl)methyl)phenyl-boronic acid (19a) 4-((5-methoxy-6-(methoxycarbonyl)-1,3-benzodiazol-1-yl)methyl)-phenyl-boronic acid (19b

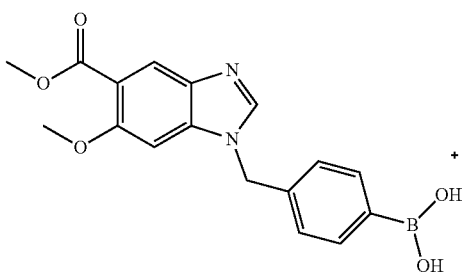

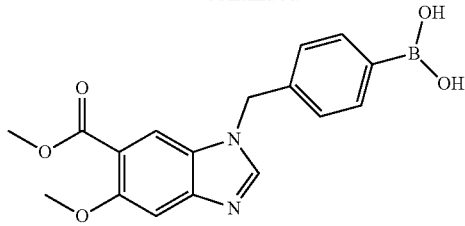

The title compounds were synthesized by the method described in example 7 except methyl 6-methoxy-1H-1,3-benzodiazole-5-carboxylate (480 mg, 1.979 mmol, 1.00 equiv, 85% purity) was used in place of 1H-1,3-benzodiazole-5-carbonitrile. Yield: 600 mg (86% purity) of a mixture of 4-((6-methoxy-5-(methoxycarbonyl)-1,3-benzodiazol-1-yl)methyl)phenyl-boronic acid (19a) and 4-((5-methoxy-6-(methoxycarbonyl)-1,3-benzodiazol-1-yl)methyl)-phenyl-boronic acid (19b). MS (ESI, pos. ion) m/z: 341.3 (M+1).

Step 4: 4-((6-carbamoyl-5-methoxy-1,3-benzodiazol-1-yl)methyl)phenylboronic acid (19c) and 4-((5-carbamoyl-6-methoxy-1,3-benzodiazol-1-yl)methyl)phenylboronic acid (19d)

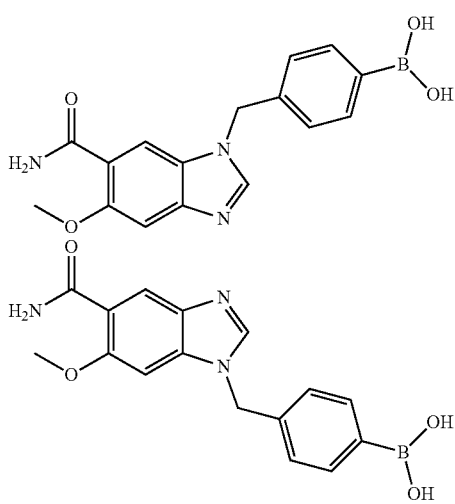

The title compounds were synthesized by the method described in Example 14 at step 2 except a mixture of 4-((6-methoxy-5-(methoxycarbonyl)-1,3-benzodiazol-1-yl)methyl)phenylboronic acid and 4-((5-methoxy-6-(methoxycarbonyl)-1,3-benzodiazol-1-yl)methyl)phenylboronic acid (250 mg, 0.712 mmol, 1.00 equiv, 97% purity) was used as starting material. The crude product was purified by prep-HPLC with the following conditions Column: XBridge Prep OBD C18 Column, 30×150 mm, 5 um; Mobile Phase A: Water (10 mmol/L ammonium bicarbonate+0.1% aqueous ammonia), Mobile Phase B: acetonitrile; Flow rate: 60 mL/min; Gradient: 10% B to 15% B in 10 min, 220 & 254 nm. The fractions containing the desired products were combined and lyophilized to give two fractions.

Fraction 1: Rt: 7.38 min. 24.4 mg (10% yield) of 4-((6-carbamoyl-5-methoxy-1,3-benzodiazol-1-yl)methyl)phenylboronic acid (19c) as a white solid. MS (ESI, pos. ion) m/z: 326.3 (M+1). $^1$H-NMR: (300 MHz, DMSO-d$_6$, ppm) δ 8.45 (s, 1H), 7.96 (s, 1H), 7.78-7.59 (m, 3H), 7.50-7.35 (m, 2H), 7.21-7.18 (m, 2H), 5.51 (s, 2H), 3.92 (s, 3H).

Fraction 2: Rt: 8.88 min. 23.9 mg (9% yield) of 4-((5-carbamoyl-6-methoxy-1,3-benzodiazol-1-yl)methyl)phenylboronic acid (19d) as an off-white solid. MS (ESI, pos. ion) m/z: 326.3 (M+1). $^1$H-NMR: (300 MHz, DMSO-d$_6$, ppm) δ 8.38 (s, 1H), 8.15-8.06 (m, 3H), 7.77-7.67 (m, 3H), 7.46 (s, 1H), 7.34-7.26 (m, 3H), 5.52 (s, 2H), 3.88 (s, 3H).

Example 20

Synthesis of (4-((6-carbamoyl-2-ethyl-1H-benzo[d]imidazol-1-yl)methyl)phenyl)boronic acid (20a) 4-((5-carbamoyl-2-ethyl-1,3-benzodiazol-1-yl)methyl)phenylboronic acid (20b

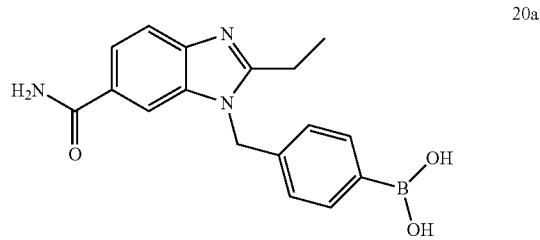

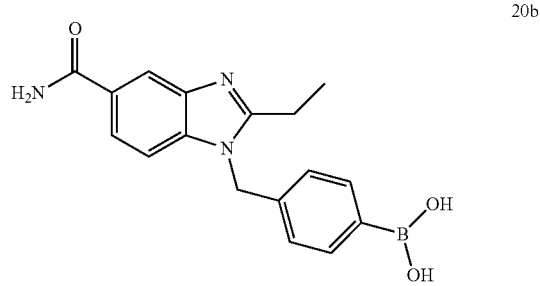

Step 1: methyl 2-ethyl-1H-1,3-benzodiazole-5-carboxylate

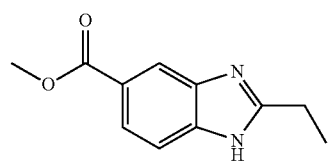

To a solution of methyl 3,4-diaminobenzoate (500 mg, 3.01 mmol, 1.00 equiv.) in N,N-dimethyl-propenamide (5 mL) was added 1H-imidazole hydrochloride (63 mg, 0.60 mmol, 0.20 equiv.) at room temperature. After stirring for 24 hours at 140° C., the reaction mixture was cooled to room temperature, diluted with ethyl acetate and washed water. The combined organic layers were dried with over sodium sulfate, filtered and concentrated under reduced pressure. The residue was purified by column chromatography (silica gel, eluent: petroleum ether/ethyl acetate=7:3) to give 0.36 g (51%) of methyl 2-ethyl-1H-1,3-benzodiazole-5-carboxylate as a brown solid. 1H-NMR: (400 MHz, DMSO-d$_6$, ppm) δ 12.79-12.33 (brs, 1H), 8.08 (s, 1H), 7.78 (dd, J=8.4, 1.6

Hz, 1H), 7.55 (d, J=8.4 Hz, 1H), 3.85 (s, 3H), 2.87 (q, J=8.0 Hz, 2H), 1.33 (t, J=7.6 Hz, 3H).

Step 2: 2-ethyl-1H-1,3-benzodiazole-5-carboxylic acid

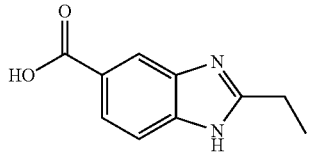

To a solution of methyl 2-ethyl-1H-1,3-benzodiazole-5-carboxylate (300 mg, 1.47 mmol, 1.00 equiv.) in methanol (5 mL) were added sodium hydroxide (176 mg, 4.41 mmol, 3.00 equiv.) and water (2 mL) at room temperature. After stirring for 1 hour at room temperature, the mixture was adjusted to pH=3 with 2 N hydrogen chloride (3 mL) and a white precipitate was formed. The solid was collected by filtration, washed with water and dried under reduced pressure to give 0.25 g (89%) of 2-ethyl-1H-1,3-benzodiazole-5-carboxylic acid as an off-white solid.

Step 3: 2-ethyl-1H-1,3-benzodiazole-5-carboxamide

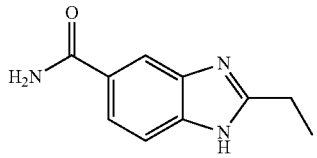

2-Ethyl-1H-1,3-benzodiazole-5-carboxylic acid (250 mg, 1.31 mmol, 1.00 equiv.) was added to thionyl chloride (15 mL), resulting in a suspension, which was stirred for 1 hour at 80° C. The mixture was evaporated under reduced pressure to give the intermediate acid chloride as a brown solid, which was suspended in dichloromethane and slowly added into a stirred solution of ammonia in methanol (10 mL, 7 M, 70 mmol, 53.26 equiv.) at room temperature. The resulting mixture was stirred for 2 hours at room temperature and concentrated under reduced pressure to give 0.23 g (92%) of 2-ethyl-1H-1,3-benzodiazole-5-carboxamide as a yellow solid.

Step 4: (4-((6-carbamoyl-2-ethyl-1H-benzo[d]imidazol-1-yl)methyl)phenyl)boronic acid (20a) and 4-((5-carbamoyl-2-ethyl-1,3-benzodiazol-1-yl)methyl)phenylboronic acid (20b

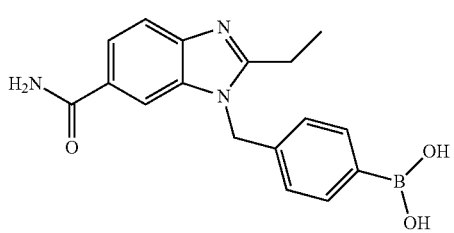

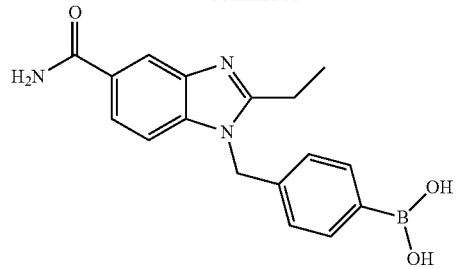

To a suspension of sodium hydride (44 mg, 1.82 mmol, 1.50 equiv.) in N, N-dimethylformamide (5 mL) was added a solution of 2-ethyl-1H-1,3-benzodiazole-5-carboxamide (230 mg, 1.22 mmol, 1.00 equiv.) in N, N-dimethylformamide (5 mL) at 0° C. After stirring for 30 minutes at 0° C., a solution of 4-(bromomethyl)phenylboronic acid (313 mg, 1.46 mmol, 1.20 equiv.) in N, N-dimethylformamide (2 mL) was added at the same temperature. The resulting mixture was further stirred for 2 hours at room temperature. The reaction mixture was quenched with 2 N hydrogen chloride (5 mL) and concentrated under reduced pressure. The residue was purified by prep-HPLC with following conditions Column: XBridge C18 OBD column, 100 Å, 19×250, 5 um; Mobile Phase A: Water (0.05% FA), Mobile Phase B: acetonitrile; Flow rate: 25 mL/min; Gradient: 7% B to 14% B in 7 min; 220 & 254 nm. The fractions containing the desired product were combined and lyophilized to give two fractions.

Fraction 1: Rt=5.35 min. 23.4 mg (5% yield) of (4-((6-carbamoyl-2-ethyl-1H-benzo[d]imidazol-1-yl)methyl)phenyl)boronic acid (20a) as a white solid. MS (ESI, pos. ion) m/z: 323.8 (M+1). $^1$H-NMR: (400 MHz, DMSO-$d_6$, ppm) δ 8.04 (d, J=1.6 Hz, 1H), 8.01 (s, 2H), 7.90 (s, 1H), 7.78-7.70 (m, 3H), 7.62 (d, J=8.4 Hz, 1H), 7.26 (s, 1H), 7.04 (d, J=7.9 Hz, 2H), 5.52 (s, 2H), 2.86 (q, J=7.5 Hz, 2H), 1.28 (t, J=7.5 Hz, 3H).

Fraction 2: Rt=7.13 min. 17.5 mg (4% yield) of 4-((5-carbamoyl-2-ethyl-1,3-benzodiazol-1-yl)methyl)phenylboronic acid (20b) as a white solid. MS (ESI, pos. ion) m/z: 324.4 (M+1). $^1$H-NMR: (400 MHz, DMSO-$d_6$, ppm) δ 12.69 (s, 0.7 HCOOH), 8.16 (d, J=1.6 Hz, 1H), 8.13 (s, 0.7HCOOH), 8.02 (s, 2H), 7.92 (s, 1H), 7.76-7.70 (m, 3H), 7.50 (d, J=8.4 Hz, 1H), 7.23 (s, 1H), 7.04 (d, J=8.1 Hz, 2H), 5.52 (s, 2H), 2.86 (q, J=7.5 Hz, 2H), 1.28 (t, J=7.5 Hz, 3H).

Example 21

Synthesis of 4-((5-(methoxycarbonyl)indazol-1-yl)methyl)phenylboronic acid (21a), 1-(4-boronobenzyl)-1H-indazole-5-carboxylic acid (21b) and 4-((5-carbamoylindazol-1-yl)methyl)phenylboronic acid (21c 21a

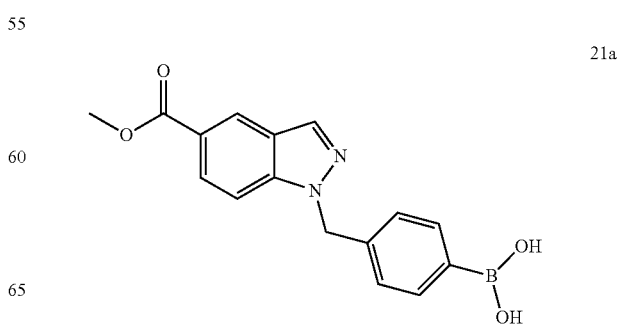

-continued

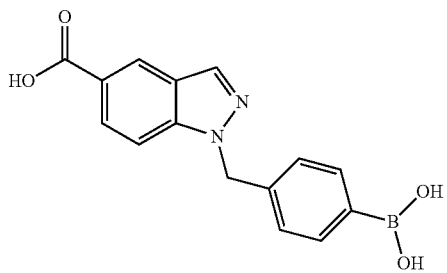

22b

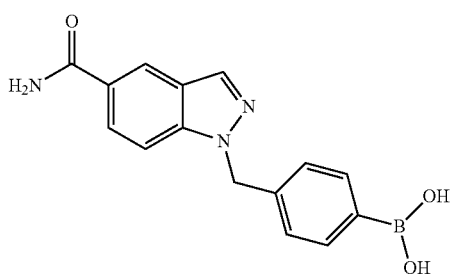

22c

Step 1: 4-((5-(methoxycarbonyl)indazol-1-yl)methyl)phenylboronic acid (21a

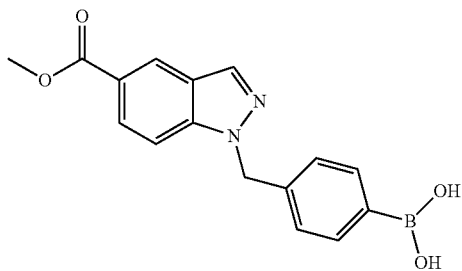 [SMILES: COC(=O)c1ccc2c(cnn2Cc2ccc(B(O)O)cc2)c1]

To a stirred solution of methyl 1H-indazole-5-carboxylate (300 mg, 1.70 mmol, 1.00 equiv) in methanol (15 mL) was added 4-(bromomethyl)phenylboronic acid (439 mg, 2.04 mmol, 1.20 equiv) and potassium carbonate (471 mg, 3.41 mmol, 2.00 equiv) at room temperature. After stirring overnight at 80° C., the resulting mixture was filtered. The filter cake was washed with methanol. The filtrate was concentrated under reduced pressure. The crude product was purified by prep-HPLC with following conditions Column: Sunfire prep C18 column, 30×150 mm, 5 um; Mobile Phase A: Water (0.1% FA), Mobile Phase B: acetonitrile; Flow rate: 60 mL/min; Gradient: 28% B to 36% B in 11 min; 220 & 254 nm. The fractions containing the desired product were combined and lyophilized to give the title compound. Fraction 1: Rt: 7.8 min. 220 mg (37% yield) of 4-((5-(methoxycarbonyl)indazol-1-yl)methyl)phenylboronic acid (21a) as a white solid. 1H-NMR: (300 MHz, DMSO-$d_6$, ppm) δ 8.51 (dd, J=1.6, 0.8 Hz, 1H), 8.32 (d, J=0.9 Hz, 1H), 8.01 (s, 2H), 7.97-7.89 (m, 1H), 7.81 (m, 1H), 7.74-7.66 (m, 2H), 7.18 (d, J=8.0 Hz, 2H), 5.71 (s, 2H), 3.87 (d, J=1.5 Hz, 3H).

Step 2: 1-((4-(dihydroxyboranyl)phenyl)methyl)indazole-5-carboxylic acid and 4-((5-carbamoylindazol-1-yl)methyl)phenylboronic acid

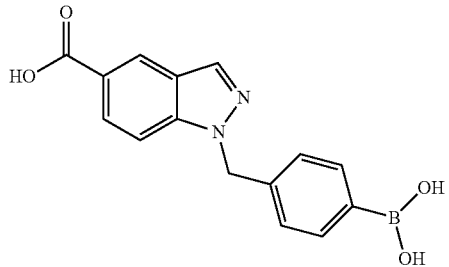

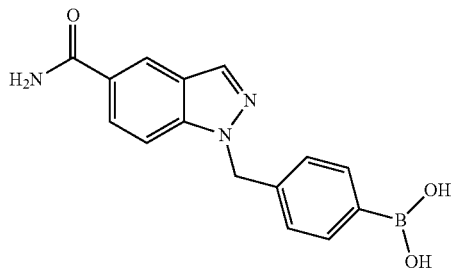

A solution of 4-((5-(methoxycarbonyl)indazol-1-yl)methyl)phenylboronic acid (21a) (220 mg, 0.64 mmol, 1.00 equiv, 90% purity) in aqueous ammonia (10 mL) was stirred for 1.5 h at room temperature. Then the reaction mixture was concentrated under reduced pressure. The crude product was purified by prep-HPLC with following conditions Column: Sunfire prep C18 column, 30×150 mm, 5 um; Mobile Phase A: Water (0.1% FA), Mobile Phase B: acetonitrile; Flow rate: 60 mL/min; Gradient: 5% B to 50% B in 7 min; 220 & 254 nm. The fractions containing the desired product were combined and lyophilized to give two fractions.

Fraction 1: Rt: 5.42 min. 32.8 mg (17%) 1-((4-(dihydroxyboranyl)phenyl)methyl)indazole-5-carboxylic acid (22c) as a white solid. MS (ESI, pos. ion) m/z: 297.2 (M+1). $^1$H-NMR: (300 MHz, DMSO-$d_6$, ppm) δ 12.79 (s, 1H), 8.50-8.42 (m, 1H), 8.33-8.25 (m, 1H), 8.04-7.87 (m, 3H), 7.82-7.67 (m, 3H), 7.24-7.14 (m, 2H), 5.71 (s, 2H).

Fraction 2: Rt: 6.50 min. 50.9 mg (27% yield) of 4-((5-carbamoylindazol-1-yl)methyl)phenylboronic acid (22d) as a white solid. MS (ESI, pos. ion) m/z: 295.9 (M+1). $^1$H-NMR: (300 MHz, DMSO-$d_6$, ppm) δ 8.37 (d, J=1.3 Hz, 1H), 8.25 (d, J=0.9 Hz, 1H), 8.01 (s, 3H), 7.91 (dd, J=8.8, 1.6 Hz, 1H), 7.78-7.67 (m, 3H), 7.33-7.27 (m, 1H), 7.22-7.13 (m, 2H), 5.70 (s, 2H).

Example 22

Synthesis of (4-((6-carbamoyl-2-methyl-1H-benzo[d]imidazol-1-yl)methyl)phenyl)boronic acid (22a) and (4-((5-carbamoyl-2-methyl-1H-benzo[d]imidazol-1-yl)methyl)phenyl)boronic acid (22b

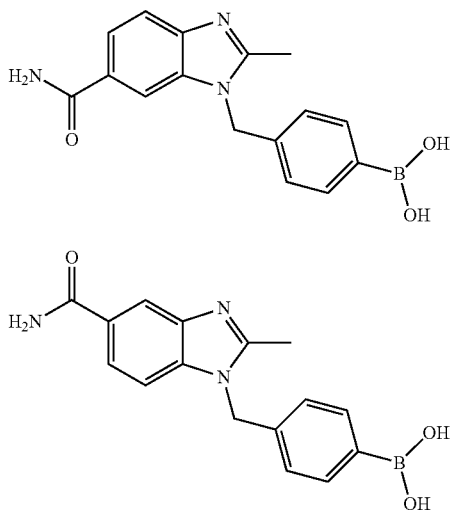

Step 1: methyl 2-methyl-1H-1,3-benzodiazole-5-carboxylate

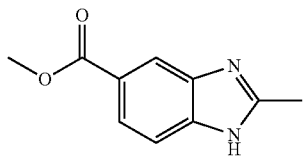

To a stirred solution of methyl 3,4-diaminobenzoate (1.00 g, 6.02 mmol, 1.00 equiv) in dimethylacetamide (15 mL) was added imidazole hydrochloride (307 mg, 3.01 mmol, 0.50 equiv) at room temperature. After stirring for 8 h at 150° C., the mixture was poured into water. The aqueous layer was extracted with methylene chloride. The organic layers were combined, dried over anhydrous sodium sulfate, filtered and evaporated under reduced pressure. The residue was purified by column chromatography (silica gel, eluent: PE/EA 4:1) to give 0.95 g (71% yield) of methyl 2-methyl-1H-1,3-benzodiazole-5-carboxylate as a brown solid.

Step 2: 2-Methyl-1H-1,3-benzodiazole-5-carboxylic acid

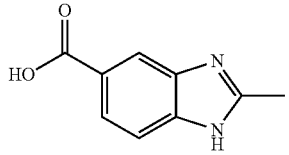

To a stirred solution of methyl 2-methyl-1H-1,3-benzodiazole-5-carboxylate (500 mg, 2.63 mmol, 1.00 equiv, 86%) in MeOH (5.00 mL) and H₂O (5.00 mL) was added NaOH (210 mg, 5.23 mmol, 2 equiv) at room temperature. After stirring for 2 h at room temperature, the mixture was acidified to pH 4~5 with concentrated hydrochloric acid at 0° C. The precipitated solid was collected by filtration, washed with water and dried in vacuo to give 300 mg (74% yield) 2-methyl-1H-1,3-benzodiazole-5-carboxylic acid.

Step 3: 2-methyl-1H-1,3-benzodiazole-5-carboxamide

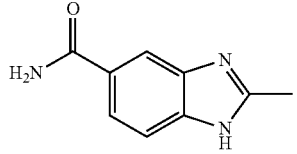

A suspension of 2-Methyl-1H-1,3-benzodiazole-5-carboxylic acid (300 mg, 1.70 mmol, 1.00 equiv) in thionyl chloride (10 mL) was stirred for 1 hour at 80° C. After cooling to room temperature, the mixture was evaporated to dryness under reduced pressure. The residue was suspended in dichloromethane (10 mL) and added into a stirring solution of ammonia in methanol (10 mL, 7 M, 70 mmol, 41.11 equiv.) at room temperature slowly. The resulting mixture was stirred for 2 hours at room temperature and concentrated under reduced pressure to give 180 mg (60% yield) of 2-methyl-1H-1,3-benzodiazole-5-carboxamide as an off-white solid. MS (ESI, pos. ion) m/z: 176.25 (M+1).

Step 4: (4-((6-carbamoyl-2-methyl-1H-benzo[d]imidazol-1-yl)methyl)phenyl)-boronic acid (22a) and (4-((5-carbamoyl-2-methyl-1H-benzo[d]imidazol-1-yl)methyl)-phenyl)boronic acid (22b

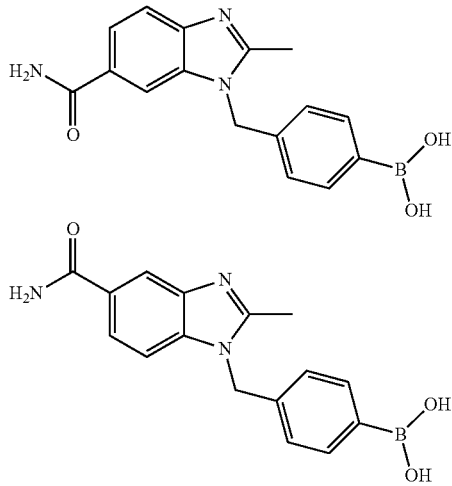

To a suspension of sodium hydride (43 mg, 1.78 mmol, 2.0 equiv.) in N, N-dimethylformamide (8 mL) was added 1H-1,3-benzodiazole-5-carboxamide (180 mg, 0.89 mmol, 1.00 equiv, 80%) at 0° C. After stirring for 30 minutes at 0° C., 4-(bromomethyl)phenylboronic acid (230 mg, 1.07 mmol, 1.20 equiv) was added at this temperature and the mixture was further stirred for 2 hours at room temperature. The mixture was quenched with 2 N hydrogen chloride and concentrated under reduced pressure. The residue was purified by prep-HPLC with Column: Sunfire prep C18 column, 30*150, 5 um; Mobile Phase A: Water (0.1% FA), Mobile Phase B: ACN; Flow rate: 60 mL/min; Gradient: 2 B to 9 B in 10 min; 254/220 nm; RT1:7.62; 9.32; RT2; Injection Volumn: ml; Number Of Runs. The fractions containing the desired product were combined and lyophilized to give two fractions.

Fraction 1: Rt: 7.62 min. 84 mg (29% yield) 4-((6-carbamoyl-2-methyl-1,3-benzodiazol-1-yl)methyl)phenylboronic acid (22a) as a white solid. MS (ESI, pos. ion) m/z: 310.3 (M+1). $^1$H NMR (300 MHz, DMSO-$d_6$) δ 12.95-12.63 (s, 0.3 HCOOH), δ 8.20-7.91 (m, 4H), 7.73 (d, J=7.8 Hz, 3H), 7.50 (d, J=8.5 Hz, 1H), 7.24 (s, 1H), 7.07 (d, J=7.9 Hz, 2H), 5.51 (s, 2H), 2.53 (s, 3H).

Fraction 2: Rt: 9.32 min. 110 mg (37% yield) 4-((5-carbamoyl-2-methyl-1,3-benzodiazol-1-yl)methyl)phenylboronic acid (22b) as a white solid. MS (ESI, pos. ion) m/z: 310.3 (M+1). $^1$H NMR (300 MHz, DMSO-$d_6$) δ 8.14 (s, 1H), 8.05 (s, 2H), 7.92 (s, 1H), 7.74 (d, J=7.7 Hz, 3H), 7.58 (d, J=8.4 Hz, 1H), 7.28 (s, 1H), 7.07 (d, J=7.7 Hz, 2H), 5.51 (s, 2H), 2.54 (d, J=2.2 Hz, 3H).

Example 23

Synthesis of 4-((6-carbamoyl-2-isopropyl-1,3-benzodiazol-1-yl)methyl)phenylboronic acid (23a) and 4-((5-carbamoyl-2-isopropyl-1,3-benzodiazol-1-yl)methyl)phenylboronic acid (23b

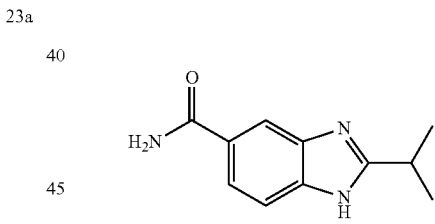

Step 1: methyl 2-isopropyl-1H-1,3-benzodiazole-5-carboxylate

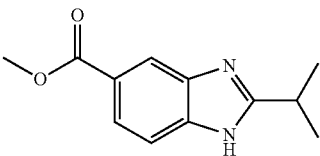 [SMILES: COC(=O)c1ccc2[nH]c(C(C)C)nc2c1]

The title compound was synthesized by the method described in step 1 of Example 22 except N,N-dimethylisobutyramide (5 mL) was used in place of dimethylacetamide.

Step 2: 2-isopropyl-1H-1,3-benzodiazole-5-carboxylic acid

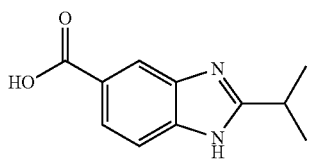

The title compound was synthesized by the method described in step 2 of Example 22 except methyl 2-isopropyl-1H-1,3-benzodiazole-5-carboxylate (220 mg) and sodium hydroxide (121 mg, 3.02 mmol 3.00 equiv.) were used.

Step 3: 2-isopropyl-1H-1,3-benzodiazole-5-carboxamide

The title compound was synthesized by the method described in step 3 of example 22 except 2-isopropyl-1H-1,3-benzodiazole-5-carboxylic acid (180 mg) was used.

Step 4: 4-((6-carbamoyl-2-isopropyl-1,3-benzodiazol-1-yl)methyl)phenylboronic acid (23a) and 4-((5-carbamoyl-2-isopropyl-1,3-benzodiazol-1-yl)methyl)phenylboronic acid (23b

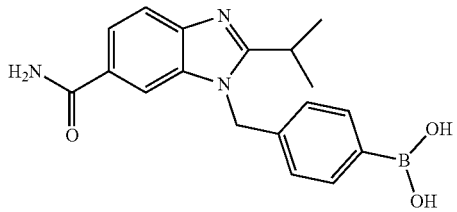

-continued

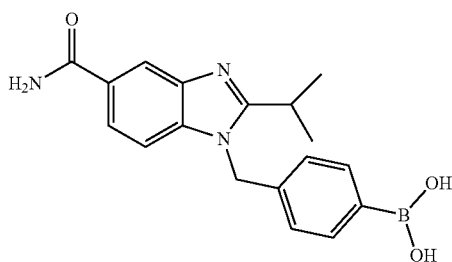

The title compound was synthesized by the method described in step 4 of example 22 except 2-isopropyl-1H-1,3-benzodiazole-5-carboxamide (160 mg) was used. The crude product was purified by prep-HPLC with following conditions Column XBridge C18 OBD column, 100 Å, 19×250, 5 um; Mobile Phase A: Water (0.1% FA), Mobile Phase B: acetonitrile; Flow rate: 25 mL/min; Gradient: 7% B to 15% B in 7 min; 220 & 254 nm. The fractions containing the desired product were combined and lyophilized to give two fractions.

Fraction 1: Rt=5.55 min. 43.4 mg (16% yield) of 4-((6-carbamoyl-2-isopropyl-1,3-benzodiazol-1-yl)methyl)phenylboronic acid (23a) as a white solid. MS (ESI, pos. ion) m/z: 338.3 (M+1). $^1$H-NMR (400 MHz, DMSO-$d_6$, ppm) δ 8.06-8.01 (m, 3H), 7.90 (s, 1H), 7.76-7.67 (m, 3H), 7.62 (d, J=8.3 Hz, 1H), 7.59 (s, 1H), 7.00 (d, J=8.0 Hz, 2H), 5.56 (s, 2H), 3.31-3.22 (m, 1H), 1.24 (d, J=6.8 Hz, 6H).

Fraction 2: Rt=7.22 min. 37.6 mg (13% yield) of 4-((5-carbamoyl-2-isopropyl-1,3-benzodiazol-1-yl)methyl)phenylboronic acid (23b) as a white solid. MS (ESI, pos. ion) m/z: 338.4 (M+1). $^1$H-NMR (400 MHz, DMSO-$d_6$, ppm) δ 8.16 (s, 1H), 8.03 (s, 2H), 7.91 (s, 1H), 7.74-7.70 (m, 3H), 7.46 (d, J=8.4 Hz, 1H), 7.24 (s, 1H), 7.00 (d, J=8.0 Hz, 2H), 5.55 (s, 2H), 3.31-3.22 (m, 1H), 1.24 (d, J=6.8 Hz, 6H)

Example 24

Synthesis of 4-((5-carbamoyl-1,3-benzodiazol-1-ylmethyl)phenylphosphonic acid

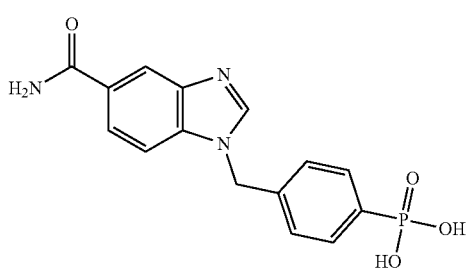 [SMILES: NC(=O)c1ccc2c(c1)ncn2Cc1ccc(P(=O)(O)O)cc1]

Step 1: methyl 3-((4-bromophenyl)methyl)-1,3-benzodiazole-5-carboxylate and methyl 1-((4-bromophenyl)methyl)-1,3-benzodiazole-5-carboxylate

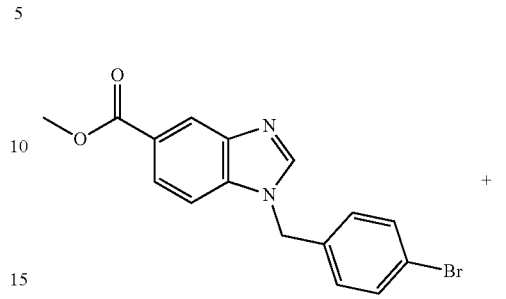

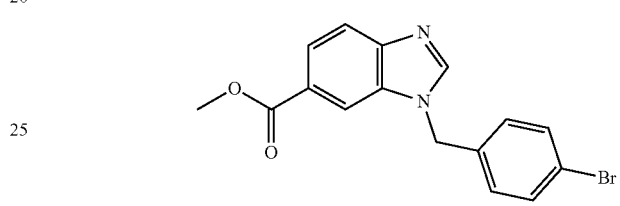

Methyl 1H-1,3-benzodiazole-5-carboxylate (1.50 g, 8.51 mmol, 1.00 equiv) was dissolved in MeOH (20.00 mL). Then 1-bromo-4-(bromomethyl)benzene (2.56 g, 10.22 mmol, 1.20 equiv) and $Cs_2CO_3$ (3.61 g, 11.07 mmol, 1.30 equiv) were added. After stirring for 12 h at room temperature, the reaction mixture was concentrated under reduced pressure, diluted with water and extracted with methylene chloride. The organic layers were combined, dried over anhydrous sodium sulfate, filtered and evaporated under reduced pressure. The residue was purified by column chromatography (silica gel, eluent: DCM/MEOH 98:2) to give 2.3 g (77% yield) of a mixture of methyl 3-((4-bromophenyl)methyl)-1,3-benzodiazole-5-carboxylate and methyl 1-((4-bromophenyl)methyl)-1,3-benzodiazole-5-carboxylate as a yellow solid Step 2: 3-((4-(diethoxyphosphoryl)phenyl)methyl)-1,3-benzodiazole-5-carboxylate and methyl 1-((4-(diethoxyphosphoryl)phenyl)methyl)-1,3-benzodiazole-5-carboxylate

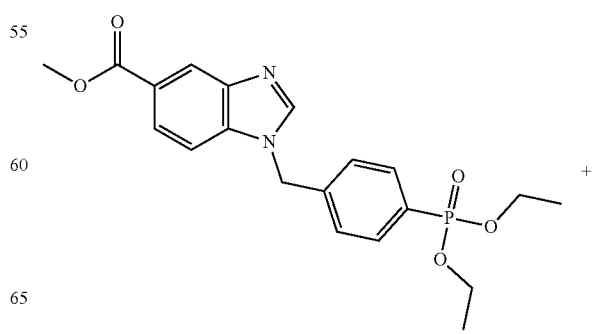

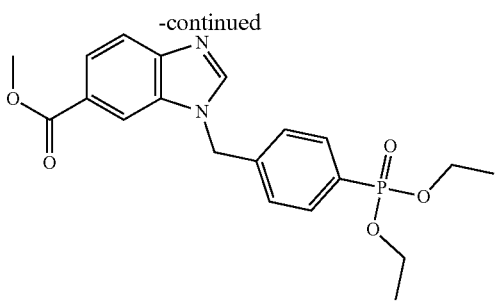

To a mixture of methyl 3-((4-bromophenyl)methyl)-1,3-benzodiazole-5-carboxylate and methyl 1-((4-bromophenyl)methyl)-1,3-benzodiazole-5-carboxylate (1.20 g, 3.44 mmol, 1.00 equiv, 99%) in THF (15.00 mL) were added diethyl phosphite (0.62 g, 4.47 mmol, 1.30 equiv), $Cs_2CO_3$ (1.68 g, 5.16 mmol, 1.50 equiv) and $Pd(PPh_3)_4$ (398 mg, 0.34 mmol, 0.10 equiv) at room temperature. The resulting mixture was irradiated for 3 h at 100° C. in a microwave reactor. The reaction mixture was concentrated under reduced pressure, diluted with water and extracted with methylene chloride. The organic layers were combined, dried over anhydrous sodium sulfate, filtered and evaporated under reduced pressure. The residue was purified by column chromatography (silica gel, eluent: DCM/MeOH 96:4) to give 0.8 g (56% yield) of a mixture of methyl 3-((4-(diethoxyphosphoryl)phenyl)methyl)-1,3-benzodiazole-5-carboxylate and methyl 1-((4-(diethoxyphosphoryl)phenyl)methyl)-1,3-benzodiazole-5-carboxylate as a yellow solid (ratio=1:1).

Step 3: diethyl 4-((5-carbamoyl-1,3-benzodiazol-1-yl)methyl)phenyl-phosphonate

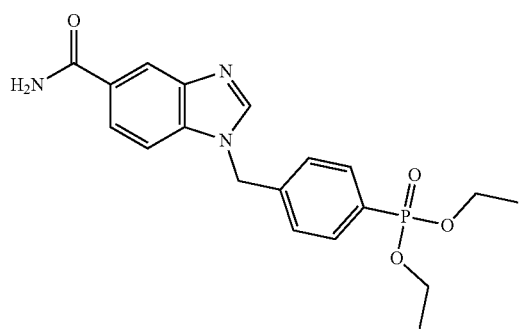 [SMILES: CCOP(=O)(OCC)c1ccc(Cn2cnc3cc(C(N)=O)ccc32)cc1]

A mixture of methyl 3-((4-(diethoxyphosphoryl)phenyl)methyl)-1,3-benzodiazole-5-carboxylate and methyl 1-((4-(diethoxyphosphoryl)phenyl)methyl)-1,3-benzodiazole-5-carboxylate (700 mg, 1.69 mmol, 1.00 equiv) was added to $NH_3$—$H_2O$ (15.00 mL). After stirring for 2 h at 80° C., the reaction mixture was concentrated under reduced pressure. The residue was purified by Column: XBridge Shield RP18 OBD Column, 30*150 mm, 5 um; Mobile Phase A: Water (0.05% $NH_3H_2O$), Mobile Phase B: ACN; Flow rate: 60 mL/min; Gradient: 13 B to 16 B in 7 min; 254/220 nm; RT 5.48; Injection Volumn: ml; Number Of Runs to give 80 mg (12% yield) diethyl 4-((5-carbamoyl-1,3-benzodiazol-1-yl)methyl)phenyl-phosphonate as a white solid. MS (ESI, pos. ion) m/z: 388.00 (M+1). $^1$H NMR (300 MHz, Methanol-$d_4$) δ 8.46 (s, 1H), 8.30 (dd, J=1.7, 0.7 Hz, 1H), 7.93-7.69 (m, 3H), 7.56-7.35 (m, 3H), 5.66 (s, 2H), 4.10 (m, 4H), 1.31 (m, 6H).

Step 4: 4-((5-carbamoyl-1,3-benzodiazol-1-yl)methyl)phenylphosphonic acid

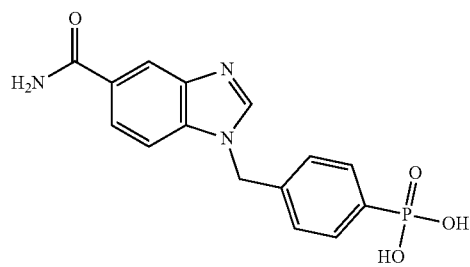 [SMILES: NC(=O)c1ccc2c(c1)ncn2Cc1ccc(P(=O)(O)O)cc1]

To a stirred solution of diethyl 4-((5-carbamoyl-1,3-benzodiazol-1-yl)methyl)phenylphosphonate (75.00 mg, 0.19 mmol, 1.00 equiv) in DCM (5.00 mL) was added bromotrimethylsilane (296.40 mg, 1.97 mmol, 10.00 equiv) dropwise at room temperature. The resulting mixture was stirred for 12 h at room temperature. The reaction was quenched by the addition of MeOH (5 mL). After concentration under reduced pressure, the crude product was washed with hexane (5 mL) and MeOH/DCM=1:1 (5 mL×2) to afford 25.3 mg (39% yield) 4-((5-carbamoyl-1,3-benzodiazol-1-yl)methyl)phenylphosphonic acid as a white solid. MS (ESI, pos. ion) m/z: 332.25 (M+1). $^1$H NMR (300 MHz, DMSO-$d_6$) δ 9.40 (d, J=4.0 Hz, 1H), 8.31 (d, J=1.5 Hz, 1H), 8.14 (s, 1H), 7.97 (dd, J=8.7, 1.5 Hz, 1H), 7.79 (d, J=8.6 Hz, 1H), 7.74-7.61 (m, 2H), 7.48 (dd, J=8.1, 3.2 Hz, 3H), 5.76 (s, 2H).

Example 25

Synthesis of diethyl (4-((4-methoxy-1H-pyrazolo[4,3-c]pyridin-1-yl)methyl)phenyl)phosphonate (25a) and 4-((4-hydroxypyrazolo[4,3-c]pyridin-1-yl)methyl)phenylphosphonic acid (25b 25a

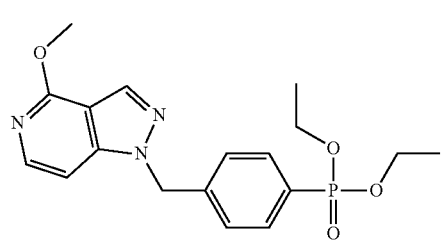

25b

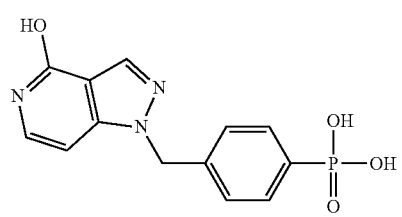

Step 1: 4-methoxy-1H-pyrazolo[4,3-c]pyridine

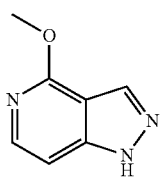

To 4-chloro-1H-pyrazolo[4,3-c]pyridine (1.00 g, 6.51 mmol, 1.00 equiv) was added NaOMe (17.00 mL, 30% in MeOH) at room temperature. The resulting mixture was stirring for 12 hours at 120° C. in an oil bath. After cooling to room temperature, the mixture was diluted with water and extracted with ethyl acetate. The combined organic layers were washed with saturated sodium chloride aqueous solution, dried over anhydrous sodium sulfate. The organic layer was concentrated under reduced pressure to afford 4-methoxy-1H-pyrazolo[4,3-c]pyridine (520 mg, 52.29% yield) as a white solid. MS (ESI, pos. ion) m/z: 149.95 (M+1).

Step 2: diethyl 4-((4-methoxypyrazolo[4,3-c]pyridin-1-yl)methyl)phenylphosphonate (96a

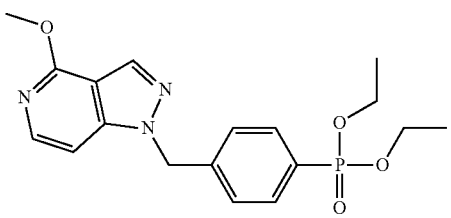 [SMILES: CCOP(=O)(OCC)c1ccc(Cn2ncc3c(OC)nccc32)cc1]

The title compound was were synthesized by the method described in step 2 of Example 55 except 4-methoxy-1H-pyrazolo[4,3-c]pyridine (250.00 mg, 1.68 mmol) and diethyl 4-(bromomethyl)phenylphosphonate (772 mg, 2.51 mmol) were used. The crude product was purified by prep-HPLC with the following conditions (Column: YMC-Actus Triart C18, 30*250.5 um; Mobile Phase A: Water (0.05% FA), Mobile Phase B: ACN:MEOH=4:1; Flow rate: 45 mL/min; Gradient: 25 B to 40 B in 10 min; 254,220 nm; RT1:6.48 min; RT2:7.75 min) to give the title compound.

Fraction 1: Rt: 6.48 min. 100 mg (15.9% yield) of diethyl 4-((4-methoxypyrazolo[4,3-c]pyridin-1-yl)methyl)phenylphosphonate (25a) as a white solid. MS (ESI, pos. ion) m/z: 376.10 (M+1). $^1$H NMR (300 MHz, DMSO-$d_6$, ppm) δ 8.42 (s, 1H), 7.86 (d, J=5.8 Hz, 1H), 7.76-7.62 (m, 2H), 7.45-7.35 (m, 2H), 7.21 (d, J=5.8 Hz, 1H), 5.61 (s, 2H), 4.05-3.91 (m, 7H), 1.20 (t, J=7.0 Hz, 6H).

Step 3: 4-((4-hydroxypyrazolo[4,3-c]pyridin-1-yl)methyl)phenylphosphonic acid (25b

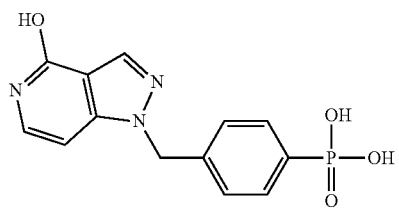 [SMILES: O=P(O)(O)c1ccc(Cn2ncc3c(O)nccc32)cc1]

The title compound was synthesized by the in step 2 of Example 35 except diethyl 4-((4-methoxypyrazolo[4,3-c]pyridin-1-yl)methyl)-phenylphosphonate (100.00 mg, 0.27 mmol) was used to give 4-((4-hydroxypyrazolo[4,3-c]pyridin-1-yl)methyl)phenylphosphonic acid (25b, 16.2 mg, 19.6%). MS (ESI, pos. ion) m/z: 306.20 (M+1). $^1$H NMR (300 MHz, DMSO-$d_6$, ppm/$D_2O$) δ 11.90 (s, 1H), 9.22 (s, 1H), 7.72-7.62 (m, 2H), 7.48-7.37 (m, 3H), 6.68 (d, J=7.2 Hz, 1H), 5.64 (s, 2H).

Example 26

Synthesis of diethyl (4-((5-carbamoyl-1H-indazol-1-yl)methyl)phenyl)phosphonate (26a) and 4-((5-carbamoylindazol-1-yl)methyl)phenylphosphonic acid (26b

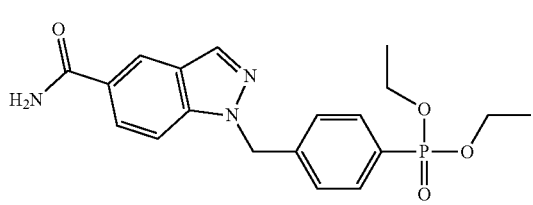

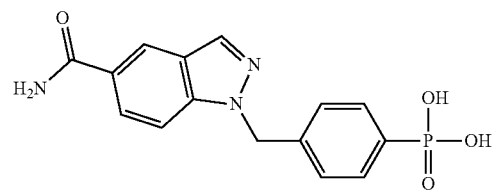

Step 1: 1H-indazole-5-carboxamide

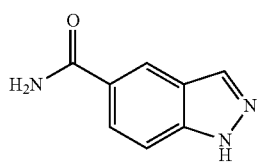 [SMILES: NC(=O)c1ccc2[nH]ncc2c1]

Methyl 1H-indazole-5-carboxylate (500 mg, 2.84 mmol, 1.00 equiv) in $NH_3 \cdot H_2O$ (10 mL) was stirred for 12 hours at 80° C. in an oil bath. After cooling to room temperature, the mixture was concentrated under reduced pressure. The resi- Step 2: diethyl 4-((5-carbamoylindazol-1-yl)methyl)phenylphosphonate (26a

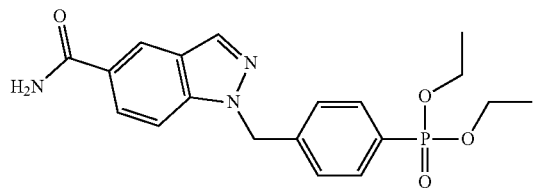 [SMILES: CCOP(=O)(OCC)c1ccc(Cn2ncc3cc(C(N)=O)ccc32)cc1]

The title compound was synthesized by the in step 2 of Example 55 except 1H-indazole-5-carboxamide (122 mg, 0.76 mmol) and 4-(bromomethyl)phenylphosphonate (348.74 mg, 1.14 mmol) were used. The crude product was purified by prep-HPLC with the following conditions (Column: YMC-Actus Triart C18, 30*250.5 um; Mobile Phase A: Water (0.05% FA), Mobile Phase B: ACN; Flow rate: 45 mL/min; Gradient: 25 B to 30 B in 7 min; 254/220 nm, RT1:6.17 min; RT2: 8.20 min). The fractions containing the desired product were combined and lyophilized to give the title compound.

Fraction 1: Rt: 6.17 min. 89 mg (44.9% yield) of diethyl 4-((5-carbamoylindazol-1-yl)methyl)phenylphosphonate (26a) as a white solid. MS (ESI, pos. ion) m/z: 388.25 (M+1). $^1$H NMR (300 MHz, DMSO-$d_6$, ppm) δ 8.38 (s, 1H), 8.31-8.25 (m, 1H), 8.00 (s, 1H), 7.93 (dd, J=8.9, 1.5 Hz, 1H), 7.77 (d, J=8.9 Hz, 1H), 7.67 (dd, J=12.9, 7.9 Hz, 2H), 7.34 (dd, J=8.0, 3.9 Hz, 3H), 5.79 (s, 2H), 3.98 (m, 4H), 1.20 (t, J=7.0 Hz, 6H).

Step 3: 4-((5-carbamoylindazol-1-yl)methyl)phenylphosphonic acid (26b

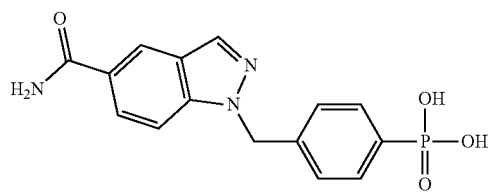 [SMILES: NC(=O)c1ccc2c(cnn2Cc2ccc(P(=O)(O)O)cc2)c1]

The title compound was synthesized by the in step 2 of Example 85 except diethyl 4-((5-carbamoylindazol-1-yl)methyl)phenyl-phosphonate (89 mg, 0.23 mmol) was used. (26b, 27.4 mg, 35.7%). MS (ESI, pos. ion) m/z: 330.15 (M-1). $^1$H NMR (300 MHz, DMSO-$d_6$, ppm) δ 8.37 (d, J=1.4 Hz, 1H), 8.26 (s, 1H), 7.98 (s, 1H), 7.91 (dd, J=8.7, 1.6 Hz, 1H), 7.74 (d, J=8.8 Hz, 1H), 7.59 (dd, J=12.5, 7.9 Hz, 2H), 7.49-6.89 (m, 3H), 5.72 (s, 2H).

Example 28

Synthesis of a mixture of (4-((5-(methylsulfonyl)-1H-benzo[d]imidazol-1-yl)methyl)phenyl)-boronic acid (28a) acid and 4-((6-(methylsulfonyl)-1H-benzo[d]imidazol-1-yl)methyl)phenyl)boronic acid (28b

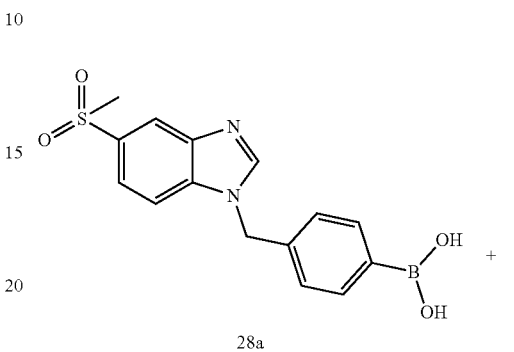

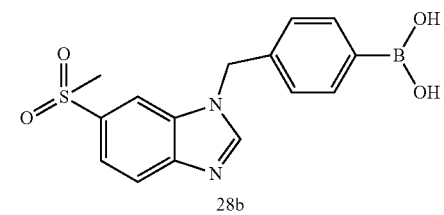

Step 1: 5-methanesulfonyl-1H-1,3-benzodiazole

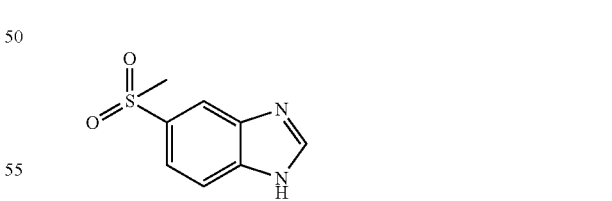

To a stirred solution of 4-methanesulfonylbenzene-1,2-diamine (150 mg, 0.81 mmol, 1.00 equiv) in N,N-dimethylformamide (4 mL) was added HMDS (130 mg, 0.805 mmol, 1.00 equiv). After stirring overnight at 120° C., the resulting mixture was concentrated under reduced pressure. The residue was dissolved in methanol (10 mL) and the precipitated solid was collected by filtration, washed with methanol and dried under vacuum to give 150 mg (84%) of 5-methanesulfonyl-1H-1,3-benzodiazole as a grey solid.

Step 2: a mixture of 4-((5-methanesulfonyl-1,3-benzodiazol-1-yl)methyl)phenylboronic acid and 4-((6-methanesulfonyl-1,3-benzodiazol-1-yl)methyl)phenylboronic acid

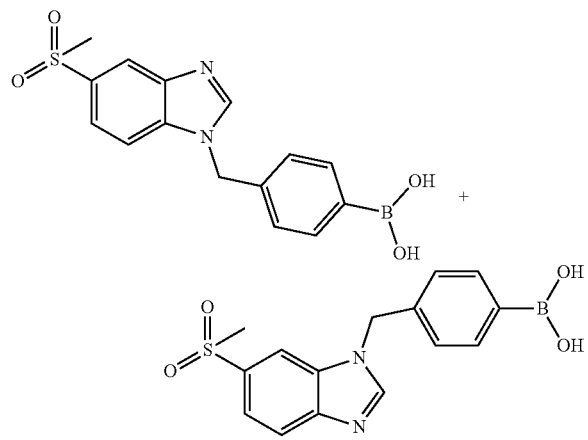

To a stirred solution of 5-methanesulfonyl-1H-1,3-benzodiazole (150 mg, 0.68 mmol, 1.00 equiv, 89%) in N,N-dimethylformamide (5 mL) were added 4-(bromomethyl)phenylboronic acid (175 mg, 0.82 mmol, 1.20 equiv) and potassium carbonate (188 mg, 1.36 mmol, 2.00 equiv) at 0° C. After stirring overnight at room temperature, the resulting mixture was concentrated under reduced pressure. The residue was dissolved in methanol (20 mL) and the solids filtered off. The filtrate was concentrated and purified by prep-HPLC with the following conditions Column: XBridge Shield RP18 OBD Column, 19×250 mm, 10 um; Mobile Phase A: Water (10 mmol/L ammonium bicarbonate), Mobile Phase B: acetonitrile; Flow rate: 25 mL/min; Gradient: 20% B to 25% B in 7 min, 220 & 254 nm. The fractions containing the desired products were combined and lyophilized to give 44.5 mg (18%) a mixture of 4-((5-methanesulfonyl-1,3-benzodiazol-1-yl)methyl)phenylboronic acid (97a) and 4-((6-methanesulfonyl-1,3-benzodiazol-1-yl)methyl)phenylboronic acid (97b) (ratio 1:1) as a white solid. MS (ESI, pos. ion) m/z: 331.2 (M+1). $^1$H-NMR: (300 MHz, DMSO-$d_6$, ppm) δ 8.71-8.67 (m, 1H), 8.22-8.15 (m, 1H), 8.05 (s, 2H), 7.92-7.73 (m, 4H), 7.28-7.25 (m, 2H), 5.64-5.59 (m, 2H), 3.20-3.18 (m, 3H).

Example 29

Synthesis of a mixture of (4-((5-cyano-1H-benzo[d]imidazol-1-yl)methyl)phenyl)phosphonic acid (29a) and (4-((6-cyano-1H-benzo[d]imidazol-1-yl)methyl)phenyl)phosphonic acid (29b

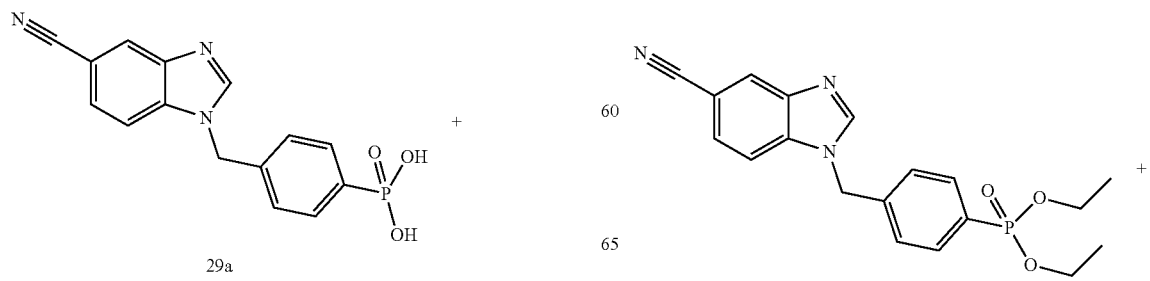

Step 1: 1-((4-bromophenyl)methyl)-1,3-benzodiazole-5-carbonitrile and 3-((4-bromophenyl)methyl)-1,3-benzodiazole-5-carbonitrile

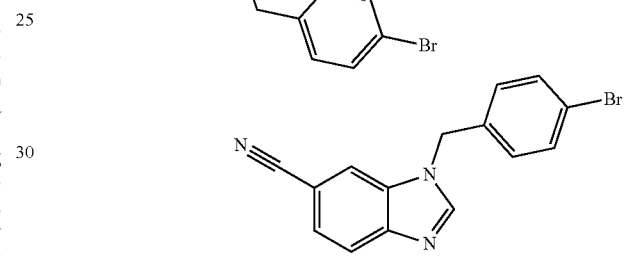

To a solution of 1H-1,3-benzodiazole-5-carbonitrile (400 mg, 2.794 mmol, 1.00 equiv) in ethanol (10 mL) were added potassium hydroxide powder (204 mg, 3.633 mmol, 1.30 equiv) and 1-bromo-4-(bromomethyl)benzene (838 mg, 3.353 mmol, 1.20 equiv). After stirring at room temperature for 12 h, the reaction mixture was diluted with water and extracted with ethyl acetate. The combined organic layers were washed with water and brine, dried over anhydrous sodium sulfate and filtered. The filtrate was concentrated under reduced pressure. The residue was purified by silica gel column chromatography (eluent: dichloromethane/methanol 97:3) to give 510 mg of a mixture of 1-((4-bromophenyl)methyl)-1,3-benzodiazole-5-carbonitrile and 3-((4-bromophenyl)methyl)-1,3-benzodiazole-5-carbonitrile as an off-white solid.

Step 2: diethyl 4-((5-cyano-1,3-benzodiazol-1-yl)methyl)phenylphosphonate and diethyl 4-((6-cyano-1,3-benzodiazol-1-yl)methyl)phenylphosphonate

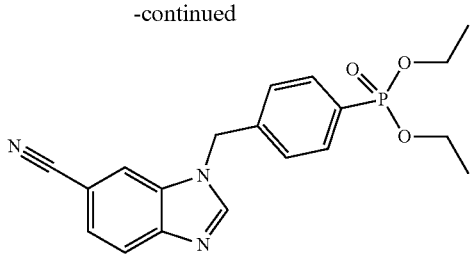

A mixture of 1-((4-bromophenyl)methyl)-1,3-benzodiazole-5-carbonitrile and 3-((4-bromophenyl)methyl)-1,3-benzodiazole-5-carbonitrile (210 mg, 0.666 mmol, 1.00 quiv, 99% purity) in tetrahydrofuran (4 mL) were added tetrakis(triphenylphosphine)palladium (0) (77 mg, 0.067 mmol, 0.10 equiv), cesium carbonate (282 mg, 0.866 mmol, 1.30 equiv) and diethylphosphonate (110 mg, 0.799 mmol, 1.20 equiv) at room temperature. The resulting mixture was irradiated at 100° C. in microwave reactor for 10 minutes. The reaction mixture was concentrated under reduced pressure. The residue was purified by silica gel column chromatography (eluent: dichloromethane/methanol 95:5) to give 225 mg (90%) of a mixture of diethyl 4-((5-cyano-1,3-benzodiazol-1-yl)methyl)phenylphosphonate and diethyl 4-((6-cyano-1,3-benzodiazol-1-yl)methyl)phenylphosphonate as a yellow solid (ratio=1:1). MS (ESI, pos. ion) m/z: 370.35 (M+1).

Step 3: (4-((5-cyano-1H-benzo[d]imidazol-1-yl)methyl)phenyl)phosphonic acid (29a) and (4-((6-cyano-1H-benzo[d]imidazol-1-yl)methyl)phenyl)phosphonic acid (29b

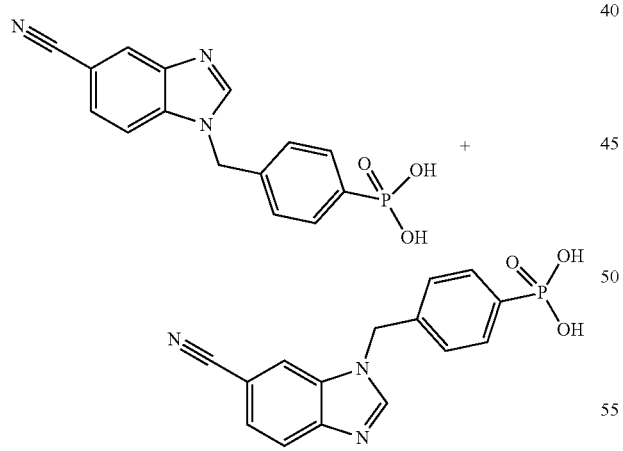

Into a mixture of diethyl 4-((5-cyano-1,3-benzodiazol-1-yl)methyl)phenylphosphonate and diethyl 4-((6-cyano-1,3-benzodiazol-1-yl)methyl)phenylphosphonate (210 mg, 0.563 mmol, 1.00 equiv, 99% purity) in dichloromethane (5 mL) was added bromotrimethylsilane (1.72 g, 11.257 mmol, 20 equiv) at room temperature. The solution was stirred for 2 h at room temperature. The reaction mixture was concentrated under reduced pressure and the residue was purified prep-HPLC with the following conditions. Column: XBridge Shield RP18 OBD Column, 19×250 mm, 10 um; Mobile Phase A: Water (10 mmol/L ammonium bicarbonate), Mobile Phase B: acetonitrile; Flow rate: 25 mL/min; Gradient: 4% B to 18% B in 7 min, 220 & 254 nm. The fractions containing the desired products were combined and lyophilized to give 119.5 mg (66%) of a mixture of (4-((5-cyano-1H-benzo[d]imidazol-1-yl)methyl)phenyl)-phosphonic acid (29a) and (4-((6-cyano-1H-benzo[d]imidazol-1-yl)methyl)phenyl)phosphonic acid (29b) as a white solid (ratio=1:1). MS (ESI, pos. ion) m/z: 314.2 (M+1). $^1$H-NMR: (300 MHz, DMSO-$d_6$, ppm) δ 8.69 (d, J=10.7 Hz, 1H), 8.22 (s, 1H), 7.84 (d, J=8.4 Hz, 1H), 7.72-7.53 (m, 3H), 7.36-6.80 (m, 4H), 5.54 (s, 2H).

Example 30

Synthesis of 4-((5-carbamoyl-4-methoxyindol-1-yl)methyl)phenylboronic acid

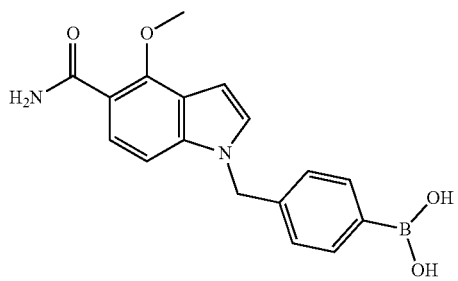

Step 1: 4-amino-5-chloro-2-methoxybenzoate

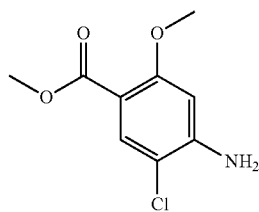

To a stirred solution of methyl 4-amino-2-methoxybenzoate (5.00 g, 27.595 mmol, 1.00 equiv) in DMF (50.00 mL) was added NCS (3.70 g, 27.709 mmol, 1.00 equiv) at room temperature. The resulting mixture was stirred for 12 h at 70° C. in an oil bath and then quenched with water at room temperature. The resulting mixture was extracted with EtOAc and the combined organic layers were washed with brine, and dried over anhydrous $Na_2SO_4$. After filtration, the filtrate was concentrated under reduced pressure and the residue was purified by silica gel column chromatography, eluted with PE/EtOAc (30:70) to afford methyl 4-amino-5-chloro-2-methoxybenzoate (4.9 g, 82.4% yield) as a yellow green solid.

Step 2: 4-amino-5-chloro-3-iodo-2-methoxybenzoate

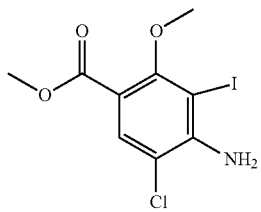

To a solution of methyl 4-amino-5-chloro-2-methoxybenzoate (0.80 g, 3.71 mmol, 1.00 equiv) in AcOH (20.00 mL) were added NIS (0.83 g, 3.71 mmol, 1.00 equiv). After stirring for 4 h at room temperature, the reaction mixture was diluted with ethyl acetate, washed with water and brine. The organic layer was dried with over sodium sulfate, filtered and concentrated under reduced pressure. The residue was purified by silica gel column chromatography (eluent: petroleum ether/ethyl acetate=6:1) to give 1.0 g (79% yield) of methyl 4-amino-5-chloro-3-iodo-2-methoxybenzoate as a white solid.

Step 3: methyl 7-chloro-4-methoxy-2-(trimethylsilyl)-1H-indole-5-carboxylate

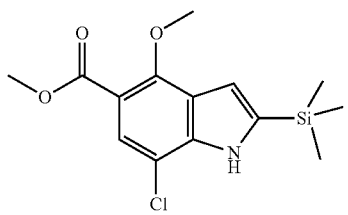

To a mixture of methyl 4-amino-5-chloro-3-iodo-2-methoxybenzoate (1.00 g, 2.93 mmol, 1.00 equiv) in THF (30.00 mL) were added ethynyltrimethylsilane (0.48 g, 5.85 mmol, 2.00 equiv), $K_2CO_3$ (0.81 g, 5.86 mmol, 2.00 equiv), X-Phos (0.28 g, 0.59 mmol, 0.20 equiv) and $Pd(PPh_3)_4$, (0.34 g, 0.29 mmol, 0.10 equiv). After stirring overnight at 80° C. under argon atmosphere, the reaction mixture was cooled to room temperature and concentrated under reduced pressure. The residue was poured into water and the aqueous layer was extracted with ethyl acetate. The organic layers were combined, dried over anhydrous sodium sulfate, filtered and evaporated under reduced pressure. The residue was purified by column chromatography on silica gel 120 g (eluent: petroleum ether-ethyl acetate 100%, 8:1) to give methyl 7-chloro-4-methoxy-2-(trimethylsilyl)-1H-indole-5-carboxylate (350 mg, 31% yield) as a brown solid.

Step 4: methyl 7-chloro-4-methoxy-1H-indole-5-carboxylate

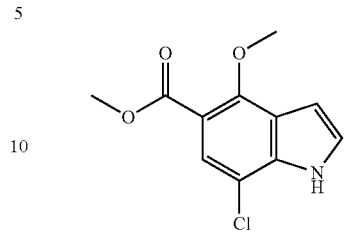

To a mixture of methyl 7-chloro-4-methoxy-2-(trimethylsilyl)-1H-indole-5-carboxylate (350.00 mg, 1.122 mmol, 1.00 equiv) in DCM (10.00 mL) was added TFA (2 mL). After stirring 3 h at room temperature, the reaction mixture was poured into water. The aqueous layer was extracted with DCM and the organic layers were combined, dried over anhydrous sodium sulfate, filtered and evaporated under reduced pressure. The residue was purified by column chromatography on silica gel (eluent: petroleum ether-ethyl acetate 100%, 8:1) to give methyl 7-chloro-4-methoxy-1H-indole-5-carboxylate (250 mg, 87% yield) as a brown solid.

Step 5: methyl 4-methoxy-1H-indole-5-carboxylate

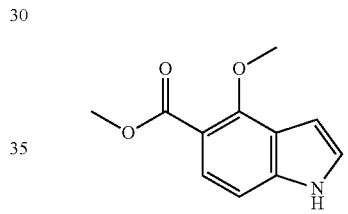

To a mixture of methyl 7-chloro-4-methoxy-1H-indole-5-carboxylate (265 mg, 1.10 mmol, 1.00 equiv) in MeOH (5.00 mL) was added Pd/C (30 mg). After stirring for 24 h, the resulting mixture was filtered through a Celite. The filter cake was washed with MeOH and the filtrate was concentrated under reduced pressure. The residue was purified by column chromatography on silica gel 40 g (eluent: petroleum ether-ethyl acetate 100%, 5:1) to give 4-methoxy-1H-indole-5-carboxamide (210 mg, 94.9% yield) as a light brown solid.

Step 6: 4-methoxy-1H-indole-5-carboxamide

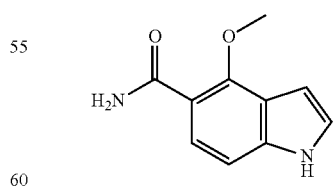

A mixture of methyl 4-methoxy-1H-indole-5-carboxylate (210 mg, 1.02 mmol, 1.00 equiv) in aqueous ammonia (10 mL) was stirred at 80° C. for 12 h. After cooling to room temperature, the reaction mixture was concentrated under reduced pressure. The residue was purified by column chromatography on silica gel 100 g (eluent: MeOH/DCM 100%, 5:95) to give 4-methoxy-1H-indole-5-carboxamide (150 mg, 77% yield) as a light brown solid.

Step 7: 4-((5-carbamoyl-4-methoxyindol-1-yl)methyl)phenylboronic acid

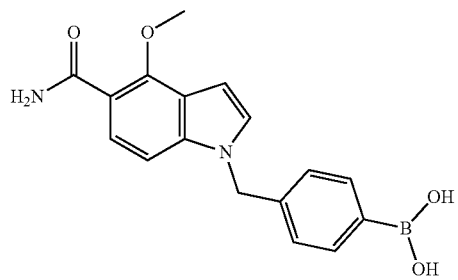

The title compound was synthesized by the in step 4 of Example 22 except 4-methoxy-1H-indole-5-carboxamide (150 mg, 0.79 mmol) was used. The crude product was purified by Prep-HPLC with the following conditions (Column: Sunfire prep C18 column, 30*150, 5 um; Mobile Phase A: Water (0.1% FA), Mobile Phase B: ACN; Flow rate: 60 mL/min; Gradient: 9 B to 35 B in 7 min; 254/220 nm; RT: 2.95 min) to afford 8.8 mg (3.3% yield) of 4-((5-carbamoyl-4-methoxyindol-1-yl)methyl)phenylboronic acid as a white solid. MS (ESI, pos. ion) m/z: 325.30 (M+1). $^1$H-NMR (300 MHz, DMSO-$d_6$, ppm) δ 8.01 (s, 2H), 7.79-7.46 (m, 5H), 7.34 (s, 1H), 7.18 (dd, J=16.9, 8.1 Hz, 3H), 6.75 (s, 1H), 5.43 (s, 2H), 4.10 (d, J=1.8 Hz, 3H).

Example 31

Synthesis of 4-((4-carbamoylindol-1-yl)methyl)phenylboronic acid

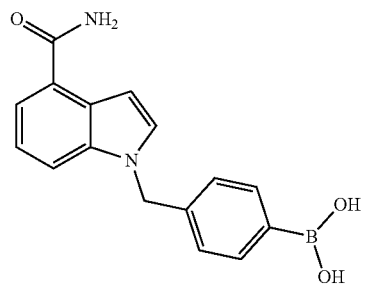

Step 1: indole-4-carboxamide

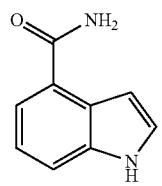

To a solution of 1H-indole-4-carbonitrile (100 mg, 0.70 mmol, 1.00 equiv) in a mixture of EtOH (4.00 mL) and H$_2$O (1.00 mL) was added Parkins catalyst (30.05 mg, 0.070 mmol, 0.10 equiv) at room temperature and stirred for 3 hours at 100° C. The mixture was cooled to room temperature and concentrated under reduced pressure to give indole-4-carboxamide (85 mg, 75%) as a light yellow solid.

Step 2: 4-((4-carbamoylindol-1-yl)methyl)phenylboronic acid

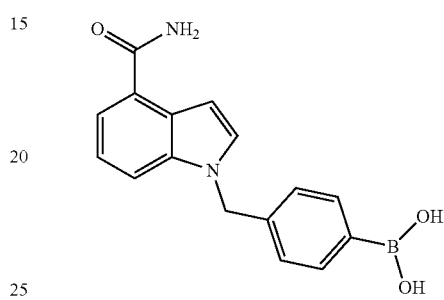

The title compound was synthesized by the in step 4 of Example 22 except indole-4-carboxamide (85 mg, 0.53 mmol) was used. The residue was purified by prep-HPLC (Column: Sunfire prep C18 column, 30*150, 5 um; Mobile Phase A: Water (0.1% FA), Mobile Phase B: ACN; Flow rate: 60 mL/min; Gradient: 18 B to 30 B in 7 min; 254/220 nm; RT: 6.93 min) to give 53.4 mg (33.1% yield) 4-((4-carbamoylindol-1-yl)methyl)phenylboronic acid as a white solid. MS (ESI, pos. ion) m/z: 295.25 (M+1). $^1$H-NMR (300 MHz, DMSO-$d_6$, ppm) δ 8.00 (d, J=4.4 Hz, 2H), 7.72 (s, 1H), 7.70-7.67 (m, 2H), 7.61-7.54 (m, 2H), 7.47 (d, J=7.3 Hz, 1H), 7.22 (s, 1H), 7.17-7.08 (m, 3H), 6.95 (d, J=3.1 Hz, 1H), 5.47 (s, 2H).

Example 32

Synthesis of 4-(imidazo[4,5-c]pyridin-3-ylmethyl)phenylboronic acid (32a) and 4-(imidazo[4,5-c]pyridin-1-ylmethyl)phenylboronic acid (32b

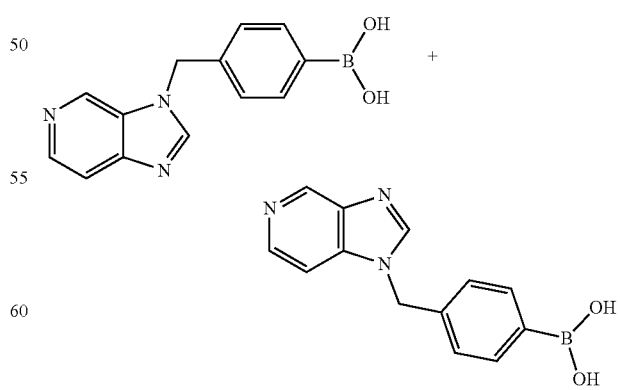

A mixture of title compounds was synthesized by the in Example 13 except 3,5-diazaindole (238 mg, 1.998 mmol, 1.00 equiv) was used. Yield: 112.1 mg (21% purity) of a mixture of 4-(imidazo[4,5-c]pyridin-3-ylmethyl)phenylboronic acid (32a) and 4-(imidazo[4,5-c]pyridin-1-ylmethyl)phenylboronic acid (32b). MS (ESI, pos. ion) m/z: 254.3 (M+1). $^1$H-NMR (300 MHz, DMSO-d$_6$, ppm) δ 9.27-9.21 (m, 1H), 8.49-8.40 (m, 1H), 8.23-8.17 (m, 1H), 7.84-7.78 (m, 3H), 7.39-7.29 (m, 2H), 5.68-5.62 (m, 2H).

Example 33

Synthesis of 4-((6-cyanoimidazo[4,5-c]pyridin-3-yl)methyl)phenylboronic acid (33a) and 4-((6-cyanoimidazo[4,5-c]pyridin-1-yl)methyl)phenylboronic acid (33b

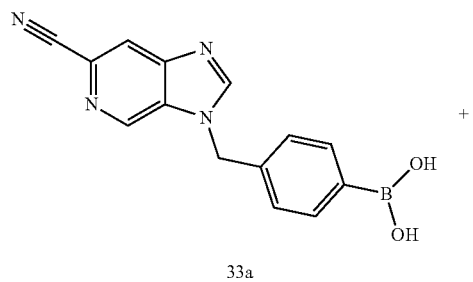

33a

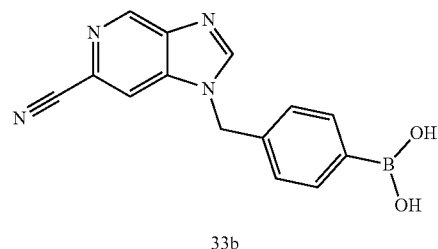

33b

Step 1: 3H-imidazo[4,5-c]pyridine-6-carbonitrile

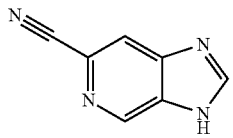 [SMILES: N#Cc1cc2nc[nH]c2cn1]

A solution of 3H-imidazo[4,5-c]pyridine-6-carboxamide (80 mg, 0.493 mmol, 1.00 equiv) in POCl$_3$ (8.00 mL) was stirred for 3 hour at 110° C. in an oil bath. After cooling to room temperature, the reaction mixture was concentrated under reduced pressure. The residue was purified by column chromatography (silica gel, eluent: EA/MEOH 85:15) to get 88 mg (55% yield) of 3H-imidazo[4,5-c]pyridine-6-carbonitrile as a white solid.

Step 2: a mixture of 4-((6-cyanoimidazo[4,5-c]pyridin-3-yl)methyl)phenylboronic acid (33a) and 4-((6-cyanoimidazo[4,5-c]pyridin-1-yl)methyl)phenylboronic acid (33b

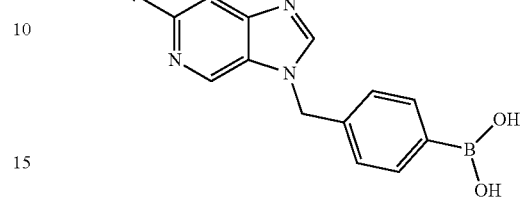

The title compounds were synthesized by the in step 4 of Example 22 except 3H-imidazo[4,5-c]pyridine-6-carbonitrile (78 mg, 0.54 mmol) was used. The crude product was purified by Prep-HPLC with the following conditions. (Column: Sunfire prep C18 column, 30*150, 5 um; Mobile Phase A: Water (0.1% FA), Mobile Phase B: ACN; Flow rate: 60 mL/min; Gradient: 5 B to 30 B in 10 min; 254/220 nm) gave 26.2 mg (34% yield) of a mixture of 4-((6-cyanoimidazo[4,5-c]pyridin-3-yl)methyl)phenylboronic acid (33a) and 4-((6-cyanoimidazo[4,5-c]pyridin-1-yl)methyl)phenylboronic acid (33b) as a white solid. MS (ESI, pos. ion) m/z: 279.20 (M+1). $^1$H NMR (300 MHz, DMSO-d6, ppm) δ 9.10 (d, J=8.7 Hz, 1H), 8.88 (dd, J=8.6, 2.5 Hz, 1H), 8.56-8.44 (m, 1H), 8.08 (s, 2H), 7.76 (d, J=7.6 Hz, 2H), 7.35 (d, J=7.6 Hz, 2H), 5.64 (d, J=23.7 Hz, 2H).

Example 34

Synthesis of 4-((5-cyanoimidazo[4,5-b]pyridin-1-yl)methyl)phenylboronic acid (34a) and 4-((5-cyanoimidazo[4,5-b]pyridin-3-yl)methyl)phenylboronic acid (34b

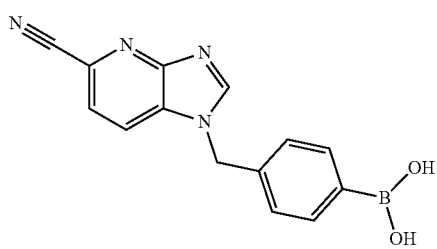

34a

-continued

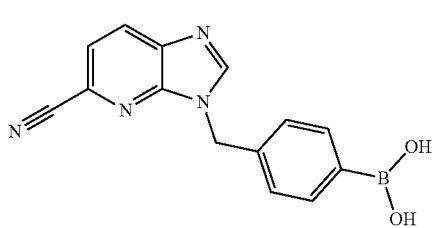
34b

Step 1: 1H-imidazo[4,5-b]pyridine-5-carbonitrile

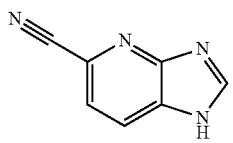 [SMILES: N#Cc1ccc2[nH]cnc2n1]

The title compound was synthesized by the in step 1 of Example 33 except 1H-imidazo[4,5-b]pyridine-5-carboxamide (150 mg, 0.93 mmol) was used. Yield: 130 mg (91.0%) as an off-white solid.

Step 2: 4-((5-cyanoimidazo[4,5-b]pyridin-1-yl)methyl)phenylboronic acid (34a) and 4-((5-cyanoimidazo[4,5-b]pyridin-3-yl)methyl)phenylboronic acid (34b

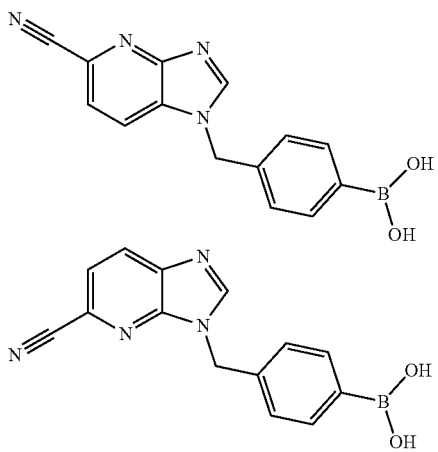

The title compounds were synthesized by the method described in step 4 of Example 22 except 1H-imidazo[4,5-b]pyridine-5-carbonitrile (150 mg, 1.04 mmol) was used. The crude product was purified by Prep-HPLC with the following conditions (Column: Sunfire prep C18 column, 30*150, 5 um; Mobile Phase A: Water (0.1% FA), Mobile Phase B: ACN; Flow rate: 60 mL/min; Gradient: 5 B to 30 B in 10 min; 254/220 nm; RT1:8.82 min; RT2: 9.12 min) to give two fractions:

Fraction 1: Rt: 8.82 min. 20.7 mg (7.07% yield) of 4-((5-cyanoimidazo[4,5-b]pyridin-3-yl)methyl)phenylboronic acid (34b) as a white solid. MS (ESI, pos. ion) m/z: 278.85 (M+1). $^1$H NMR (300 MHz, DMSO-d6, ppm) δ 8.98 (s, 1H), 8.23 (d, J=8.2 Hz, 1H), 8.07 (s, 2H), 7.89 (d, J=8.3 Hz, 1H), 7.75 (d, J=7.8 Hz, 2H), 7.31 (d, J=7.8 Hz, 2H), 5.61 (s, 2H).

Fraction 2: Rt: 9.12 min. 16.4 mg (5.42% yield) of 4-((5-cyanoimidazo[4,5-b]pyridin-1-yl)methyl)phenylboronic acid (34a) as a white solid. MS (ESI, pos. ion) m/z: 279.20 (M+1). $^1$H-NMR (400 MHz, DMSO-d$_6$, ppm) δ 8.94 (s, 1H), 8.36 (d, J=8.2 Hz, 1H), 8.07 (s, 2H), 7.93 (d, J=8.2 Hz, 1H), 7.78-7.72 (m, 2H), 7.29 (d, J=7.7 Hz, 2H), 5.56 (s, 2H).

Example 35

Synthesis of 4-((4-hydroxyindol-1-yl)methyl)phenylboronic acid

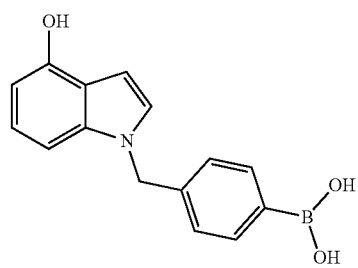

Step 1: 4-((4-methoxyindol-1-yl)methyl)phenylboronic acid

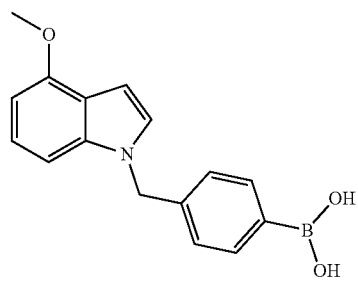

The title compound was synthesized by the method described in step 4 of Example 22 except 4-methoxy-1H-indole (200 mg, 1.36 mmol) was used. Yield: 200 mg (52.0%) as a light brown solid.

Step 2: 4-((4-hydroxyindol-1-yl)methyl)phenylboronic acid

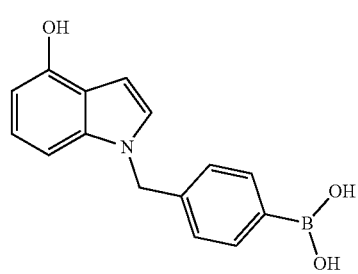

To a solution of 4-((4-methoxyindol-1-yl)methyl)phenylboronic acid (180 mg, 0.640 mmol, 1.00 equiv) in DCM (5.00 mL) was added BBr$_3$ (1.00 mL). The resulting mixture was stirred for 2 h at room temperature and then concentrated under reduced pressure. The crude product was purified by Prep-HPLC under the following conditions (Column: XSelect CSH Prep C18 OBD Column, 19*250 mm, 5 um; Mobile Phase A: Water (0.1% FA), Mobile Phase B: ACN; Flow rate: 20 mL/min; Gradient: 41 B to 42 B in 7 min; 254/220 nm; RT: 6.3 min) to afford 17.8 mg (9.3% yield) of 4-((4-hydroxyindol-1-yl)methyl)phenylboronic acid as a white solid. MS (ESI, pos. ion) m/z: 268.10 (M+1). $^1$H NMR (300 MHz, DMSO-d6, ppm) δ 9.40 (s, 1H), 8.01 (s, 2H), 7.74-7.65 (m, 2H), 7.31 (d, J=3.2 Hz, 1H), 7.11 (d, J=7.8 Hz, 2H), 6.92-6.78 (m, 2H), 6.52 (dd, J=3.2, 0.6 Hz, 1H), 6.37 (dd, J=6.7, 1.7 Hz, 1H), 5.34 (s, 2H).

Example 36

Synthesis of 4-((4-hydroxy-1,3-benzodiazol-1-yl)methyl)phenylboronic acid (36a) and 4-((7-hydroxy-1,3-benzodiazol-1-yl)methyl)phenylboronic acid (36b

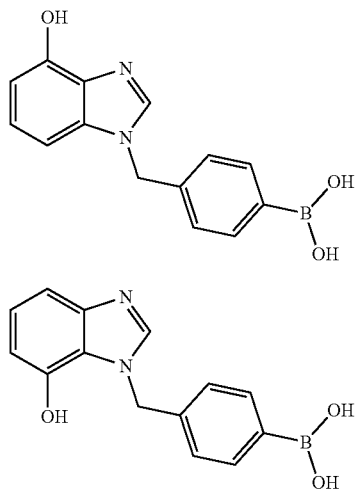

36a

36b

Step 1: 4-((4-methoxyindol-1-yl)methyl)phenylboronic acid and 4-((7-methoxy-1,3-benzodiazol-1-yl)methyl)phenylboronic acid

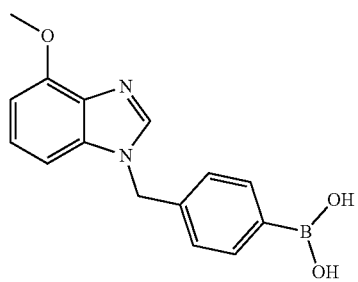 [SMILES: COc1cccc2c1ccn2Cc1ccc(B(O)O)cc1]

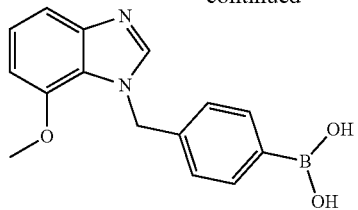

The title compounds were synthesized by the method described in step 4 of Example 22 except 4-methoxy-1H-1,3-benzodiazole (200 mg, 1.35 mmol) was used. Yield: 220 mg (57.2%) of a mixture of 4-((4-methoxyindol-1-yl)methyl)phenylboronic acid and 4-((7-methoxy-1,3-benzodiazol-1-yl)methyl)phenylboronic acid (ratio=1:1) as a light brown solid.

Step 2: 4-((4-hydroxy-1,3-benzodiazol-1-yl)methyl)phenylboronic acid (36a) and 4-((7-hydroxy-1,3-benzodiazol-1-yl)methyl)phenylboronic acid (36b

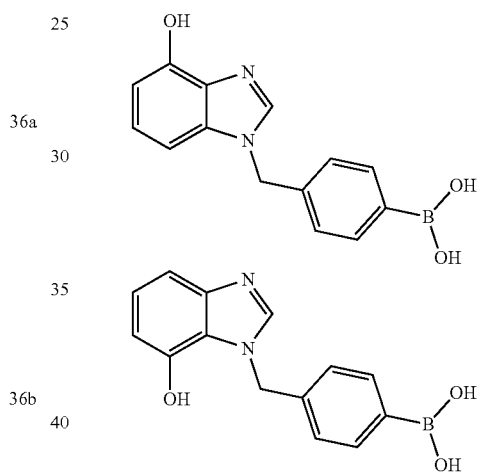

The title compounds were synthesized by the method described in step 2 of example 35 except 4-((4-methoxy-1,3-benzodiazol-1-yl)methyl)phenylboronic acid (150 mg, 0.532 mmol) was used. The crude product was purified by Prep-HPLC with the following conditions (Column: XBridge C18 OBD Prep Column, 19 mm×250 mm; Mobile Phase A: Water (10 MMOL/L NH4HCO3+0.1% NH$_3$·H$_2$O), Mobile Phase B: ACN; Flow rate: 25 mL/min; Gradient: 10 B to 30 B in 7 min; 254/220 nm; RT1:6.67 min; RT2: 6.99 min) to afford two fractions:

Fraction 1: Rt: 6.67 min. 41.2 mg (28.0% yield) of 4-((7-hydroxy-1,3-benzodiazol-1-yl)methyl)phenylboronic acid (36b) as a white solid. MS (ESI, pos. ion) m/z: 269.25 (M+1). $^1$H NMR (300 MHz, DMSO-d6, ppm) δ 9.97 (s, 1H), 8.25 (s, 1H), 8.01 (s, 2H), 7.85-7.65 (m, 2H), 7.26-7.06 (m, 3H), 6.96 (t, J=7.9 Hz, 1H), 6.59 (dd, J=7.7, 1.0 Hz, 1H), 5.63 (s, 2H).

Fraction 2: Rt: 6.99 min. 11.9 mg (8.1% yield) of 4-((4-hydroxy-1,3-benzodiazol-1-yl)methyl)phenylboronic acid (36a) as a white solid. MS (ESI, pos. ion) m/z: 269.30 (M+1). $^1$H NMR (400 MHz, DMSO-d$_6$, ppm) δ 9.77 (s, 1H), 8.24 (s, 1H), 8.03 (s, 2H), 7.77-7.69 (m, 2H), 7.22 (d, J=8.0 Hz, 2H), 6.90 (t, J=7.9 Hz, 2H), 6.54 (dd, J=7.6, 1.1 Hz, 1H), 5.43 (s, 2H).

Example 37

Synthesis of 4-((4-hydroxy-2-methylimidazo[4,5-c]pyridin-1-yl)methyl)phenylboronic acid (37a) and 4-((4-hydroxy-2-methylimidazo[4,5-c]pyridin-3-yl)methyl)phenylboronic acid (37b

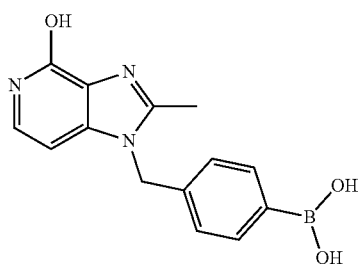

37a

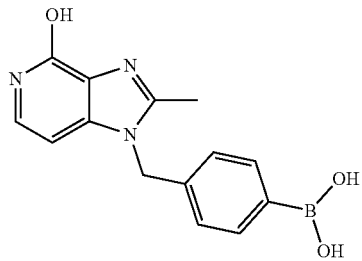

37b

Step 1: 4-methoxy-2-methyl-1H-imidazo[4,5-c]pyridine

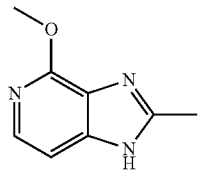

To a stirred solution of 2-methoxypyridine-3,4-diamine (300 mg, 2.156 mmol, 1.00 equiv) in MeOH (5.00 mL) were added Pd/C (210 mg, 1.078 mmol, 0.5 equiv) and acetaldehyde (95 mg, 1.617 mmol, 1.50 equiv). After stirring for 12 hours at 120° C. in an oil bath, the mixture was concentrated under reduced pressure. After stirring for 24 h, the resulting mixture was filtered through a Celite and the filter cake was washed with MeOH. The filtrate was concentrated under reduced pressure and the residue was purified by column chromatography (silica gel, eluent: ethyl acetate/petroleum ether 3:2) to give 4-methoxy-2-methyl-1H-imidazo[4,5-c]pyridine (300 mg, 56.3% yield) as a white solid.

Step 2: 4-((4-hydroxy-2-methylimidazo[4,5-c]pyridin-1-yl)methyl)phenylboronic acid (37a) and 4-((4-hydroxy-2-methylimidazo[4,5-c]pyridin-3-yl)methyl)phenylboronic acid (37b

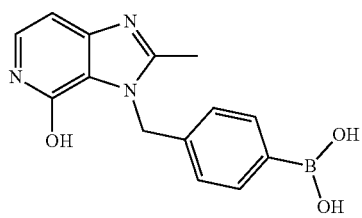

NaH (101 mg, 4.204 mmol, 2 equiv) was placed into a three-neck flask which was purged with nitrogen at room temperature. A solution of 4-methoxy-2-methyl-1H-imidazo[4,5-c]pyridine (343 mg, 2.10 mmol, 1.00 equiv) in DMF (6.00 mL) was added at 0° C. After stirring for 30 min, 4-(bromomethyl)phenylboronic acid (542 mg, 2.522 mmol, 1.20 equiv) was added at 0° C. The mixture was stirred for additional 1 h at room temperature, then quenched with hydrochloric acid (3 N, 5.0 mL) and concentrated under reduced pressure. The crude product was purified by Prep-HPLC with the following conditions (Column: XBridge C18 OBD Prep Column, 100 Å, 5 μm, 19 mm×250 mm; Mobile Phase A: Water (0.05% FA), Mobile Phase B: ACN; Flow rate: 25 mL/min; Gradient: 5 B to 12 B in 7 min; 254/220 nm; RT1:7.13 min; RT2: 8.42 min) to afford two fractions:

Fraction 1: Rt: 7.13 min. 32.7 mg (5.3% yield) of 4-((4-hydroxy-2-methylimidazo[4,5-c]pyridin-3-yl)methyl)phenylboronic acid (37b). MS (ESI, pos. ion) m/z: 284.25 (M+1). $^1$H NMR (400 MHz, DMSO-d6, ppm) δ 11.27 (d, J=5.8 Hz, 1H), 8.06 (s, 2H), 7.73 (d, J=7.7 Hz, 2H), 7.09 (dd, J=11.1, 7.1 Hz, 3H), 6.51 (d, J=7.0 Hz, 1H), 5.73 (s, 2H), 2.35 (s, 3H).

Fraction 2: Rt: 8.42 min. 3.7 mg (0.6% yield) of 4-((4-hydroxy-2-methylimidazo[4,5-c]pyridin-1-yl)methyl)phenylboronic acid (37a) as a white solid. MS (ESI, pos. ion) m/z: 284.25 (M+1). $^1$H NMR (400 MHz, DMSO-d6, ppm) δ 11.12 (s, 1H), 8.45 (s, 2H), 7.73 (d, J=7.6 Hz, 2H), 7.05 (d, J=7.6 Hz, 3H), 6.52 (d, J=7.0 Hz, 1H), 5.38 (s, 2H), 2.39 (s, 3H).

Example 38

Synthesis of 4-((2-ethyl-4-hydroxyimidazo[4,5-c]pyridin-1-yl)methyl)phenylboronic acid (38a) and 4-((2-ethyl-4-hydroxyimidazo[4,5-c]pyridin-3-yl)methyl)phenylboronic acid (38b

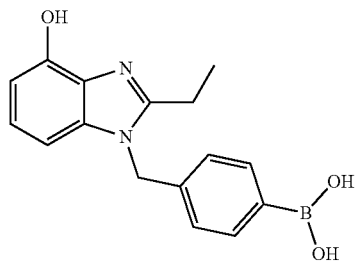
38a

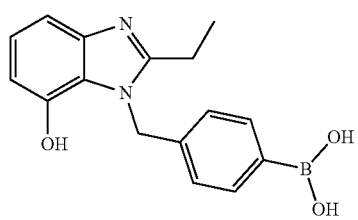
38b

Step 1: 2-ethyl-4-methoxy-1H-imidazo[4,5-c]pyridine

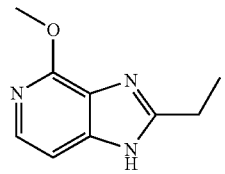

The compound was synthesized by the at step 1 of Example 37 except 2-methoxypyridine-3,4-diamine (500 mg, 3.59 mmol) and propionaldehyde (208 mg, 3.59 mmol) were used. Yield: 200 mg (30.8%).

Step 2: 4-((2-ethyl-4-hydroxyimidazo[4,5-c]pyridin-1-yl)methyl)phenylboronic acid (38a) and 4-((2-ethyl-4-hydroxyimidazo[4,5-c]pyridin-3-yl)methyl) phenylboronic acid (38b

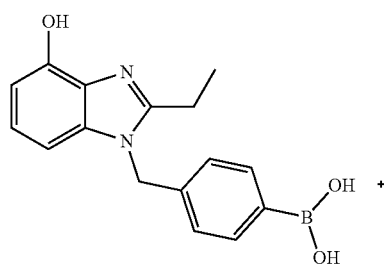 +

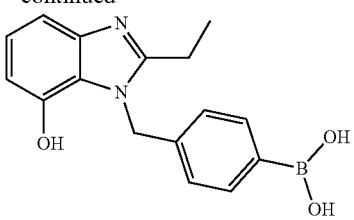

The title compounds were synthesized by the in step 2 of Example 37 except 2-ethyl-4-methoxy-1H-imidazo[4,5-c]pyridine (350 mg, 1.975 mmol) was used. The crude product was purified by Prep-HPLC with the following conditions (Column: Sunfire prep C18 column, 30*150, 5 um; Mobile Phase A: Water (0.1% FA), Mobile Phase B: ACN; Flow rate: 60 mL/min; Gradient: 8 B to 25 B in 10 min; 254/220 nm; RT1:5.08 min; RT2: 6.10 min) to afford two fractions:

Fraction 1: Rt: 5.08 min. 12.7 mg (2.1% yield) of 4-((2-ethyl-4-hydroxyimidazo[4,5-c]pyridin-3-yl)methyl)phenylboronic acid (38b). MS (ESI, pos. ion) m/z: 298.25 (M+1). $^1$H NMR (400 MHz, DMSO-d6, ppm) δ 11.27 (d, J=5.7 Hz, 1H), 8.15 (d, J=39.2 Hz, 2H), 7.73 (d, J=7.6 Hz, 2H), 7.13-7.03 (m, 3H), 6.55 (d, J=6.9 Hz, 1H), 5.75 (s, 2H), 2.67 (q, J=7.5 Hz, 2H), 1.16 (t, J=7.5 Hz, 3H).

Fraction 2: Rt: 6.10 min. 13.8 mg (2.3% yield) of 4-((2-ethyl-4-hydroxyimidazo[4,5-c]pyridin-1-yl)methyl)phenylboronic acid (38a) as a white solid. MS (ESI, pos. ion) m/z: 298.20 (M+1). $^1$H-NMR (400 MHz, DMSO-d$_6$, ppm) δ 11.11 (d, J=5.5 Hz, 1H), 8.10 (s, 2H), 7.74 (d, J=7.8 Hz, 2H), 7.06 (dd, J=29.5, 7.0 Hz, 3H), 6.52 (d, J=7.0 Hz, 1H), 5.39 (s, 2H), 2.71 (q, J=7.5 Hz, 2H), 1.21 (t, J=7.4 Hz, 3H).

Example 39

Synthesis of 4-((4-hydroxy-2-isopropylimidazo[4,5-c]pyridin-1-yl)methyl)phenylboronic acid (39a) and 4-((4-hydroxy-2-isopropylimidazo[4,5-c]pyridin-3-yl)methyl)phenylboronic acid with formic acid (39a

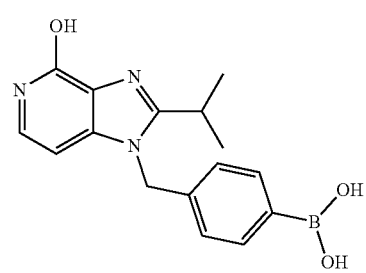
39a

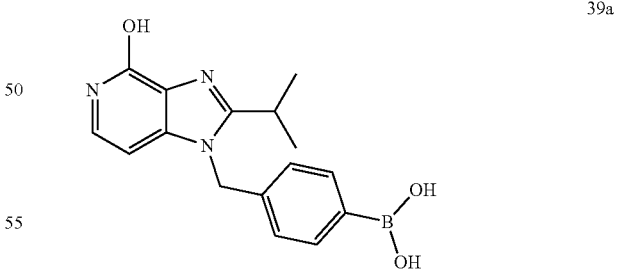
39b

Step 1: 2-isopropyl-4-methoxy-1H-imidazo[4,5-c]pyridine

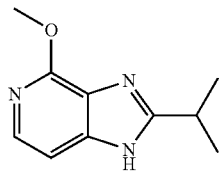

The title compounds were synthesized by the method described in step 1 of Example 37 except 2-methoxypyridine-3,4-diamine (500 mg, 3.59 mmol) and isobutyraldehyde (285 mg, 3.952 mmol) were used. Yield: 370 mg (46.2%). MS (ESI, pos. ion) m/z: 192.25 (M+1).

Step 2: 4-((2-isopropyl-4-methoxyimidazo[4,5-c]pyridin-1-yl)methyl)phenylboronic acid (39a) and 4-((2-isopropyl-4-methoxyimidazo[4,5-c]pyridin-3-yl)methyl)phenylboronic acid (39b

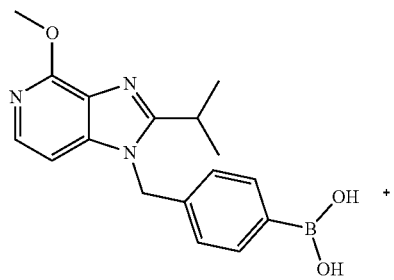

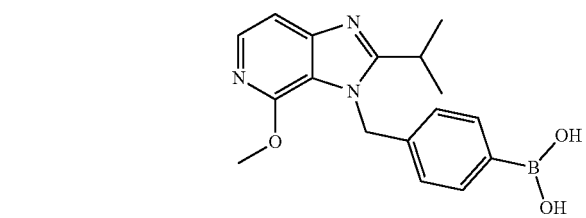

The compounds were synthesized by the in step 4 in Example 22 except 2-isopropyl-4-methoxy-1H-imidazo[4,5-c]pyridine (370 mg, 1.935 mmol) was used and the residue was dissolved in methanol (5 mL) and filtered. The filtrate was concentrated under reduced pressure to give 420 mg (58.6% yield) of a mixture of 4-((2-isopropyl-4-methoxyimidazo[4,5-c]pyridin-1-yl)methyl)phenylboronic acid and 4-((2-isopropyl-4-methoxyimidazo[4,5-c]pyridin-3-yl)methyl)phenylboronic acid (ratio=1:1) as a brown solid. MS (ESI, pos. ion) m/z: 325.90 (M+1).

Step 3: 4-((4-hydroxy-2-isopropylimidazo[4,5-c]pyridin-1-yl)methyl)phenylboronic (39a) and 4-((4-hydroxy-2-isopropylimidazo[4,5-c]pyridin-3-yl)methyl)phenylboronic acid formate (39a

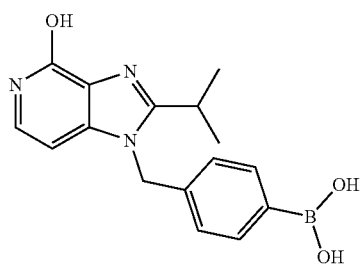

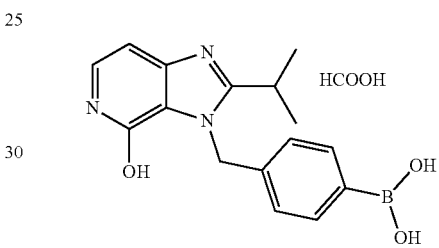

To a solution of a mixture of 4-((2-isopropyl-4-methoxyimidazo[4,5-c]pyridin-3-yl)methyl)phenylboronic acid and 4-((2-isopropyl-4-methoxyimidazo[4,5-c]pyridin-1-yl)methyl)phenylboronic acid) (420 mg, 1.033 mmol, 1.00 equiv, 80%) in ACN (10.00 mL) was added TMSI (1.29 g, 6.458 mmol, 5 equiv) at room temperature. The resulting mixture was stirred for 2 hours at 90° C. After cooling down to room temperature, the reaction mixture was concentrated under reduced pressure. The residue was purified by prep-HPLC (Column: Sunfire prep C18 column, 30*150, 5 um; Mobile Phase A: Water (0.1% FA), Mobile Phase B: ACN; Flow rate: 60 mL/min; Gradient: 9 B to 20 B in 10 min; 254/220 nm; RT1: 8.12 min; RT2: 8.90 min) to give two fractions:

Fraction 1: Rt: 8.12 min. 74.2 mg (19.5% yield) of 4-((4-hydroxy-2-isopropylimidazo[4,5-c]pyridin-3-yl)methyl)phenylboronic acid (39b) as a formate salt (light yellow solid). MS (ESI, pos. ion) m/z: 312.25 (M+1). $^1$H NMR (400 MHz, DMSO-d6, ppm) δ11.27 (d, J=5.8 Hz, 1H), 8.14 (s, 1H), 8.03 (s, 2H), 7.73 (d, J=7.9 Hz, 2H), 7.09 (dd, J=16.9, 7.1 Hz, 3H), 6.56 (d, J=6.9 Hz, 1H), 5.80 (s, 2H), 3.10 (m, 1H), 1.12 (d, J=6.7 Hz, 6H).

Fraction 2: Rt: 8.90 min. 108.3 mg (33.0% yield) 4-((4-hydroxy-2-isopropylimidazo[4,5-c]pyridin-1-yl)methyl)phenylboronic acid (39a) as an off-white solid. MS (ESI, pos. ion) m/z: 312.30 (M+1). $^1$H-NMR (400 MHz, DMSO-d$_6$, ppm) δ11.11 (d, J=5.9 Hz, 1H), 8.05 (s, 2H), 7.74 (d, J=7.8 Hz, 2H), 7.10 (t, J=6.5 Hz, 1H), 7.00 (d, J=7.8 Hz, 2H), 6.57-6.44 (m, 1H), 5.44 (s, 2H), 3.19-3.09 (m, 1H), 1.18 (d, J=6.8 Hz, 6H).

Example 40

Synthesis of 4-((4-hydroxy-2-methylpyrrolo[3,2-c]pyridin-1-yl)methyl)phenylboronic acid

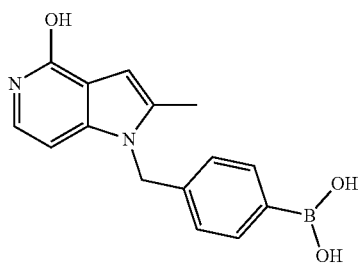

Step 1: 4-methoxy-2-methyl-1H-pyrrolo[3,2-c]pyridine

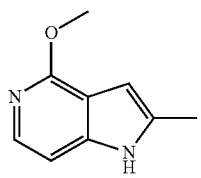

To a stirred solution 3-iodo-2-methoxypyridin-4-amine (500 mg, 2.00 mmol, 1.00 equiv) in THF (10 mL) were added K$_2$CO$_3$ (552 mg, 4.0 mmol, 2.00 equiv), Pd(PPh$_3$)$_4$ (231 mg, 0.200 mmol, 0.10 equiv), XPhos (191 mg, 0.400 mmol, 0.20 equiv) and propyne (1 M in THF) (6.00 mL, 6.000 mmol, 3.00 equiv) under argon atmosphere. The reaction mixture was refluxed for 8 h. After evaporation under reduced pressure to remove THF, the residue was purified by flash chromatography on silica gel column (PE/EtOAc, gradient 100:0 to 85:15) to give 4-methoxy-2-methyl-1H-pyrrolo[3,2-c]pyridine (150 mg, 35.6%) as a brown solid. MS (ESI, pos. ion) m/z: 163.25 (M+1).

Step 2: 4-((4-methoxy-2-methylpyrrolo[3,2-c]pyridin-1-yl)methyl)phenylboronic acid

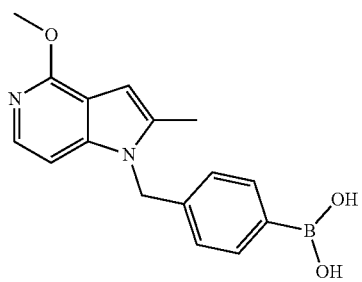 [SMILES: COc1nccc2c1cc(C)n2Cc1ccc(B(O)O)cc1]

This compound was synthesized by the same at step 4 in Example 22 except 4-methoxy-2-methyl-1H-pyrrolo[3,2-c]pyridine (150 mg, 0.712 mmol) was used. Yield: 150 mg (66.2%) as a light brown solid. MS (ESI, pos. ion) m/z: 297.30 (M+1).

Step 3: 4-((4-hydroxy-2-methylpyrrolo[3,2-c]pyridin-1-yl)methyl)phenylboronic acid

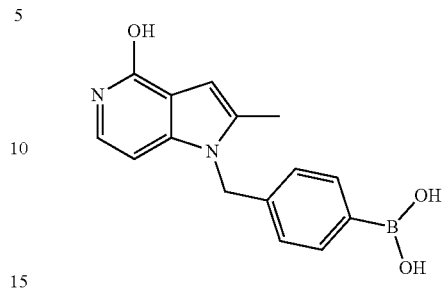

To a solution of 4-((4-methoxy-2-methylpyrrolo[3,2-c]pyridin-1-yl)methyl)phenylboronic acid (150 mg, 0.52 mmol, 1.00 equiv) in ACN (5 mL) was added TMSI (0.5 mL). After stirring for 1 h at 90° C., the reaction mixture was concentrated under reduced pressure. The crude product was purified by Prep-HPLC with the following conditions (Column: XBridge Prep OBD C18 Column, 19*250 mm, 5 um; Mobile Phase A: Water (10 MMOL/L NH4HCO3+0.1% NH3·H2O), Mobile Phase B: ACN; Flow rate: 20 mL/min; Gradient: 15 B to 70 B in 7 min; 254/220 nm; RT: 6.3 min) to afford 4-((4-hydroxy-2-methylpyrrolo[3,2-c]pyridin-1-yl)methyl)phenylboronic acid (25.8 mg, 17.6% yield) as a white solid. MS (ESI, pos. ion) m/z: 283.25 (M+1). $^1$H NMR (300 MHz, DMSO-d$_6$, ppm) δ 10.63 (d, J=5.5 Hz, 1H), 8.02 (s, 2H), 7.77-7.68 (m, 2H), 7.12 (d, J=7.8 Hz, 2H), 6.96-6.86 (m, 2H), 6.42 (d, J=7.1 Hz, 1H), 5.23 (s, 2H), 2.31 (d, J=1.0 Hz, 3H).

Example 41

Synthesis of 4-((5-carbamoyl-2-methylpyrrolo[3,2-b]pyridin-1-yl)methyl)phenylboronic acid

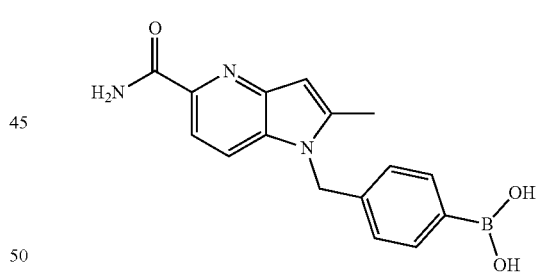

Step 1: 2-methyl-1H-pyrrolo[3,2-b]pyridine-5-carboxamide

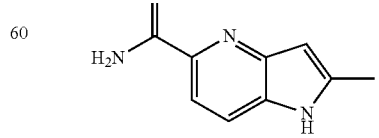

To a solution of 5-chloro-2-methyl-1H-pyrrolo[3,2-b]pyridine (500.00 mg, 3.001 mmol, 1.00 equiv) in 7 M NH$_3$ (g) in MeOH (15.00 mL) was added Pd(dppf)Cl$_2$ CH$_2$Cl$_2$ (122.54 mg, 0.150 mmol, 0.05 equiv). The resulting mixture was purged with carbon monoxide for 5 minutes and stirred 6 hours at 120° C. under carbon monoxide (20 atm.) atmosphere. The mixture was cooled to room temperature and concentrated under reduced pressure. The residue was purified by column chromatography (silica gel, eluent: petroleum ether/ethyl acetate 1:1) to give 400 mg (72.2% yield) of 2-methyl-1H-pyrrolo[3,2-b]pyridine-5-carboxamide as a light yellow solid.

Step 2: 4-((5-carbamoyl-2-methylpyrrolo[3,2-b]pyridin-1-yl)methyl)phenylboronic acid

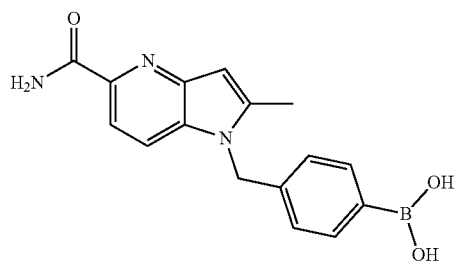 [SMILES: Cc1cc2nc(C(N)=O)ccc2n1Cc1ccc(B(O)O)cc1]

The title compound was synthesized by the in step 4 of Example 22 except 2-methyl-1H-pyrrolo[3,2-b]pyridine-5-carboxamide (150 mg, 0.856 mmol) was used. The residue was purified by prep-HPLC (Column: XBridge C18 OBD Prep Column, 100 mm×5 um, 19 mm×250 mm; Mobile Phase A: Water (0.05% FA), Mobile Phase B: ACN; Flow rate: 25 mL/min; Gradient: 20 B to 30 B in 7 min; 254/220 nm) to give 67.3 mg (25.1% yield) of 4-((5-carbamoyl-2-methylpyrrolo[3,2-b]pyridin-1-yl)methyl)phenylboronic acid as a white solid. MS (ESI, pos. ion) m/z: 310.25 (M+1). $^1$H NMR (400 MHz, DMSO-d6, ppm) δ 8.00 (s, 3H), 7.92 (d, J=8.5 Hz, 1H), 7.80 (d, J=8.5 Hz, 1H), 7.71 (d, J=7.8 Hz, 2H), 7.38 (d, J=3.3 Hz, 1H), 6.96 (d, J=7.8 Hz, 2H), 6.54 (s, 1H), 5.50 (s, 2H), 2.44 (s, 3H).

Example 42

Synthesis of 4-((5-cyano-2-methylpyrrolo[3,2-b]pyridin-1-yl)methyl)phenylboronic acid

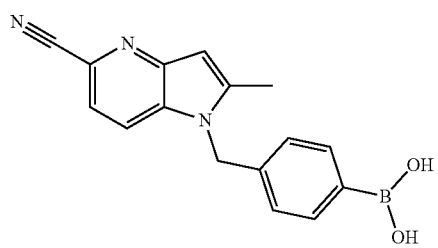 [SMILES: Cc1cc2nc(C#N)ccc2n1Cc1ccc(B(O)O)cc1]

Step 1: 2-methyl-1H-pyrrolo[3,2-b]pyridine-5-carbonitrile

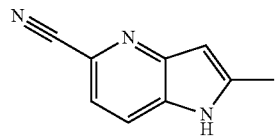

The title compound was synthesized by the in step 1 of Example 33 except 2-methyl-1H-pyrrolo[3,2-b]pyridine-5-carboxamide (250 mg, 1.43 mmol) was used. Yield: 75 mg (78.0%) as a brown solid.

Step 2: 4-((5-cyano-2-methylpyrrolo[3,2-b]pyridin-1-yl)methyl)phenylboronic acid

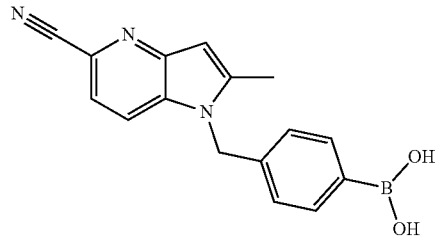 [SMILES: Cc1cc2nc(C#N)ccc2n1Cc1ccc(B(O)O)cc1]

The title compound was synthesized by the e in step 4 of Example 22 except 2-methyl-1H-pyrrolo[3,2-b]pyridine-5-carbonitrile (175 mg, 1.113 mmol) was used and the residue was purified by prep-HPLC prep-HPLC (Column: XBridge C18 OBD Prep Column, 100 mm×5 um, 19 mm×250 mm; Mobile Phase A: Water (0.05% FA), Mobile Phase B: ACN; Flow rate: 25 mL/min; Gradient: 30 B to 40 B in 7 min; 254, 220 nm) to give 4-((5-cyano-2-methylpyrrolo[3,2-b]pyridin-1-yl)methyl)phenylboronic acid (74.5 mg, 22.5% yield) as a white solid. MS (ESI, pos. ion) m/z: 292.25 (M+1). $^1$H NMR (400 MHz, DMSO-d6, ppm) δ 8.07-7.99 (m, 3H), 7.71 (d, J=7.7 Hz, 2H), 7.65 (d, J=8.4 Hz, 1H), 6.96 (d, J=7.7 Hz, 2H), 6.62 (s, 1H), 5.54 (s, 2H), 2.45 (s, 3H).

Example 43

Synthesis of 4-((5-carbamoyl-2-isopropylpyrrolo[3,2-b]pyridin-1-yl)methyl)phenylboronic acid

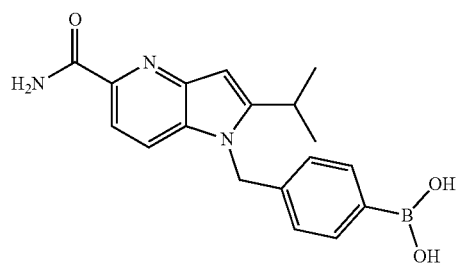 [SMILES: CC(C)c1cc2nc(C(N)=O)ccc2n1Cc1ccc(B(O)O)cc1]

175

Step 1: 6-chloro-2-(3-methylbut-1-yn-1-yl)pyridin-3-amine

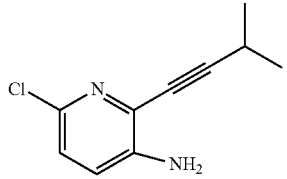

To a solution of 6-chloro-2-iodopyridin-3-amine (900 mg, 3.537 mmol, 1.00 equiv) in ACN (10.00 mL) were added TEA (8 mL), CuI (33.68 mg, 0.177 mmol, 0.05 equiv), Pd(PPh₃)₄ (408.71 mg, 0.354 mmol, 0.10 equiv) and 1-butyne, 3-methyl- (265 mg, 3.891 mmol, 1.1 equiv) at room temperature under argon atmosphere. After stirring for 20 hours at room temperature, the mixture was concentrated under reduced pressure and the residue was purified by column chromatography (silica gel, eluent: petroleum ether/ethyl acetate 2:3) to give 6-chloro-2-(3-methylbut-1-yn-1-yl)pyridin-3-amine (620 mg, 90% yield) as a light brown solid.

Step 2: 5-chloro-2-isopropyl-1H-pyrrolo[3,2-b]pyridine

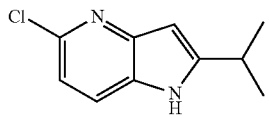

To a solution of 6-chloro-2-(3-methylbut-1-yn-1-yl)pyridin-3-amine (580 mg, 2.980 mmol, 1.00 equiv) in dry DMF (5.00 mL) was added t-BuOK (669 mg, 5.959 mmol, 2 equiv) at room temperature. After stirred for 4 hours at room temperature, the reaction mixture was poured into cool water and a brown precipitate was formed. The solid was collected by filtration, washed with water and dried in air to give 5-chloro-2-isopropyl-1H-pyrrolo[3,2-b]pyridine (440 mg, 75.9% yield) as a brown solid

Step 3: 2-isopropyl-1H-pyrrolo[3,2-b]pyridine-5-carboxamide

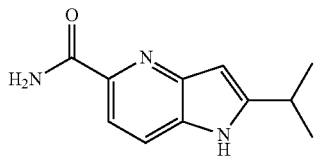

The title compound was synthesized by the in step 1 of example 41 except 5-chloro-2-isopropyl-1H-pyrrolo[3,2-b]pyridine (500 mg, 2.569 mmol) was used. Yield: 390 mg (63.7%) as a yellow solid.

176

Step 4: 4-((5-carbamoyl-2-isopropylpyrrolo[3,2-b]pyridin-1-yl)methyl)phenylboronic acid

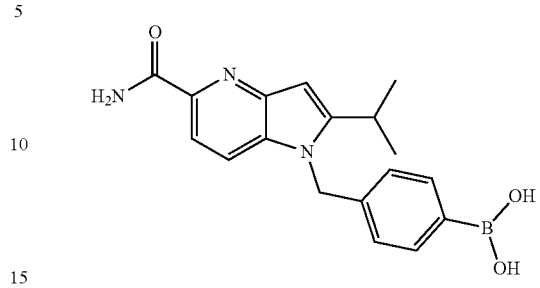

The title compound was synthesized by the in step 4 of Example 22 except 2-isopropyl-1H-pyrrolo[3,2-b]pyridine-5-carboxamide (150 mg, 0.74 mmol) was used. The crude product was purified by Prep-HPLC with the following conditions (Column: Sunfire prep C18 column, 30*150, 5 um; Mobile Phase A: Water (0.1% FA), Mobile Phase B: ACN; Flow rate: 60 mL/min; Gradient: 20 B to 38 B in 7 min; 254/220 nm) to afford 4-((5-carbamoyl-2-isopropylpyrrolo[3,2-b]pyridin-1-yl)methyl)phenylboronic acid (76.1 mg, 29.5% yield) as a yellow solid. MS (ESI, pos. ion) m/z: 338.30 (M+1). ¹H NMR (400 MHz, DMSO-d6, ppm) δ 7.98 (d, J=15.7 Hz, 3H), 7.89-7.74 (m, 2H), 7.67 (d, J=7.7 Hz, 2H), 7.40 (d, J=3.2 Hz, 1H), 6.87 (d, J=7.7 Hz, 2H), 6.54 (s, 1H), 5.54 (s, 2H), 3.09 (sept, J=6.8 Hz, 1H), 1.22 (d, J=6.7 Hz, 6H).

Example 44

Synthesis of 4-((5-cyano-2-isopropypyrrolo[3,2-b]pyridin-1-yl)methyl)phenylboronic acid

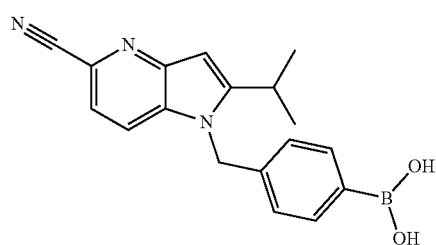 [SMILES: CC(C)c1cc2nc(C#N)ccc2n1Cc1ccc(B(O)O)cc1]

Step 1: 2-isopropyl-1H-pyrrolo[3,2-b]pyridine-5-carbonitrile

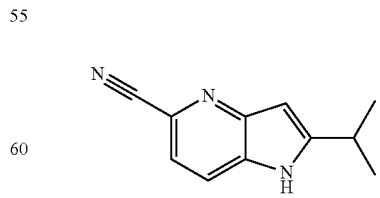

The title compound was synthesized by the in step 1 in Example 33 except 2-isopropyl-1H-pyrrolo[3,2-b]pyridine-5-carboxamide (150 mg, 0.74 mmol) was used. Yield: 35 mg, (15.8%). MS (ESI, pos. ion) m/z: 186.20 (M+1).

Step 2: 4-((5-cyano-2-isopropylpyrrolo[3,2-b]pyridin-1-yl)methyl)phenylboronic acid

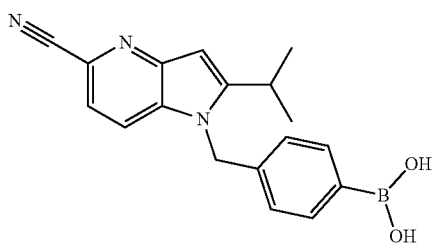 [SMILES: CC(C)c1cc2nc(C#N)ccc2n1Cc1ccc(B(O)O)cc1]

The title compound was synthesized by the in step 4 of Example 22 except 2-isopropyl-1H-pyrrolo[3,2-b]pyridine-5-carbonitrile (35 mg, 0.19 mmol) was used. The crude product was purified by Prep-HPLC with the following conditions (Column: Sunfire prep C18 column, 30*150, 5 um; Mobile Phase A: Water (0.1% FA), Mobile Phase B: ACN; Flow rate: 60 mL/min; Gradient: 15 B to 65 B in 7 min; 254/220 nm) to afford 4-((5-cyano-2-isopropylpyrrolo[3,2-b]pyridin-1-yl)methyl)phenylboronic acid (38.6 mg, 63.3% yield) as a white solid. MS (ESI, pos. ion) m/z: 320.30 (M+1). $^1$H NMR (400 MHz, DMSO-d6, ppm) δ 8.06-7.87 (m, 3H), 7.65 (m, 3H), 6.88 (d, J=7.9 Hz, 2H), 6.64 (s, 1H), 5.57 (s, 2H), 3.11 (sept, J=6.8 Hz, 1H), 1.21 (d, J=6.7 Hz, 6H).

Example 45

Synthesis of 4-((4-chloro-1,3-benzodiazol-1-yl)methyl)phenylboronic acid (45a) and 4-((7-chloro-1,3-benzodiazol-1-yl)methyl)phenylboronic acid (45b

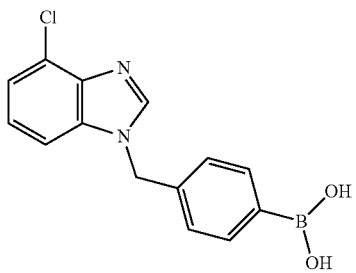

45a

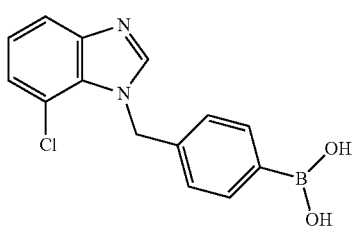

45b

Step 1: 4-chloro-1H-1,3-benzodiazole

To a suspension of 3-chlorobenzene-1,2-diamine (200 mg, 1.403 mmol, 1.00 equiv) in H$_2$O (5.00 mL) was added HCOOH (129 mg, 2.805 mmol, 2.0 equiv). The resulting mixture was stirred for 3 hours at 100° C. After cooling to room temperature, the reaction mixture was adjusted to pH=9 with 2 M sodium hydroxide and extracted with dichloromethane. The combined organic layers were washed with water and brine, dried over anhydrous magnesium sulfate and filtered. The filtrate was evaporated to dryness to give 4-chloro-1H-1,3-benzodiazole (180 mg, 84.1% yield) as a brown yellow solid.

Step 2: 4-((4-chloro-1,3-benzodiazol-1-yl)methyl)phenylboronic acid (45a) and 4-((7-chloro-1,3-benzodiazol-1-yl)methyl)phenylboronic acid (45b

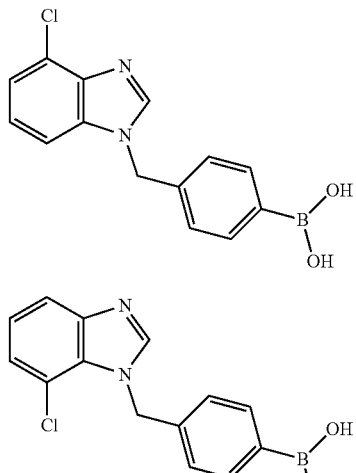

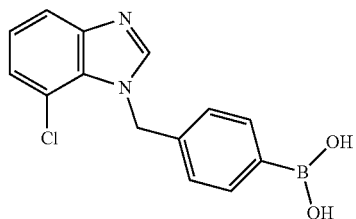

The title compounds were synthesized by the in step 4 of Example 22 except 4-chloro-1H-1,3-benzodiazole (180 mg, 1.18 mmol) was used. The residue was purified by prep-HPLC (Column: YMC-Actus Triart C18, 30*250.5 um; Mobile Phase A: Water (0.05% FA), Mobile Phase B: ACN; Flow rate: 45 mL/min; Gradient: 20 B to 30 B in 7 min; 254,220 nm; RT1: 6.45 min; RT2: 7.58 min) to afford two fractions:

Fraction 1: Rt: 6.45 min. 30.0 mg (7.6% yield) of 4-((4-chloro-1,3-benzodiazol-1-yl)methyl)phenylboronic acid (45a) as an off-white solid. MS (ESI, pos. ion) m/z: 287.15 (M+1). $^1$H NMR (400 MHz, DMSO-d$_6$, ppm) δ 8.50 (s, 1H), 8.07 (s, 2H), 7.75-7.63 (m, 2H), 7.47 (m, 1H), 7.30-7.12 (m, 4H), 5.51 (s, 2H).

Fraction 2: Rt: 7.58 min. 33.3 mg (8.4% yield) of 4-((7-chloro-1,3-benzodiazol-1-yl)methyl)phenylboronic acid (45b) as an off-white solid. MS (ESI, pos. ion) m/z: 287.10

(M+1). 1H-NMR (400 MHz, DMSO-$d_6$, ppm) δ 8.49 (d, J=12.1 Hz, 1H), 8.04 (s, 2H), 7.75-7.63 (m, 3H), 7.29-7.14 (m, 2H), 7.00 (d, J=7.8 Hz, 2H), 5.75 (s, 2H).

Example 46

Synthesis of 4-((4,6-dichloro-1,3-benzodiazol-1-yl)methyl)phenylboronic acid (46a) and 4-((5,7-dichloro-1,3-benzodiazol-1-yl)methyl)phenylboronic acid (46a

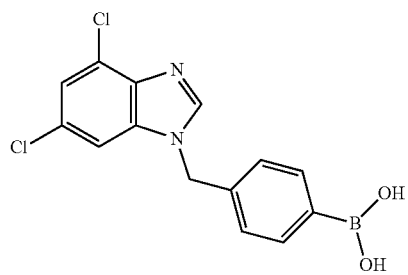

46a

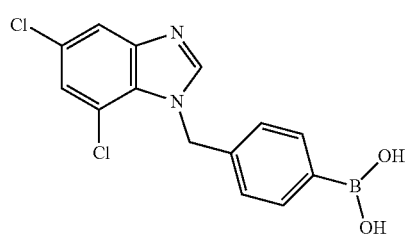

46b

Step 1: 4,6-dichloro-1H-1,3-benzodiazole

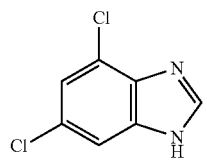 [SMILES: Clc1cc(Cl)c2nc[nH]c2c1]

The title compound was synthesized by the in step 1 of Example 45 except 3,5-dichlorobenzene-1,2-diamine (300.00 mg, 1.70 mmol) was used. Yield: 280 mg (88.4%) as a light yellow solid.

Step 2: 4-((4,6-dichloro-1,3-benzodiazol-1-yl)methyl)phenylboronic acid and 4-((5,7-dichloro-1,3-benzodiazol-1-yl)methyl)phenylboronic acid

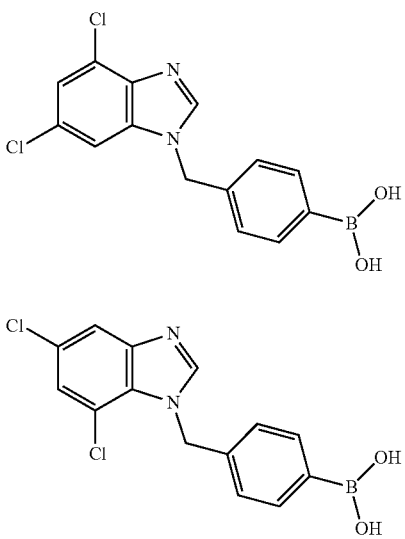 [SMILES: OB(O)c1ccc(Cn2cnc3c(Cl)cc(Cl)cc32)cc1 ; OB(O)c1ccc(Cn2cnc3cc(Cl)cc(Cl)c32)cc1]

The title compounds were synthesized by the method described in step 4 of Example 22 except 4,6-dichloro-1H-1,3-benzodiazole (150 mg, 0.802 mmol) was used. The residue was purified by prep-HPLC (Column: Sunfire prep C18 column, 30*150, 5 um; Mobile Phase A: Water (0.1% FA), Mobile Phase B: ACN; Flow rate: 60 mL/min; Gradient: 35 B to 40 B in 10 min; 254/220 nm; RT1: 7.03 min; RT2: 8.47 min) to afford two fractions:

Fraction 1: Rt: 7.03 min. 27.9 mg (10.3% yield) of 4-((5,7-dichloro-1,3-benzodiazol-1-yl)methyl)phenylboronic acid (46b) as a white solid. MS (ESI, pos. ion) m/z: 321.20 (M+1). $^1$H NMR (400 MHz, DMSO-d6, ppm) δ 8.56 (s, 1H), 8.02 (s, 2H), 7.78 (d, J=1.9 Hz, 1H), 7.70 (d, J=7.9 Hz, 2H), 7.36 (d, J=1.8 Hz, 1H), 7.00 (d, J=7.8 Hz, 2H), 5.74 (s, 2H).

Fraction 2: Rt: 8.47 min. 17.4 mg (6.8% yield) give 4-((4,6-dichloro-1,3-benzodiazol-1-yl)methyl)phenylboronic acid (46a) as a white solid. MS (ESI, pos. ion) m/z: 321.15 (M+1). $^1$H-NMR (400 MHz, DMSO-d6, ppm) δ 8.56 (s, 1H), 8.11 (s, 2H), 7.76-7.65 (m, 3H), 7.39 (d, J=1.8 Hz, 1H), 7.25 (d, J=7.7 Hz, 2H), 5.51 (s, 2H).

Example 47

Synthesis of 4-((4-fluoro-1,3-benzodiazol-1-yl)methyl)phenylboronic acid (47a) and 4-((7-fluoro-1,3-benzodiazol-1-yl)methyl)phenylboronic acid (47b

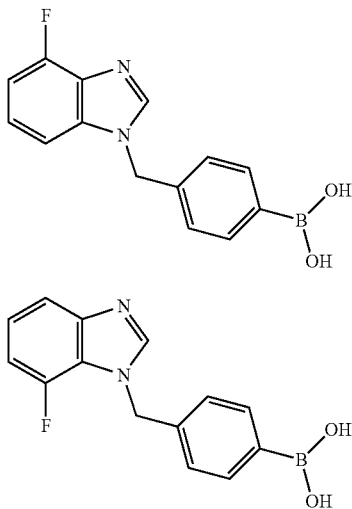

47a

47b

The title compounds were synthesized by the method described in step 4 of Example 22 except 4-fluoro-1H-1,3-benzodiazole (150 mg, 1.102 mmol) was used. The residue was purified by prep-HPLC (Column: Sunfire prep C18 column, 30*150, 5 um; Mobile Phase A: Water (0.1% FA), Mobile Phase B: ACN; Flow rate: 60 mL/min; Gradient: 10 B to 35 B in 10 min; 254/220 nm; RT1: 8.3 min; RT2: 8.98 min) to afford two fractions:

Fraction 1: Rt: 8.30 min. 57.7 mg (18.8% yield) of 4-((4-fluoro-1,3-benzodiazol-1-yl)methyl)phenylboronic acid (47a) as a white solid. MS (ESI, pos. ion) m/z: 271.20 (M+1). $^1$H NMR (400 MHz, DMSO-d6, ppm) δ 8.45 (s, 1H), 8.03 (s, 2H), 7.75-7.68 (m, 2H), 7.33 (m, 1H), 7.27-7.21 (m, 1H), 7.17 (m, 2H), 6.99 (m, 1H), 5.51 (s, 2H).

Fraction 2: Rt: 8.98 min. 90.4 mg (29.5% yield) give 4-((7-fluoro-1,3-benzodiazol-1-yl)methyl)phenylboronic acid (47b) as a white solid. MS (ESI, pos. ion) m/z: 271.25 (M+1). $^1$H-NMR (400 MHz, DMSO-d6, ppm) δ 8.45 (s, 1H), 8.06 (s, 2H), 7.74-7.68 (m, 2H), 7.49 (d, J=8.1 Hz, 1H), 7.15 (m, 3H), 7.01 (dd, J=11.5, 8.0 Hz, 1H), 5.55 (s, 2H).

Example 48

Synthesis of 4-(imidazo[4,5-b]pyridin-1-ylmethyl)phenylboronic acid (48a) and 4-(imidazo[4,5-b]pyridin-3-ylmethyl)phenylboronic acid (48b

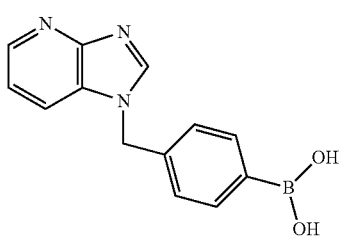

48a

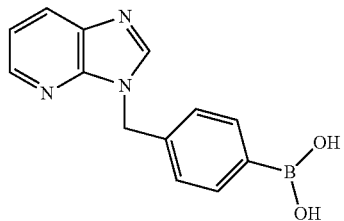

48b

The title compounds were synthesized by the method described in step 4 of Example 22 except 3H-imidazo[4,5-b]pyridine (150.00 mg, 1.259 mmol) was used. The residue was purified by prep-HPLC (Column: XBridge C18 OBD Prep Column, 100 Å, 5 μm, 19 mm×250 mm; Mobile Phase A: Water (0.05% FA), Mobile Phase B: ACN; Flow rate: 25 mL/min; Gradient: 7 B to 17 B in 7 min; 254, 220 nm; RT1: 7.70 min; RT2: 9.88 min) to afford two fractions:

Fraction 1: Rt: 7.70 min. 55.9 mg (16.3% yield) of 4-(imidazo[4,5-b]pyridin-1-ylmethyl)phenylboronic acid (48a) as a white solid. MS (ESI, pos. ion) m/z: 254.25 (M+1). $^1$H NMR (400 MHz, DMSO-d6, ppm) δ 8.65 (s, 1H), 8.38 (dd, J=4.7, 1.5 Hz, 1H), 8.05 (s, 2H), 7.93 (dd, J=8.1, 1.6 Hz, 1H), 7.75-7.69 (m, 2H), 7.39-7.10 (m, 3H), 5.52 (s, 2H).

Fraction 2: Rt: 9.88 min. 73.3 mg (22.7% yield) give 4-(imidazo[4,5-b]pyridin-3-ylmethyl)phenylboronic acid (48b) as a white solid. MS (ESI, pos. ion) m/z: 254.20 (M+1). $^1$H-NMR (400 MHz, DMSO-d6, ppm) δ 8.59 (s, 1H), 8.35 (dd, J=4.8, 1.5 Hz, 1H), 8.09 (dd, J=8.1, 1.5 Hz, 1H), 8.02 (d, J=4.5 Hz, 2H), 7.74-7.67 (m, 2H), 7.31-7.22 (m, 3H), 5.49 (s, 2H).

Example 49

Synthesis of 4-((2-isopropylimidazo[4,5-b]pyridin-1-yl)methyl)phenylboronic acid (49a) and 4-((2-isopropylimidazo[4,5-b]pyridin-3-yl)methyl)phenylboronic acid (49b

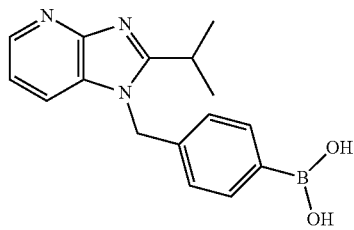

49a

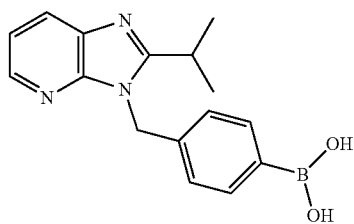

49b

Step 1: 2-isopropyl-1H-imidazo[4,5-b]pyridine

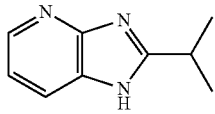

The title compound was synthesized by the method described in step 1 of Example 37 except pyridine-2,3-diamine (300 mg, 2.749 mmol) and isobutyraldehyde (198 mg, 2.749) were used. The crude product was purified by column chromatography (silica gel, eluent: ethyl acetate/ petroleum ether 3:2) to afford 2-isopropyl-1H-imidazo[4,5-b]pyridine (210 mg, 26.1% yield) as a yellow solid.

Step 2: 4-((2-isopropylimidazo[4,5-b]pyridin-1-yl) methyl)phenylboronic acid and 4-((2-isopropylimidazo[4,5-b]pyridin-3-yl)methyl)phenylboronic acid

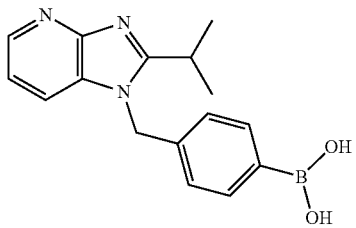

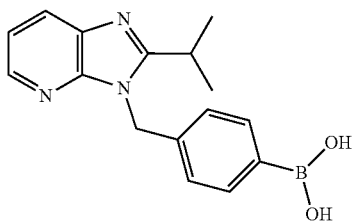

The title compounds were synthesized by the method described in step 4 of Example 22 except 2-isopropyl-1H-imidazo[4,5-b]pyridine (210 mg, 1.30 mmol) was used. The residue was purified by prep-HPLC (The residue was purified by prep-HPLC (Column: XBridge C18 OBD Prep Column, 100 Å, 5 μm, 19 mm×250 mm; Mobile Phase A: Water (0.05% FA), Mobile Phase B: ACN; Flow rate: 25 mL/min; Gradient: 10 B to 35 B in 8 min; 254,220 nm; RT1: 3.60 min; RT2: 6.72 min) to afford two fractions:

Fraction 1: Rt: 3.60 min. 8.0 mg (2.0% yield) of 4-((2-isopropylimidazo[4,5-b]pyridin-1-yl)methyl)phenylboronic acid (49a) as a white solid. MS (ESI, pos. ion) m/z: 296.30 (M+1). $^1$H NMR (400 MHz, DMSO-d6, ppm) δ 8.28-7.93 (m, 4H), 7.75-7.67 (m, 2H), 7.39 (d, J=7.9 Hz, 2H), 7.12 (dd, J=7.6, 6.3 Hz, 1H), 5.80 (s, 2H), 3.20-3.08 (m, 1H), 1.32 (d, J=6.9 Hz, 6H).

Fraction 2: Rt: 6.72 min. 14.6 mg (3.6% yield) give 4-((2-isopropylimidazo[4,5-b]pyridin-3-yl)methyl)phenylboronic acid (49b) as a brown solid. MS (ESI, pos. ion) m/z: 296.25 (M+1). $^1$H-NMR (400 MHz, DMSO-d6, ppm) δ 8.28 (d, J=4.8 Hz, 1H), 8.14-7.86 (m, 3H), 7.69 (d, J=7.6 Hz, 2H), 7.25 (dd, J=7.9, 4.8 Hz, 1H), 7.06 (d, J=7.7 Hz, 2H), 5.54 (s, 2H), 3.22 (d, J=6.7 Hz, 1H), 1.18 (d, J=6.7 Hz, 6H).

Example 50

Synthesis of 4-((7-chloroimidazo[4,5-c]pyridin-3-yl) methyl)phenylboronic acid (50a) and 4-((7-chloroimidazo[4,5-c]pyridin-1-yl)methyl)phenylboronic acid (50b

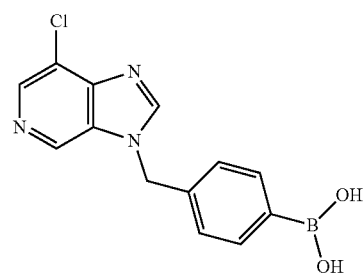

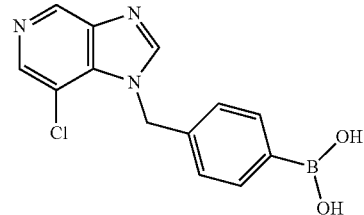

The title compounds were synthesized by the method described in step 4 of Example 22 except 7-chloro-3H-imidazo[4,5-c]pyridine (150 mg, 0.977 mmol) was used. The residue was purified by prep-HPLC (The residue was purified by prep-HPLC (Column: XBridge C18 OBD Prep Column, 100 Å, 5 μm, 19 mm×250 mm; Mobile Phase A: Water (10 MMOL/L NH$_4$HCO$_3$+0.1% NH$_3$·H$_2$O), Mobile Phase B: ACN; Flow rate: 25 mL/min; Gradient: 20 B to 30 B in 7 min; 254/220 nm; RT1: 6.58 min; RT2: 6.72 min) to afford two fractions:

Fraction 1: Rt: 6.58 min. 12.6 mg (4.5% yield) of 4-((7-chloroimidazo[4,5-c]pyridin-3-yl)methyl)phenylboronic acid (50a) as a white solid. MS (ESI, pos. ion) m/z: 287.85 (M+1). $^1$H NMR (400 MHz, DMSO-d6, ppm) δ 9.25 (d, J=1.3 Hz, 1H), 8.56 (d, J=1.3 Hz, 1H), 8.37 (s, 2H), 8.23 (s, 1H), 7.80-7.73 (m, 2H), 7.40 (d, J=7.9 Hz, 2H), 5.66 (s, 2H).

Fraction 2: Rt: 6.72 min. 29.6 mg (10.5% yield) give 4-((7-chloroimidazo[4,5-c]pyridin-1-yl)methyl)phenylboronic acid (50b) as a white solid. MS (ESI, pos. ion) m/z: 288.20 (M+1). $^1$H-NMR (400 MHz, DMSO-d6, ppm) δ 8.96 (s, 1H), 8.66 (s, 1H), 8.32 (s, 1H), 8.05 (s, 2H), 7.74-7.72 (d, J=7.9 Hz, 2H), 7.08-7.06 (d, J=7.9 Hz, 2H), 5.77 (s, 2H).

Example 51

Synthesis of 4-((7-chloro-2-isopropylimidazo[4,5-c]pyridin-3-yl)methyl)phenylboronic acid

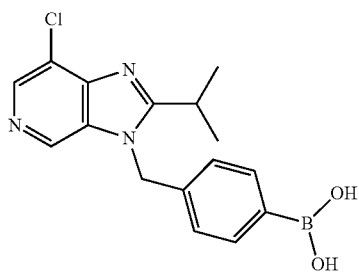 [SMILES: CC(C)c1nc2c(Cl)cncc2n1Cc1ccc(B(O)O)cc1]

Step 1: 7-chloro-2-isopropyl-3H-imidazo[4,5-c]pyridine

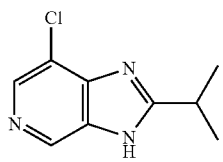

To a stirred solution of 5-chloropyridine-3,4-diamine (300 mg, 2.09 mmol, 1.00 equiv) in N,N-dimethylisobutyramide (6.00 mL, 0.21 mmol, 0.02 equiv) was added imidazole hydrochloride (328 mg, 3.13 mmol, 1.50 equiv) at room temperature. After stirring for 24 hours at 140° C., the mixture was diluted with water and extracted with ethyl acetate. The combined organic layers were washed brine, dried over anhydrous sodium sulfate, filtered and concentrated under reduced pressure. The residue was purified by column chromatography (silica gel, eluent: ethyl acetate/petroleum ether 9:11) to get 7-chloro-2-isopropyl-3H-imidazo[4,5-c]pyridine (150 mg, 34.9% yield) as a yellow solid Step 2: 4-((7-chloro-2-isopropylimidazo[4,5-c]pyridin-3-yl)methyl)phenylboronic

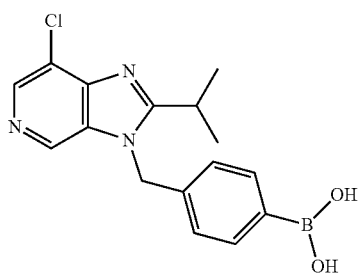 [SMILES: CC(C)c1nc2c(Cl)cncc2n1Cc1ccc(B(O)O)cc1]

The title compound was synthesized by the method described in step 4 of Example 22 except 7-chloro-2-isopropyl-3H-imidazo[4,5-c]pyridine (150 mg, 0.77 mmol) was used. The residue was purified by prep-HPLC (Column: YMC-Actus Triart C18, 30*250, 5 um; Mobile Phase A: Water (0.05% FA), Mobile Phase B: ACN; Flow rate: 45 mL/min; Gradient: 5 B to 22 B in 7 min; 254,220 nm) to afford 4-((7-chloro-2-isopropylimidazo[4,5-c]pyridin-3-yl) methyl)phenylboronic acid (30.7 mg, 11.9% yield) as a white solid. MS (ESI, pos. ion) m/z: 330.20 (M+1). $^1$H NMR (400 MHz, DMSO-d$_6$, ppm) δ 8.98 (s, 1H), 8.46 (s, 1H), 8.10 (d, J=16.3 Hz, 2H), 7.77 (d, J=7.8 Hz, 2H), 7.37 (d, J=7.8 Hz, 2H), 5.61 (s, 2H), 3.19-3.11 (m, 1H), 1.42-1.18 (m, 6H).

Example 52

Synthesis of 4-((4-hydroxy-2-methyl-1,3-benzodiazol-1-yl)methyl)phenylboronic acid with 2.0 formic acid (52a), 4-((7-methoxy-2-methyl-1,3-benzodiazol-1-yl)methyl)phenylboronic acid (52b) and 4-((4-methoxy-2-methyl-1,3-benzodiazol-1-yl)methyl)phenylboronic acid (52c

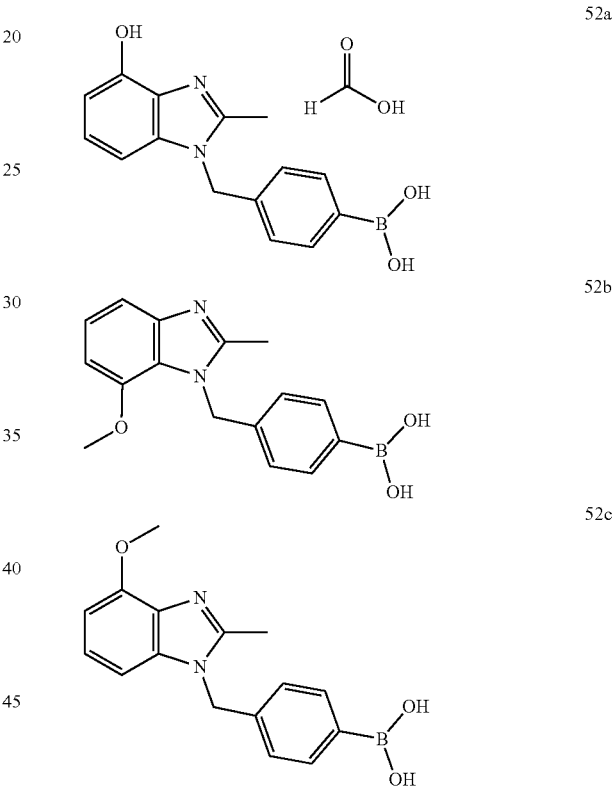

Step 1: 4-methoxy-2-methyl-1H-1,3-benzodiazole

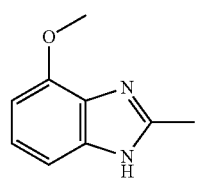

The title compound was synthesized by the method described in step 4 of Example 37 except 3-methoxybenzene-1,2-diamine (500 mg, 3.62 mmol) was used. Yield: 250 mg (27.5%) as a white solid. MS (ESI, pos. ion) m/z: 163.25 (M+1).

Step 2: 4-((7-methoxy-2-methyl-1,3-benzodiazol-1-yl)methyl)phenylboronic acid (52b) and 4-((4-methoxy-2-methyl-1,3-benzodiazol-1-yl)methyl)phenylboronic acid (52c

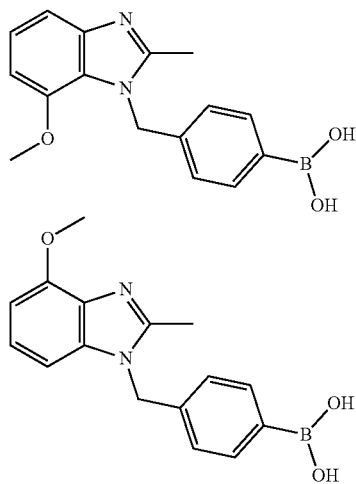

The title compounds were synthesized by the method described in step 4 of Example 22 except 4-methoxy-2-methyl-1H-1,3-benzodiazole (0.25 g, 1.54 mmol) was used. The residue was purified by prep-HPLC (Column: YMC-Actus Triart C18, 30*250.5 um; Mobile Phase A: Water (10 MMOL/L NH4HCO3+0.1% NH3·H2O), Mobile Phase B: ACN; Flow rate: 45 mL/min; Gradient: 20 B to 30 B in 7 min; 254,220 nm; RT1: 9.05 min; RT2: 11.02 min) to afford two fractions:

Fraction 1: Rt: 9.05 min. 22.2 mg (4.8% yield) give and 4-((7-methoxy-2-methyl-1,3-benzodiazol-1-yl)methyl)phenylboronic acid (52b) as a white solid. MS (ESI, pos. ion) m/z: 296.90 (M+1). $^1$H-NMR (400 MHz, DMSO-d6, ppm) δ 7.99 (s, 2H), 7.75-7.66 (m, 2H), 7.13-6.94 (dd, J=8.1, 0.9 Hz, 1H), 7.04 (t, J=8.0 Hz, 1H), 7.00-6.94 (m, 2H), 6.73 (dd, J=7.9, 0.9 Hz, 1H), 5.60 (s, 2H), 3.78 (s, 3H), 2.39 (s, 3H).

Fraction 2: Rt: 11.02 min. 110 mg (23.7% yield) of 4-((4-methoxy-2-methyl-1,3-benzodiazol-1-yl)methyl)phenylboronic acid (52c) as a white solid. MS (ESI, pos. ion) m/z: 296.90 (M+1). $^1$H NMR (400 MHz, DMSO-d6, ppm) δ 8.01 (s, 2H), 7.73-7.66 (m, 2H), 7.08-6.96 (m, 4H), 6.65 (dd, J=7.3, 1.5 Hz, 1H), 5.41 (s, 2H), 3.90 (s, 3H), 2.45 (s, 3H).

Step 3: 4-((4-hydroxy-2-methyl-1,3-benzodiazol-1-yl)methyl)phenylboronic acid with 2.0 formic acid (52a

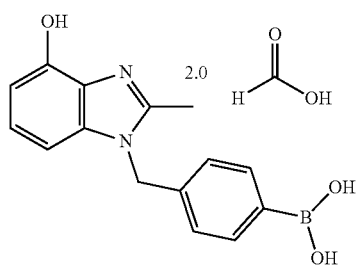

The title compound was synthesized by the method described in step 2 of example 35 except 4-((4-methoxy-2-methyl-1,3-benzodiazol-1-yl)methyl)phenyl-boronic acid (80 mg, 0.27 mmol) was used. The residue was purified by prep-HPLC (Column: YMC-Actus Triart C18, 30*250.5 um; Mobile Phase A: Water (0.1% FA), Mobile Phase B: ACN; Flow rate: 45 mL/min; Gradient: 5 B to 30 B in 7 min; 254/220 nm; RT1: 5.78 min) to afford 4-((4-hydroxy-2-methyl-1,3-benzodiazol-1-yl)methyl)phenylboronic acid: formic acid (52a, 16.3 mg, 21.4% yield) as a white solid. MS (ESI, pos. ion) m/z: 282.90 (M+1). $^1$H-NMR (400 MHz, DMSO-d6, ppm) δ 9.63 (s, 1H), 8.15 (s, 2H), 8.06 (s, 1H), 7.72 (d, J=7.8 Hz, 2H), 7.06 (d, J=7.8 Hz, 2H), 6.96-6.78 (m, 2H), 6.51 (dd, J=7.7, 1.1 Hz, 1H), 5.40 (s, 2H), 2.48 (s, 3H)

Example 53

Synthesis of 4-((4-carbamoylimidazo[4,5-c]pyridin-1-yl)methyl)phenylboronic acid

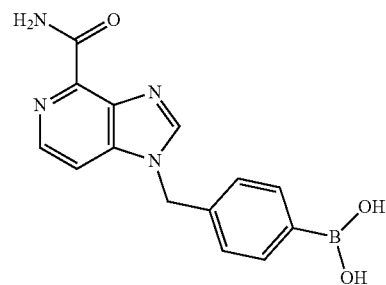

Step 1: 1H-imidazo[4,5-c]pyridine-4-carboxamide

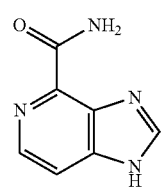 [SMILES: NC(=O)c1nccc2[nH]cnc12]

The title compound was synthesized by the method described in step 1 of Example 41 except 4-chloro-1H-imidazo[4,5-c]pyridine (220 mg, 1.43 mmol) was used. Yield: 160 mg (50.1%) as a purple solid. MS (ESI, pos. ion) m/z: 162.99 (M+1).

Step 2: 4-((4-carbamoylimidazo[4,5-c]pyridin-1-yl)methyl)phenylboronic acid

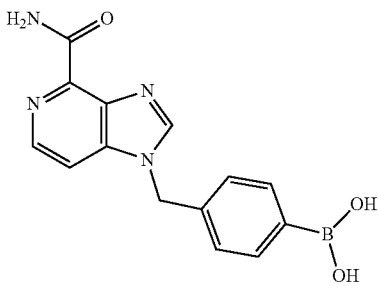

The title compound was synthesized by the method described in step 4 of Example 22 except 1H-imidazo[4,5-c]pyridine-4-carboxamide (82.00 mg, 0.506 mmol) was used. The residue was purified by prep-HPLC (Column: YMC-Actus Triart C18, 30*250.5 um; Mobile Phase A: Water (10 MMOL/L NH4HCO3+0.1% NH3·H2O), Mobile Phase B: ACN; Flow rate: 45 mL/min; Gradient: 20 B to 30 B in 7 min; 254/220 nm; RT: 9.05 min) Column: Sunfire prep C18 column, 30*150, 5 um; Mobile Phase A: Water (0.1% FA), Mobile Phase B: ACN; Flow rate: 60 mL/min; Gradient: 4 B to 12 B in 7.5 min; 254/220 nm) to afford 4-((4-carbamoylimidazo[4,5-c]pyridin-1-yl)methyl)phenylboronic acid (19.2 mg, 12.8% yield) as a white solid. MS (ESI, pos. ion) m/z: 297.25 (M+1). $^1$H-NMR (400 MHz, DMSO-d6, ppm) δ 8.72 (s, 1H), 8.58 (s, 1H), 8.38 (d, J=5.4 Hz, 1H), 8.08 (s, 2H), 7.80-7.67 (m, 4H), 7.30-7.20 (m, 2H), 5.58 (s, 2H).

Example 54

Synthesis of 4-((4-fluoropyrrolo[2,3-b]pyridin-1-yl)methyl)phenylboronic acid

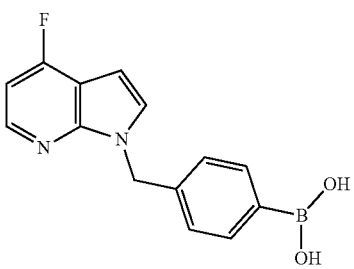 [SMILES: OB(O)c1ccc(Cn2ccc3c(F)ccnc32)cc1]

The title compound was synthesized by the method described in step 4 of Example 22 except 4-fluoro-1H-pyrrolo[2,3-b]pyridine (150 mg, 1.102 mmol) was used. The residue was purified by prep-HPLC (Column: YMC-Actus Triart C18, 30*250.5 um; Mobile Phase A: Water (0.05% FA), Mobile Phase B: ACN:MEOH=4:1; Flow rate: 45 mL/min; Gradient: 35 B to 55 B in 7 min; 254/220 nm; RT: 7.27 min) to afford 4-((4-fluoropyrrolo[2,3-b]pyridin-1-yl)methyl)phenylboronic acid (157.9 mg, 50.8% yield) as a white solid. MS (ESI, pos. ion) m/z: 271.10 (M+1). $^1$H-NMR (400 MHz, DMSO-d6, ppm) δ 8.33-8.22 (m, 1H), 8.01 (d, J=1.9 Hz, 2H), 7.71 (d, J=7.9 Hz, 3H), 7.18 (d, J=7.5 Hz, 2H), 7.02 (dd, J=10.8, 5.6 Hz, 1H), 6.62 (t, J=2.7 Hz, 1H), 5.51 (s, 2H).

Example 55

Synthesis of 4-((4-methoxypyrazolo[4,3-c]pyridin-1-yl)methyl)phenylboronic acid (55a), and 4-((4-hydroxypyrazolo[4,3-c]pyridin-1-yl)methyl)phenylboronic acid (55b

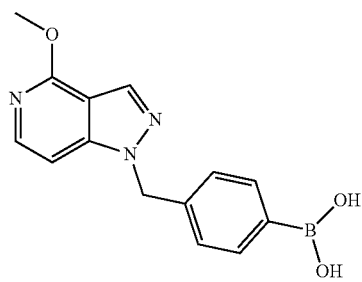

55a

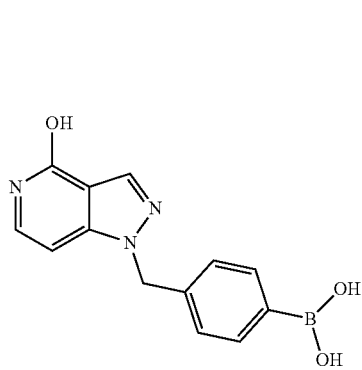

55b

Step 1: 4-methoxy-1H-pyrazolo[4,3-c]pyridine

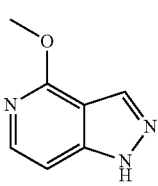

To a solution of 30% NaOMe in MeOH (10.00 mL) was added 4-chloro-1H-pyrazolo[4,3-c]pyridine (500.00 mg, 1 equiv). The resulting mixture was stirred for 2 h at 140° C. After cooling to room temperature, the reaction mixture was quenched with water and extracted with ethyl acetate. The combined organic layers were washed with water and brine, dried over sodium sulfate, filtered and concentrated under reduced pressure to give 4-methoxy-1H-pyrazolo[4,3-c]pyridine (300 mg, 60.54% yield) as a yellow solid Step 2: 4-((4-methoxypyrazolo[4,3-c]pyridin-1-yl)methyl)phenylboronic acid (55a)

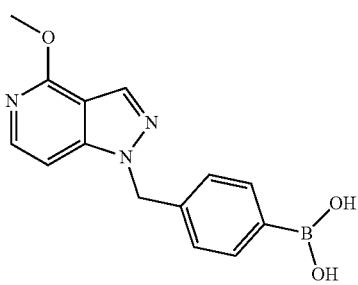

To a solution of 4-methoxy-1H-pyrazolo[4,3-c]pyridine (280 mg, 1.840 mmol, 1.00 equiv, 98%) in DMF (10.00 mL) were added 4-(bromomethyl)phenylboronic acid (474 mg, 2.21 mmol, 1.2 eq) and cesium carbonate (1.20 g, 3.68 mmol, 2 eq). After stirring for 2 h at room temperature, the reaction mixture was concentrated under reduced pressure. The residue was purified by Column: Sunfire prep C18 column, 30*150, 5 um; Mobile Phase A: Water (0.1% FA), Mobile Phase B: ACN; Flow rate: 60 mL/min; Gradient: 20 B to 30 B in 10 min; 254/220 nm; RT1: 5.02 min; RT2: 9.17 min) to give 100 mg (18.4% yield) of 4-((4-methoxypyrazolo[4,3-c]pyridin-1-yl)methyl)phenylboronic acid (55a) as a white solid. MS (ESI, pos. ion) m/z: 284.25 (M+1). $^1$H NMR (300 MHz, DMSO-$d_6$, ppm) δ 8.18 (s, 1H), 8.02 (s, 2H), 7.90 (d, J=6.1 Hz, 1H), 7.72 (d, J=7.7 Hz, 2H), 7.32 (d, J=6.1 Hz, 1H), 7.16 (d, J=7.5 Hz, 2H), 5.64 (s, 2H), 4.00 (s, 3H).

Step 3: 4-((4-hydroxypyrazolo[4,3-c]pyridin-1-yl)methyl)phenylboronic acid

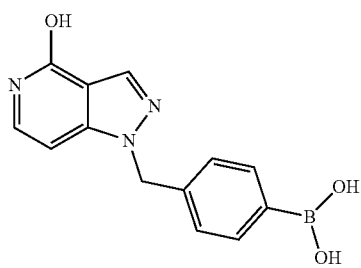

Into a solution of 4-((4-methoxypyrazolo[4,3-c]pyridin-1-yl)methyl)phenylboronic acid (55a, 85.00 mg, 0.300 mmol, 1.00 equiv) in ACN (5 mL) was added TMSI (1.0 mL. After stirring for 1 h at 90° C., the reaction mixture was concentrated under reduced pressure. The crude product was purified by Prep-HPLC with the following conditions (Column: XSelect CSH Prep C18 OBD Column, 19*250 mm, 5 um; Mobile Phase A: Water (0.1% FA), Mobile Phase B: ACN; Flow rate: 20 mL/min; Gradient: 10 B to 71 B in 7 min; 254/220 nm; RT: 5.83 min) to afford 4-((4-hydroxypyrazolo[4,3-c]pyridin-1-yl)methyl)phenylboronic acid (55c, 57.0 mg, 67.8% yield) as a white solid. MS (ESI, pos. ion) m/z: 270.20 (M+1). $^1$H-NMR (400 MHz, DMSO-d6, ppm) $^1$H NMR (300 MHz, DMSO-$d_6$) δ 11.05 (d, J=5.7 Hz, 1H), 8.06 (d, J=0.8 Hz, 2H), 7.82-7.69 (m, 2H), 7.25-7.12 (m, 3H), 6.70-6.61 (m, 1H), 5.54 (s, 2H).

Example 56

Synthesis of 4-((5-(methylcarbamoyl)-1,3-benzodiazol-1-yl)methyl)phenylboronic acid (56a) and 4-((6-(methylcarbamoyl)-1,3-benzodiazol-1-yl)methyl)phenylboronic acid (56b

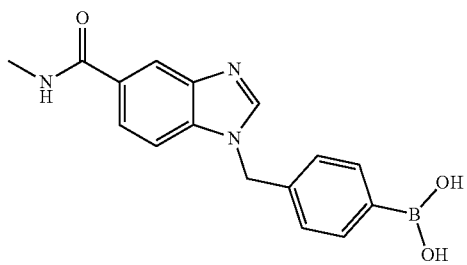

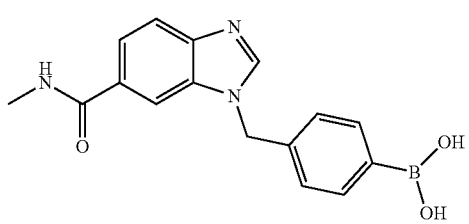

Step 1: N-methyl-1H-1,3-benzodiazole-5-carboxamide

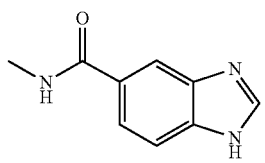

Methyl 1H-1,3-benzodiazole-5-carboxylate (500 mg, 1.00 equiv) was dissolved in a solution of $CH_3NH_2$ (10.00 mL, 30% in MeOH). After stirring overnight at 80° C., the reaction mixture was cooled to room temperature and concentrated under reduced pressure. The residue was purified by column chromatography on silica gel 100 g (eluent: petroleum ether-ethyl acetate 100%, 1:3) to give N-methyl-1H-1,3-benzodiazole-5-carboxamide (300 mg, 60.3% yield) as an off-white solid.

Step 2: 4-((5-(methylcarbamoyl)-1,3-benzodiazol-1-yl)methyl)phenylboronic acid (56a) and 4-((6-(methylcarbamoyl)-1,3-benzodiazol-1-yl)methyl)phenylboronic (56b

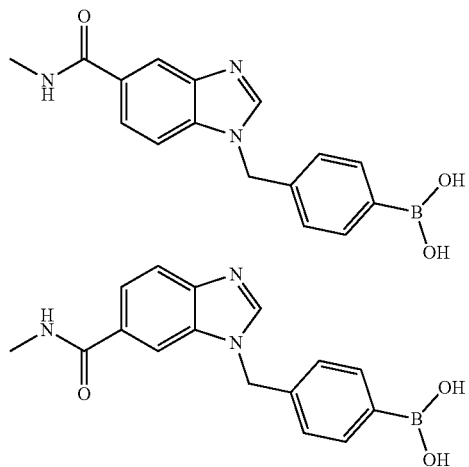

The title compounds were synthesized by the method described in step 2 of Example 55 except N-methyl-1H-1,3-benzodiazole-5-carboxamide (200 mg, 1.142 mmol) was used. Two fractions were obtained:

Fraction 1: Rt: 5.02 min. 77.7 mg (21.8% yield) of 4-((6-(methylcarbamoyl)-1,3-benzodiazol-1-yl)methyl)phenylboronic acid (56b) as a white solid. MS (ESI, pos. ion) m/z: 310.30 (M+1). $^1$H NMR (300 MHz, DMSO-$d_6$, ppm) δ 8.56 (s, 1H), 8.43-8.34 (m, 1H), 8.03 (s, 3H), 7.79-7.68 (m, 4H), 7.31-7.20 (m, 2H), 5.55 (s, 2H), 2.79 (d, J=4.5 Hz, 3H).

Fraction 2: Rt: 6.65 min. 41.3 mg (11.5% yield) 4-((5-(methylcarbamoyl)-1,3-benzodiazol-1-yl)methyl)phenylboronic acid (56a) as a white solid. MS (ESI, pos. ion) m/z: 310.30 (M+1). $^1$H NMR (300 MHz, DMSO-$d_6$, ppm) δ 8.53 (s, 1H), 8.38 (t, J=4.5 Hz, 1H), 8.20 (d, J=1.5 Hz, 1H), 8.03 (s, 2H), 7.74 (dd, J=8.3, 1.5 Hz, 3H), 7.56 (dd, J=8.5, 0.7 Hz, 1H), 7.31-7.22 (m, 2H), 5.53 (s, 2H), 2.80 (d, J=4.5 Hz, 3H).

Example 57

Synthesis of diethyl 4-((4-methoxyindol-1-yl)methyl)phenylphosphonate (57a), 4-((4-methoxyindol-1-yl)methyl)phenylphosphonic acid (57b) and 4-((4-hydroxyindol-1-yl)methyl)phenylphosphonic acid (57c

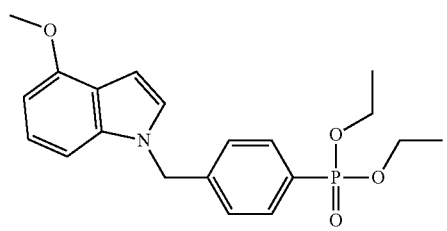

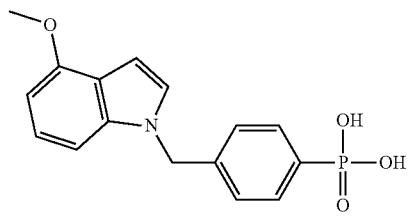

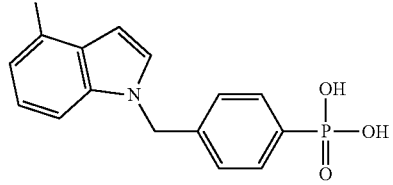

Step 1: diethyl 4-((4-methoxyindol-1-yl)methyl)phenylphosphonate (57a

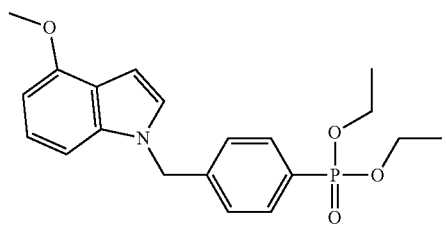 [SMILES: CCOP(=O)(OCC)c1ccc(Cn2ccc3c(OC)cccc32)cc1]

The title compound was synthesized by the method described in step 2 of Example 55 except 4-methoxy-1H-indole (250 mg, 1.70 mmol) and diethyl 4-(bromomethyl)phenylphosphonate (782 mg, 2.55 mmol) were used to give diethyl 4-((4-methoxyindol-1-yl)methyl)phenylphosphonate (57a, 355 mg, 55.0%) as a yellow solid. MS (ESI, pos. ion) m/z: 374.25 (M+1). $^1$H NMR (300 MHz, DMSO-$d_6$, ppm) δ 7.71-7.58 (m, 2H), 7.40 (d, J=3.1 Hz, 1H), 7.27 (dd, J=8.1, 3.9 Hz, 2H), 7.09-6.96 (m, 2H), 6.60-6.48 (m, 2H), 5.49 (s, 2H), 3.97 (dqd, J=8.3, 7.0, 2.7 Hz, 4H), 3.87 (s, 3H), 1.20 (t, J=7.0 Hz, 6H).

Step 2: 4-((4-methoxyindol-1-yl)methyl)phenylphosphonic acid (57b

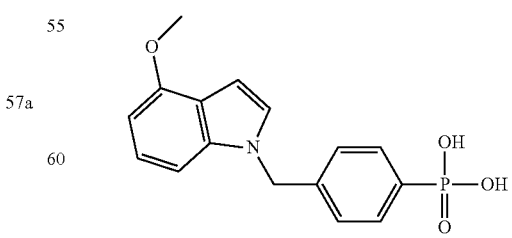

The title compound was synthesized by the method described in step 2 of Example 85 except diethyl 4-((4-methoxyindol-1-yl)methyl)phenylphosphonate (170.00 mg, 0.46 mmol) was used to give 4-((4-methoxyindol-1-yl)methyl)phenylphosphonic acid (57b, 85 mg, 50.0%) as an off-white solid. MS (ESI, pos. ion) m/z: 318.05 (M+1). $^1$H NMR (300 MHz, DMSO-d$_6$, ppm) δ 7.59 (dd, J=12.8, 7.8 Hz, 2H), 7.39 (d, J=3.2 Hz, 1H), 7.20 (d, J=7.7 Hz, 2H), 7.01 (d, J=5.7 Hz, 2H), 6.52 (d, J=11.2 Hz, 2H), 5.44 (s, 2H), 3.87 (s, 3H).

Step 3:
4-((4-hydroxyindol-1-yl)methyl)phenylphosphonic acid (57c

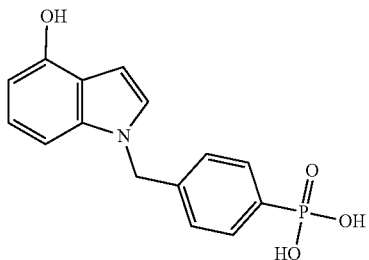 [SMILES: O=P(O)(O)c1ccc(Cn2ccc3c(O)cccc32)cc1]

The title compound was synthesized by the method described in step 2 of Example 35 except 4-((4-methoxyindol-1-yl)methyl)phenylphosphonic acid (70.00 mg, 0.22 mmol) was used to give 4-((4-methoxyindol-1-yl)methyl)phenylphosphonic acid (57c, 20.3 mg, 50.0%). MS (ESI, pos. ion) m/z: 304.05 (M+1). $^1$H NMR (300 MHz, DMSO-d$_6$/D20, ppm) δ 7.63-7.50 (m, 2H), 7.29 (d, J=3.5 Hz, 1H), 7.19 (d, J=7.8 Hz, 2H), 6.98-6.70 (m, 2H), 6.51 (d, J=3.1 Hz, 1H), 6.38 (d, J=7.4 Hz, 1H), 5.33 (s, 2H).

Example 58

Synthesis of 4-((6-carbamoylimidazo[4,5-c]pyridin-3-yl)methyl)phenylboronic acid (58a) and 4-((6-carbamoylimidazo[4,5-c]pyridin-1-yl)methyl)phenylboronic acid (58b

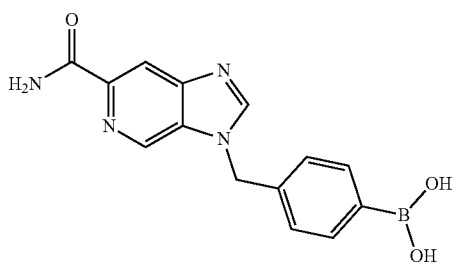
58a

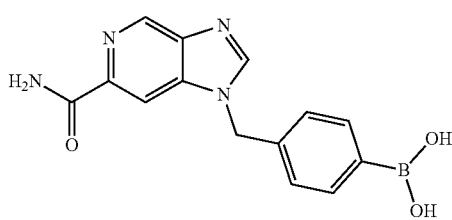
58b

Step 1: 3H-imidazo[4,5-c]pyridine-6-carboxamide

Methyl 3H-imidazo[4,5-c]pyridine-6-carboxylate (200 mg, 1.13 mmol) was dissolved in NH$_3$—H$_2$O (10 mL) in a sealed tube. The resulting mixture was stirred for 2 hours at 80° C. The reaction mixture was cooled to room temperature and evaporated to dryness to give 3H-imidazo[4,5-c]pyridine-6-carboxamide (180 mg, 98.3% yield) as a light yellow solid.

Step 2: 4-((6-carbamoylimidazo[4,5-c]pyridin-3-yl)methyl)phenylboronic acid (58a) and 4-((6-carbamoylimidazo[4,5-c]pyridin-1-yl)methyl)phenylboronic acid (58b

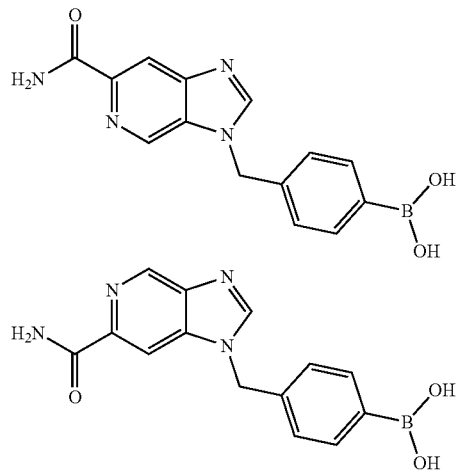

The title compounds were synthesized by the method described in step 2 of Example 55 except 3H-imidazo[4,5-c]pyridine-6-carboxamide (80 mg, 0.493 mmol). Two fractions were obtained:

Fraction 1: Rt: 13.05 min. 28.9 mg (18.9% yield) of 4-((6-carbamoylimidazo[4,5-c]pyridin-1-yl)methyl)phenylboronic acid (58b) as a white solid. MS (ESI, pos. ion) m/z: 297.30 (M+1). $^1$H NMR (300 MHz, DMSO-d$_6$, ppm) δ 8.98 (d, J=1.0 Hz, 1H), 8.72 (s, 1H), 8.24 (s, 1H), 8.14 (d, J=2.7 Hz, 1H), 8.08 (d, J=4.4 Hz, 2H), 7.75 (d, J=7.7 Hz, 2H), 7.60 (d, J=3.1 Hz, 1H), 7.26 (d, J=7.7 Hz, 2H), 5.66 (s, 2H).

Fraction 2: Rt: 14.0 min. 21.2 mg (13.9% yield) 4-((6-carbamoylimidazo[4,5-c]pyridin-3-yl)methyl)phenylboronic acid (58a) as a white solid. MS (ESI, pos. ion) m/z: 297.30 (M+1). $^1$H NMR (300 MHz, DMSO-d$_6$, ppm) δ 8.88 (s, 1H), 8.76 (s, 1H), 8.28 (s, 1H), 8.11-8.03 (m, 3H), 7.76 (d, J=7.8 Hz, 2H), 7.56 (s, 1H), 7.35 (d, J=7.7 Hz, 2H), 5.67 (s, 2H).

Example 59

Synthesis of 4-((6-(methylcarbamoyl)imidazo[4,5-c]pyridin-3-yl)methyl)phenylboronic acid (59a) and 4-((6-(methylcarbamoyl)imidazo[4,5-c]pyridin-1-yl)methyl)phenylboronic acid (59b

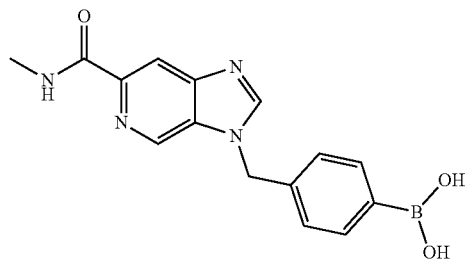

59a

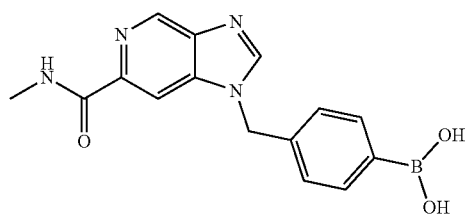

59b

Step 1: N-methyl-3H-imidazo[4,5-c]pyridine-6-carboxamide

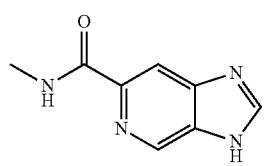

To a solution of 3H-imidazo[4,5-c]pyridine-6-carboxylic acid (250 mg, 1.5 mmol, 1.00 equiv) in DMF (5.00 mL) were added HATU (641 mg, 1.69 mmol, 1.1 equiv), TEA (465 mg, 4.60 mmol, 3 equiv) and methylamine (71 mg, 2.30 mmol, 1.5 equiv) at room temperature. The resulting mixture was stirred for 1.0 h at room temperature. The mixture was concentrated under reduced pressure and the residue was purified by column chromatography (silica gel, eluent: ethyl acetate/methanol 19:1) to give N-methyl-3H-imidazo[4,5-c]pyridine-6-carboxamide (120 mg, 44.5% yield) as a brown solid. MS (ESI, pos. ion) m/z: 177.20 (M+1).

Step 2: 4-((6-(methylcarbamoyl)imidazo[4,5-c]pyridin-3-yl)methyl)phenylboronic acid (59a) and 4-((6-(methylcarbamoyl)imidazo[4,5-c]pyridin-1-yl)methyl)phenylboronic acid (59b

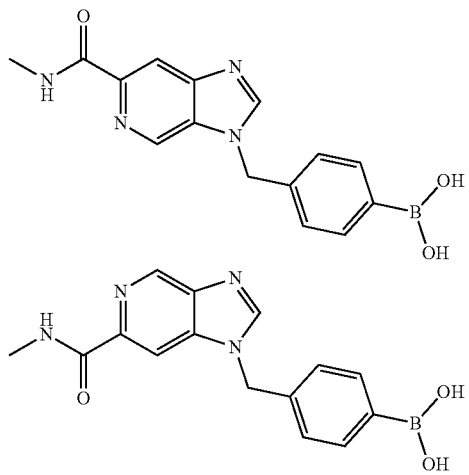

The title compounds were synthesized by the method described in step 2 of Example 55 except N-methyl-3H-imidazo[4,5-c]pyridine-6-carboxamide (120 mg, 0.681 mmol) was used. Two fractions were obtained:

Fraction 1: Rt: 13.05 min. 27.9 mg (13.2% yield) of 4-((6-(methylcarbamoyl)imidazo[4,5-c]pyridin-1-yl)methyl)phenylboronic acid (59b) as a white solid. MS (ESI, pos. ion) m/z: 311.05 (M+1). $^1$H NMR (300 MHz, DMSO-$d_6$, ppm) δ 8.98 (s, 1H), 8.78 (d, J=6.2 Hz, 1H), 8.71 (s, 1H), 8.21 (s, 1H), 8.06 (d, J=2.2 Hz, 2H), 7.75 (d, J=7.6 Hz, 2H), 7.26 (d, J=7.3 Hz, 2H), 5.66 (s, 2H), 2.82 (d, J=4.1 Hz, 3H).

Fraction 2: Rt: 14.0 min. 32.6 mg (15.0% yield) 4-((6-(methylcarbamoyl)imidazo[4,5-c]pyridin-3-yl)methyl)phenylboronic acid (59a) as a white solid. MS (ESI, pos. ion) m/z: 311.05 (M+1). $^1$H NMR (300 MHz, DMSO-$d_6$, ppm) δ 8.89 (s, 1H), 8.75 (s, 1H), 8.68 (s, 1H), 8.26 (s, 1H), 8.07 (s, 2H), 7.76 (d, J=7.4 Hz, 2H), 7.34 (d, J=7.6 Hz, 2H), 5.67 (s, 2H), 2.83 (s, 3H).

Example 60

Synthesis of 4-((4-amino-5-carbamoyl-1,3-benzodiazol-1-yl)methyl)phenylboronic acid

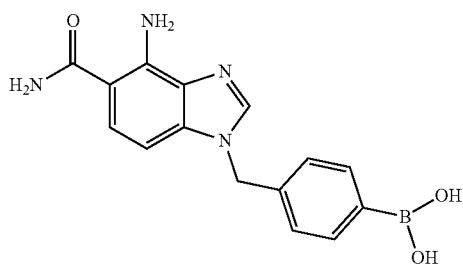

Step 1: 5-methyl-4-nitro-1H-1,3-benzodiazole and 5-methyl-6-nitro-1H-1,3-benzodiazole

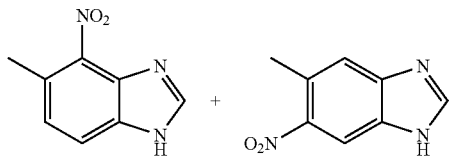

5-Methylbenzimidazole (6.0 g, 45.40 mmol) was dissolved in concentrated $H_2SO_4$ (20 mL) and cooled to 0° C. $KNO_3$ (1.68 g, 16.646 mmol, 1.10 equiv) was added portionwise. After stirring for 2 h, the reaction mixture was poured over ice and $Na_2CO_3$ was added to adjust pH>8. The aqueous layer was extracted with EtOAc and the combined organic layers were dried over $Na_2SO_4$, filtered and concentrated under reduced pressure The resulting yellow solid was recrystallized from 50% MeOH/water (80 mL) to afford a mixture of 5-methyl-4-nitro-1H-1,3-benzodiazole and 5-methyl-6-nitro-1H-1,3-benzodiazole (2.0 g, 74.6% yield) as a yellow solid.

Step 2: 4-nitro-1H-1,3-benzodiazole-5-carboxylic acid and 6-nitro-1H-1,3-benzodiazole-5-carboxylic acid

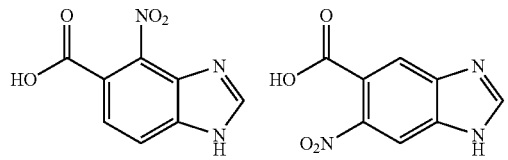

A mixture of 5-methyl-4-nitro-1H-1,3-benzodiazole and 5-methyl-6-nitro-1H-1,3-benzodiazole (2.00 g, 11.289 mmol, 1.00 equiv) was dissolved in water (30.00 mL) and t-BuOH (30.00 mL). $KMnO_4$ (7.14 g, 45.156 mmol, 4 equiv) was added and after stirring for 24 h at 90° C., the resulting mixture was filtered. The filtrate was concentrated under reduced pressure. The mixture was poured into water and the aqueous layer was extracted with ethyl acetate. The organic layers were combined, dried over anhydrous sodium sulfate, filtered and evaporated under reduced pressure. The residue was purified by column chromatography (silica gel, eluent: DCM/MEOH 90:10) to give a mixture of 4-nitro-1H-1,3-benzodiazole-5-carboxylic acid and 6-nitro-1H-1,3-benzodiazole-5-carboxylic acid (500 mg, 21.4% yield).

Step 3: 4-nitro-1H-benzo[d]imidazole-5-carboxamide and 6-nitro-1H-benzo[d]imidazole-5-carboxamide

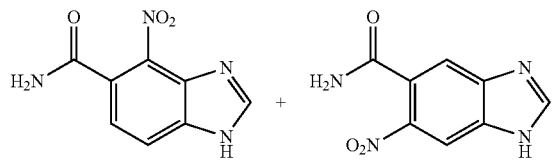 [SMILES: NC(=O)c1ccc2[nH]cnc2c1[N+](=O)[O-] ; NC(=O)c1cc2nc[nH]c2cc1[N+](=O)[O-]]

The title compound was synthesized by the method described at step 3 of Example 23 except a mixture of 4-nitro-1H-1,3-benzodiazole-5-carboxylic acid and 6-nitro-1H-1,3-benzodiazole-5-carboxylic acid (500 mg, 2.41 mmol) was used. to give a mixture of 4-nitro-1H-benzo[d]imidazole-5-carboxamide and 6-nitro-1H-benzo[d]imidazole-5-carboxamide 150 mg (32.1% yield)

Step 4: (4-((5-carbamoyl-4-nitro-1H-benzo[d]imidazol-1-yl)methyl)phenyl)boronic acid and (4-((5-carbamoyl-6-nitro-1H-benzo[d]imidazol-1-yl)methyl)phenyl)boronic acid

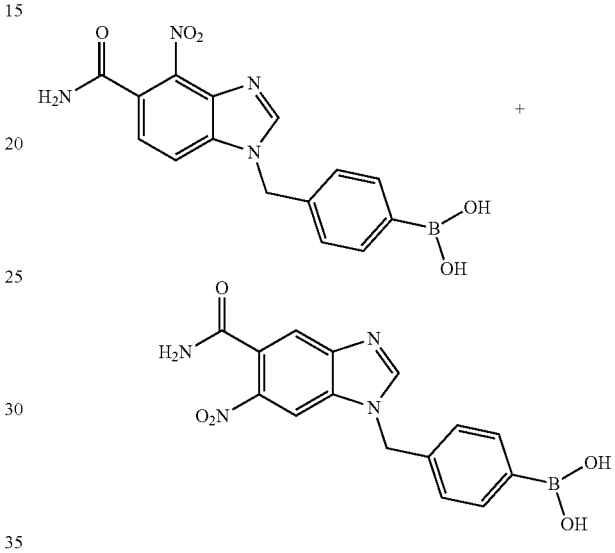

The title compounds were synthesized by the method described in step 2 of Example 55 except a mixture of 4-nitro-1H-benzo[d]imidazole-5-carboxamide and 6-nitro-1H-benzo[d]imidazole-5-carboxamide (150 mg 0.73 mmol) was used. to give a mixture (4-((5-carbamoyl-4-nitro-1H-benzo[d]imidazol-1-yl)methyl)phenyl)boronic acid and (4-((5-carbamoyl-6-nitro-1H-benzo[d]imidazol-1-yl)methyl)phenyl)boronic acid (150 mg, 32.1% yield).

Step 5: 4-((4-amino-5-carbamoyl-1,3-benzodiazol-1-yl)methyl)phenylboronic acid

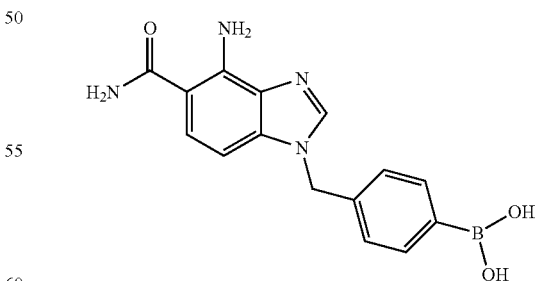

Into a solution of a mixture of (4-((5-carbamoyl-4-nitro-1H-benzo[d]imidazol-1-yl)methyl)phenyl)boronic acid and (4-((5-carbamoyl-6-nitro-1H-benzo[d]imidazol-1-yl)methyl)phenyl)boronic acid (100 mg, 0.294 mmol, 1.00 equiv) in MeOH (5 mL) was added Pd/C (20 mg). After stirring for 60 h at room temperature, the resulting mixture was filtered through a Celite. The filtrate was concentrated under reduced pressure. The crude product was purified by Prep-HPLC with the following conditions (Column: XBridge Prep OBD C18 Column, 19*250 mm, 5 um; Mobile Phase A: Water (10MMOL/L NH4HCO3+0.1% NH3·H2O), Mobile Phase B: ACN; Flow rate: 20 mL/min; Gradient: 8 B to 15 B in 12 min; 254/220 nm; RT: 7.8 min) to afford 4-((4-amino-5-carbamoyl-1,3-benzodiazol-1-yl)methyl)phenylboronic acid (3.2 mg, 3.1% yield) as a white solid. MS (ESI, pos. ion) m/z: 311.30 (M+1). $^1$H NMR (400 MHz, DMSO-d$_6$) δ 8.25 (s, 1H), 8.04 (d, J=4.2 Hz, 2H), 7.79-7.69 (m, 4H), 7.34 (d, J=7.9 Hz, 2H), 7.11 (s, 1H), 6.84 (s, 1H), 6.07 (s, 2H), 5.33 (s, 2H).

Example 61

Synthesis of 4-((5-carbamoylimidazo[4,5-b]pyridin-1-yl)methyl)phenylboronic acid (61a) and 4-((5-carbamoylimidazo[4,5-b]pyridin-3-yl)methyl)phenylboronic acid (61b

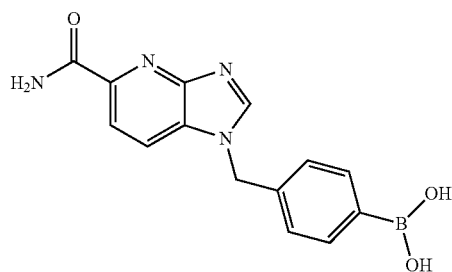
61a

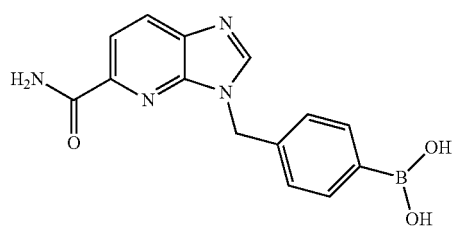
61b

Step 1: 1H-imidazo[4,5-b]pyridine-5-carboxamide

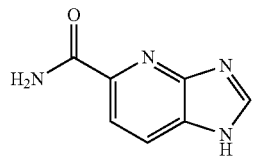 [SMILES: NC(=O)c1ccc2[nH]cnc2n1]

The title compound was synthesized by the method described in step 1 of Example 58 except methyl 1H-imidazo[4,5-b]pyridine-5-carboxylate (400 mg, 2.26 mmol) was used. Yield: 350 mg (83.1%) as a light yellow solid.

Step 2: 4-((5-carbamoylimidazo[4,5-b]pyridin-1-yl)methyl)phenylboronic acid (61a) and 4-((5-carbamoylimidazo[4,5-b]pyridin-3-yl)methyl)phenylboronic acid (61b

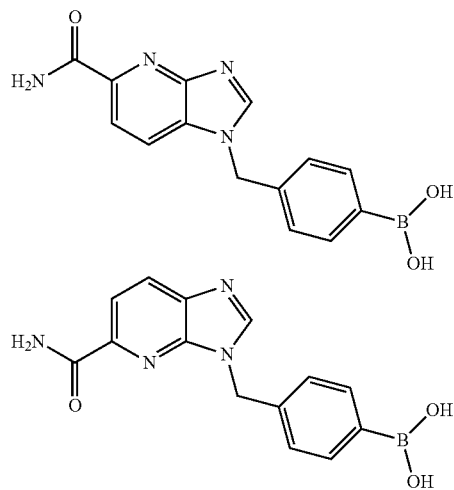

The title compounds were synthesized by the method described in step 2 of Example 55 except 1H-imidazo[4,5-b]pyridine-5-carboxamide (100 mg, 0.62 mmol) was used. Two fractions were obtained:

Fraction 1: Rt: 13.05 min. 40.4 mg (21.3% yield) of 4-((5-carbamoylimidazo[4,5-b]pyridin-1-yl)methyl)phenylboronic acid (61a) as a white solid. MS (ESI, pos. ion) m/z: 297.25 (M+1). $^1$H NMR (300 MHz, DMSO-d$_6$, ppm)) δ 8.83 (s, 1H), 8.17-8.05 (m, 4H), 7.98 (d, J=8.4 Hz, 1H), 7.75 (d, J=7.8 Hz, 2H), 7.56-7.49 (m, 1H), 7.30 (d, J=7.7 Hz, 2H), 5.58 (s, 2H).

Fraction 2: Rt: 14.0 min. 44.8 mg (23.6% yield) of 4-((5-carbamoylimidazo[4,5-b]pyridin-3-yl)methyl)phenylboronic acid (61b) as a white solid. MS (ESI, pos. ion) m/z: 297.30 (M+1). $^1$H NMR (300 MHz, DMSO-d$_6$, ppm) δ 8.78 (s, 1H), 8.26-8.18 (m, 2H), 8.09 (d, J=4.0 Hz, 2H), 7.99 (d, J=8.3 Hz, 1H), 7.74 (d, J=7.7 Hz, 2H), 7.66 (d, J=2.8 Hz, 1H), 7.42 (d, J=7.7 Hz, 2H), 5.60 (s, 2H).

Example 62

Synthesis of 4-((2-ethyl-4-hydroxypyrrolo[3,2-c]pyridin-1-yl)methyl)phenylboronic acid

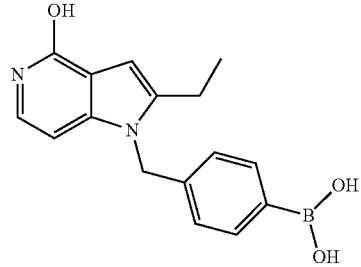 [SMILES: CCc1cc2c(O)nccc2n1Cc1ccc(B(O)O)cc1]

Step 1: 2-ethyl-4-methoxy-1H-pyrrolo[3,2-c]pyridine

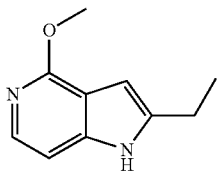

Into a stirred solution 3-iodo-2-methoxypyridin-4-amine (2.00 g, 7.999 mmol, 1.00 equiv) in THF (400 mL) were added $K_2CO_3$ (2.21 g, 15.998 mmol, 2.00 equiv), $Pd(PPh_3)_4$ (0.92 g, 0.800 mmol, 0.10 equiv) and XPhos (0.76 g, 1.600 mmol, 0.20 equiv) under 1-butyne (3.00 equiv) atmosphere. The reaction mixture was refluxed for 24 h. After concentration under reduced pressure, the residue was purified by flash chromatography on silica gel column (PE/EtOAc, gradient 100:0 to 85:15) and to give 2-ethyl-4-methoxy-1H-pyrrolo[3,2-c]pyridine (350 mg, 23.1% yield) as a brown solid.

Step 2: 4-((2-ethyl-4-methoxypyrrolo[3,2-c]pyridin-1-yl)methyl)phenylboronic acid

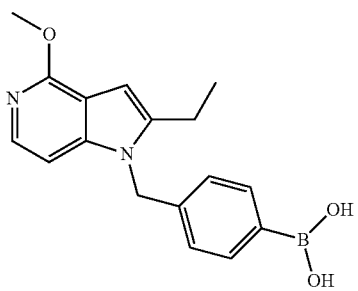 [SMILES: CCc1cc2c(OC)nccc2n1Cc1ccc(B(O)O)cc1]

The title compounds were synthesized by the method described in step 2 of Example 55 except 2-ethyl-4-methoxy-1H-pyrrolo[3,2-c]pyridine (250.00 mg, 1.419 mmol) was used. Yield: 268 mg (58.2% yield) as a white solid.

Step 3: 4-((2-ethyl-4-hydroxypyrrolo[3,2-c]pyridin-1-yl)methyl)phenylboronic acid

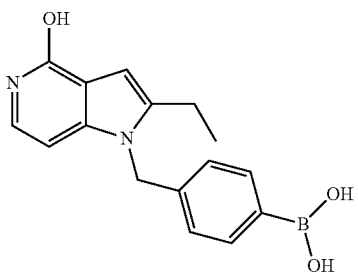 [SMILES: CCc1cc2c(O)nccc2n1Cc1ccc(B(O)O)cc1]

The title compounds were synthesized by the method described in step 3 of Example 55 except 4-((2-ethyl-4-methoxypyrrolo[3,2-c]pyridin-1-yl)methyl)phenylboronic acid (268 mg, 0.864 mmol) was used. Yield: 75.9 mg (29.3%) as a white solid. MS (ESI, pos. ion) m/z: 297.10 (M+1); $^1H$ NMR (300 MHz, DMSO-$d_6$, ppm) δ 10.62 (d, J=4.9 Hz, 1H), 8.01 (s, 2H), 7.73 (d, J=7.7 Hz, 2H), 7.12 (d, J=7.7 Hz, 2H), 6.93 (d, J=9.0 Hz, 2H), 6.42 (d, J=7.2 Hz, 1H), 5.24 (s, 2H), 2.76 (q, J=7.4 Hz, 2H), 1.19 (t, J=7.4 Hz, 3H).

Example 63

Synthesis of 4-((4-hydroxy-2-isopropylpyrrolo[3,2-c]pyridin-1-yl)methyl)phenylboronic acid

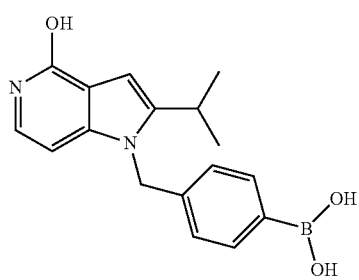

Step 1: 2-isopropyl-4-methoxy-1H-pyrrolo[3,2-c]pyridine

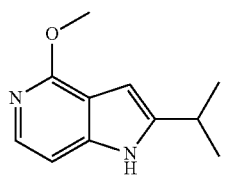

The title compound was synthesized by the method described in step 1 of Example 37 except 3-iodo-2-methoxypyridin-4-amine (0.60 g, 2.40 mmol) and 3-methyl-1-butyne (0.33 g, 4.799 mmol) were used. Yield: 0.25 g (54.8%) as a brown solid.

Step 2: 4-((2-isopropyl-4-methoxypyrrolo[3,2-c]pyridin-1-yl)methyl)phenylboronic acid

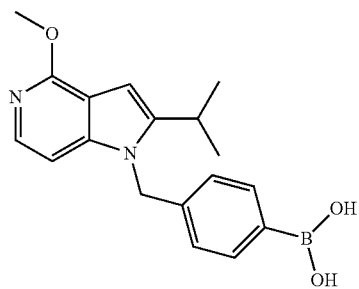 [SMILES: COc1nccc2c1cc(C(C)C)n2Cc1ccc(B(O)O)cc1]

The title compound was synthesized by the method described in step 2 of Example 55 except 2-isopropyl-4-methoxy-1H-pyrrolo[3,2-c]pyridine (250 mg, 1.314 mmol)

was used. Yield: 230 mg (54.0%) as a light brown solid. MS (ESI, pos. ion) m/z: 325.35 (M+1).

Step 3: 4-((4-hydroxy-2-isopropylpyrrolo[3,2-c]pyridin-1-yl)methyl)phenylboronic acid

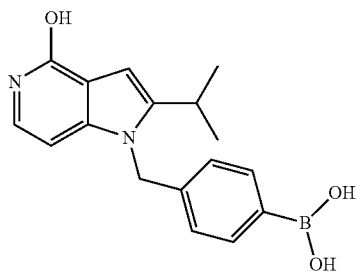 [SMILES: CC(C)c1cc2c(O)nccc2n1Cc1ccc(B(O)O)cc1]

The title compound was synthesized by the method described in step 3 of Example 55 except 4-((2-isopropyl-4-methoxypyrrolo[3,2-c]pyridin-1-yl)methyl)phenylboronic acid (130.00 mg, 0.30 mmol) was used. Yield: 75.9 mg (29.3%) as a white solid. MS (ESI, pos. ion) m/z: 311.25 (M+1). $^1$H NMR (300 MHz, DMSO-d$_6$, ppm) δ 10.75 (d, J=5.2 Hz, 1H), 8.00 (s, 2H), 7.71 (d, J=7.8 Hz, 2H), 6.92 (dd, J=17.2, 7.1 Hz, 3H), 6.39 (d, J=7.6 Hz, 2H), 5.37 (s, 2H), 2.92 (sept, J=6.7 Hz, 1H), 1.15 (d, J=6.7 Hz, 6H).

Example 64

Synthesis of 4-((5-carbamoyl-4-methoxy-1,3-benzodiazol-1-yl)methyl)phenylboronic acid (64a) and 4-((5-carbamoyl-4-hydroxy-1,3-benzodiazol-1-yl)methyl)phenylboronic acid with 0.5 para-toluene sulfonic acid (64b 64a

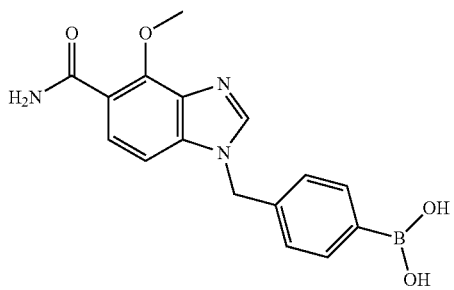

64b

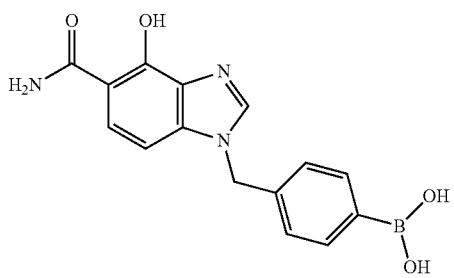

0.5 p-TsOH

Step 1: methyl 4-methoxy-1H-1,3-benzodiazole-5-carboxylate

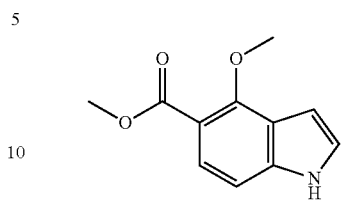

To a solution of methyl 3,4-diamino-2-methoxybenzoate (0.50 g, 2.548 mmol, 1.00 equiv) in DMF (10.00 mL) was added 1H-imidazole hydrochloride (0.35 g, 1 equiv). After stirring at 140° C. for 24 h, the reaction mixture was diluted with water and extracted with ethyl acetate. The combined organic layers were washed with brine, dried over anhydrous sodium sulfate and filtered. The filtrate was concentrated under reduced pressure and the residue was purified by silica gel column chromatography (eluent: EA/PE 1:3) to give methyl 4-methoxy-1H-1,3-benzodiazole-5-carboxylate (0.4 g, 76.1% yield).

Step 2: 4-methoxy-1H-1,3-benzodiazole-5-carboxamide

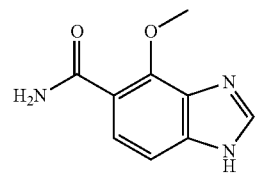

A mixture methyl 4-methoxy-1H-1,3-benzodiazole-5-carboxylate (0.40 g, 1 equiv) in NH$_3$H$_2$O (10.00 mL) was stirred at 80° C. for 48 h. After cooling the reaction mixture to room temperature the reaction mixture was concentrated under reduced pressure. The residue was purified by column chromatography on silica gel 40 g (eluent: petroleum ether-ethyl acetate 100%, 2:1) to give 4-methoxy-1H-1,3-benzodiazole-5-carboxamide (0.25 g, 36.2% yield) as a light brown solid.

Step 3: 4-((5-carbamoyl-4-methoxy-1,3-benzodiazol-1-yl)methyl)phenylboronic acid

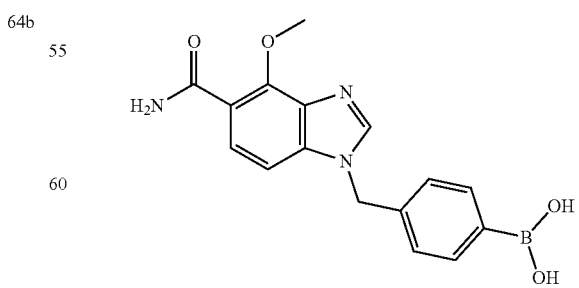

The title compound was synthesized by the method described in step 2 of Example 55 except 4-methoxy-1H-1, 3-benzodiazole-5-carboxamide (250 mg, 1.31 mmol) was used to give (120 mg, 20% yield) as a white solid. MS (ESI, pos. ion) m/z: 326.30 (M+1). $^1$H NMR (300 MHz, DMSO-d$_6$, ppm) δ 8.45 (t, J=1.8 Hz, 1H), 8.05 (d, J=2.5 Hz, 2H), 7.78-7.64 (m, 4H), 7.43 (s, 1H), 7.22 (dd, J=16.8, 8.2 Hz, 3H), 5.50 (s, 2H), 4.43 (t, J=1.8 Hz, 3H).

Step 4: 4-((5-carbamoyl-4-hydroxy-1,3-benzodiazol-1-yl)methyl)phenylboronic acid; para-toluene sulfonate (64b

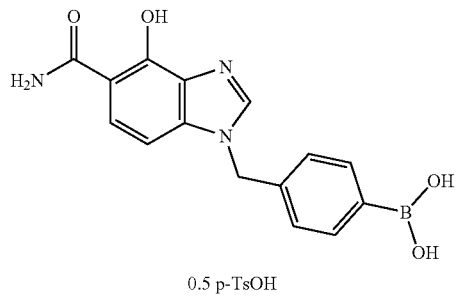 [SMILES: NC(=O)c1ccc2c(ncn2Cc2ccc(B(O)O)cc2)c1O]

0.5 p-TsOH

To a solution of 4-((5-carbamoyl-4-methoxy-1,3-benzodiazol-1-yl)methyl)phenylboronic acid (85 mg, 0.261 mmol, 1.00 equiv) in acetonitrile (5 mL) were added LiI (70.0 mg, 0.523 mmol, 2.00 equiv) and p-toluenesulfonic acid (90 mg, 0.523 mmol, 2.00 equiv). After stirring for 2 hours at 85° C., the reaction mixture was cooled down to RT and concentrated under reduced pressure. The crude product was purified by Prep-HPLC under the following conditions (Column: Sunfire prep C18 column, 30*150, 5 um; Mobile Phase A: Water (0.1% FA), Mobile Phase B: ACN; Flow rate: 60 mL/min; Gradient: 5 B to 36 B in 7 min; 254/220 nm; RT1:6 min) to give 4-((5-carbamoyl-4-hydroxy-1,3-benzodiazol-1-yl)methyl)phenylboronic acid with 0.5 para-toluene sulfonic acid (64b, 21.1 mg, 16.0% yield) as a white solid. MS (ESI, pos. ion) m/z: 312.25 (M+1). $^1$H NMR (300 MHz, DMSO-d$_6$/D$_2$O, ppm) δ 8.75 (s, 1H), 7.75-7.65 (m, 3H), 7.49 (d, J=7.7 Hz, 1H), 7.27 (d, J=7.6 Hz, 2H), 7.15 (d, J=7.8 Hz, 1H), 7.02 (d, J=8.8 Hz, 1H), 5.52 (s, 2H), 2.27 (s, 2H).

Example 65

Synthesis of 4-(imidazo[4,5-b]pyrazin-1-ylmethyl)phenylboronic acid

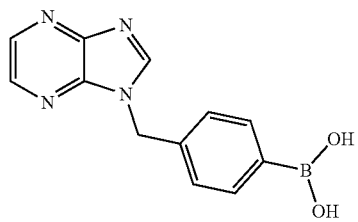 [SMILES: OB(O)c1ccc(Cn2cnc3nccnc32)cc1]

The title compound was synthesized by the method described in step 2 of Example 55 except 1H-imidazo[4,5-b]pyrazine (150 mg, 1.249 mmol) was used. Yield: 172.4 mg (42.6%) as an off-white solid. MS (ESI, pos. ion) m/z: 255.20 (M+1). $^1$H NMR (300 MHz, DMSO-d$_6$, ppm) δ 8.95 (s, 1H), 8.52 (d, J=2.7 Hz, 1H), 8.40 (d, J=2.7 Hz, 1H), 8.03 (s, 2H), 7.79-7.69 (m, 2H), 7.31-7.25 (m, 2H), 5.52 (s, 2H).

Example 66

Synthesis of 4-(pyrrolo[2,3-b]pyrazin-5-ylmethyl)phenylboronic acid

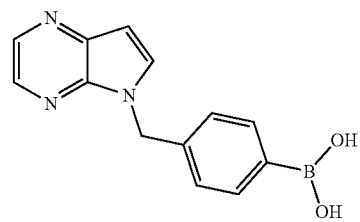

The title compound was synthesized by the method described in step 2 of Example 55 except 5H-pyrrolo[2,3-b]pyrazine (200.00 mg, 1.679 mmol) was used. Yield: 190 mg (44.7%) as a white solid. MS (ESI, pos. ion) m/z: 253.90 (M+1). $^1$H NMR (300 MHz, DMSO-d$_6$, ppm) δ 8.42 (m, 1H), 8.26 (m, 1H), 8.05-7.98 (m, 2H), 7.77-7.66 (m, 2H), 7.23-7.15 (m, 2H), 6.69 (m, 1H), 5.48 (d, J=3.4 Hz, 2H).

Example 67

Synthesis of 4-((2-carbamoylpyrrolo[2,3-b]pyrazin-5-yl)methyl)phenylboronic acid

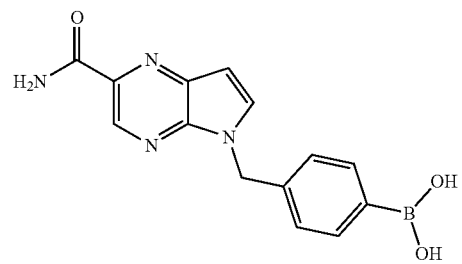 [SMILES: NC(=O)c1cnc2c(ccn2Cc2ccc(B(O)O)cc2)n1]

Step 1: 5H-pyrrolo[2,3-b]pyrazine-2-carboxamide

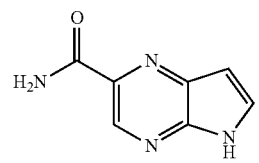 [SMILES: NC(=O)c1cnc2[nH]ccc2n1]

The title compound was synthesized by the method described in step 1 of Example 41 except 2-bromo-5H-pyrrolo[2,3-b]pyrazine (500 mg, 2.525 mmol) was used. Yield: 500 mg (90.0%) as a brown solid.

Step 2: 4-((2-carbamoylpyrrolo[2,3-b]pyrazin-5-yl)methyl)phenylboronic acid

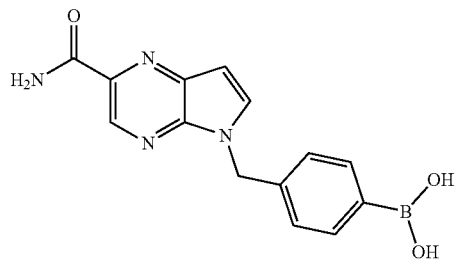 [SMILES: NC(=O)c1cnc2c(ccn2Cc2ccc(B(O)O)cc2)n1]

The title compound was synthesized by the method described in step 2 of Example 55 except 5H-pyrrolo[2,3-b]pyrazine-2-carboxamide (300 mg, 1.85 mmol) was used. Yield: 131.3 mg (23.0%) as an orange solid. MS (ESI, pos. ion) m/z: 297.25 (M+1). $^1$H NMR (300 MHz, DMSO-$d_6$, ppm) δ 8.94 (s, 1H), 8.23-8.13 (m, 2H), 8.03 (s, 2H), 7.73 (d, J=7.5 Hz, 2H), 7.63 (s, 1H), 7.22 (d, J=7.5 Hz, 2H), 6.81 (d, J=3.2 Hz, 1H), 5.55 (s, 2H).

Example 68

Synthesis of 4-((6-carbamoylimidazo[4,5-b]pyridin-3-yl)methyl)phenylboronic acid (68a) and 4-((6-carbamoylimidazo[4,5-b]pyridin-1-yl)methyl)phenylboronic acid (68b

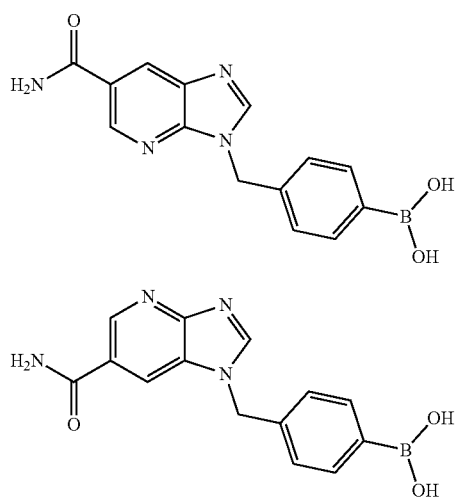

Step 1: 3H-imidazo[4,5-b]pyridine-6-carboxamide

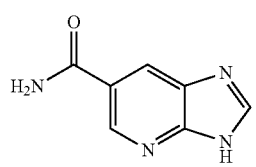 [SMILES: NC(=O)c1cnc2[nH]cnc2c1]

The title compound was synthesized by the method described in step 1 of Example 41 except 6-bromo-3H-imidazo[4,5-b]pyridine (500.00 mg, 2.525 mmol) was used. Yield: 480 mg (90.5%) as a brown solid. MS (ESI, pos. ion) m/z: 163.10 (M+1).

Step 2: 4-((6-carbamoylimidazo[4,5-b]pyridin-3-yl)methyl)phenylboronic acid (68a) and 4-((6-carbamoylimidazo[4,5-b]pyridin-1-yl)methyl)phenylboronic acid (68b

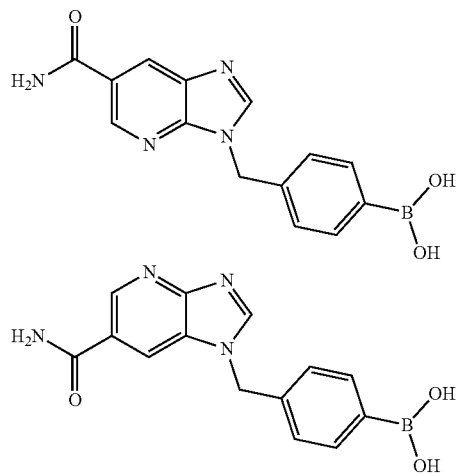

The title compounds were synthesized by the method described in step 2 of Example 55 except 3H-imidazo[4,5-b]pyridine-6-carboxamide (490 mg, 3.022 mmol) was used. Two fractions were obtained:

Fraction 1: Rt: 3.53 min. 34.7 mg (3.9% yield) 4-((6-carbamoylimidazo[4,5-b]pyridin-3-yl)methyl)phenylboronic acid (68a) as a white solid. MS (ESI, pos. ion) m/z: 297.10 (M+1). $^1$H NMR (300 MHz, DMSO-$d_6$, ppm) δ 8.89 (s, 1H), 8.72 (d, J=1.9 Hz, 1H), 8.57 (d, J=2.2 Hz, 1H), 8.14 (s, 1H), 8.05 (d, J=1.9 Hz, 2H), 7.74 (d, J=7.6 Hz, 2H), 7.52 (s, 1H), 7.28 (d, J=7.7 Hz, 2H), 5.55 (s, 2H).

Fraction 2: Rt: 4.00 min. 4.2 mg (0.5% yield) afford 4-((6-carbamoylimidazo[4,5-b]pyridin-1-yl)methyl)phenylboronic acid (68b) as a white solid. MS (ESI, pos. ion) m/z: 297.10 (M+1) $^1$H NMR (300 MHz, DMSO-$d_6$, ppm) δ 8.95 (s, 1H), 8.80 (s, 1H), 8.38 (s, 1H), 8.25 (s, 3H), 7.79-7.67 (m, 3H), 7.44 (d, J=7.7 Hz, 2H), 5.94 (s, 2H).

Example 69

Synthesis of (4-((1H-benzo[d]imidazol-1-yl)methyl)phenyl)boronic acid

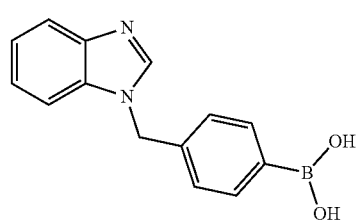 [SMILES: OB(O)c1ccc(Cn2cnc3ccccc32)cc1]

The title compound was synthesized by the method described in step 2 of Example 55 except benzimidazole (234.00 mg, 1.981 mmol) was used. Yield: 221.4 mg (44.2%) as a white solid. MS (ESI, pos. ion) m/z: 253.25 (M+1). $^1$H NMR (300 MHz, DMSO-$d_6$, ppm) δ 8.53 (d, J=11.8 Hz, 1H), 8.05 (d, J=1.8 Hz, 1H), 7.83 (d, J=7.4 Hz, 1H), 7.73 (t, J=7.0 Hz, 2H), 7.55-7.46 (m, 1H), 7.30-7.15 (m, 4H), 5.51 (d, J=5.8 Hz, 2H).

Example 70

Synthesis of 4-((6-methoxypurin-9-yl)methyl)phenylboronic acid (70a) and 4-((6-methoxypurin-7-yl)methyl)phenylboronic acid (70b

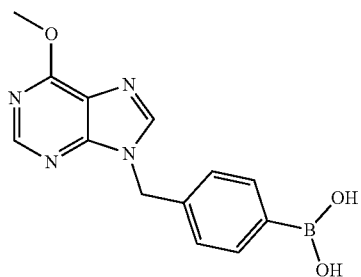

70a

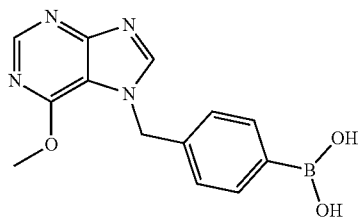

70b

Step 1: 4-((6-methoxypurin-9-yl)methyl)phenylboronic acid (70a) and 4-((6-methoxypurin-7-yl)methyl)phenylboronic acid (70b

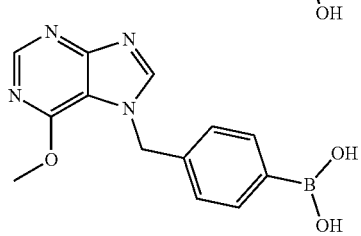

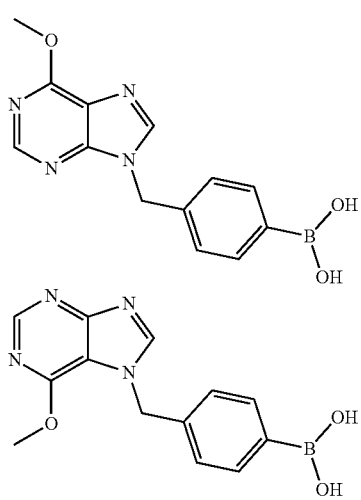

The title compounds were synthesized by the method described in step 2 of Example 55 except 6-methoxy-9H-purine (200 mg, 1.332 mmol) was used. Two fractions were obtained:

Fraction 1: Rt: 8.5 min. 140 mg (35.9% yield) of 4-((6-methoxypurin-9-yl)methyl)phenylboronic acid (70a) as a white solid. MS (ESI, pos. ion) m/z: 285.25 (M+1). $^1$H NMR (300 MHz, DMSO-$d_6$, ppm) δ 8.51 (d, J=6.0 Hz, 2H), 8.03 (s, 2H), 7.76-7.68 (m, 2H), 7.27-7.20 (m, 2H), 5.46 (s, 2H), 4.07 (s, 3H).

Fraction 2: Rt: 8.9 min. 72.2 mg (18.8% yield) of 4-((6-methoxypurin-7-yl)methyl)phenylboronic acid (70b) as a white solid. MS (ESI, pos. ion) m/z: 285.25 (M+1). $^1$H NMR (300 MHz, DMSO-$d_6$, ppm) δ 8.67 (s, 1H), 8.52 (s, 1H), 8.03 (s, 2H), 7.76-7.69 (m, 2H), 7.24-7.17 (m, 2H), 5.54 (s, 2H), 4.02 (s, 3H).

Example 71

Synthesis of (4-((4-oxo-3,4-dihydro-7H-pyrrolo[2,3-d]pyrimidin-7-yl)methyl)phenyl)boronic acid

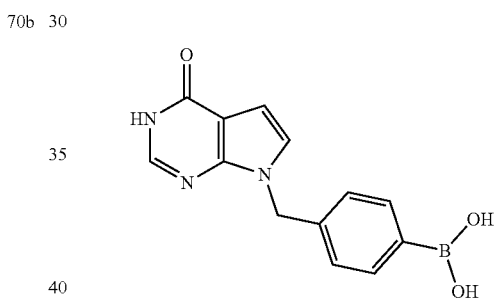

Step 1: 4-((4-methoxypyrrolo[2,3-d]pyrimidin-7-yl)methyl)phenylboronic acid

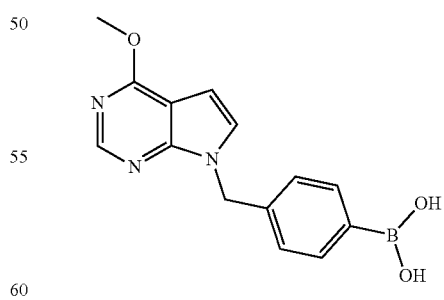

The title compound was synthesized by the method described in step 2 of Example 55 except 4-methoxy-7H-pyrrolo[2,3-d]pyrimidine (200 mg, 1.341 mmol) was used. Yield: 270 mg (71.1%). MS (ESI, pos. ion) m/z: 284.15 (M+1).

Step 2: (4-((4-oxo-3,4-dihydro-7H-pyrrolo[2,3-d]pyrimidin-7-yl)methyl)phenyl)boronic acid

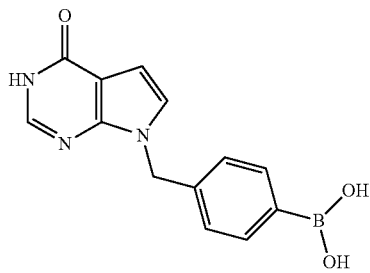 [SMILES: O=c1[nH]cnc2c1ccn2Cc1ccc(B(O)O)cc1]

The title compound was synthesized by the method described in step 2 of Example 35 except 4-((4-methoxypyrrolo[2,3-d]pyrimidin-7-yl)methyl)phenylboronic acid (270.00 mg, 0.95 mmol) was used. Yield: 129.9 mg (50.2%) as a white solid. MS (ESI, pos. ion) m/z: 270.30 (M+1). $^1$H NMR (300 MHz, DMSO-$d_6$, ppm) δ 11.90 (s, 1H), 8.00 (s, 2H), 7.88 (d, J=3.6 Hz, 1H), 7.73-7.66 (m, 2H), 7.14 (d, J=7.9 Hz, 3H), 6.48 (d, J=3.3 Hz, 1H), 5.32 (s, 2H).

Example 72

Synthesis of 4-((4-hydroxypyrrolo[2,3-b]pyridin-1-yl)methyl)phenylboronic acid

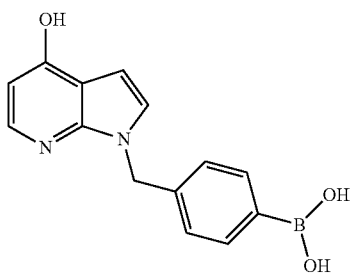 [SMILES: OB(O)c1ccc(Cn2ccc3c(O)ccnc32)cc1]

Step 1: 4-((4-methoxypyrrolo[2,3-b]pyridin-1-yl)methyl)phenylboronic acid

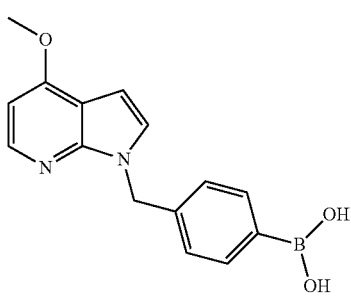 [SMILES: COc1ccnc2c1ccn2Cc1ccc(B(O)O)cc1]

The title compound was synthesized by the method described in step 2 of Example 55 except 4-methoxy-1H-pyrrolo[2,3-b]pyridine (200 mg, 1.35 mmol) was used. Yield: 270 mg (70.9%) as white solid. MS (ESI, pos. ion) m/z: 283.10 (M+1).

Step 2: 4-((4-hydroxypyrrolo[2,3-b]pyridin-1-yl)methyl)phenylboronic acid

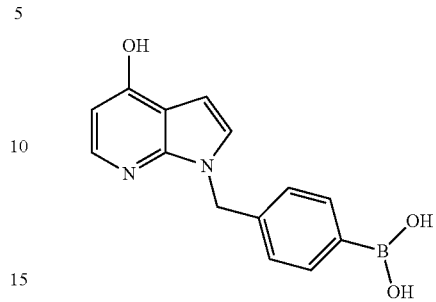

The title compound was synthesized by the method described in step 2 of Example 35 except 4-((4-methoxypyrrolo[2,3-b]pyridin-1-yl)methyl)phenylboronic acid (230.00 mg, 0.81 mmol) was used. Yield: 47.8 mg (21.4%) as a white solid. MS (ESI, pos. ion) m/z: 267.05 (M-1). $^1$H NMR (300 MHz, DMSO-$d_6$/$D_2O$, ppm)$^1$H NMR (400 MHz, DMSO-$d_6$) δ 7.95 (s, 1H), 7.69 (d, J=7.8 Hz, 2H), 7.31 (d, J=13.6 Hz, 1H), 7.14 (d, J=7.6 Hz, 2H), 6.49 (d, J=13.9 Hz, 2H), 6.05 (s, 1H), 5.40 (s, 2H).

Example 73

Synthesis of 4-((2-carbamoylpyrrolo[3,2-d]pyrimidin-5-yl)methyl)phenylboronic acid

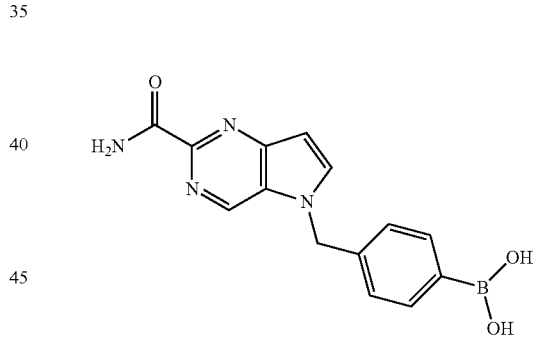

Step 1: 5H-pyrrolo[3,2-d]pyrimidine-2-carboxamide

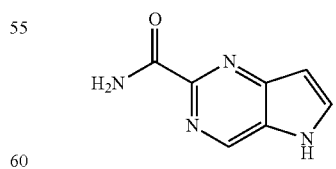

The title compound was synthesized by the method described in step 1 of Example 41 except 2-chloro-5H-pyrrolo[3,2-d]pyrimidine (300 mg, 1.95 mmol) was used. Yield: 227 mg (63.8%) as a brown solid. MS (ESI, pos. ion) n/z: 162.9 (M+1).

Step 2: 4-((2-carbamoylpyrrolo[3,2-d]pyrimidin-5-yl)methyl)phenylboronic acid

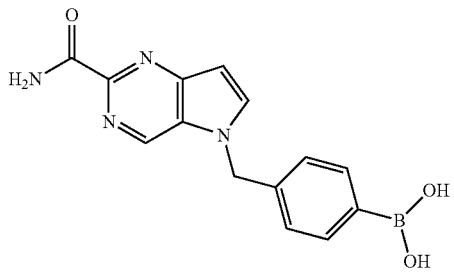 [SMILES: NC(=O)c1ncc2c(ccn2Cc2ccc(B(O)O)cc2)n1]

The title compound was synthesized by the method described in step 2 of Example 55 except 5H-pyrrolo[3,2-d]pyrimidine-2-carboxamide (100.00 mg, 0.62 mmol) was used. Yield: 4.2 mg (2.3%) as a white solid. MS (ESI, pos. ion) m/z: 297.30 (M+1). $^1$H NMR (400 MHz, DMSO-$d_6$) δ 9.12 (s, 1H), 8.38-7.99 (m, 4H), 7.74 (d, J=7.7 Hz, 2H), 7.57 (s, 1H), 7.26 (d, J=7.7 Hz, 2H), 6.78 (d, J=3.2 Hz, 1H), 5.61 (s, 2H).

Example 74

Synthesis of 4-((7-chloroimidazo[4,5-b]pyridin-3-yl)methyl)phenylboronic acid (74a) and 4-((7-chloroimidazo[4,5-b]pyridin-1-yl)methyl)phenylboronic acid (74b

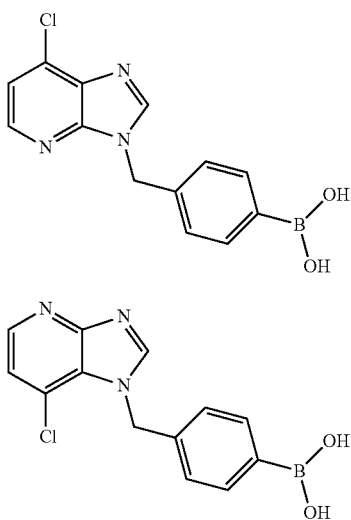

The title compounds were synthesized by the method described in step 2 of Example 55 except 7-chloro-3H-imidazo[4,5-b]pyridine (300.00 mg, 1.954 mmol) was used. Two fractions were obtained:

Fraction 1: Rt: 4.92 min. 36.2 mg (6.1% yield) of 4-((7-chloroimidazo[4,5-b]pyridin-3-yl)methyl)phenylboronic acid (74a) as a white solid. MS (ESI, pos. ion) m/z: 288.20 (M+1). $^1$H NMR (300 MHz, DMSO-$d_6$) δ 8.72 (s, 1H), 8.33 (d, J=5.2 Hz, 1H), 8.04 (d, J=3.3 Hz, 2H), 7.78-7.69 (m, 2H), 7.46 (d, J=5.2 Hz, 1H), 7.32-7.23 (m, 2H), 5.53 (s, 2H).

Fraction 2: Rt: 5.08 min. 23.3 mg (4.0% yield) of 4-((7-chloroimidazo[4,5-b]pyridin-1-yl)methyl)phenylboronic acid (74) as a white solid. MS (ESI, pos. ion) m/z: 288.20 (M+1). $^1$H NMR (300 MHz, DMSO-$d_6$, ppm) δ 8.78 (s, 1H), 8.38 (d, J=5.2 Hz, 1H), 8.04 (d, J=3.4 Hz, 2H), 7.78-7.69 (m, 2H), 7.37 (d, J=5.2 Hz, 1H), 7.07 (d, J=7.9 Hz, 2H), 5.75 (s, 2H).

Example 75

Synthesis of 4-((5-chloro-1,3-benzodiazol-1-yl)methyl)phenylboronic acid (75a) and 4-((6-chloro-1,3-benzodiazol-1-yl)methyl)phenylboronic acid. (75b

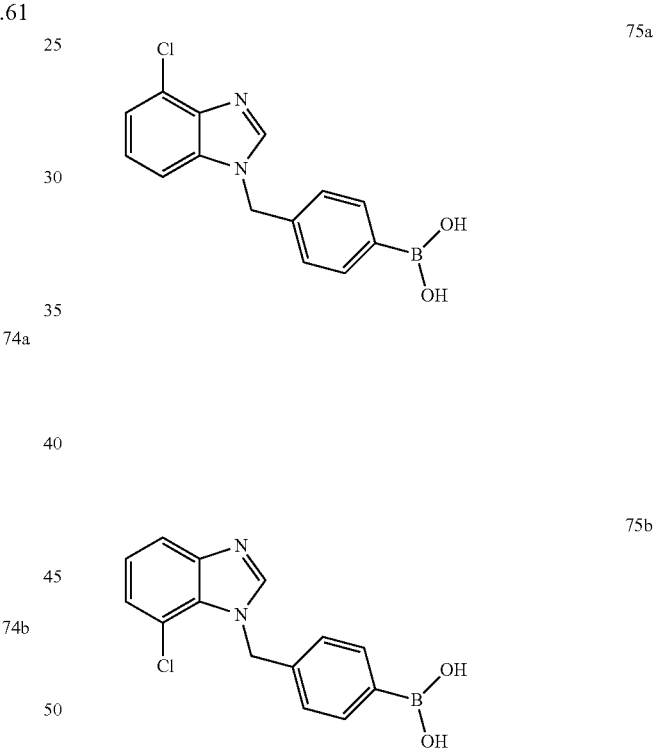

The title compounds were synthesized by the method described in step 2 of Example 55 except 5-chloro-1H-benzo[d]imidazole (150 mg, 0.97 mmol) was used. Yield: 92.3 mg (32.0%) of a mixture 4-((5-chloro-1,3-benzodiazol-1-yl)methyl)phenylboronic acid and 4-((6-chloro-1,3-benzodiazol-1-yl)methyl)phenylboronic acid (ratio=1:1) as a white solid. MS (ESI, pos. ion) m/z: 287.20 (M+1). 1H NMR (300 MHz, DMSO-d6, ppm) δ 8.50 (d, J=7.4 Hz, 1H), 8.05 (d, J=1.5 Hz, 2H), 7.81-7.63 (m, 3H), 7.54 (d, J=8.6 Hz, 1H), 7.32-7.18 (m, 3H), 5.53 (s, 2H).

Example 76

Synthesis of 4-((4-cyano-1,3-benzodiazol-1-yl)methyl)phenylboronic acid (76a) and 4-((7-cyano-1,3-benzodiazol-1-yl)methyl)phenylboronic acid. (76b

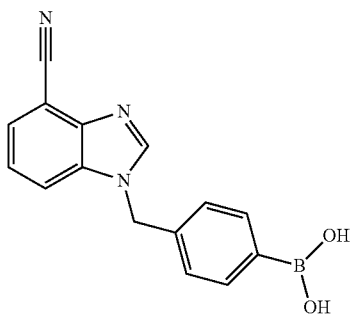

76a

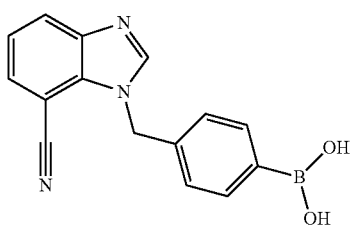

76b

The title compounds were synthesized by the method described in step 2 of Example 55 except 1H-benzo[d]imidazole-4-carbonitrile (120 mg, 0.84 mmol) was used. The crude product was purified by prep-HPLC (Column: C18 Column, 19*250 mm, 5 um; Mobile Phase A: Water (10 mmoL/L NH$_4$HCO$_3$+0.1% NH$_3$·H$_2$O), Mobile Phase B: ACN; Flow rate: 20 mL/min; Gradient: 14 B to 20 B in 12 min; 254/220 nm; RT1=7.32 min; RT2=8.00 min) to give two fractions:

Fraction 1: Rt: 7.32 min. 48.6 mg (14.5% yield) of 4-((4-cyano-1,3-benzodiazol-1-yl)methyl)phenylboronic acid as an off-white solid. MS (ESI, pos. ion) m/z: 278.20 (M+1). $^1$H NMR (300 MHz, DMSO-d$_6$/D$_2$O, ppm) δ 8.63 (s, 1H), 7.77 (dd, J=42.8, 7.6 Hz, 4H), 7.50-6.92 (m, 3H), 5.55 (s, 2H).

Fraction 2: Rt: 8.00 min. 7.6 mg (2.3% yield) of 4-((7-cyano-1,3-benzodiazol-1-yl)methyl)phenylboronic acid (7.6 mg) as an off-white solid. MS (ESI, pos. ion) m/z: 278.20 (M+1). $^1$H NMR (300 MHz, DMSO-d$_6$, ppm) 8.14-8.04 (m, 1H), 8.06 (s, 3H), 7.79-7.70 (m, 3H), 7.45-7.26 (m, 1H), 7.10 (d, J=7.8 Hz, 2H), 5.76 (s, 2H).

Example 77

Synthesis of 4-((4-aminoimidazo[4,5-c]pyridin-1-yl)methyl)phenylboronic acid

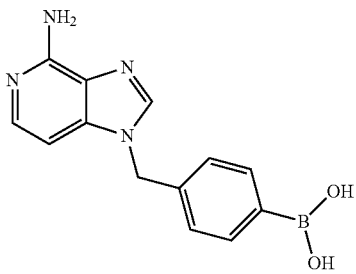 [SMILES: Nc1nccc2c1ncn2Cc1ccc(B(O)O)cc1]

The title compound was synthesized by the method described in step 2 of Example 55 except 1H-imidazo[4,5-c]pyridin-4-amine (300 mg, 2.24 mmol) was used. The crude product was purified by prep-HPLC with the following conditions (Column: C18 column, 30*150, 5 um; Mobile Phase A: Water (0.1% FA), Mobile Phase B: ACN; Flow rate: 60 mL/min; Gradient: 1 B to 15 B in 8 min; 254/220 nm) to afford 4-((4-aminoimidazo[4,5-c]pyridin-1-yl)methyl)phenylboronic acid (160.9 mg, 26.7% yield) as a white solid. MS (ESI, pos. ion) m/z: 269.20 (M+1). $^1$H NMR (300 MHz, DMSO-d$_6$/D$_2$O, ppm) δ 8.34 (s, 1H), 8.18 (s, 1H), 7.73 (d, J=7.8 Hz, 2H), 7.61 (d, J=6.1 Hz, 1H), 7.24 (d, J=8.0 Hz, 2H), 6.84 (d, J=6.1 Hz, 1H), 5.44 (s, 2H).

Example 78

Synthesis of 4-((4-amino-1,3-benzodiazol-1-yl)methyl)phenylboronic acid

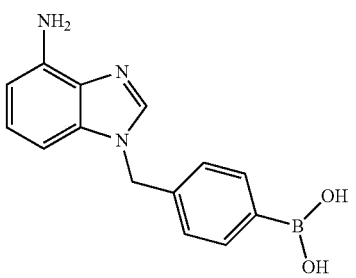 [SMILES: Nc1cccc2c1ncn2Cc1ccc(B(O)O)cc1]

The title compound was synthesized by the method described in step 2 of Example 55 except 1H-1,3-benzodiazol-4-amine (100 mg, 0.75 mmol) was used. The crude product was purified by prep-HPLC with the following conditions (Column: C18 column, 30*150, 5 um; Mobile Phase A: Water (10 mmoL/L NH$_4$HCO$_3$+0.1% NH$_3$·H$_2$O), Mobile Phase B: ACN; Flow rate: 45 mL/min; Gradient: 15 B to 35 B in 7 min; 254,220 nm) to afford 4-((4-amino-1,3-benzodiazol-1-yl)methyl)phenylboronic acid (37.2 mg, 19% yield) as a white solid. MS (ESI, pos. ion) m/z: 268.25 (M+1). $^1$H NMR (300 MHz, DMSO-d$_6$, ppm) δ 8.16 (s, 1H), 8.02 (s, 2H), 7.73 (d, J=7.8 Hz, 2H), 7.21 (d, J=7.8 Hz, 2H), 6.86 (t, J=7.8 Hz, 1H), 6.60 (dd, J=8.1, 1.0 Hz, 1H), 6.35 (dd, J=7.6, 0.9 Hz, 1H), 5.39 (s, 2H), 5.26 (s, 2H).

Example 79

Synthesis of 4-((5-methoxyimidazo[4,5-b]pyridin-1-yl)methyl)phenylboronic acid (79a), 4-((5-methoxyimidazo[4,5-b]pyridin-3-yl)methyl)phenylboronic acid (79b), and (4-((5-hydroxy-1H-imidazo[4,5-b]pyridin-1-yl)methy)phenyl)boronic acid (79c

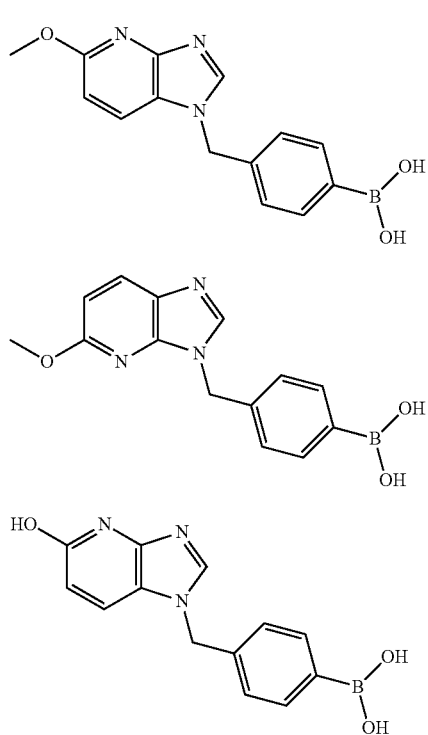

Step 1: 6-methoxypyridine-2,3-diamine

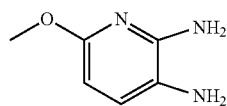

The title compound was synthesized by the method described in step 5 of Example 30 except 6-methoxy-2-nitropyridin-3-amine (2.00 g, 11.83 mmol) was used. Yield: 910 mg (45.6%). MS (ESI, pos. ion) m/z: 139.90 (M+1).

Step 2: 5-methoxy-1H-imidazo[4,5-b]pyridine

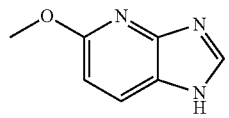

A solution of 6-methoxypyridine-2,3-diamine (910 mg, 6.54 mmol, 1.00 equiv) in formic acid (30 mL) was stirring for 8 hours at 105° C. in an oil bath. After cooling to room temperature, the mixture was concentrated under reduced pressure and the residue was purified by column chromatography (silica gel, eluent: ethyl acetate/petroleum ether 100:0) to get 5-methoxy-1H-imidazo[4,5-b]pyridine (810 mg, 78.6% yield) as a pink solid.

Step 3: 4-((5-methoxyimidazo[4,5-b]pyridin-1-yl)methyl)phenylboronic acid (79a) and 4-((5-methoxyimidazo[4,5-b]pyridin-3-yl)methyl)phenylboronic acid (79b

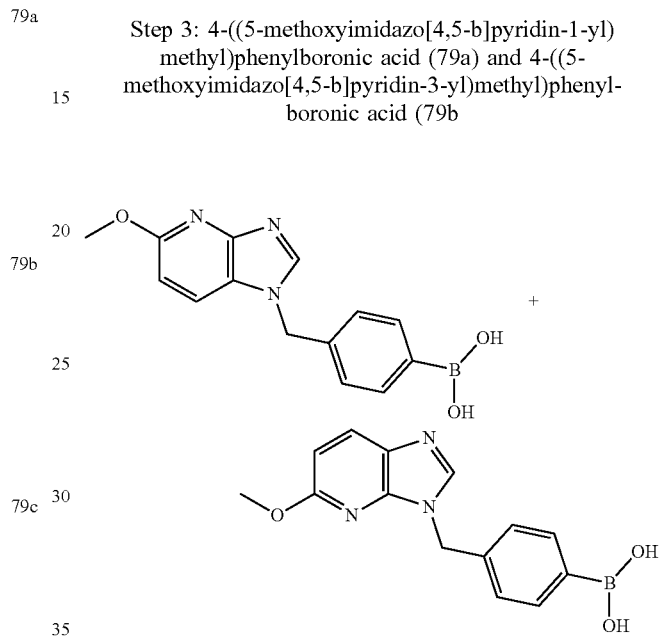

The title compounds were synthesized by the method described in step 2 of Example 55 except 5-methoxy-1H-imidazo[4,5-b]pyridine (810 mg, 5.43 mmol) was used. The crude product was purified by prep-HPLC with the following conditions (Column: C18 Column, 30×150 mm 5 um; Mobile Phase A: Water (0.1% FA), Mobile Phase B: ACN; Flow rate: 60 mL/min; Gradient: 16 B to 20 B in 10 min; 254/220 nm; RT1:7.8 min; RT2: 9.0 min). The fractions containing the desired product were combined and lyophilized to give two fractions:

Fraction 1: Rt: 7.8 min. 310 mg (17.2% yield) of 4-((5-methoxyimidazo[4,5-b]pyridin-1-yl)methyl)phenylboronic acid (79a) as a white solid. MS (ESI, pos. ion) m/z: 284.25 (M+1). $^1$H NMR (300 MHz, DMSO-d6, ppm) δ 8.47 (s, 1H), 8.04 (d, J=3.3 Hz, 2H), 7.86 (d, J=8.7 Hz, 1H), 7.79-7.70 (m, 2H), 7.25 (d, J=7.8 Hz, 2H), 6.68 (d, J=8.7 Hz, 1H), 5.49 (s, 2H), 3.87 (s, 3H).

Fraction 2: Rt: 9.0 min. 254.2 mg (15.9% yield) of 4-((5-methoxyimidazo[4,5-b]pyridin-3-yl)methyl)phenylboronic acid (79b) as a white solid. MS (ESI, pos. ion) m/z: 284.20 (M+1). $^1$H NMR (300 MHz, DMSO-d6, ppm) δ 8.39 (s, 1H), 8.07-7.95 (m, 3H), 7.75 (d, J=7.9 Hz, 2H), 7.37 (dd, J=7.7, 5.8 Hz, 2H), 6.71 (d, J=8.6 Hz, 1H), 5.42 (s, 2H), 3.90 (d, J=4.4 Hz, 3H).

Step 4: (4-((5-hydroxy-1H-imidazo[4,5-b]pyridin-1-yl)methyl)phenyl)boronic acid (79c

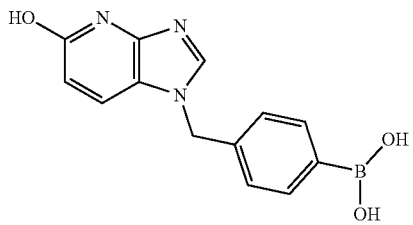 [SMILES: OB(O)c1ccc(Cn2cnc3nc(O)ccc32)cc1]

To a stirred solution of 4-((5-methoxyimidazo[4,5-b]pyridin-1-yl)methyl)phenylboronic acid (100 mg, 0.353 mmol, 1.00 equiv) in DCM (4.00 mL) was added BBr$_3$ (3.00 mL) at room temperature. After stirring for 3 days at room temperature, the mixture was concentrated under reduced pressure. The crude product was purified by prep-HPLC under following conditions (Column: XBridge Prep OBD C18 Column, 30×150 mm 5 um; Mobile Phase A: Water (0.1% FA), Mobile Phase B: ACN; Flow rate: 60 mL/min; Gradient: 3 B to 30 B in 7 min; 254/220 nm) to afford 4-((5-hydroxyimidazo[4,5-b]pyridin-1-yl)methyl)phenylboronic acid (65.4 mg, 66.9% yield) as a white solid. MS (ESI, pos. ion) m/z: 270.20 (M+1). $^1$H NMR (300 MHz, DMSO-d$_6$, ppm) δ 11.63 (s, 1H), 8.21 (s, 1H), 8.06 (s, 2H), 7.75 (d, J=7.6 Hz, 2H), 7.69 (d, J=9.1 Hz, 1H), 7.25 (d, J=7.5 Hz, 2H), 6.20 (d, J=9.2 Hz, 1H), 5.41 (s, 2H).

Example 80

Synthesis of (4-((5-carbamoyl-1H-benzo[d]imidazol-1-yl)methyl)-3-methylphenyl)boronic acid (80a) and (4-((6-carbamoyl-1H-benzo[d]imidazol-1-yl)methyl)-3-methylphenyl)boronic acid (80b 80a
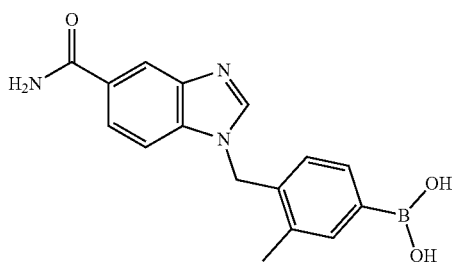

80b
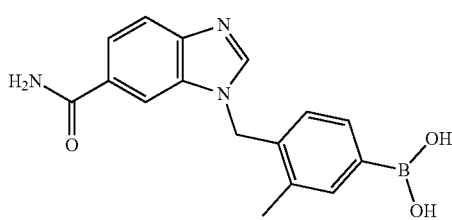

Step 1: methyl 1-(4-bromo-2-methylbenzyl)-1H-benzo[d]imidazole-5-carboxylate and methyl 1-(4-bromo-2-methylbenzyl)-1H-benzo[d]imidazole-6-carboxylate

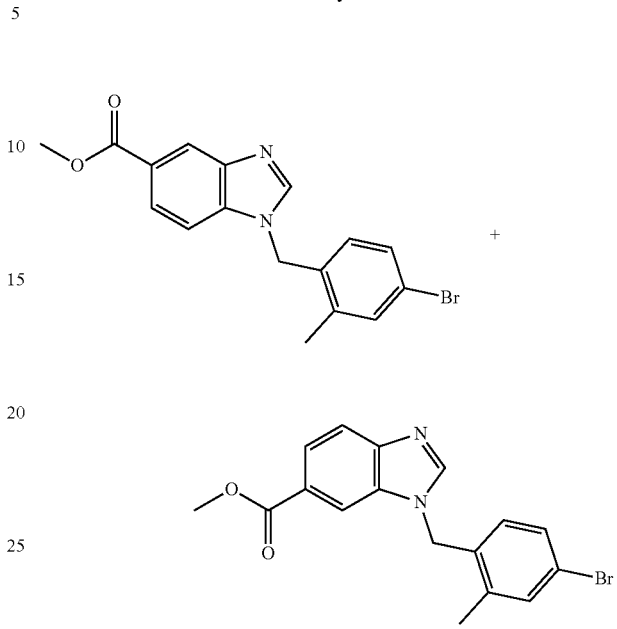

Methyl 1H-benzo[d]imidazole-5-carboxylate (1.60 g, 9.082 mmol, 1.00 equiv) was dissolved in MeOH (30.00 mL). 4-Bromo-1-(bromomethyl)-2-methylbenzene (2.88 g, 10.898 mmol, 1.20 equiv) and Cs$_2$CO$_3$ (3.85 g, 11.806 mmol, 1.30 equiv) were added. After stirring for 12 h at room temperature, the reaction mixture was concentrated under reduced pressure. The residue was poured into water and the aqueous layer was extracted with ethyl acetate. The organic layers were combined, dried over anhydrous sodium sulfate, filtered and evaporated under reduced pressure. The residue was purified by column chromatography (silica gel, eluent: DCM/MEOH 97:3) to give 2.7 g (81.9% yield) of a mixture of 1-(4-bromo-2-methylbenzyl)-1H-benzo[d]imidazole-5-carboxylate and methyl 1-(4-bromo-2-methylbenzyl)-1H-benzo[d]imidazole-6-carboxylate as a yellow solid.

Step 2: methyl 1-(2-methyl-4-(4,4,5,5-tetramethyl-1,3,2-dioxaborolan-2-yl)benzyl)-1H-benzo[d]imidazole-5-carboxylate and methyl 1-(2-methyl-4-(4,4,5,5-tetramethyl-1,3,2-dioxaborolan-2-yl)benzyl)-1H-benzo[d]imidazole-6-carboxylate

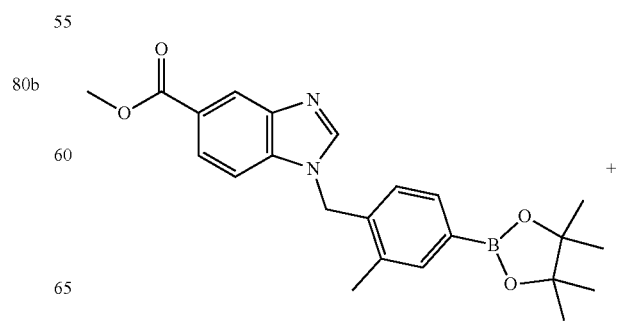

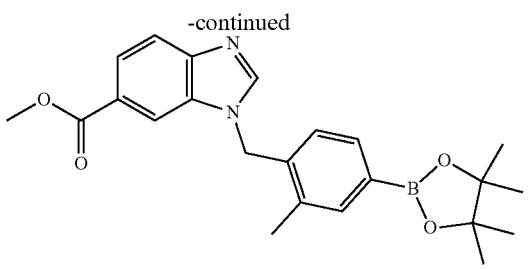

To a mixture of 1-(4-bromo-2-methylbenzyl)-1H-benzo[d]imidazole-5-carboxylate and methyl 1-(4-bromo-2-methylbenzyl)-1H-benzo[d]imidazole-6-carboxylate (1.50 g, 4.134 mmol, 1.00 equiv, 99%) in dioxane (20.00 mL) were added bis(pinacolato)diboron (2.14 g, 8.268 mmol, 2.00 equiv), KOAc (1.01 g, 10.335 mmol, 2.50 equiv) and, Pd(dppf)Cl$_2$·CH$_2$Cl$_2$ (338 mg, 0.413 mmol, 0.10 equiv) at room temperature. After stirring for 6.5 h at 90° C., the reaction mixture was concentrated under reduced pressure. The residue was purified by column chromatography (silica gel, eluent: EA:PE 1:2) to give a mixture of methyl 1-(2-methyl-4-(4,4,5,5-tetramethyl-1,3,2-dioxaborolan-2-yl)benzyl)-1H-benzo[d]imidazole-5-carboxylate and methyl 1-(2-methyl-4-(4,4,5,5-tetramethyl-1,3,2-dioxaborolan-2-yl)benzyl)-1H-benzo[d]imidazole-6-carboxylate 1.4 g (79% yield) as an yellow oil.

Step 3: (4-((5-(methoxycarbonyl)-1H-benzo[d]imidazol-1-yl)methyl)-3-methylphenyl)boronic acid and (4-((6-(methoxycarbonyl)-1H-benzo[d]imidazol-1-yl)methyl)-3-methylphenyl)boronic acid

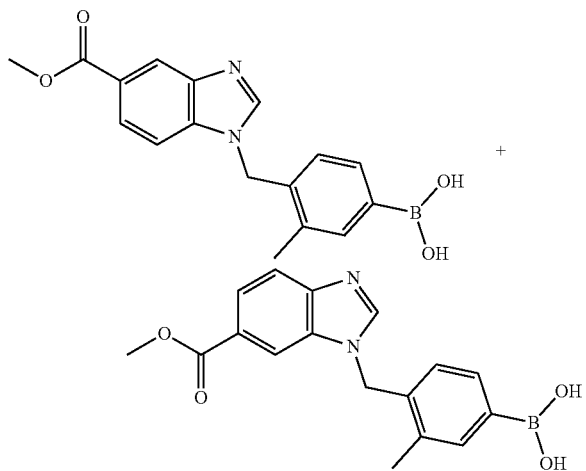

To a solution of 1-(2-methyl-4-(4,4,5,5-tetramethyl-1,3,2-dioxaborolan-2-yl)benzyl)-1H-benzo[d]imidazole-5-carboxylate and methyl 1-(2-methyl-4-(4,4,5,5-tetramethyl-1,3,2-dioxaborolan-2-yl)benzyl)-1H-benzo[d]imidazole-6-carboxylate (1.40 g, 3.446 mmol, 1.00 equiv) in THF (20 mL) and H$_2$O (5 mL) was added NaIO$_4$ (2.21 g, 10.337 mmol, 3.00 equiv) at room temperature. The resulting mixture was stirred for 30 minutes at room temperature, then 3 N HCl (10.00 mL) was added. After stirring for 4 hours at room temperature, the reaction mixture was poured water and extracted with ethyl acetate. The combined organic layers were washed with brine, dried over anhydrous sodium sulfate, filtered and concentrated under reduced pressure. The residue was purified by column chromatography (silica gel, eluent: ethyl acetate/methanol 19:1) to give a mixture of (4-((5-(methoxycarbonyl)-1H-benzo[d]imidazol-1-yl)methyl)-3-methylphenyl)boronic acid and (4-((6-(methoxycarbonyl)-1H-benzo[d]imidazol-1-yl)methyl)-3-methylphenyl)boronic acid 0.8 g (71% yield) as a light yellow solid.

Step 4: (4-((5-carbamoyl-1H-benzo[d]imidazol-1-yl)methyl)-3-methylphenyl)boronic acid (80a) and (4-((6-carbamoyl-1H-benzo[d]imidazol-1-yl)methyl)-3-methylphenyl)boronic acid 80b

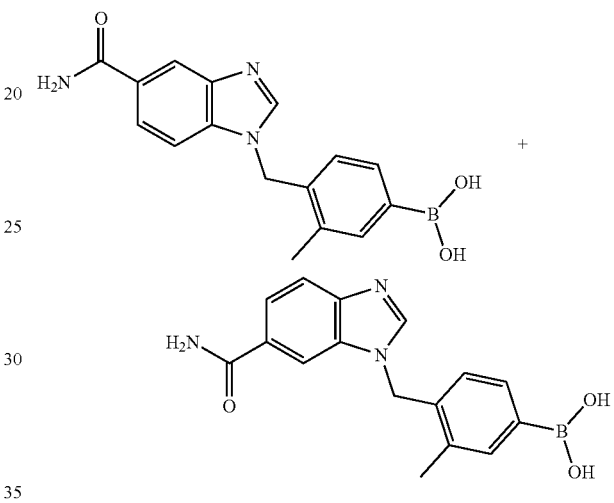

A mixture of 4-((5-(methoxycarbonyl)-1,3-benzodiazol-1-yl)methyl)-3-methyl-phenylboronic acid and 4-((6-(methoxycarbonyl)-1,3-benzodiazol-1-yl)methyl)-3-methylphenylboronic acid (120 mg, 0.370 mmol, 1.00 equiv) was dissolved in aqueous ammonia (10 mL). After stirring at 80° C. for 24 h, the reaction mixture was concentrated under reduced pressure. The residue was purified prep-HPLC with the following conditions (column: Sunfire prep C18 column, 30*150, 5 um; Mobile Phase A: Water (10 mmoL/L NH$_4$HCO$_3$+0.1% NH$_3$·H$_2$O), Mobile Phase B: ACN; Flow rate: 25 mL/min; Gradient: 15 B to 25 B in 7 min; 254,220 nm; RT1:6.68 min; RT2:7.22 min.). The fractions containing the desired products were combined and lyophilized to give two fractions:

Fraction 1: Rt: 6.68 min. 9.4 mg (7.8% yield) of (4-((5-carbamoyl-1H-benzo[d]imidazol-1-yl)methyl)-3-methylphenyl)boronic acid (80a) as a white solid. MS (ESI, pos. ion) m/z: 310.3 (M+1). $^1$H NMR (300 MHz, DMSO-d6, ppm) δ 8.42-8.25 (m, 2H), 8.09-7.94 (m, 3H), 7.77 (d, J=8.2 Hz, 1H), 7.63 (s, 1H), 7.55-7.40 (m, 2H), 7.27 (s, 1H), 6.68 (d, J=7.8 Hz, 1H), 5.56 (s, 2H), 2.31 (d, J=2.6 Hz, 3H).

Fraction 2: Rt: 7.22 min. 5.8 mg (5.1% yield) of (4-((6-carbamoyl-1H-benzo[d]imidazol-1-yl)methyl)-3-methylphenyl)boronic acid (80b) as a white solid. MS (ESI, pos. ion) m/z: 310.3 (M+1). $^1$H-NMR (300 MHz, DMSO-d$_6$, ppm) δ 8.37 (d, J=2.1 Hz, 1H), 8.28 (s, 1H), 8.09-7.94 (m, 3H), 7.77 (d, J=8.2 Hz, 1H), 7.63 (s, 1H), 7.55-7.40 (m, 2H), 7.27 (s, 1H), 6.68 (d, J=7.8 Hz, 1H), 5.56 (s, 2H), 2.31 (d, J=2.6 Hz, 3H).

Example 81

Synthesis of 4-((4-(difluoromethyl)-1,3-benzodiazol-1-yl)methyl)phenylboronic acid

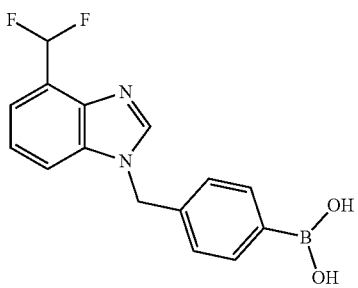 [SMILES: OB(O)c1ccc(Cn2cnc3c(C(F)F)cccc32)cc1]

Step 1: 1H-1,3-benzodiazol-4-ylmethanol

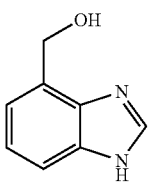 [SMILES: OCc1cccc2[nH]cnc12]

To a stirred solution of 1H-1,3-benzodiazole-4-carboxylic acid (2.00 g, 12.34 mmol, 1.00 equiv) in THF (30.00 mL) was added LiAlH$_4$ (9 mL, 2.5 M in THF) in portions at −70° C. under argon gas atmosphere. After stirring for 12 hours at room temperature, the reaction mixture was quenched with methanol at room temperature. and concentrated under reduced pressure. The residue was purified by column chromatography (silica gel, eluent: ethyl acetate/petroleum ether 3:7) to afford 1H-1,3-benzodiazol-4-ylmethanol (1.20 g, 66.0% yield) as an orange solid.

Step 2: 1H-1,3-benzodiazole-4-carbaldehyde

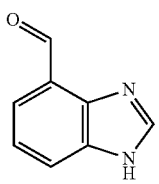 [SMILES: O=Cc1cccc2[nH]cnc12]

To a stirred solution of 1H-1,3-benzodiazol-4-ylmethanol (1.20 g, 8.10 mmol, 1.00 equiv) in DCM (25.00 mL) was added Dess-Martin (6870.32 mg, 16.20 mmol, 2.00 equiv) at room temperature. After stirring for 12 hours at room temperature, saturated sodium thiosulfate solution (100 mL) was added. The mixture was extracted with DCM and the combined organic layers were washed saturated sodium chloride aqueous solution, dried over anhydrous sodium sulfate, filtered and concentrated under reduced pressure. The residue was purified by column chromatography (silica gel, eluent: petroleum ether/ethyl acetate 42:58) to give 1H-1,3-benzodiazole-4-carbaldehyde (400 mg, 33.8%) as a white solid.

Step 3: 1-((4-bromophenyl)methyl)-1,3-benzodiazole-4-carbaldehyde

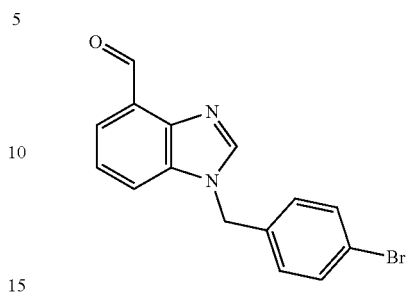

The title compound was synthesized by the method described in step 2 of Example 55 except 1H-1,3-benzodiazole-4-carbaldehyde (400.00 mg, 2.74 mmol) and 1-bromo-4-(bromomethyl)benzene (1.03 g, 4.12 mmo) were used. The crude product was purified by column chromatography (silica gel, eluent: petroleum ether/ethyl acetate 4:6) to give 1-((4-bromophenyl)methyl)-1,3-benzodiazole-4-carbaldehyde (400 mg, 43.1% yield) as a white solid.

Step 4: 1-((4-bromophenyl)methyl)-4-(difluoromethyl)-1,3-benzodiazole

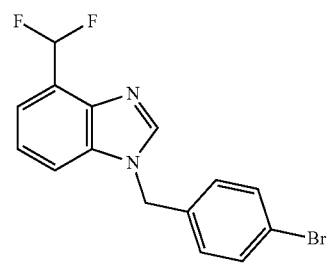 [SMILES: FC(F)c1cccc2c1ncn2Cc1ccc(Br)cc1]

To a stirred solution of 1-((4-bromophenyl)methyl)-1,3-benzodiazole-4-carbaldehyde (420 mg, 1.33 mmol, 1.00 equiv) in DCE (10 mL) was added BAST (Bis(2-methoxyethyl)aminosulfur Trifluoride, 0.5 mL) at room temperature. After stirring for 12 hours at room temperature, the resulting mixture was concentrated under reduced pressure, diluted with water and extracted with ethyl acetate. The combined organic layers were washed saturated sodium chloride aqueous solution, dried over anhydrous sodium sulfate, filtered and concentrated under reduced pressure. The residue was purified by column chromatography (silica gel, eluent: petroleum ether/ethyl acetate 32:68) to give a crude product, which was further purified by prep-HPLC with the following conditions (Column: Sunfire prep C18, 30*250, 5 um; Mobile Phase A: Water (10 mmolL/L NH$_4$HCO$_3$+0.1% NH$_3$·H$_2$O), Mobile Phase B: ACN; Flow rate: 45 mL/min; Gradient: 54 B to 95 B in 8 min; 254/220 nm; RT1:7.3 min) to afford 1-((4-bromophenyl)methyl)-4-(difluoromethyl)-1,3-benzodiazole (120 mg, 25.3% yield) as a white solid.

Step 5: 4-(difluoromethyl)-1-((4-(4,4,5,5-tetramethyl-1,3,2-dioxaborolan-2-yl)phenyl)-methyl)-1,3-benzodiazole

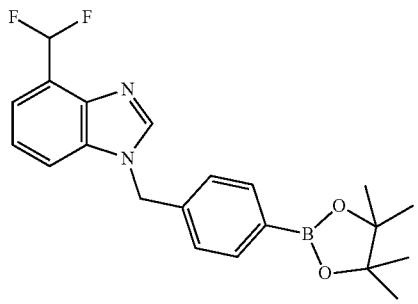 [SMILES: CC1(C)OB(c2ccc(Cn3cnc4c(C(F)F)cccc43)cc2)OC1(C)C]

To a stirred mixture of 1-((4-bromophenyl)methyl)-4-(difluoromethyl)-1,3-benzodiazole (120 mg, 0.36 mmol, 1.00 equiv) in dioxane (10 mL) were added KOAc (70 mg, 0.71 mmol, 2.00 equiv), Bis(pinacolato)diboron (180 mg, 0.1 equiv) and Pd(dppf)Cl$_2$ (26 mg, 0.036 mmol, 0.10 equiv) at room temperature under argon atmosphere. After stirring for 12 hours at 100° C. in an oil bath, the resulting mixture was concentrated under reduced pressure. The residue was purified by column chromatography (silica gel, eluent: petroleum ether/ethyl acetate 3:7) to give 4-(difluoromethyl)-1-((4-(4,4,5,5-tetramethyl-1,3,2-dioxaborolan-2-yl)phenyl)methyl)-1,3-benzodiazole (130 mg, 86.41% yield) as a white solid.

Step 6: 4-((4-(difluoromethyl)-1,3-benzodiazol-1-yl)methyl)phenylboronic acid

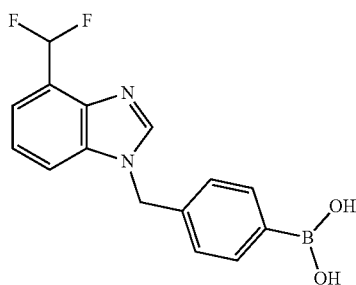

The title compound was synthesized by the method described in step 3 of Example 80 except 4-(difluoromethyl)-1-((4-(4,4,5,5-tetramethyl-1,3,2-dioxaborolan-2-yl)phenyl)methyl)-1,3-benzodiazole (110.00 mg, 0.29 mmol) was used. The crude product was purified by Prep-HPLC with the following conditions (Column: Sunfire prep C18 column, 30*150, 5 um; Mobile Phase A: Water (0.1% FA), Mobile Phase B: ACN; Flow rate: 60 mL/min; Gradient: 10 B to 50 B in 7 min; 254/220 nm) to afford 4-((4-(difluoromethyl)-1,3-benzodiazol-1-yl)methyl)phenylboronic acid (10.8 mg, 12.3% yield) as an off-white solid. MS (ESI, pos. ion) m/z: 303.05 (M+1). $^1$H NMR (300 MHz, DMSO-d$_6$, ppm) δ 8.55 (s, 1H), 8.03 (s, 2H), 7.72 (m, 3H), 7.31 (m, 5H), 5.56 (s, 2H).

Example 82

Synthesis of 3,5-difluoro-4-((4-hydroxyimidazo[4,5-c]pyridin-1-yl)methyl)phenylboronic acid

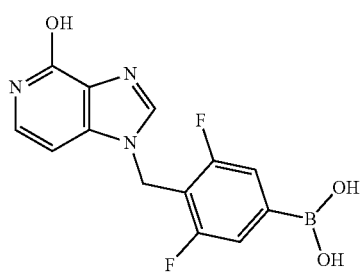 [SMILES: OB(O)c1cc(F)c(Cn2cnc3c(O)nccc32)c(F)c1]

Step 1: 4-methoxy-1H-imidazo[4,5-c]pyridine

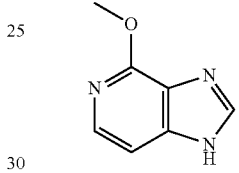

A solution of 4-chloro-1H-imidazo[4,5-c]pyridine (1.00 g, 6.51 mmol, 1.00 equiv) in sodium methanolate (17 mL, 30% in MeOH) was stirred for 12 hours at 120° C. After cooling to room temperature, the mixture was diluted with water and extracted with ethyl acetate. The combined organic layers were washed saturated sodium chloride aqueous solution, dried over anhydrous sodium sulfate, filtered and concentrated under reduced pressure to afford 4-methoxy-1H-imidazo[4,5-c]pyridine (520 mg, 50%) as a white solid Step 2: 1-((4-bromo-2,6-difluorophenyl)methyl)-4-methoxyimidazo[4,5-c]pyridine

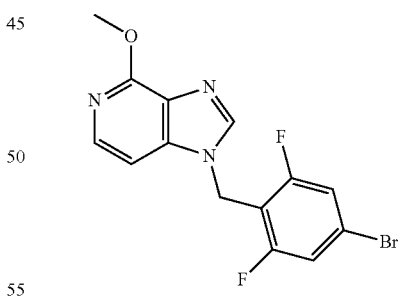

The title compound was synthesized by the method described in step 1 of Example 80 except 4-methoxy-1H-imidazo[4,5-c]pyridine (520 mg, 3.49 mmol) and 5-bromo-2-(bromomethyl)-1,3-difluorobenzene (1.20 g, 4.18 mmol) were used. The crude product was purified by prep-HPLC with the following conditions (Column: Sunfire prep C18 column, 30*150, 5 um; Mobile Phase A: Water (0.1% FA), Mobile Phase B: ACN; Flow rate: 60 mL/min; Gradient: 10 B to 50 B in 7 min; 254/220 nm) to afford 1-((4-bromo-2,6-difluorophenyl)methyl)-4-methoxyimidazo[4,5-c]pyridine (420 mg, 33.4% yield) as a white solid.

Step 3: 1-((2,6-difluoro-4-(4,4,5,5-tetramethyl-1,3,2-dioxaborolan-2-yl)phenyl)methyl)-4-methoxyimidazo[4,5-c]pyridine

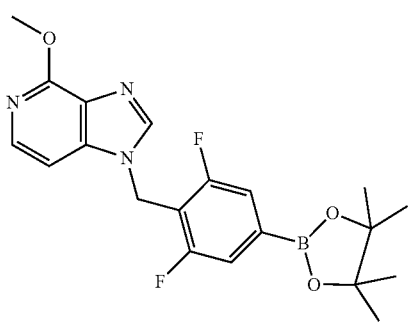 [SMILES: COc1nccc2c1ncn2Cc1c(F)cc(B2OC(C)(C)C(C)(C)O2)cc1F]

The title compound was synthesized by the method described in step 2 of Example 80 except 1-((4-bromo-2,6-difluorophenyl)methyl)-4-methoxyimidazo[4,5-c]pyridine (370 mg, 1.05 mmol) was used. Yield: 400 mg (81.6%). MS (ESI, pos. ion) m/z: 401.90 (M+1).

Step 4: 3,5-difluoro-4-((4-hydroxyimidazo[4,5-c]pyridin-1-yl)methyl)phenylboronic acid

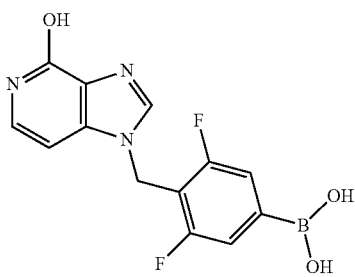 [SMILES: OB(O)c1cc(F)c(Cn2cnc3c(O)nccc32)c(F)c1]

The title compound was synthesized by the method described in step 3 of Example 80 except 1-((4-bromo-2,6-difluorophenyl)methyl)-4-methoxyimidazo[4,5-c]pyridine (370 mg, 1.05 mmol) was used. Yield: 23.2 mg (16.0%). MS (ESI, pos. ion) m/z: 306.00 (M+1). H NMR (300 MHz, DMSO-$d_6$, ppm) δ 11.22 (s, 1H), 8.48 (s, 2H), 8.07 (s, 1H), 7.47 (d, J=8.3 Hz, 2H), 7.20 (t, J=5.8 Hz, 1H), 6.46 (d, J=7.0 Hz, 1H), 5.50 (s, 2H).

Example 83

Synthesis of 3,5-difluoro-4-((4-hydroxypyrrolo[3,2-c]pyridin-1-yl)methyl)phenylboronic acid

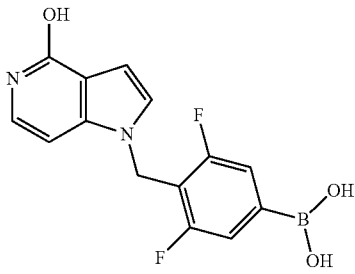 [SMILES: OB(O)c1cc(F)c(Cn2ccc3c(O)nccc32)c(F)c1]

Step 1: 4-methoxy-1H-pyrrolo[3,2-c]pyridine

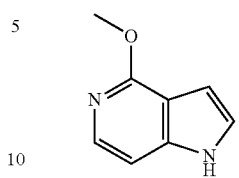

The title compound was synthesized by the method described in step 1 of Example 82 except 4-chloro-1H-pyrrolo[3,2-c]pyridine (2.00 g, 13.11 mmol) was used. Yield: 840 mg (38.2%). MS (ESI, pos. ion) m/z: 149.15 (M+1).

Step 2: 1-((4-bromo-2,6-difluorophenyl)methyl)-4-methoxypyrrolo[3,2-c]pyridine

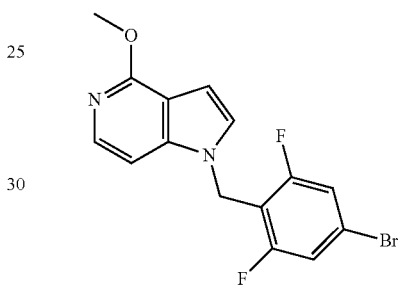

The title compound was synthesized by the method described in step 1 of Example 80 except 4-methoxy-1H-pyrrolo[3,2-c]pyridine (0.80 g, 5.40 mmol) and 5-bromo-2-(bromomethyl)-1,3-difluorobenzene (1.70 g, 5.939 mmol) were used. The crude product was purified by column chromatography (silica gel, eluent: DCM/MEOH 98:2) to give 1-((4-bromo-2,6-difluorophenyl)methyl)-4-methoxy-pyrrolo[3,2-c]pyridine (1.1 g, 57.7% yield) as an off-white solid. MS (ESI, pos. ion) m/z: 353.17 (M+1).

Step 3: 1-((2,6-difluoro-4-(4,4,5,5-tetramethyl-1,3,2-dioxaborolan-2-yl)phenyl)methyl)-4-methoxypyrrolo[3,2-c]pyridine

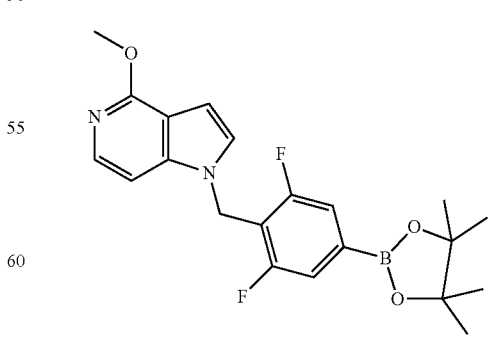

The title compound was synthesized by the method described in step 2 of Example 80 except 1-((4-bromo-2,6-difluorophenyl)methyl)-4-methoxypyrrolo[3,2-c]pyridine (500 mg, 1.42 mmol) was used. Yield: 310 mg (54.2%). MS (ESI, pos. ion) m/z: 401.10 (M+1).

Step 4: 3,5-difluoro-4-((4-hydroxypyrrolo[3,2-c]pyridin-1-yl)methyl)phenylboronic acid

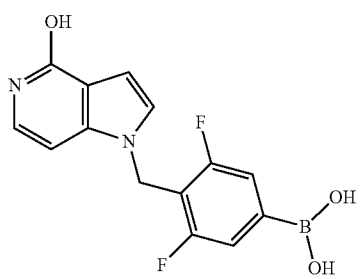 [SMILES: OB(O)c1cc(F)c(Cn2ccc3c(O)nccc32)c(F)c1]

The title compound was synthesized by the method described in step 3 of Example 80 except 1-((2,6-difluoro-4-(4,4,5,5-tetramethyl-1,3,2-dioxaborolan-2-yl)phenyl)methyl)-4-methoxypyrrolo[3,2-c]pyridine (150.00 mg, 0.41 mmol) was used. Yield: 23.8 mg (20.6%). MS (ESI, pos. ion) m/z: 305.05 (M+1). H NMR (300 MHz, DMSO-$d_6$, ppm) δ 10.81 (s, 1H), 8.42 (s, 2H), 7.42 (d, J=8.4 Hz, 2H), 7.04 (d, J=7.0 Hz, 2H), 6.50 (dd, J=14.4, 5.2 Hz, 2H), 5.35 (s, 2H).

Example 84

Synthesis of 4-((4-(fluoromethyl)-1,3-benzodiazol-1-yl)methyl)phenylboronic acid

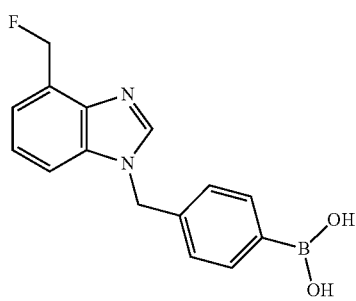 [SMILES: OB(O)c1ccc(Cn2cnc3c(CF)cccc32)cc1]

Step 1: 1H-1,3-benzodiazol-4-ylmethanol

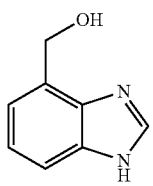

To a stirred solution of 1H-1,3-benzodiazole-4-carboxylic acid (1.83 g, 11.29 mmol, 1.00 equiv) in THF (30 mL) was added LiAlH₄ (9 mL, 2.5 mol/L) in portions at –70° C. under argon gas atmosphere. After stirring overnight at room temperature, the reaction was quenched with methanol at room temperature. The resulting mixture was concentrated under reduced pressure and the residue was purified by column chromatography (silica gel, eluent: ethyl acetate/petroleum ether 3:7) to afford 1H-1,3-benzodiazol-4-ylmethanol (1.1 g, 48.0% yield) as an orange solid.

Step 2: (1-((4-bromophenyl)methyl)-1,3-benzodiazol-4-yl)methanol

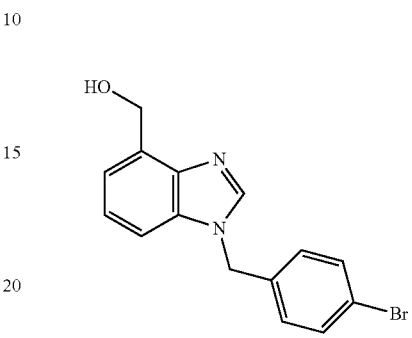

The title compound was synthesized by the method described in step 2 of Example 55 except 1H-1,3-benzodiazol-4-ylmethanol (300 mg, 2.03 mmol) and 1-bromo-4-(bromomethyl)benzene (557 mg, 2.23 mmol) were used. The crude product was purified by column chromatography (silica gel, eluent: DCE/MEOH 95:5) to afford (1-((4-bromophenyl)methyl)-1,3-benzodiazol-4-yl)methanol (350 mg, 52.6% yield) as a brown oil. MS (ESI, pos. ion) m/z: 317.10 (M+1).

Step 3: 1-((4-bromophenyl)methyl)-4-(fluoromethyl)-1,3-benzodiazole

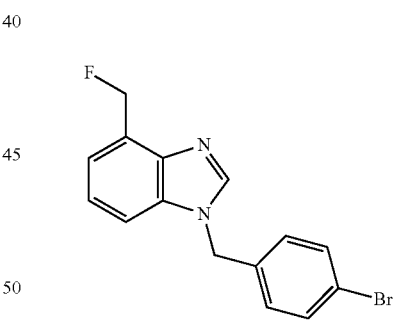

To a stirred solution of (1-((4-bromophenyl)methyl)-1,3-benzodiazol-4-yl)methanol (300 mg, 0.95 mmol, 1.00 equiv) in DCE (8.00 mL) were added BAST (0.70 mL) at room temperature. After stirring for 3 hours at room temperature, the mixture was poured water (100 mL) and extracted with ethyl acetate. The combined organic layers were dried over anhydrous sodium sulfate, filtered and concentrated under reduced pressure. The residue was purified by column chromatography (silica gel, eluent: ethyl acetate/petroleum ether 50:50) to get 1-((4-bromophenyl)methyl)-4-(fluoromethyl)-1,3-benzodiazole (160 mg, 70.8% yield) as a brown solid.

Step 4: 4-(fluoromethyl)-1-((4-(4,4,5,5-tetramethyl-1,3,2-dioxaborolan-2-yl)phenyl)methyl)-1,3-benzodiazole

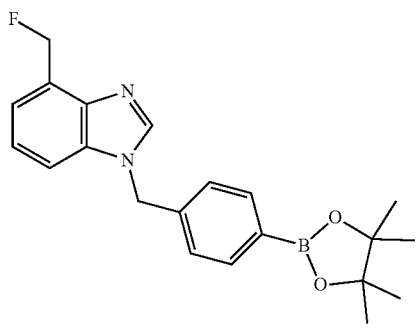 [SMILES: CC1(C)OB(c2ccc(Cn3cnc4c(CF)cccc43)cc2)OC1(C)C]

The title compound was synthesized by the method described in step 2 of Example 80 except 1-((4-bromophenyl) methyl)-4-(fluoromethyl)-1,3-benzodiazole (160 mg, 0.50 mmol) was used. The crude product was purified by column chromatography (silica gel, eluent: ethyl acetate/petroleum ether 40:60) to give 4-(fluoromethyl)-1-((4-(4,4,5,5-tetramethyl-1,3,2-dioxaborolan-2-yl)phenyl)methyl)-1,3-benzodiazole (146 mg, 74.0% yield) as an off-white solid.

Step 5: 4-((4-(fluoromethyl)-1,3-benzodiazol-1-yl)methyl)phenylboronic acid

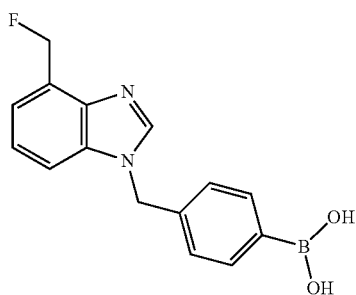 [SMILES: OB(O)c1ccc(Cn2cnc3c(CF)cccc32)cc1]

The title compound was synthesized by the method described in step 3 of Example 80 except 4-(fluoromethyl)-1-((4-(4,4,5,5-tetramethyl-1,3,2-dioxaborolan-2-yl)phenyl)methyl)-1,3-benzodiazole (126 mg, 0.34 mmol) was used. Yield: 24.6 mg (24.3%). MS (ESI, pos. ion) m/z: 285.25 (M+1). $^1$H NMR (300 MHz, DMSO-$d_6$, ppm) δ 8.49 (s, 1H), 8.00 (s, 2H), 7.77-7.69 (m, 2H), 7.54 (m, 1H), 7.33-7.19 (m, 4H), 5.85 (s, 1H), 5.69 (s, 1H), 5.53 (s, 2H).

Example 85

Synthesis of 4-((4-bromo-5-fluoropyrrolo[2,3-d]pyrimidin-7-yl)methyl)phenylphosphonic acid (85a) and 4-((5-fluoro-4-oxo-3H-pyrrolo[2,3-d]pyrimidin-7-yl)methyl)phenylphosphonic acid (85b)

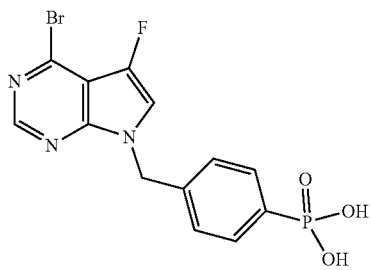

85a

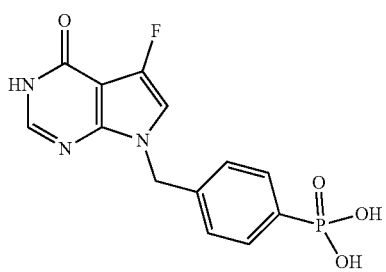

85b

Step 1: diethyl 4-((4-chloro-5-fluoropyrrolo[2,3-d]pyrimidin-7-yl)methyl)phenyl-phosphonate

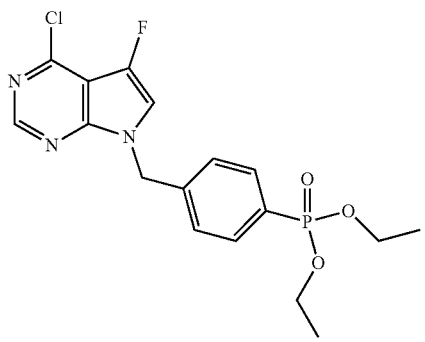 [SMILES: CCOP(=O)(OCC)c1ccc(Cn2cc(F)c3c(Cl)ncnc32)cc1]

The title compound was synthesized by the method described in step 4 of Example 22 except 4-chloro-5-fluoro-7H-pyrrolo[2,3-d]pyrimidine (0.55 g, 3.21 mmol) and diethyl 4-(bromomethyl)phenylphosphonate (1.18 g, 3.84 mmol) were used. Yield: 600 mg (47.1%). MS (ESI, pos. ion) m/z: 398.10 (M+1).

Step 2: 4-((4-bromo-5-fluoropyrrolo[2,3-d]pyrimidin-7-yl)methyl)phenylphosphonic acid (85a

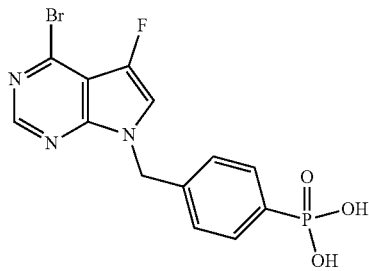 [SMILES: O=P(O)(O)c1ccc(Cn2cc(F)c3c(Br)ncnc32)cc1]

To a solution of diethyl 4-((4-chloro-5-fluoropyrrolo[2,3-d]pyrimidin-7-yl)-methyl)phenylphosphonate (540 mg, 1.36 mmol, 1.00 equiv) in DCM (10.00 mL) was added bromotrimethylsilane (2 mL). After stirring overnight at RT, the reaction mixture was evaporated under reduced pressure. The crude product was purified by prep-HPLC underfollowing conditions (Column: XBridge Prep OBD C18 Column, 19*250 mm, 5 um; Mobile Phase A: Water (10 mmoL/L NH$_4$HCO$_3$+0.1% NH$_3$·H$_2$O), Mobile Phase B: ACN; Flow rate: 20 mL/min; Gradient: 8 B to 64 B in 7 min; 254/220 nm) to afford 400 mg 4-((4-bromo-5-fluoropyrrolo[2,3-d]pyrimidin-7-yl)methyl)phenylphosphonic acid (85a) as a white solid. MS (ESI, pos. ion) m/z: 386.15 (M+1). $^1$H NMR (400 MHz, DMSO-d$_6$, ppm) δ 8.63 (s, 1H), 7.90 (d, J=2.2 Hz, 1H), 7.54 (m, 7.9 Hz, 2H), 7.15 (d, J=2.5 Hz, 2H), 5.43 (s, 2H).

Step 3: 4-((5-fluoro-4-oxo-3H-pyrrolo[2,3-d]pyrimidin-7-yl)methyl)phenylphosphonic acid (85b

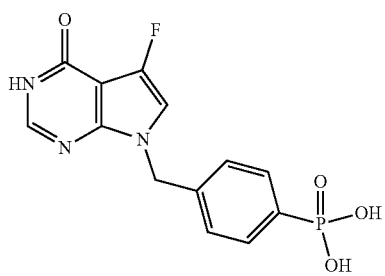

To a solution of 4-((4-bromo-5-fluoropyrrolo[2,3-d]pyrimidin-7-yl)methyl)phenyl-phosphonic acid (100.00 mg, 0.31 mmol) in THF (5.00 mL) was added HCl (5.00 mL, 1M). After stirring for 3 hours at 80° C., the reaction mixture was evaporated under reduced pressure. The crude product was purified by Prep-HPLC under following conditions (Column: XBridge Prep OBD C18 Column, 19*250 mm, 5 um; Mobile Phase A: Water (10 mmoL/L NH$_4$HCO$_3$+0.1% NH$_3$·H$_2$O), Mobile Phase B: ACN; Flow rate: 20 mL/min; Gradient: 8 B to 64 B in 7 min; 254/220 nm) to afford 4-((5-fluoro-4-oxo-3H-pyrrolo[2,3-d]pyrimidin-7-yl)methyl)phenylphosphonic acid (85b, 5.5 mg, 6.0% yield). MS (ESI, pos. ion) m/z: 324.25 (M+1). $^1$H NMR (300 MHz, DMSO-d6/D20, ppm) 67.91 (s, 1H), 7.58 (dd, J=12.2, 7.7 Hz, 2H), 7.20-7.09 (m, 3H), 5.28 (s, 2H).

Example 86

Synthesis of 4-((4-amino-5-fluoropyrrolo[2,3-d]pyrimidin-7-yl)methyl)phenylphosphonic acid

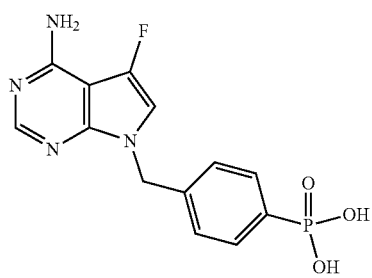 [SMILES: Nc1ncnc2c1c(F)cn2Cc1ccc(P(=O)(O)O)cc1]

4-((4-bromo-5-fluoropyrrolo[2,3-d]pyrimidin-7-yl)methyl)phenylphosphonic acid (100 mg, 0.29 mmol, 1.00 equiv) was dissolved in MeOH (3 mL) and aqueous ammonia (10 mL). After stirring at 80° C. for 5 h, the reaction mixture was cooled to room temperature and concentrated under reduced pressure. The residue was purified by prep-HPLC under following conditions (Column: XBridge Prep OBD C18 Column, 19*250 mm, 5 um; Mobile Phase A: Water (10 mmoL/L NH$_4$HCO$_3$+0.1% NH$_3$·H$_2$O), Mobile Phase B: ACN; Flow rate: 25 mL/min; Gradient: 5 B to 18 B in 7 min; 254,220 nm) to give 4-((4-amino-5-fluoropyrrolo[2,3-d]pyrimidin-7-yl)methyl)phenylphosphonic acid (56.4 mg) as a white solid. MS (ESI, pos. ion) m/z: 323.25 (M+1). $^1$H NMR (300 MHz, DMSO-d$_6$, ppm) δ 8.09 (s, 1H), 7.53 (dd, J=11.7, 7.8 Hz, 2H), 7.18 (d, J=2.3 Hz, 1H), 7.10 (dd, J=8.2, 2.8 Hz, 2H), 6.96 (s, 2H), 5.26 (s, 2H).

Example 87

Synthesis of diethyl 4-((5-carbamoyl-2-methyl-1,3-benzodiazol-1-yl)methyl)phenylphosphonate (87a), diethyl 4-((6-carbamoyl-2-methyl-1,3-benzodiazol-1-yl)methyl)phenylphosphonate (87b) and 4-((5-carbamoyl-2-methyl-1,3-benzodiazol-1-yl)methyl)phenylphosphonic acid (87c

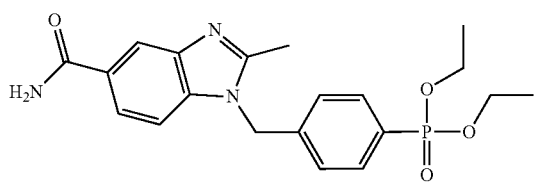

87a

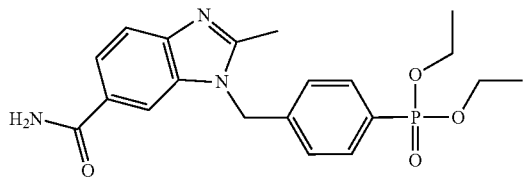

87b

Step 3: diethyl 4-((5-carbamoyl-2-methyl-1,3-benzodiazol-1-yl)methyl)phenylphosphonate (87a) and diethyl 4-((6-carbamoyl-2-methyl-1,3-benzodiazol-1-yl)methyl)phenylphosphonate (87b

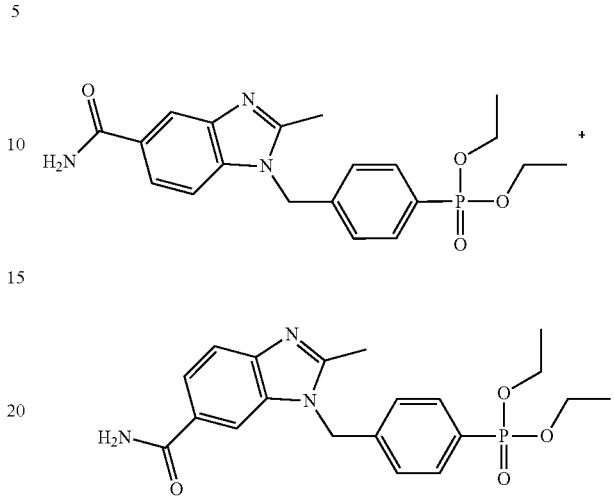

The title compounds were synthesized by the method described in step 2 of Example 55 except (2-methyl-1H-1,3-benzodiazole-5-carboxamide (200 mg, 1.14 mmol) and diethyl 4-(bromomethyl)phenylphosphonate (421 mg, 1.37 mmol) were used. The crude product was purified by prep-HPLC with the following conditions (Column: Sunfire prep C18 column, 30*150, 5 um; Mobile Phase A: Water (10 mmoL/L H$_4$HCO$_3$+0.1% NH$_3$·H$_2$O), Mobile Phase B: ACN; Flow rate: 45 mL/min; Gradient: 18 B to 23 B in 7 min; 254,220 nm; RT1=6.83 min, RT2=7.50 min). The fractions containing the desired product were combined and lyophilized to give two fractions:

Fraction 1: Rt: 6.83 min. 100 mg (12.5% yield) of diethyl 4-((5-carbamoyl-2-methyl-1,3-benzodiazol-1-yl)methyl)phenylphosphonate (87a) as a white solid. MS (E SI, pos. ion) m/z: 402.25 (M+1). $^1$H NMR (300 MHz, DMSO-d6, ppm) δ 8.15 (d, J=1.6 Hz, 1H), 7.95 (s, 1H), 7.80-7.61 (m, 3H), 7.50 (d, J=8.5 Hz, 1H), 7.30-7.20 (m, 3H), 5.61 (s, 2H), 3.98 (m, 4H), 2.53 (s, 3H), 1.20 (t, J=7.0 Hz, 6H).

Fraction 2: Rt: 7.50 min. 63.4 mg (9.14% yield) of diethyl 4-((6-carbamoyl-2-methyl-1,3-benzodiazol-1-yl)methyl)phenylphosphonate (87b) as a white solid. MS (ESI, pos. ion) m/z: 402.25 (M+1). $^1$H NMR (300 MHz, DMSO-d6, ppm) δ 8.04 (d, J=1.6 Hz, 1H), 7.90 (s, 1H), 7.80-7.63 (m, 3H), 7.60 (d, J=8.4 Hz, 1H), 7.2 (s, 3H), 5.62 (s, 2H), 4.09-3.86 (m, 4H), 2.53 (s, 3H), 1.20 (t, J=7.0 Hz, 6H).

Step 3: 4-((5-carbamoyl-2-methyl-1,3-benzodiazol-1-yl)methyl)phenylphosphonic acid (87c

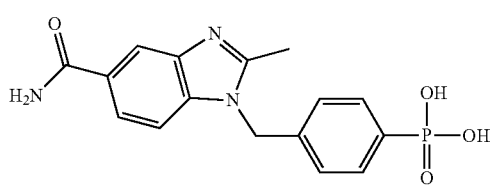

The title compound was synthesized by the method described in step 2 of Example 85 except diethyl 4-((5-

87c

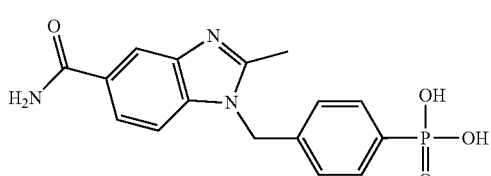

Step 1: methyl 2-methyl-1H-1,3-benzodiazole-5-carboxylate

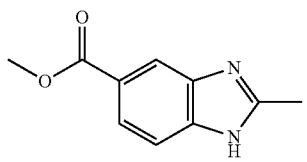

To a stirred solution of methyl 3,4-diaminobenzoate (2.00 g, 12.00 mmol, 1.0 equiv) in dimethylacetamide (25 mL) was added imidazole hydrochloride (1.00 g, 9.57 mmol, 0.79 equiv) at room temperature. After stirring for 12 hours at 120° C. in an oil bath, the mixture was diluted with water and extracted with ethyl acetate. The combined organic layers were washed with saturated sodium chloride aqueous solution, dried over anhydrous sodium sulfate, filtered and concentrated under reduced pressure. The residue was purified by column chromatography (silica gel, eluent: Petroleum ether/ethyl acetate 10:1) to give methyl 2-methyl-1H-1,3-benzodiazole-5-carboxylate (1.71 g, 73.1%) as a white solid.

Step 2: 2-methyl-1H-1,3-benzodiazole-5-carboxamide

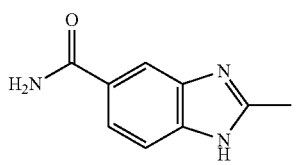

A solution of methyl 2-methyl-1H-1,3-benzodiazole-5-carboxylate (500.00 mg, 2.63 mmol, 1 equiv) in NH$_3$·H$_2$O (15 mL) was stirring for 24 hours at 80° C. in an oil bath. After cooling to room temperature, the mixture was concentrated under reduced pressure. The residue was purified by column chromatography (silica gel, eluent: dichloromethane/methanol 92:8) to afford 2-methyl-1H-1,3-benzodiazole-5-carboxamide (200 mg, 42.6% yield) as a yellow solid.

carbamoyl-2-methyl-1,3-benzodiazol-1-yl)methyl)phenylphosphonate (90 mg, 0.22 mmol) was used. The crude product was purified by prep-HPLC with the following conditions (Column: YMC-Actus Triart C18, 30*250.5 um; Mobile Phase A: Water (0.05% FA), Mobile Phase B: ACN:MEOH=4:1; Flow rate: 45 mL/min; Gradient: 2 B to 20 B in 7 min; 254,220 nm) to afford 4-((5-carbamoyl-2-methyl-1,3-benzodiazol-1-yl)methyl)phenylphosphonic acid (23.6 mg, 27.3% yield) as a white solid. MS (ESI, pos. ion) m/z: 346.10 (M+1). $^1$H NMR (300 MHz, DMSO-d6/D$_2$O, ppm) δ 8.14 (s, 1H), 7.77 (d, J=8.5 Hz, 1H), 7.68-7.44 (m, 3H), 7.2 (s, 2H), 5.58 (s, 2H), 2.60 (s, 3H).

Example 88

Synthesis of 4-((5-carbamoyl-6-methoxy-1,3-benzodiazol-1-yl)methyl)phenylphosphonic acid

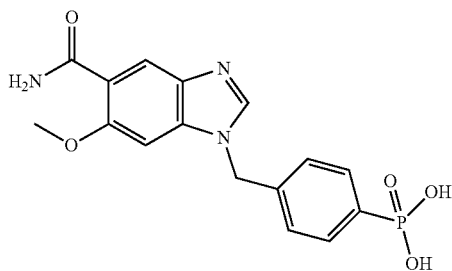 [SMILES: COc1cc2c(cc1C(N)=O)ncn2Cc1ccc(P(=O)(O)O)cc1]

Step 1: methyl 4,5-diamino-2-methoxybenzoate

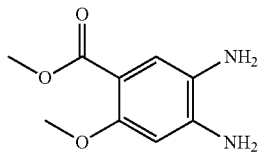

The title compound was synthesized by the method described in step 5 of Example 30 except methyl 4-amino-2-methoxy-5-nitrobenzoate (1.00 g, 4.42 mmol) was used. Yield: 760 mg (85.6%).

Step 2: methyl 6-methoxy-1H-1,3-benzodiazole-5-carboxylate

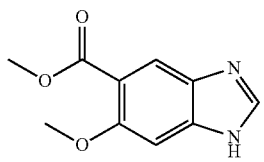

To a solution of methyl 4,5-diamino-2-methoxybenzoate (700 mg, 3.49 mmol, 1.0 equiv) in DMF (10.00 mL) was added imidazole hydrochloride (368 mg, 3.49 mmol, 1.0 equiv). After stirring for 24 h at 150° C. the reaction mixture was diluted with water and extracted with ethyl acetate. The combined organic layers were washed with brine, dried over anhydrous sodium sulfate and filtered. The filtrate was concentrated under reduced pressure to give methyl 6-methoxy-1H-1,3-benzodiazole-5-carboxylate (500 mg, 68.0% yield) as a yellow oil.

Step 3: 6-methoxy-1H-1,3-benzodiazole-5-carboxamide

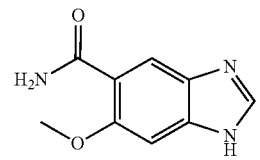

The title compound was synthesized by the method described in step 2 of Example 87 except methyl 6-methoxy-1H-1,3-benzodiazole-5-carboxylate (500 mg, 2.43 mmol) was used. Yield: 280 mg (70.2%).

Step 4: diethyl 4-((5-carbamoyl-6-methoxy-1,3-benzodiazol-1-yl)methyl)phenylphosphonate

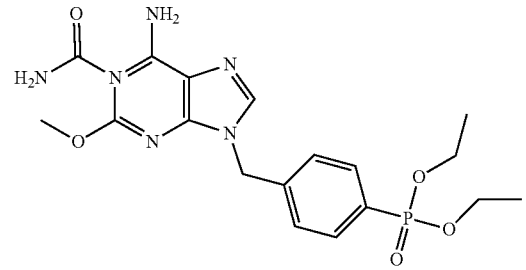

The title compound was synthesized by the method described in step 2 of Example 55 except 6-methoxy-1H-1,3-benzodiazole-5-carboxamide (230 mg, 1.20 mmol) and diethyl 4-(bromomethyl)phenylphosphonate (369 mg, 1.20 mmol) were used. The crude product was purified by prep-HPLC under following conditions (Column: Sunfire prep C18 column, 30*150, 5 um; Mobile Phase A: Water (0.05% FA), Mobile Phase B: ACN; Flow rate: 45 mL/min; Gradient: 17 B to 27 B in 10 min; 254,220 nm) to give 50 mg (10% yield) of diethyl 4-((5-carbamoyl-6-methoxy-1,3-benzodiazol-1-yl)methyl)phenylphosphonate as a white solid. MS (ESI, pos. ion) m/z: 418.30 (M+1).

Step 5: 4-((5-carbamoyl-6-methoxy-1,3-benzodiazol-1-yl)methyl)phenylphosphonic acid

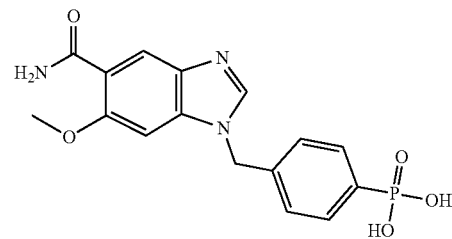 [SMILES: COc1cc2c(cc1C(N)=O)ncn2Cc1ccc(P(=O)(O)O)cc1]

The title compound was synthesized by the method described in step 2 of Example 85 except diethyl 4-((5-carbamoyl-6-methoxy-1,3-benzodiazol-1-yl)methyl)phenylphosphonate (50 mg 0.12 mmol) was used. The crude product was purified by prep-HPLC under following conditions (Column: YMC-Actus Triart C18, 30*250.5 um; Mobile Phase A: Water (0.05% FA), Mobile Phase B: ACN:MEOH=4:1; Flow rate: 45 mL/min; Gradient: 2 B to 20 B in 7 min; 254,220 nm) to afford 4-((5-carbamoyl-6-methoxy-1,3-benzodiazol-1-yl)methyl)phenylphosphonic acid (21.2 mg, 46.58% yield) as a white solid. MS (ESI, pos. ion) m/z: 362.2 (M+1). $^1$H NMR (400 MHz, DMSO-d6, ppm) δ 8.67 (s, 1H), 8.08 (s, 1H), 7.69-7.59 (m, 3H), 7.51 (s, 1H), 7.40 (dd, J=8.2, 3.2 Hz, 2H), 7.32 (s, 1H), 5.60 (s, 2H), (s, 3H).

Example 89

Synthesis of diethyl 4-((5-carbamoylimidazo[4,5-b]pyridin-1-yl)methyl)phenylphosphonate (89a), diethyl 4-((5-carbamoylimidazo[4,5-b]pyridin-3-yl)methyl)phenylphosphonate (89b) and 4-((5-carbamoylimidazo[4,5-b]pyridin-1-yl)methyl)phenylphosphonic acid (89c

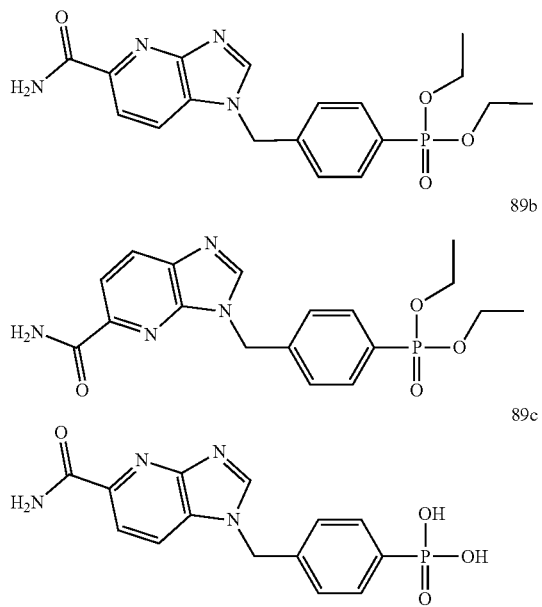

Step 1: 1H-imidazo[4,5-b]pyridine-5-carboxamide

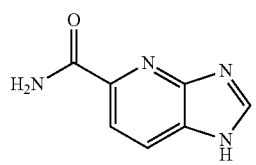 [SMILES: NC(=O)c1ccc2[nH]cnc2n1]

The title compound was synthesized by the method described in step 1 of Example 41 except 5-bromo-1H-imidazo[4,5-b]pyridine (500 mg, 2.53 mmol) was used. The crude product was purified by column chromatography (silica gel, eluent: dichloromethane/methyl alcohol 9:1) to afford 1H-imidazo[4,5-b]pyridine-5-carboxamide (400 mg, 84.9% yield) as a brown solid.

Step 2: diethyl 4-((5-carbamoylimidazo[4,5-b]pyridin-1-yl)methyl)phenylphosphonate (89a) and diethyl 4-((5-carbamoylimidazo[4,5-b]pyridin-3-yl)methyl)phenylphosphonate (89b

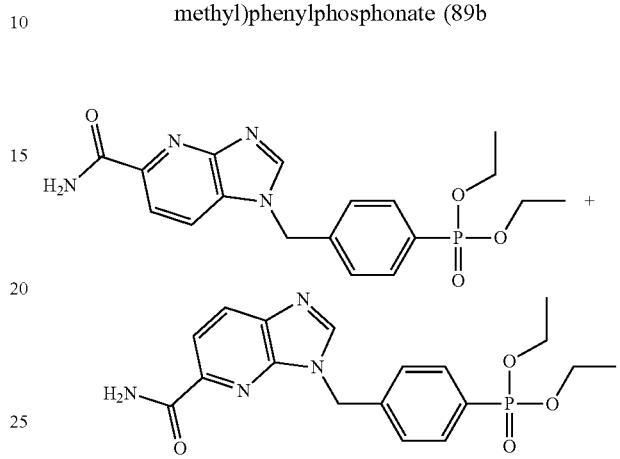

The title compounds were synthesized by the method described in step 2 of Example 55 except 1H-imidazo[4,5-b]pyridine-5-carboxamide (400 mg, 2.47 mmol) and diethyl 4-(bromomethyl)phenylphosphonate (1.14 g, 3.70 mmol) were used. The crude product was purified by prep-HPLC under following conditions (Column: Sunfire prep C18 column, 30*150, 5 um; Mobile Phase A: Water (0.1% FA), Mobile Phase B: ACN:MEOH=4:1; Flow rate: 45 mL/min; Gradient: 25 B to 30 B in 7 min; 254,220 nm; RT1:6.17 min; RT2: 8.20 min). The fractions containing the desired product were combined and lyophilized to give two fractions:

Fraction 1: Rt: 6.17 min. 160 mg (18.2% yield) of diethyl 4-((5-carbamoylimidazo[4,5-b]pyridin-1-yl)methyl)phenylphosphonate (89A) as a white solid. MS (ESI, pos. ion) m/z: 389.10 (M+1). $^1$H NMR (300 MHz, DMSO-d6, ppm) δ 8.85 (s, 1H), 8.15 (s, 2H), 8.00 (d, J=8.0 Hz, 1H), 7.70 (dd, J=13.0, 7.7 Hz, 2H), 7.57-7.36 (m, 3H), 5.69 (s, 2H), 3.98 (m, 4H), 1.20 (m, 6H).

Fraction 2: Rt: 8.20 min. 81.6 mg (8.47% yield) of diethyl 4-((5-carbamoylimidazo[4,5-b]pyridin-3-yl)methyl)phenylphosphonate (89b) as a white oil. MS (ESI, pos. ion) m/z: 388.80 (M+1). $^1$H NMR (300 MHz, DMSO-d6, ppm) δ 8.81 (d, J=1.9 Hz, 1H), 8.23 (d, J=7.2 Hz, 2H), 8.01 (dd, J=8.3, 1.9 Hz, 1H), 7.72-7.55 (m, 5H), 5.70 (s, 2H), 3.97 (t, J=7.6 Hz, 4H), 1.30-1.18 (m, 6H).

Step 3: 4-((5-carbamoylimidazo[4,5-b]pyridin-1-yl)methyl)phenylphosphonic acid (89c

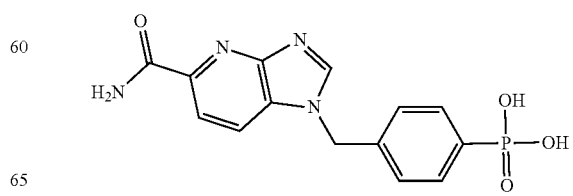

The title compound was synthesized by the method described in step 2 of Example 85 except diethyl 4-((5-carbamoylimidazo[4,5-b]pyridin-1-yl)methyl)phenylphosphonate (110 mg, 0.28 mmol) was used. The crude product was purified by prep-HPLC with the following conditions (Column: YMC-Actus Triart C18, 30*250.5 um; Mobile Water (0.05% FA), Mobile Phase B: ACN; Flow rate: 45 mL/min; Gradient: 5 B to 14 B in 7 min; 254,220 nm) to afford 4-((5-carbamoylimidazo[4,5-b]pyridin-1-yl)methyl) phenylphosphonic acid (89c, 27.1 mg, 27.9% yield) as a white solid. MS (ESI, pos. ion) m/z: 333.05 (M+1). $^1$H NMR (300 MHz, DMSO-d6/D$_2$O, ppm) δ 9.03 (d, J=2.0 Hz, 1H), 8.21-8.11 (m, 2H), 8.08-7.98 (m, 1H), 7.72-7.56 (m, 3H), 7.43 (d, J=7.7 Hz, 2H), 5.67 (s, 2H).

Example 90

Synthesis of diethyl 4-((5-(methylcarbamoyl)-1,3-benzodiazol-1-yl)methyl)phenylphosphonate (90a), diethyl 4-((6-(methylcarbamoyl)-1,3-benzodiazol-1-yl)methyl)phenylphosphonate (90b), 4-((5-(methylcarbamoyl)-1,3-benzodiazol-1-yl)methyl)phenylphosphonic acid (90c) and ethoxy (4-((5-(methylcarbamoyl)-1,3-benzodiazol-1-yl)methyl)phenyl)phosphinic acid (90d Step 1: N-methyl-1H-1,3-benzodiazole-5-carboxamide

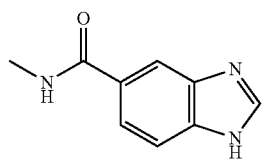

The title compound was synthesized by the method described in step 2 of Example 14 except methyl 1H-1,3-benzodiazole-5-carboxylate (500 mg, 2.84 mmol) and 30% methylamine in MeOH (10.00 mL) were used. Yield: 500 mg (90.70%). MS (ESI, pos. ion) m/z: 176.25 (M+1).

Step 2: diethyl 4-((5-(methylcarbamoyl)-1,3-benzodiazol-1-yl)methyl)phenylphosphonate (90a) and diethyl 4-((6-(methylcarbamoyl)-1,3-benzodiazol-1-yl)methyl)phenylphosphonate (90b

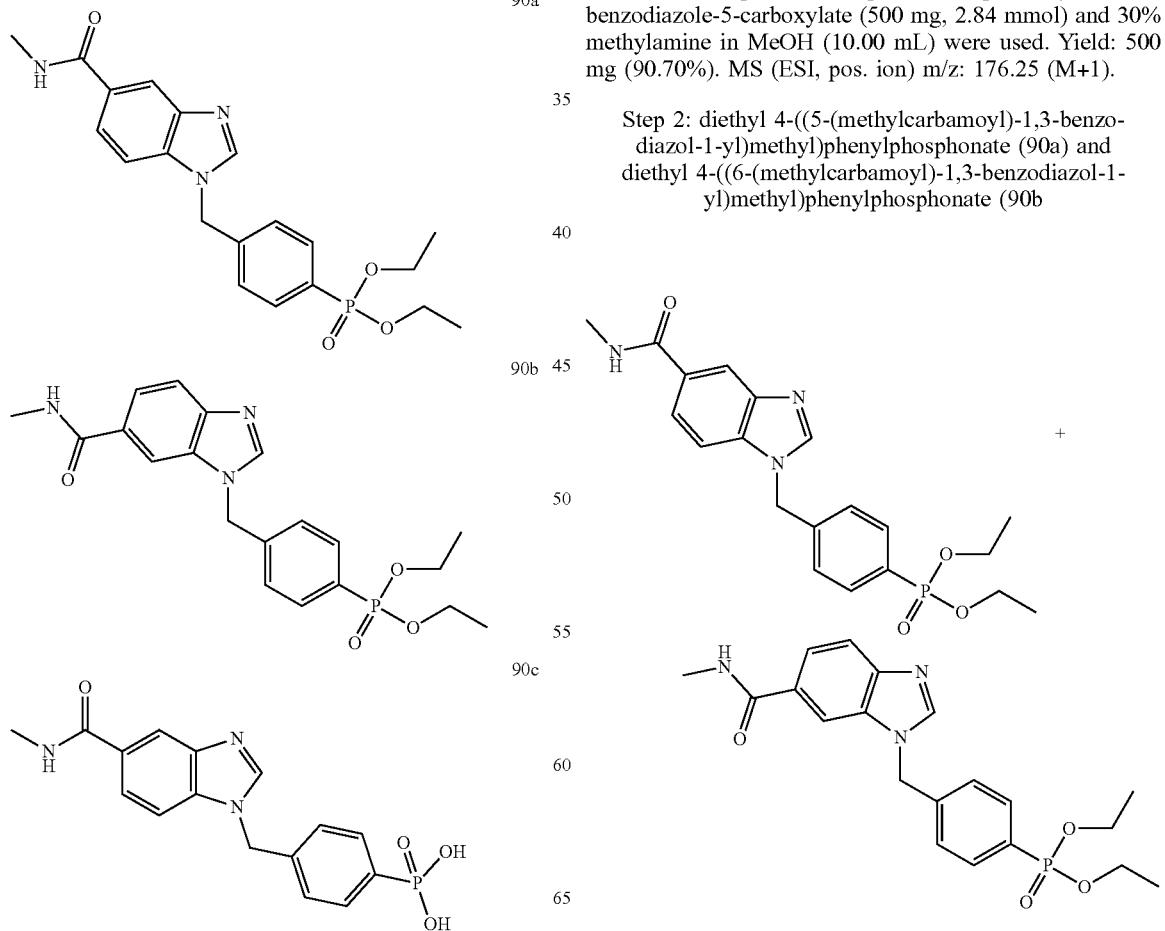

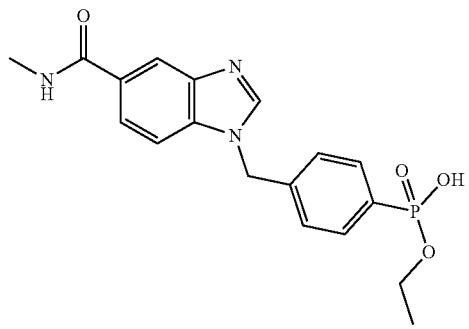

The title compounds were synthesized by the method described in step 2 of Example 55 except N-methyl-1H-1,3-benzodiazole-5-carboxamide (200 mg, 1.14 mmol) and diethyl 4-(bromomethyl)phenylphosphonate (526 mg, 1.71 mmol) were used. The crude product was purified by prep-HPLC under following conditions (Column: XBridge prep OBD C18 Column, 30×150 mm 5 um; Mobile Phase A: Water (10 mmoL/L NH$_4$HCO$_3$+0.1% NH$_3$·H$_2$O), Mobile Phase B: ACN; Flow rate: 60 mL/min; Gradient: 18 B to 19 B in 15 min; 254/220 nm, RT1:10.08 min; RT2: 12.3 min). The fractions containing the desired product were combined and lyophilized to give two fractions:

Fraction 1: Rt: 10.08 min. 150 mg (31.8% yield) of diethyl 4-((5-(methylcarbamoyl)-1,3-benzodiazol-1-yl)methyl)phenylphosphonate (90a) as a white solid. MS (ESI, pos. ion) m/z: 402.30 (M+1). $^1$H NMR (400 MHz, DMSO-d$_6$, ppm) δ 8.51 (s, 1H), 8.39 (d, J=4.7 Hz, 1H), 8.18 (dd, J=1.7, 0.7 Hz, 1H), 7.76-7.61 (m, 3H), 7.54 (dd, J=8.6, 0.7 Hz, 1H), 7.44-7.36 (m, 2H), 5.61 (s, 2H), 3.95 (m, 4H), 2.80-2.74 (m, 3H), 1.18 (t, J=7.0 Hz, 6H).

Fraction 2: Rt: 12.3 min. 120 mg (25.9% yield) of diethyl 4-((6-(methylcarbamoyl)-1,3-benzodiazol-1-yl)methyl)phenylphosphonate (90b) as a white solid. MS (ESI, pos. ion) m/z: 402.3 (M+1). $^1$H NMR (400 MHz, DMSO-d$_6$, ppm) δ 8.53 (s, 1H), 8.38 (d, J=4.7 Hz, 1H), 8.01 (t, J=1.2 Hz, 1H), 7.75-7.63 (m, 4H), 7.38 (dd, J=8.2, 3.7 Hz, 2H), 5.63 (s, 2H), 3.95 (m, 4H), 2.76 (d, J=4.5 Hz, 3H), 1.18 (t, J=7.1 Hz, 6H).

Step 3: 4-((5-(methylcarbamoyl)-1,3-benzodiazol-1-yl)methyl)phenylphosphonic acid (90c) and ethoxy (4-((5-(methylcarbamoyl)-1,3-benzodiazol-1-yl)methyl)phenyl)phosphinic acid (90d

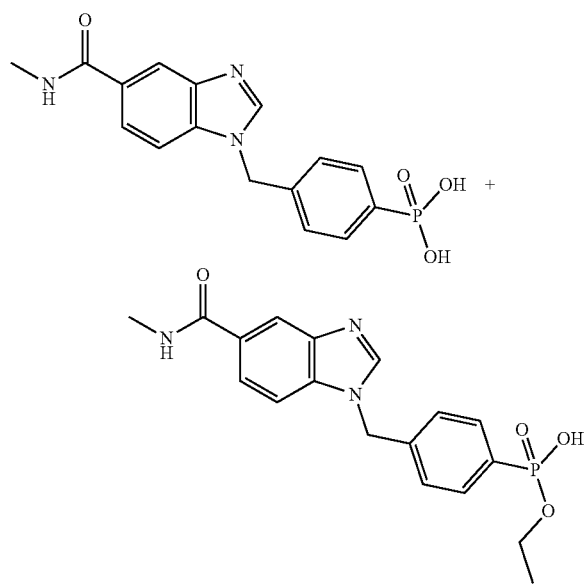

The title compounds were synthesized by the method described in step 2 of Example 85 except diethyl 4-((5-(methylcarbamoyl)-1,3-benzodiazol-1-yl)methyl)phenylphosphonate (150 mg, 0.37 mmol) was used. The crude product was purified by prep-HPLC under following conditions (Column: YMC-Actus Triart C18, 30*250.5 um; Mobile Phase A: Water (0.1% FA), Mobile Phase B: ACN; Flow rate: 45 mL/min; Gradient: 5 B to 17 B in 5 min; 254,220 nm; RT1:4.92 min, RT2: 5.05 min). The fractions containing the desired product were combined and lyophilized to give two fractions:

Fraction 1: Rt: 4.92 min. 7.2 mg (5.6% yield) of 4-((5-(methylcarbamoyl)-1,3-benzodiazol-1-yl)methyl)phenylphosphonic acid (90c) as an off-white solid. MS (ESI, pos. ion) m/z: 344.05 (M-1). $^1$H NMR (300 MHz, DMSO-d6, ppm) δ 8.86 (s, 1H), 8.48 (d, J=4.8 Hz, 1H), 8.22 (s, 1H), 7.81 (d, J=9.0 Hz, 1H), 7.72-7.59 (m, 3H), 7.41 (dd, J=8.1, 3.3 Hz, 2H), 5.65 (s, 2H), 2.84-2.77 (m, 3H).

Fraction 2: Rt: 5.05 min. 3.3 mg (2.2% yield) of ethoxy (4-((5-(methylcarbamoyl)-1,3-benzodiazol-1-yl)methyl)phenyl)phosphinic acid (90d) as a white solid. MS (ESI, pos. ion) m/z: 374.25 (M+1). $^1$H NMR (300 MHz, DMSO-d6, ppm)$^1$H NMR (300 MHz, DMSO-d6, ppm) δ 8.53 (s, 1H), 8.41 (s, 1H), 8.20 (s, 1H), 7.79-7.51 (m, 5H), 7.38 (s, 2H), 5.60 (s, 2H), 3.80 (m, 2H), 2.80 (d, J=4.1 Hz, 3H), 1.15-1.11 (d, J=6.9 Hz, 3H).

Example 91

Synthesis of 4-((6-(methylcarbamoyl)-1,3-benzodiazol-1-yl)methyl)phenylphosphonic acid (91a) and ethoxy(4-((6-(methylcarbamoyl)-1,3-benzodiazol-1-yl)methyl)phenyl)phosphinic acid (91b

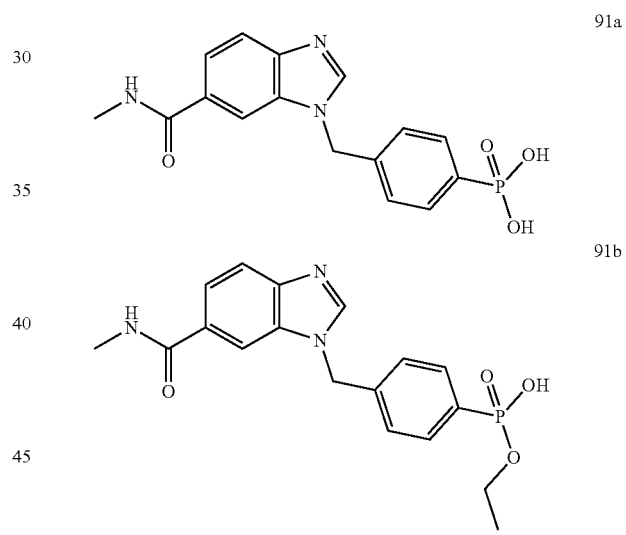

The title compound was synthesized by the method described in step 2 of Example 85 except diethyl 4-((6-(methylcarbamoyl)-1,3-benzodiazol-1-yl)methyl)phenylphosphonate (100 mg, 0.25 mmol) was used. The crude product was purified by prep-HPLC under conditions (Column: YMC-Actus Triart C18, 30*250.5 um; Mobile Phase A: Water (0.1% FA), Mobile Phase B: ACN; Flow rate: 45 mL/min; Gradient: 5 B to 17 B in 5 min; 254,220 nm; RT1:6.13 min, RT2: 7.25 min). The fractions containing the desired product were combined and lyophilized to give two fractions:

Fraction 1: Rt: 6.13 min. 28.8 mg (27.5% yield) of 4-((6-(methylcarbamoyl)-1,3-benzodiazol-1-yl)methyl)phenylphosphonic acid (91a). MS (ESI, pos. ion) m/z: 346.20 (M+1). $^1$H NMR (300 MHz, DMSO-d6, ppm) δ 8.55 (s, 1H), 8.40 (s, 1H), 8.02 (s, 1H), 7.72 (s, 2H), 7.65 (dd, J=12.8, 7.8 Hz, 2H), 7.35 (d, J=5.4 Hz, 2H), 5.61 (s, 2H), 2.79 (d, J=4.2 Hz, 3H).

Fraction 2: Rt: 7.25 min. 24.5 mg (21.4% yield) of ethoxy(4-((6-(methylcarbamoyl)-1,3-benzodiazol-1-yl)methyl)phenyl)phosphinic acid (91b). MS (ESI, pos. ion) m/z: 374.25 (M+1). $^1$H NMR (300 MHz, DMSO-d6, ppm) δ 8.55 (s, 1H), 8.40 (s, 1H), 8.03 (s, 1H), 7.72 (s, 2H), 7.65 (s, 2H), 7.36 (s, 2H), 5.62 (s, 2H), 3.80 (s, 2H), 2.79 (d, J=4.3 Hz, 3H), 1.12 (t, J=7.0 Hz, 3H).

Example 92

Synthesis of diethyl 4-((4-methoxy-1,3-benzodiazol-1-yl)methyl)phenylphosphonate (92a), diethyl (4-((7-methoxy-1H-benzo[d]imidazol-1-yl)methyl)phenyl)phosphonate (92b), diethyl (4-((4-hydroxy-1H-benzo[d]imidazol-1-yl)methyl)phenyl)phosphonate (92c), and (4-((4-hydroxy-1H-benzo[d]imidazol-1-yl)methyl)phenyl)phosphonic acid (92d

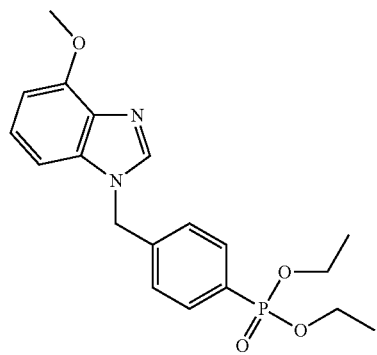

92a

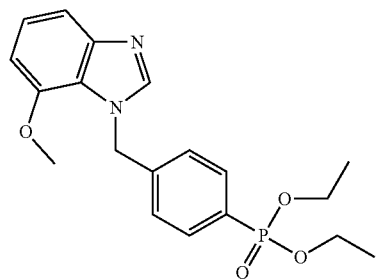

92b

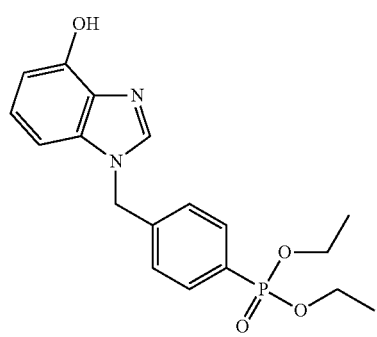 [SMILES: CCOP(=O)(OCC)c1ccc(Cn2cnc3c(O)cccc32)cc1]

92c

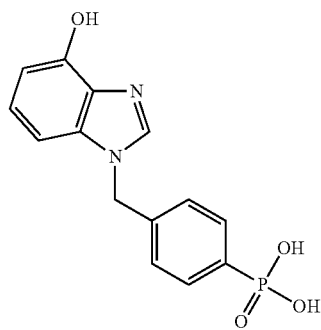 [SMILES: O=P(O)(O)c1ccc(Cn2cnc3c(O)cccc32)cc1]

92d

Step 1: diethyl 4-((4-methoxy-1,3-benzodiazol-1-yl)methyl)phenylphosphonate (92a) and diethyl 4-((4-methoxy-1,3-benzodiazol-1-yl)methyl)phenylphosphonate (92b The title compounds were synthesized by the method described in step 2 of Example 55 except 4-methoxy-1H-1,3-benzodiazole (200 mg, 1.35 mmol) and 4-(bromomethyl)phenylphosphonate (622 mg, 2.03 mmol) were used. The crude product was purified by prep-HPLC under following conditions (Column: XBridge prep OBD C18 Column, 30×150 mm 5 um; Mobile Phase A: Water (10 mmoL/L NH$_4$HCO$_3$+0.1% NH$_3$·H$_2$O), Mobile Phase B: ACN; Flow rate: 60 mL/min; Gradient: 18 B to 19 B in 15 min; 254/220 nm, RT1:6.50 min; RT2: 7.22 min). The fractions containing the desired product were combined and lyophilized to give two fractions:

Fraction 1: Rt: 6.50 min. 100 mg (19.8% yield) of diethyl 4-((4-methoxy-1,3-benzodiazol-1-yl)methyl)phenylphosphonate (92a) as a white solid. MS (ESI, pos. ion) m/z: 375.10 (M+1). $^1$H NMR (400 MHz, DMSO-d$_6$, ppm) δ 8.28 (s, 1H), 7.71-7.60 (m, 2H), 7.40-7.32 (m, 2H), 7.10 (t, J=7.9 Hz, 1H), 7.03 (dd, J=8.1, 1.0 Hz, 1H), 6.69 (dd, J=7.8, 1.0 Hz, 1H), 5.54 (s, 2H), 3.95 (m, 7H), 1.17 (t, J=7.1 Hz, 6H).

Fraction 2: Rt: 7.22 min. 120.9 mg (23.6% yield) of diethyl 4-((7-methoxy-1,3-benzodiazol-1-yl)methyl)phenylphosphonate (92b) as a white solid. MS (ESI, pos. ion) m/z: 375.30 (M+1). $^1$H NMR (400 MHz, DMSO-$d_6$, ppm) δ 8.30 (s, 1H), 7.70-7.59 (m, 2H), 7.34-7.26 (m, 2H), 7.23 (dd, J=8.2, 0.8 Hz, 1H), 7.12-7.08 (m, 1H), 6.78-6.71 (m, 1H), 5.64 (s, 2H), 3.95 (m, 4H), 3.76 (s, 3H), 1.17 (t, J=7.0 Hz, 6H).

Step 2: diethyl 4-((4-hydroxy-1,3-benzodiazol-1-yl)methyl)phenylphosphonate (92c

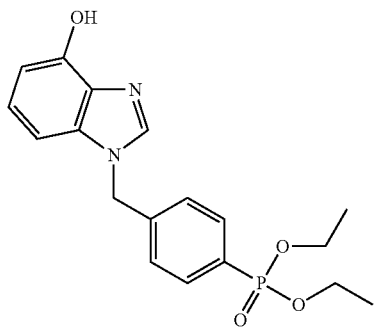

To a solution of diethyl 4-((4-methoxy-1,3-benzodiazol-1-yl)methyl)phenyl-phosphonate (100 mg, 0.27 mmol, 1.00 equiv) in DCM (5.00 mL) was added BBr$_3$ (0.50 mL, 5.289 mmol, 19.80 equiv). After stirring overnight at room temperature, the reaction mixture was evaporated under reduced pressure. The crude product was purified by prep-HPLC under following conditions (Column: XBridge Prep OBD C18 Column, 19*250 mm, 5 um; Mobile Phase A: Water (10 mmoL/L NH$_4$HCO$_3$+0.1% NH$_3$·H$_2$O), Mobile Phase B: ACN; Flow rate: 20 mL/min; Gradient: 8 B to 64 B in 7 min; 254/220 nm) to afford diethyl 4-((4-hydroxy-1,3-benzodiazol-1-yl)methyl)phenylphosphonate (92c, 52 mg, 54.02%). MS (ESI, pos. ion) m/z: 361.10 (M+1).

Step 3: (4-((4-hydroxy-1H-benzo[d]imidazol-1-yl)methyl)phenyl)phosphonic acid (92d

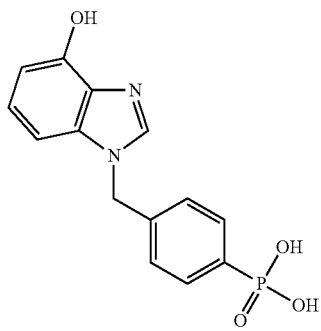

The title compound was synthesized by the method described in step 2 of Example 85 except diethyl 4-((4-hydroxy-1,3-benzodiazol-1-yl)methyl)phenylphosphonate (52.00 mg, 0.144 mmol) was used. The crude product was purified by prep-HPLC under following conditions (Column: XBridge prep OBD C18 Column, 30×150 mm 5 um; Mobile Phase A: Water (10 mmoL/L NH$_4$HCO$_3$+0.1% NH$_3$·H$_2$O), Mobile Phase B: ACN; Flow rate: 60 mL/min; Gradient: 18 B to 19 B in 15 min; 254/220 nm) to afford (4-((4-hydroxy-1H-benzo[d]imidazol-1-yl)methyl)phenyl)phosphonic acid (92d, 17.9 mg, 38.2%) as a white solid. MS (ESI, pos. ion) m/z: 305.05 (M+1). $^1$H NMR (300 MHz, DMSO-$d_6$, ppm) δ 10.00 (s, 1H), 8.47 (s, 1H), 7.70-7.57 (m, 2H), 7.36 (s, 2H), 7.26 (s, 1H), 7.14-6.97 (m, 1H), 6.91 (d, J=8.1 Hz, 2H), 6.60 (d, J=7.9 Hz, 1H), 5.53 (s, 2H).

Example 93

Synthesis of 4-((5-carbamoylindol-1-yl)methyl)phenylphosphonic acid

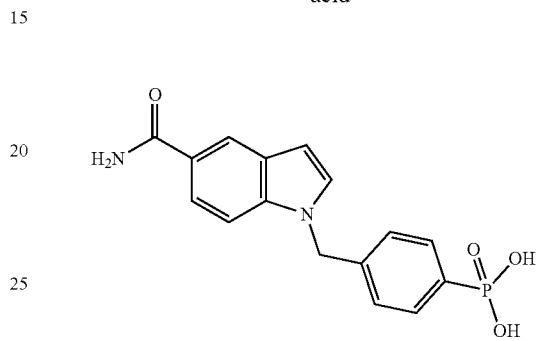

Step 1: indole-5-carboxamide

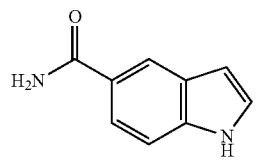 [SMILES: NC(=O)c1ccc2[nH]ccc2c1]

The title compound was synthesized by the method described in step 2 of Example 14 except methyl 1H-1,3-benzodiazole-5-carboxylate (2.00 g, 11.42 mmol) was used. The residue was purified by column chromatography (silica gel, EA/PE 7:1) to afford indole-5-carboxamide (0.6 g, 33% yield) as a grey solid. MS (ESI, pos. ion) m/z: 161.25 (M+1).

Step 2: diethyl 4-((5-carbamoylindol-1-yl)methyl)phenylphosphonate

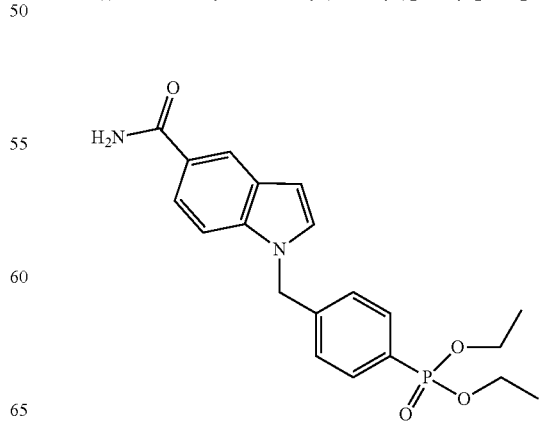

The title compound was synthesized by the method described in step 2 of Example 55 except indole-5-carboxamide (130 mg, 0.81 mmol) and diethyl 4-(bromomethyl)phenylphosphonate (374 mg, 1.22 mmol) were used. The residue was purified by column chromatography (silica gel, eluent: ethyl acetate/petroleum ether 89:11) to give diethyl 4-((5-carbamoylindol-1-yl)methyl)phenylphosphonate (162 mg, 33.1% yield) as a yellow solid. MS (ESI, pos. ion) m/z: 387.25 (M+1).

Step 3:
4-((5-carbamoylindol-1-yl)methyl)phenylphosphonic acid

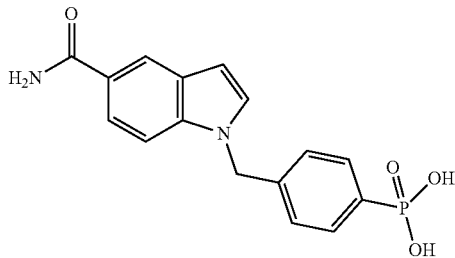 [SMILES: NC(=O)c1ccc2c(ccn2Cc2ccc(P(=O)(O)O)cc2)c1]

The title compound was synthesized by the method described in step 2 of Example 85 except diethyl 4-((5-carbamoylindol-1-yl)methyl)-phenylphosphonate (162.00 mg, 0.42 mmol) was used. Yield: 18.0 mg, (12.8%) as a pink solid. MS (ESI, pos. ion) m/z: 331.25 (M+1). $^1$H NMR (300 MHz, DMSO-$d_6$, ppm) δ 8.17 (d, J=1.6 Hz, 1H), 7.83 (s, 1H), 7.72-7.52 (m, 4H), 7.45 (d, J=8.7 Hz, 1H), 7.24 (dd, J=8.1, 3.3 Hz, 2H), 7.11 (s, 1H), 6.60 (d, J=3.1 Hz, 1H), 5.51 (s, 2H).

Example 94

Synthesis of 4-((5-carbamoyl-3-chloroindol-1-yl)methyl)phenylphosphonic acid

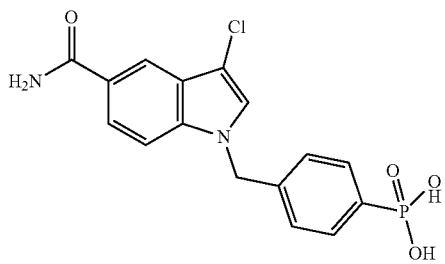 [SMILES: NC(=O)c1ccc2c(c1)c(Cl)cn2Cc1ccc(P(=O)(O)O)cc1]

Step 1: 3-chloro-1H-indole-5-carboxamide

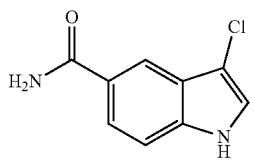

To a stirred solution of indole-5-carboxamide (0.30 g, 1.873 mmol, 1.00 equiv) in MeOH (12.00 mL) was added NCS (0.30 g, 2.0 mmol, 1.20 equiv) at room temperature. After stirring for 12 hours at room temperature, the resulting mixture was concentrated under reduced pressure. The residue was purified by column chromatography (silica gel, eluent: ethyl acetate/petroleum ether 44:56) to afford 3-chloro-1H-indole-5-carboxamide (0.38 g, 90% yield) as a yellow solid. MS (ESI, pos. ion) m/z: 195.02 (M+1) Step 2: diethyl 4-((5-carbamoyl-3-chloroindol-1-yl)methyl)phenylphosphonate

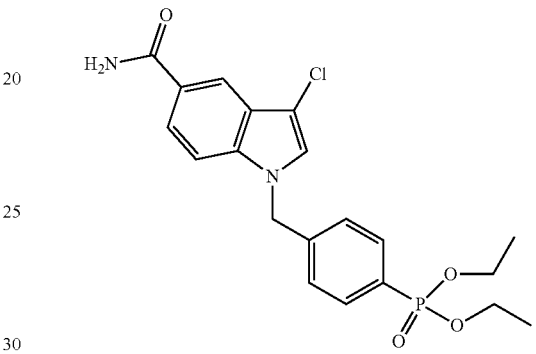

The title compound was synthesized by the method described in step 2 of Example 55 except 3-chloro-1H-indole-5-carboxamide (150 mg, 0.77 mmol) and diethyl 4-(bromomethyl)phenylphosphonate (291 mg, 0.948 mmol) were used. Yield: 300 mg (91.0%) as a yellow solid. MS (ESI, pos. ion) m/z: 421.25 (M+1).

Step 3: 4-((5-carbamoyl-3-chloroindol-1-yl)methyl)phenylphosphonic acid

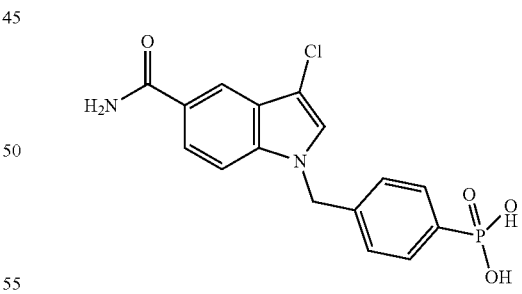

The title compound was synthesized by the method described in step 2 of Example 85 except diethyl 4-((5-carbamoyl-3-chloroindol-1-yl)methyl)-phenylphosphonate (150 mg, 0.356 mmol) was used. Yield: 33.1 mg (23.0%). MS (ESI, pos. ion) m/z: 365.04 (M+1). $^1$H NMR (300 MHz, DMSO-$d_6$, ppm) δ 8.13 (d, J=1.6 Hz, 1H), 7.99 (s, 1H), 7.83 (s, 1H), 7.76 (dd, J=8.7, 1.7 Hz, 1H), 7.67-7.52 (m, 3H), 7.26 (m, 3H), 5.49 (s, 2H).

Example 95

Synthesis of 4-((5-hydroxypyrrolo[3,2-b]pyridin-1-yl)methyl)phenylboronic acid

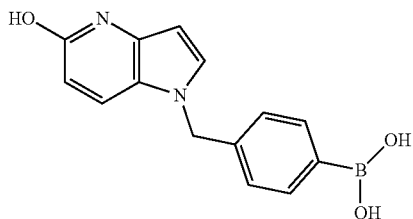

Step 1: 4-((5-methoxypyrrolo[3,2-b]pyridin-1-yl)methyl)phenylboronic acid

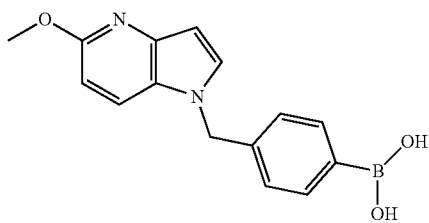 [SMILES: COc1ccc2c(ccn2Cc2ccc(B(O)O)cc2)n1]

To a solution of 5-methoxy-1H-pyrrolo[3,2-b]pyridine (150 mg, 1.012 mmol, 1.00 equiv) in DMF (5.00 mL) were added 4-(bromomethyl)phenylboronic acid (261 mg, 1.215 mmol, 1.20 equiv) and $Cs_2CO_3$ (660 mg, 2.025 mmol, 2.00 equiv). After stirring for 2 h at room temperature, the resulting mixture was filtered, and the filter cake was washed with MeOH. The filtrate was concentrated under reduced pressure. The residue was purified prep-HPLC under following condition (Column: YMC-Actus Triart C18, 30*250.5 um; Mobile Phase A: Water (0.05% FA), Mobile Phase B: ACN; Flow rate: 45 mL/min; Gradient: 16 B to 46 B in 7 min; 254,220 nm) to give 4-((5-methoxypyrrolo[3,2-b]pyridin-1-yl)methyl)phenylboronic acid (95 mg, 33% yield) as a white solid. MS (ESI, pos. ion) m/z: 283.25 (M+1). $^1$H NMR (300 MHz, DMSO-$d_6$, ppm) δ 8.01 (d, J=3.2 Hz, 2H), 7.78 (d, J=8.8 Hz, 1H), 7.71 (d, J=7.9 Hz, 2H), 7.65 (d, J=3.1 Hz, 1H), 7.14 (d, J=7.8 Hz, 2H), 6.54 (d, J=8.8 Hz, 1H), 6.45 (d, J=3.0 Hz, 1H), 5.40 (s, 2H), 3.84 (s, 3H).

Step 2: 4-((5-hydroxypyrrolo[3,2-b]pyridin-1-yl)methyl)phenylboronic acid

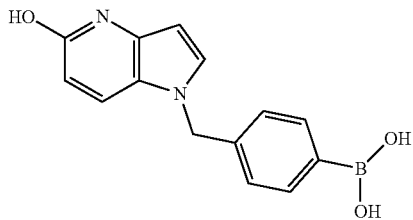

The title compound was synthesized by the method described in step 4 of Example 79 except 4-((5-methoxyimidazo[4,5-b]pyridin-1-yl)methyl)phenylboronic acid (66 mg, 0.233 mmol) was used. The crude product was purified by prep-HPLC under following conditions (Column: C18 column, 30*150, 5 um; Mobile Phase A: Water (0.1% FA), Mobile Phase B: ACN; Flow rate: 60 mL/min; Gradient: 1 B to 15 B in 8 min; 254/220 nm) to afford 4-((5-hydroxypyrrolo[3,2-b]pyridin-1-yl)methyl)phenylboronic acid (25.7 mg, 40.7% yield) as a white solid. MS (ESI, pos. ion) m/z: 269.25 (M+1). $^1$H NMR (300 MHz, DMSO-$d_6$/$D_2O$, ppm) δ 11.45 (s, 1H), 8.03 (s, 2H), 7.72 (d, J=7.8 Hz, 2H), 7.65 (d, J=9.5 Hz, 1H), 7.34 (d, J=2.9 Hz, 1H), 7.14 (d, J=7.8 Hz, 2H), 6.02-5.93 (m, 2H), 5.30 (s, 2H).

Example 96

Synthesis of 4-((5-carbamoyl-2-isopropylimidazo[4,5-b]pyridin-3-yl)methyl)phenylboronic acid (96a) and 4-((5-carbamoyl-2-isopropylimidazo[4,5-b]pyridin-1-yl)methyl)phenylboronic acid (96b

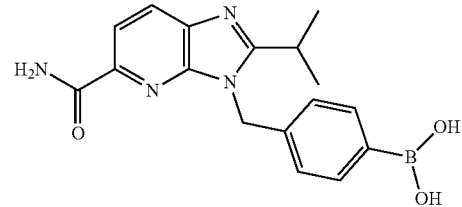

96a

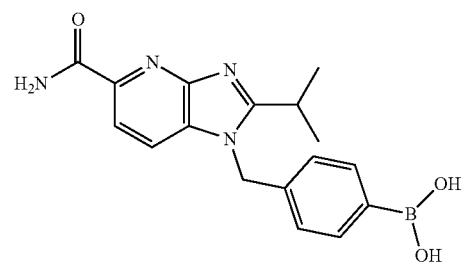

96b

Step 1: 5-chloro-2-isopropyl-1H-imidazo[4,5-b]pyridine

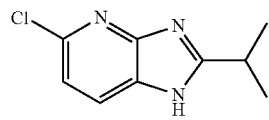

A solution of 6-chloropyridine-2,3-diamine (1.0 g, 6.96 mmol) in acetic acid (20 mL) was stirred for 12 hours at 135° C. in an oil-bath. After cooling to room temperature, the precipitate was collected by filtration, washed with MeOH and dried in vacuo to give 5-chloro-2-isopropyl-1H-imidazo[4,5-b]pyridine (1.1 g, 77%) as a brown solid.

Step 2: 2-isopropyl-1H-imidazo[4,5-b]pyridine-5-carboxamide

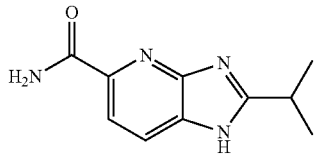

To a stirred solution of NH$_3$ (g) (80.00 mL, 7 M) in MeOH were added 5-chloro-2-isopropyl-1H-imidazo[4,5-b]pyridine (1.10 g, 5.6 mmol, 1.00 equiv) and Pd(dppf)Cl$_2$ (523 mg, 0.716 mmol, 0.10 equiv) at room temperature. After stirring for 12 hours at 120° C. in the 20 atm high pressure reactor filled with carbon monoxide, the mixture was concentrated under reduced pressure. The residue was purified by column chromatography (silica gel, eluent: DCM/MEOH 95:5) to give 2-isopropyl-1H-imidazo[4,5-b]pyridine-5-carboxamide (769 mg, 55% yield) as a brown solid.

Step 3: 4-((5-carbamoyl-2-isopropylimidazo[4,5-b]pyridin-3-yl)methyl)phenylboronic acid (96a) and 4-((5-carbamoyl-2-isopropylimidazo[4,5-b]pyridin-1-yl)methyl)phenylboronic acid (96b

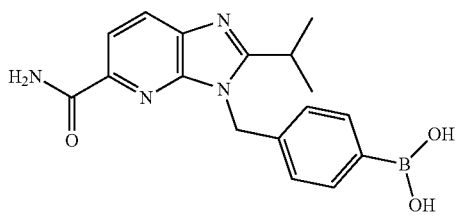

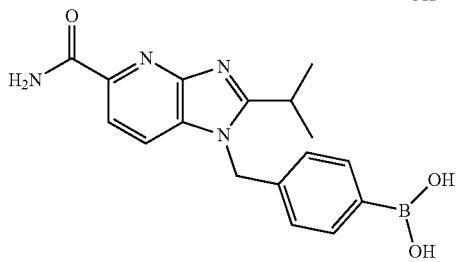

The title compounds were synthesized by the method described in step 2 of Example 55 except 2-isopropyl-1H-imidazo[4,5-b]pyridine-5-carboxamide (150 mg, 0.734 mmol) was used. The crude product was purified by prep-HPLC under following conditions (Column: C18 column, 30*150, 5 um; Mobile Phase A: Water (10 mmoL/L NH$_4$HCO$_3$+0.1% NH$_3$·H$_2$O), Mobile Phase B: ACN; Flow rate: 45 mL/min; Gradient: 15 B to 35 B in 7 min; 254,220 nm; RT1:3.2 min; RT2: 4.5 min). The fractions containing the desired product were combined and lyophilized to give two fractions:

Fraction 1: Rt: 3.2 min. 87.2 mg (34.8% yield) of 4-((5-carbamoyl-2-isopropylimidazo[4,5-b]pyridin-3-yl)methyl)phenylboronic acid (96a) as a white solid. MS (ESI, pos. ion) m/z: 339.25 (M+1). $^1$H NMR (300 MHz, DMSO-d6/D$_2$O, ppm) δ 8.11 (d, J=8.3 Hz, 1H), 7.98 (d, J=8.2 Hz, 1H), 7.70 (d, J=7.9 Hz, 2H), 7.12 (d, J=7.8 Hz, 2H), 5.66 (s, 2H), 3.22 (p, J=6.8 Hz, 1H), 1.17 (d, J=6.7 Hz, 6H).

Fraction 2: Rt: 4.5 min. 78.1 mg (31.4% yield) of 4-((5-carbamoyl-2-isopropylimidazo[4,5-b]pyridin-1-yl)methyl)phenylboronic acid (96b) as a white solid. MS (ESI, pos. ion) m/z: 339.25 (M+1). $^1$H NMR (300 MHz, DMSO-d6/D$_2$O, ppm) $^1$H NMR (300 MHz, DMSO-d$_6$) δ 7.95 (q, J=8.4 Hz, 2H), 7.69 (d, J=7.7 Hz, 2H), 7.03 (d, J=7.7 Hz, 2H), 5.56 (s, 2H), 3.30 (p, J=6.8 Hz, 1H), 1.23 (d, J=6.7 Hz, 6H).

Example 97

Synthesis of diisopropyl 4-((5-carbamoylimidazo[4,5-b]pyridin-1-yl)methyl)phenylphosphonate (97a) and diisopropyl 4-((5-carbamoylimidazo[4,5-b]pyridin-3-yl)methyl)phenylphosphonate (97b

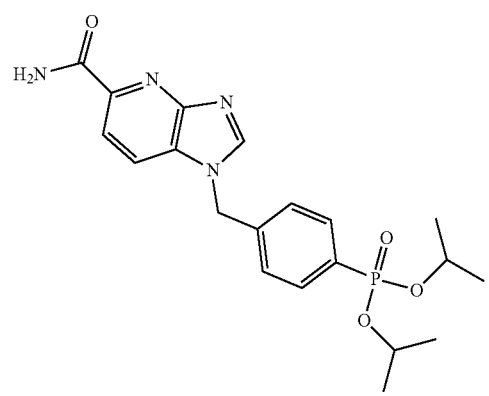

97a

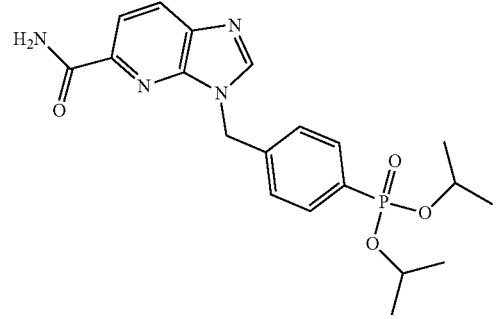

97b

Step 1: diisopropyl 4-methylphenylphosphonate

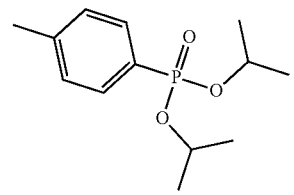 [SMILES: Cc1ccc(P(=O)(OC(C)C)OC(C)C)cc1]

To a stirred solution of 1-iodo-4-methylbenzene (2.00 g, 9.173 mmol, 1.00 equiv) in ACN (60 mL) were added diisopropyl phosphite (2.88 g, 17.33 mmol, 1.89 equiv) and sodium tert-butoxide (1.76 g, 18.35 mmol, 2.00 equiv) at room temperature. After stirring for 2 days at room temperature under an UV light, the reaction mixture was concentrated under reduced pressure. The residue was purified by column chromatography (silica gel, eluent: ethyl acetate/petroleum ether 64:36) to give diisopropyl 4-methylphenylphosphonate (1.7 g, 72.3% yield) as a colorless oil.

Step 2: diisopropyl 4-(bromomethyl)phenylphosphonate

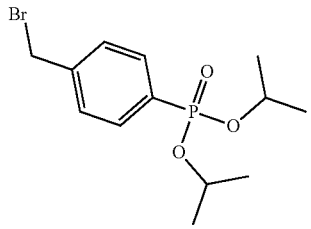 [SMILES: CC(C)OP(=O)(OC(C)C)c1ccc(CBr)cc1]

To a stirred solution of diisopropyl 4-methylphenylphosphonate (2.00 g, 7.80 mmol, 1.00 equiv) in CCl$_4$ (50.00 mL) were added NBS (1.39 g, 7.81 mmol, 1.00 equiv) and BPO (0.20 g, 0.780 mmol, 0.10 equiv) at room temperature. After stirring for 12 hours at 70° C., the reaction mixture was cooled to room temperature and concentrated under reduced pressure. The residue was purified by column chromatography (silica gel, eluent: EA/PE 70:30) to give diisopropyl 4-(bromomethyl)phenylphosphonate (1.3 g, 49.7% yield) as an colorless oil.

Step 3: diisopropyl 4-((5-carbamoylimidazo[4,5-b]pyridin-1-yl)methyl)phenylphosphonate (97a) and diisopropyl 4-((5-carbamoylimidazo[4,5-b]pyridin-3-yl)methyl)phenylphosphonate (97b

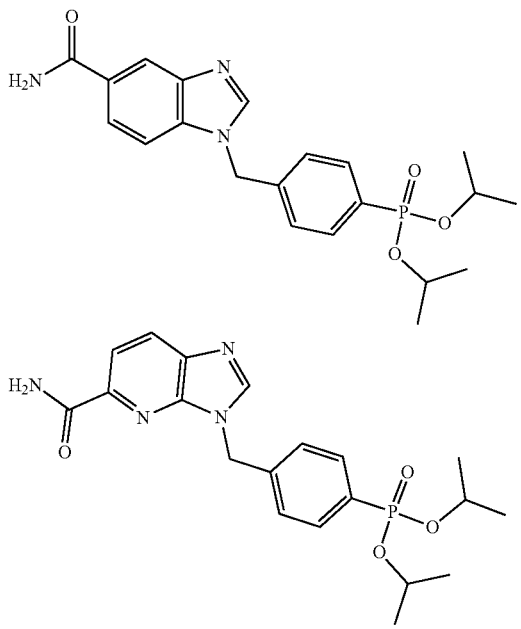

The title compounds were synthesized by the method described in step 2 of Example 55 except 2-methyl-1H-imidazo[4,5-b]pyridine-5-carboxamide (150 mg, 0.851 mmol) and diisopropyl 4-(bromomethyl)phenylphosphonate (372 mg, 1.11 mmol) were used. The crude product was purified by prep-HPLC under the following conditions (Column: C18 column, 30*150, 5 um; Mobile Phase A: Water (10 mmoL/L NH$_4$HCO$_3$+0.1% NH$_3$·H$_2$O), Mobile Phase B: ACN; Flow rate: 45 mL/min; Gradient: 30 B to 35 B in 9 min; 254,220 nm; RT1:5.5 min; RT2: 6.3 min). The fractions containing the desired product were combined and lyophilized to give two fractions:

Fraction 1: Rt: 5.5 min. 39.4 mg (10.0% yield) of diisopropyl 4-((5-carbamoylimidazo[4,5-b]-pyridin-1-yl)methyl)phenylphosphonate (97a) as a white solid. MS (ESI, pos. ion) m/z: 417.35 (M+1). $^1$H NMR (300 MHz, DMSO-d$_6$, ppm) δ 8.84 (s, 1H), 8.18-8.07 (m, 2H), 7.99 (d, J=8.3 Hz, 1H), 7.75-7.44 (m, 5H), 5.68 (s, 2H), 4.52 (m, 2H), 1.26 (d, J=6.2 Hz, 6H), 1.14 (d, J=6.2 Hz, 6H).

Fraction 2: Rt: 6.3 min. 28.7 mg (7.4% yield) of diisopropyl 4-((5-carbamoylimidazo[4,5-b]-pyridin-3-yl)methyl)phenylphosphonate (97b) as a white solid. MS (ESI, pos. ion) m/z: 417.25 (M+1). $^1$H NMR (300 MHz, DMSO-d$_6$, ppm) δ 8.80 (s, 1H), 8.27-8.17 (m, 2H), 8.00 (d, J=8.2 Hz, 1H), 7.76-7.63 (m, 3H), 7.57 (m, 2H), 5.69 (s, 2H), 4.52 (m, 2H), 1.25 (d, J=6.1 Hz, 6H), 1.14 (d, J=6.2 Hz, 6H).

Example 98

Synthesis of 1-((4-(di((isopropoxycarbonyl)oxy)methoxyphosphoryl)phenyl)methyl)imidazo[4,5-b]pyridine-5-carboxamide

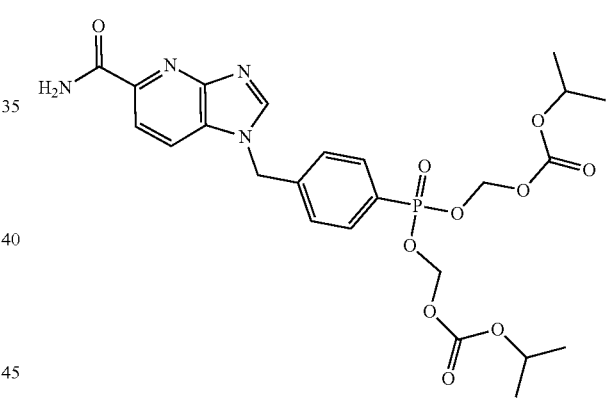

To a stirred solution of 4-((5-carbamoylimidazo[4,5-b]pyridin-1-yl)methyl)phenylphosphonic acid (100 mg, 0.301 mmol) in NMP (4.00 mL) were added TEA (0.42 mL, 4.134 mmol, 10.00 equiv) and chloromethyl isopropyl carbonate (459 mg, 3.01 mmol, 10.00 equiv) at room temperature. After stirring for 12 h at 50° C., the mixture was concentrated under reduced pressure. The crude product was purified by prep-HPLC under the following conditions (Column: XBridge Prep OBD C18 Column, 30×150 mm 5 um; Mobile Phase A: Water (10 mmoL/L NH$_4$HCO$_3$+0.1% NH$_3$·H$_2$O), Mobile Phase B: ACN; Flow rate: 60 mL/min; Gradient: 10 B to 70 B in 7 min; 254/220 nm) to afford 1-((4-(di((isopropoxycarbonyl)oxy)methoxyphosphoryl)phenyl)-methyl)imidazo[4,5-b]pyridine-5-carboxamide (36.8 mg, 19.8% yield) as a white solid. MS (ESI, pos. ion) m/z: 565.40 (M+1). $^1$H NMR (300 MHz, DMSO-d$_6$, ppm) δ 8.85 (s, 1H), 8.13 (d, J=8.3 Hz, 2H), 7.99 (d, J=8.4 Hz, 1H), 7.69 (m, 2H), 7.58-7.47 (m, 3H), 5.72-5.56 (m, 6H), 4.69 (p, J=6.2 Hz, 2H), 1.11 (m, 12H).

Example 99

Synthesis of ((4-((5-carbamoylimidazo[4,5-b]pyridin-1-yl)methyl)phenyl(((2,2-dimethyl-propanoyl)oxy)methoxy)phosphoryl)oxy)methyl 2,2-dimethylpropanoate

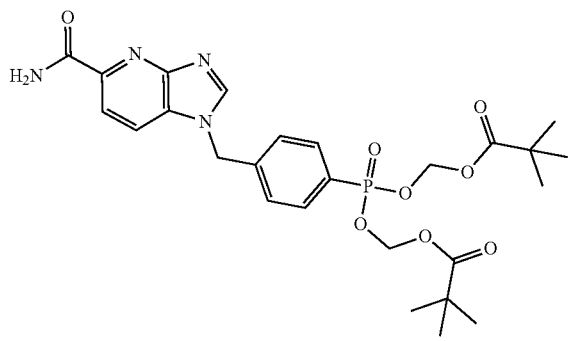 [SMILES: CC(C)(C)C(=O)OCOP(=O)(OCOC(=O)C(C)(C)C)c1ccc(Cn2cnc3nc(C(N)=O)ccc32)cc1]

The title compound was synthesized by the method described in of Example 103 below except chloromethyl 2,2-dimethylpropanoate (680 mg, 4.515 mmol) was used. Yield: 52.8 mg (20.2%). MS (ESI, pos. ion) m/z: 561.45 (M+1). $^1$H NMR (300 MHz, DMSO-$d_6$, ppm) δ 8.86 (s, 1H), 8.16-8.10 (m, 2H), 7.99 (d, J=8.4 Hz, 1H), 7.68 (dd, J=13.7, 8.0 Hz, 2H), 7.57-7.52 (m, 3H), 5.81-5.48 (m, 6H), 0.90 (s, 18H).

Example 100

Synthesis of 4-((5-hydroxyimidazo[4,5-b]pyridin-1-yl)methyl)phenylphosphonic acid

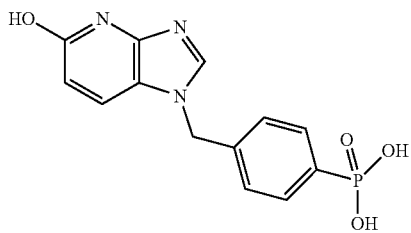 [SMILES: O=P(O)(O)c1ccc(Cn2cnc3nc(O)ccc32)cc1]

Step 1: diethyl 4-((5-methoxyimidazo[4,5-b]pyridin-1-yl)methyl)phenylphosphonate

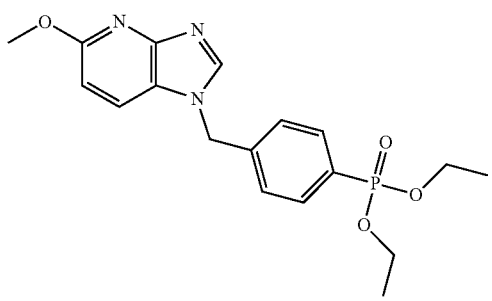 [SMILES: CCOP(=O)(OCC)c1ccc(Cn2cnc3nc(OC)ccc32)cc1]

The title compound was synthesized by the method described in step 2 of Example 55 except 5-methoxy-1H-imidazo[4,5-b]pyridine (250 mg, 1.676 mmol) and diethyl 4-(bromomethyl)phenylphosphonate (566 mg, 1.844 mmol) were used. The crude product was purified by prep-HPLC under the following conditions (Column: C18 column, 30*150, 5 um; Mobile Phase A: Water (10 mmoL/L NH$_4$HCO$_3$+0.1% NH$_3$·H$_2$O), Mobile Phase B: ACN; Flow rate: 45 mL/min; Gradient: 25 B to 35 B in 10 min; 254/220 nm) to afford diethyl 4-((5-methoxyimidazo[4,5-b]pyridin-1-yl)methyl)phenylphosphonate (149 mg, 23.7% yield) as a brown oil. MS (ESI, pos. ion) m/z: 376.25 (M+1)

Step 2: 4-((5-hydroxyimidazo[4,5-b]pyridin-1-yl)methyl)phenylphosphonic acid

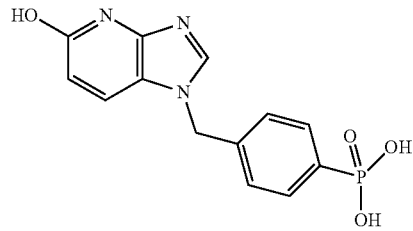 [SMILES: O=P(O)(O)c1ccc(Cn2cnc3nc(O)ccc32)cc1]

The title compound was synthesized by the method described in step 2 of Example 85 except diethyl 4-((5-methoxyimidazo[4,5-b]pyridin-1-yl)methyl)phenylphosphonate (149 mg, 0.397 mmol) was used. The crude product was purified by prep-HPLC under following conditions (Column: C18 column, 30*150, 5 um; Mobile Phase A: Water (10 mmoL/L NH$_4$HCO$_3$+0.1% NH$_3$·H$_2$O), Mobile Phase B: ACN; Flow rate: 45 mL/min; Gradient: Gradient: 20 B to 30 B in 7 min; 254/220 nm) to afford 4-((5-hydroxyimidazo[4,5-b]pyridin-1-yl)methyl)phenylphosphonic acid (39.0 mg, 28.7% yield) as a white solid. MS (ESI, pos. ion) m/z: 306.20 (M+1). $^1$H NMR (300 MHz, DMSO-$d_6$/D$_2$O, ppm) δ 8.16 (s, 1H), 7.69 (d, J=9.3 Hz, 1H), 7.61-7.50 (m, 2H), 7.17 (dd, J=8.2, 2.7 Hz, 2H), 6.20 (d, J=9.3 Hz, 1H), 5.34 (s, 2H).

Example 101

Synthesis of diphenyl 4-((5-hydroxyimidazo[4,5-b]pyridin-1-yl)methyl)phenylphosphonate (101a) and diphenyl 4-((5-hydroxyimidazo[4,5-b]pyridin-3-yl)methyl)phenylphosphonate (101b 101a

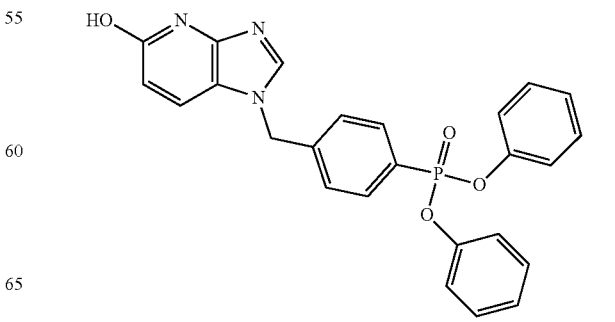

-continued

101b

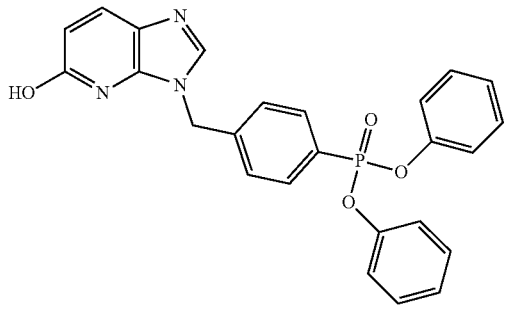

Step 1: 6-(benzyloxy)-3-nitropyridin-2-amine

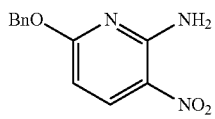 [SMILES: Nc1nc(OCc2ccccc2)ccc1[N+](=O)[O-]]

To a mixture of 6-chloro-3-nitropyridin-2-amine (10.00 g, 57.62 mmol, 1.00 equiv) and benzyl alcohol (12.46 g, 115.23 mmol, 2.00 equiv) in DMF (150.00 mL) was added slowly NaH (4.61 g, 115.23 mmol, 2.00 equiv, 60%) at 0° C. After stirring overnight at room temperature, the reaction mixture was quenched with ice water. The precipitated solids were collected by filtration, washed with water and dried in vacuo to give 6-(benzyloxy)-3-nitropyridin-2-amine (12 g, 84.9% yield) as a brown solid.

Step 2: 6-(benzyloxy)pyridine-2,3-diamine

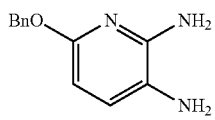 [SMILES: Nc1ccc(OCc2ccccc2)nc1N]

To a stirred solution of 6-(benzyloxy)-3-nitropyridin-2-amine (13.00 g, 53.01 mmol, 1.00 equiv) in H₂O (78.00 mL) and isopropyl alcohol (230.00 mL) were added Fe (8.88 g, 159.01 mmol, 3.00 equiv) and NH₄Cl (12.8 g, 238.54 mmol, 4.50 equiv) at room temperature. After stirring for 4 hours at 100° C. in an oil bath, the mixture was filtered through a Celite and the filter cake was washed with ethyl acetate. The filtrate was concentrated under reduced pressure and extracted with ethyl acetate. The combined organic layers were washed with brine, dried over anhydrous sodium sulfate, filtered and concentrated under reduced pressure. The residue was purified by column chromatography (silica gel, eluent: ethyl acetate/petroleum ether 71:29) to give 6-(benzyloxy)pyridine-2,3-diamine (6.3 g, 50.2% yield) as a brown solid.

Step 3: 5-(benzyloxy)-1H-imidazo[4,5-b]pyridine

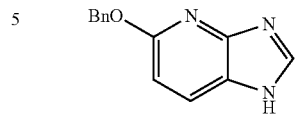

To a stirred solution of 6-(benzyloxy)pyridine-2,3-diamine (12.00 g, 55.75 mmol, 1.00 equiv) in trimethoxymethane (250.00 mL) was added TFA (1.00 mL) at room temperature. After stirring for 12 h at room temperature, the mixture was concentrated under reduced pressure. The residue was washed with dichloride/n-hexane (1:2, 150 mL×2) to give 5-(benzyloxy)-1H-imidazo[4,5-b]pyridine (10 g, 79.6% yield) as a brown solid.

Step 4: diphenyl 4-((5-(benzyloxy)imidazo[4,5-b]pyridin-1-yl)methyl)phenylphosphonate and diphenyl 4-((5-(benzyloxy)imidazo[4,5-b]pyridin-3-yl)methyl)phenylphosphonate

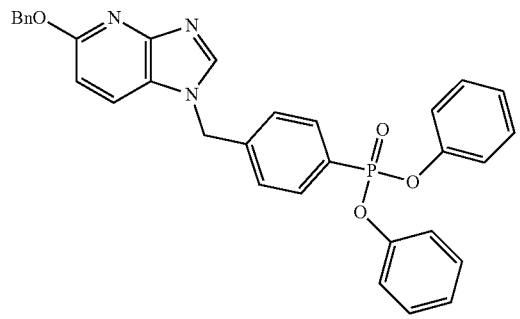

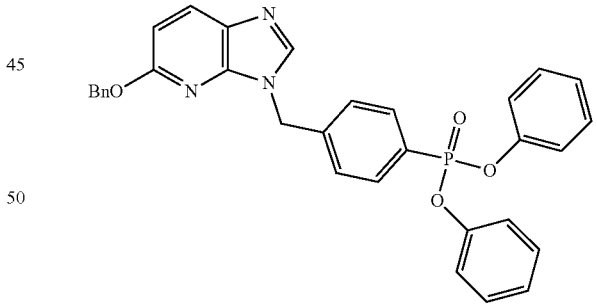

The title compounds were synthesized by the method described in step 1 of Example 2 except 5-(benzyloxy)-1H-imidazo[4,5-b]pyridine (500 mg, 2.22 mmol) and 4-(bromomethyl)phenylphosphonate (984 mg, 2.44 mmol) were used. The residue was purified by column chromatography (silica gel, eluent: ethyl acetate/petroleum ether 100:0) to give a mixture of diphenyl 4-((5-(benzyloxy)imidazo[4,5-b]pyridin-1-yl)methyl)phenylphosphonate and diphenyl 4-((5-(benzyloxy)imidazo[4,5-b]pyridin-3-yl)methyl)phenylphosphonate (645 mg, 53.1% yield, ratio=1:2) as a brown oil. MS (ESI, pos. ion) m/z: 548.15 (M+1).

Step 5: diphenyl 4-((5-hydroxyimidazo[4,5-b]pyridin-1-yl)methyl)phenylphosphonate (101a) and diphenyl 4-((5-hydroxyimidazo[4,5-b]pyridin-3-yl)methyl)phenylphosphonate (101b

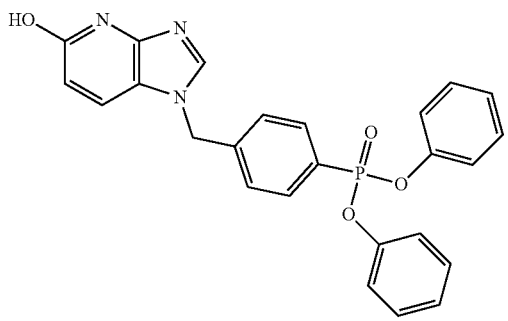

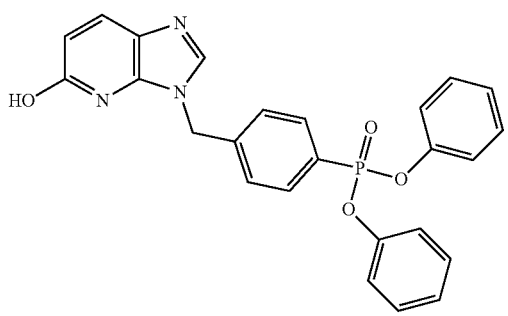

To a mixture of diphenyl 4-((5-(benzyloxy)imidazo[4,5-b]pyridin-3-yl)methyl)phenyl-phosphonate and diphenyl 4-((5-(benzyloxy)imidazo[4,5-b]pyridin-3-yl)methyl)phenyl-phosphonate (600 mg, 1.1 mmol) in MeOH (25.00 mL) was added Pd/C (200 mg) at room temperature. After stirring for 12 hours at room temperature, the resulting mixture was filtered through a Celite, and the filter cake was washed with MeOH. The filtrate was concentrated under reduced pressure. The crude product was purified by prep-HPLC under following conditions (Column: X Bridge Shield RP18 OBD Column, 30*150 mm, 5 um; Mobile Phase A: Water (0.05% $NH_3H_2O$), Mobile Phase B: ACN; Flow rate: 60 mL/min; Gradient: 26 B to 33 B in 12 min; 254/220 nm; RT1:10.05; RT2:11.0). The fractions containing the desired product were combined and lyophilized to give two fractions:

Fraction 1: Rt: 10.05 min. 30.9 mg (5.6% yield) of diphenyl 4-((5-hydroxyimidazo[4,5-b]pyridin-1-yl)methyl)phenylphosphonate (106a) as a white solid. MS (ESI, pos. ion) m/z: 458.25 (M+1). $^1$H NMR (300 MHz, DMSO-d6, ppm) δ 11.62 (s, 1H), 8.21 (s, 1H), 7.92 (dd, J=13.7, 8.0 Hz, 2H), 7.65 (d, J=9.2 Hz, 1H), 7.43 (dd, J=8.1, 4.2 Hz, 2H), 7.34 (t, J=7.9 Hz, 4H), 7.22-7.12 (m, 6H), 6.20 (d, J=9.2 Hz, 1H), 5.52 (s, 2H).

Fraction 2: Rt: 11.0 min. 79.6 mg (14.2% yield) of diphenyl 4-((5-hydroxyimidazo[4,5-b]pyridin-3-yl)methyl)phenylphosphonate (106b) as a white solid. MS (ESI, pos. ion) m/z: 458.25 (M+1). $^1$H NMR (300 MHz, DMSO-d6, ppm) δ 10.77 (s, 1H), 8.25 (s, 1H), 7.90 (dd, J=13.1, 8.0 Hz, 3H), 7.35 (t, J=7.8 Hz, 6H), 7.17 (d, J=8.2 Hz, 6H), 6.53 (d, J=8.6 Hz, 1H), 5.47 (s, 2H).

Biological Examples

Example 1

Measurement of pNP-TMP Hydrolysis by ENPP1 p-Nitrophenyl thymidine 5'-monophosphate (pNP-TMP) is a synthesized substrate for ENPP1. The ENPP1 enzyme activity assay with pNP-TMP substrate was conducted as follows:

First, in a 60 μl reaction, 7.5 ng purified ENPP1 was mixed with compounds of Formula (I) (test compound) ranging from 13.7 pM to 10 μM. Incubation of ENPP1 with compounds was set at 25° C. for 10 min. Reactions with DMSO only (with ENPP1 but no compound) gave the fastest reaction (MAX Activity). For each compound dilution, wells with assay buffer (50 mM Tris-HCl, pH8.8, 250 mM NaCl, 0.1 mg/ml BSA, 1% DMSO) only but no ENPP1 were included as controls for subtraction of test compound derived absorbance at 405 nm.

Second, after the 10 minutes ENPP1 and test compound incubation the assay was initiated by transferring 50 μl of the above mentioned ENPP1/test compound reaction into 50 μl of 1 mM pNP-TMP in assay buffer results in a 100 μl total reaction in clear bottom 96 well plates. Absorbance at 405 nm was recorded immediately in kinetic mode by PerkinElmer 2300 Enspire multimode plate reader.

For each inhibitor, the specific ENPP1 activity was calculated using the following equation: ENPP1 activity (pmol/min/μg)=Adjusted Vmax (OD405 nm/min)×conversion factor (pmol/OD405 nm)/amount of enzyme (μg)

Adjusted $Vmax=V_0×(Km+(S))/(S)$. In this assay, Km=232 μM, (S)=500 μM. Adjusted $Vmax=1.464×V_0$.

$V_0$=(OD405 nm with ENPP1−OD405 nm ENPP1 blank)/minutes. OD405 nm was plotted, with blank subtracted, against time (minutes), the initial linear rate is $V_0$. blank subtracted, against time (minutes), the initial linear rate is $V_0$.

The conversion factor (pmol/OD405 nm), was determined by plotting the amount of standard, 4-Nitrophenol (Sigma-Aldrich, Catalog #241326), against absorbance at 405 nm. The slope is the conversion factor. The percent ENPP1 activity for each sample was calculated using the following equation:

% enzyme activity=sample enzyme activity/MAX Activity×100%.

To determine the $IC_{50}$ for each compound, compound concentration values and percent enzyme activity values were inserted into GraphPad Prism (GraphPad Prism version 7.0 for Windows, GraphPad Software, La Jolla California USA, www.graphpad.com), and Prism's Transform analysis was used to convert the x-axis values (compound concentration) to logarithms. A sigmoidal variable slope nonlinear regression analysis was performed using the following equation: Y=Bottom+(Top−Bottom)/(1+10^(Log $IC_{50}$−X)*HillSlope)).

$K_i$ values for each compound were calculated from the observed $IC_{50}$ from GraphPad analysis using the Cheng-Prusoff equation: $K_i=IC_{50}/(1+(S)/K_M)$. (S) here is 500 μM and $K_M$ is determined to be 232 μM.

Ki for a representative compound of Formula (I) in Compound Table 1 above is provided in Table 2 below:

TABLE 2

| Ki (pNP-TMP) | | |
|---|---|---|
| Group A (<10 nM) | Group B (<100 nM) | Group C (<1000 nM) |
| Cpd. 9, 15, 17, 36, 37, 59, 70, 77, 96, 106, 125, 127, 144, 146 | Cpd. 1, 5, 23, 65, 41, 32, 34, 55, 56, 63, 64, 73, 75, 95, 105, 107, 134, 136, 138, 150 | Cpd. 3, 7, 12, 24, 49, 74, 98, 130, 142, 143 |

Example 2

Measurement of 2'3'-cGAMP Hydrolysis by ENPP1

ENPP1 catalyzes the hydrolysis of 2'3'-cGAMP into 5'-AMP and 5'-GMP, and hence the ENPP1 enzyme activity with 2'3'-cGAMP as substrate is monitored by measurement of the product 5'-AMP. The AMP-Glo assay kit from Promega (catalog number V5012) is used for measurement of 5'-AMP production.

First, an ENPP1 and test compound incubation is set up in assay buffer (50 mM Tris-HCl, pH8.8, 250 mM NaCl, 0.1 mg/ml BSA, 1% DMSO) with following conditions: ENPP1 concentration: 1.25 nM; test compound concentration ranging from 68 pM to 20 µM. This incubation is carried out at 25° C. for 10 min.

Second, after the 10 minute ENPP1 and test compound incubation, prepare on a separate plate, 15 µl of the substrate 2'3'-cGAMP at 200 µM in assay buffer. Then, 15 µl of the ENPP1/Compound incubation is transferred to the 200 µM 2'3'-cGAMP solution to initiate the reaction. The 30 µl mixture is incubated for 30 min at 25° C. In all these assays a DMSO control without compound is included which gave the maximum 5'-AMP production (MAX RLU). After 30 min the reaction is stopped by heating at 90° C. for 3 min.

Third, the Promega AMP-Glo kit is used to detect 5'-AMP production as a measurement of ENPP1 enzyme activity. To do this 10 µl of the above mentioned 30 µl total reaction per sample is transferred into 384 well white solid assay plate for measurement of 5'-AMP production. For each well, 10 µl of AMP-Glo Reagent I is added, mixed well, and incubated for 1 hour at 25° C. At this time AMP detection solution is prepared and 20 µl is added per well, and the resulting solution is incubated for 1 hr at 25° C. Duplicates are run for each inhibitor concentration. Luminescence signal (relative luminescence units, RLU) is recorded using a PerkinElmer 2300 Enspire multimode plate reader.

The % inhibition is calculated using the following equation: % inhibition=(MAX RLU−sample RLU)/MAX RLU× 100%.

$IC_{50}$ values of compounds are determined by loading compound concentration data and percent inhibition values into GraphPad Prism (GraphPad Prism version 7.0 for Windows, GraphPad Software, La Jolla California USA, www.graphpad.com) and conducted a Sigmoidal variable slope nonlinear regression fitting.

$K_i$ values for each compound are calculated from the observed $IC_{50}$ from GraphPad analysis using the Cheng-Prusoff equation: $K_i=IC_{50}/(1+(S)/K_M)$. (S) here is 100 µM and $K_M$ is 32 µM.

Formulation Examples

The following are representative pharmaceutical formulations containing a compound of the present disclosure.

Tablet Formulation

The following ingredients are mixed intimately and pressed into single scored tablets.

| Ingredient | Quantity per tablet mg |
|---|---|
| compound of this disclosure | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
|---|---|
| compound of this disclosure | 200 |
| lactose spray dried | 148 |
| magnesium stearate | 2 |

Injectable Formulation

Compound of the disclosure (e.g., compound 1) in 2% HPMC, 1% Tween 80 in DI water, pH 2.2 with MSA, q.s. to at least 20 mg/mL.

Inhalation Composition

To prepare a pharmaceutical composition for inhalation delivery, 20 mg of a compound disclosed herein is mixed with 50 mg of anhydrous citric acid and 100 mL of 0.9% sodium chloride solution. The mixture is incorporated into an inhalation delivery unit, such as a nebulizer, which is suitable for inhalation administration.

Topical Gel Composition

To prepare a pharmaceutical topical gel composition, 100 mg of a compound disclosed herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution Composition

To prepare a pharmaceutical ophthalmic solution composition, 100 mg of a compound disclosed herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 10 g of a compound disclosed herein is mixed with 30 mL of a 0.05M phosphate buffer solution (pH 4.4). The solution is placed in a nasal administrator designed to deliver 100 ul of spray for each application.

What is claimed:
1. A compound selected from the group consisting of:
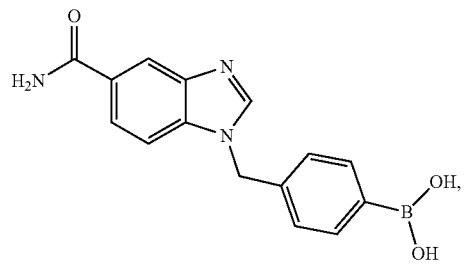
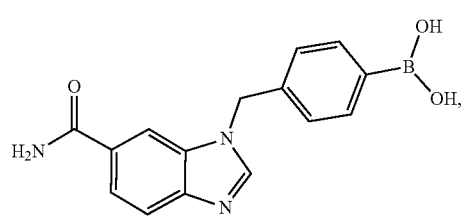
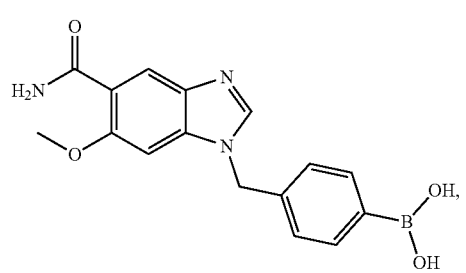
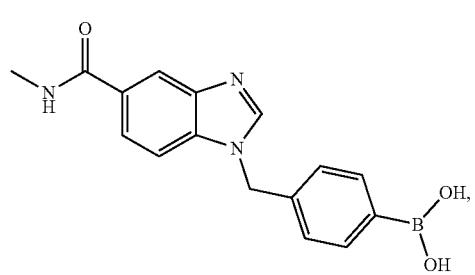
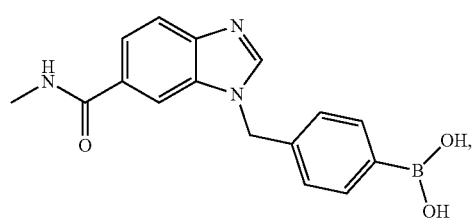
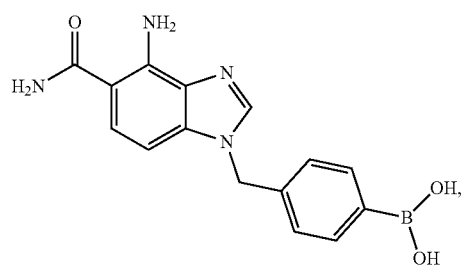
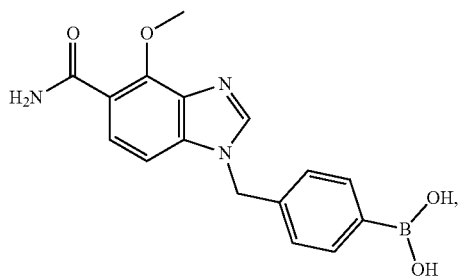
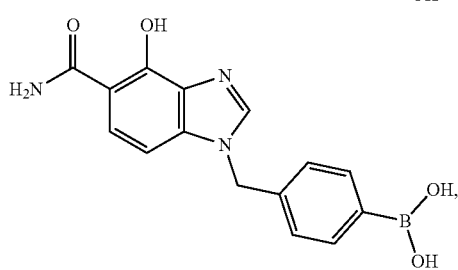
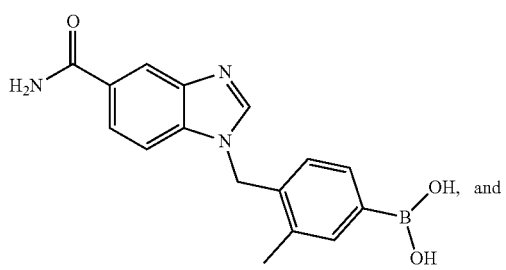
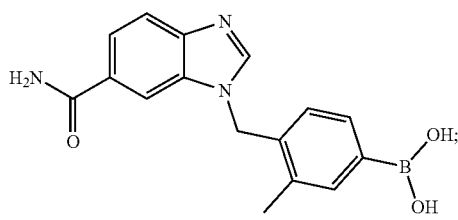
or a pharmaceutically acceptable salt thereof.
2. A compound selected from the group consisting of:
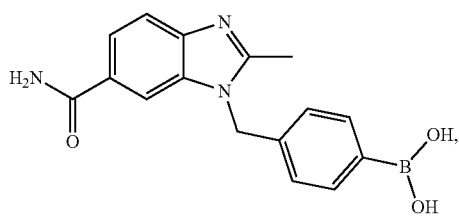
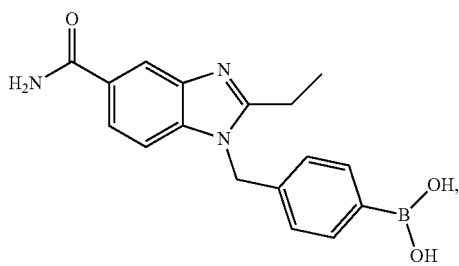

-continued

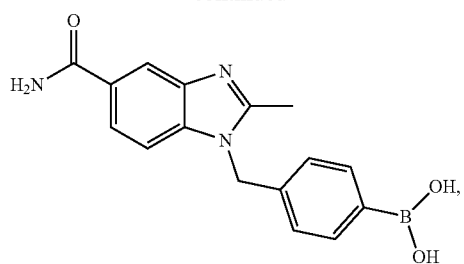

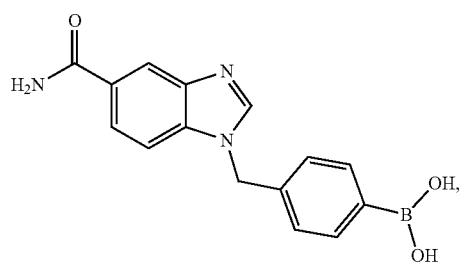

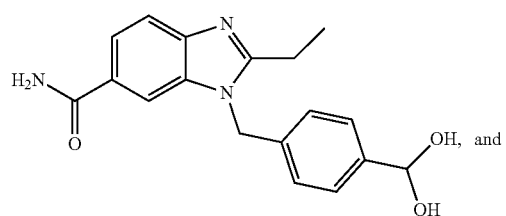

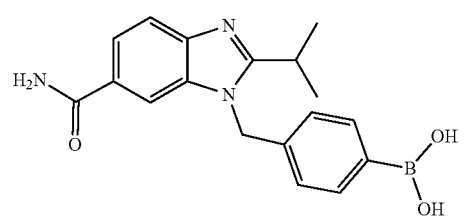

or a pharmaceutically acceptable salt thereof.

3. The compound of claim 2, having the formula:

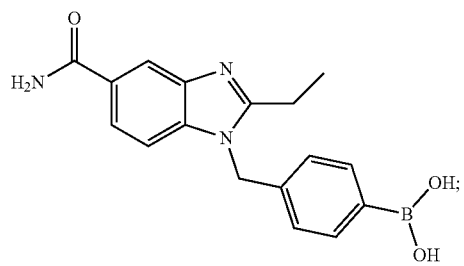 [SMILES: CCc1nc2cc(C(N)=O)ccc2n1Cc1ccc(B(O)O)cc1]

or a pharmaceutically acceptable salt thereof.

4. The compound of claim 2, having the formula:

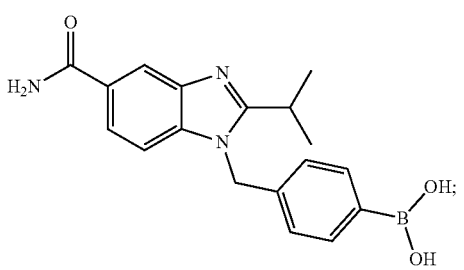 [SMILES: CC(C)c1nc2cc(C(N)=O)ccc2n1Cc1ccc(B(O)O)cc1]

or a pharmaceutically acceptable salt thereof.

5. The compound of claim 2, having the formula:

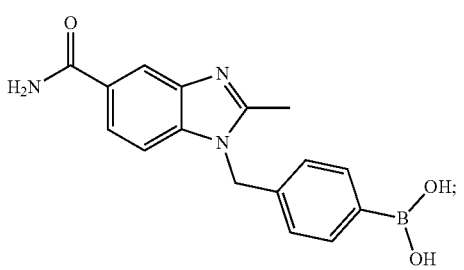 [SMILES: Cc1nc2cc(C(N)=O)ccc2n1Cc1ccc(B(O)O)cc1]

or a pharmaceutically acceptable salt thereof.

6. The compound of claim 1, having the formula:

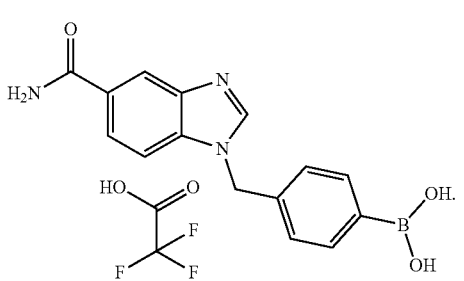

7. The compound of claim 2, having the formula:

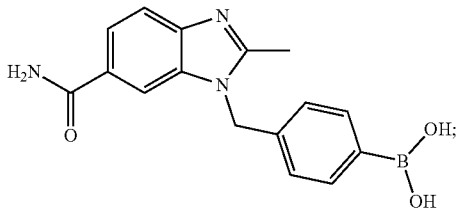 [SMILES: Cc1nc2ccc(C(N)=O)cc2n1Cc1ccc(B(O)O)cc1]

or a pharmaceutically acceptable salt thereof.

8. The compound of claim 2, having the formula:

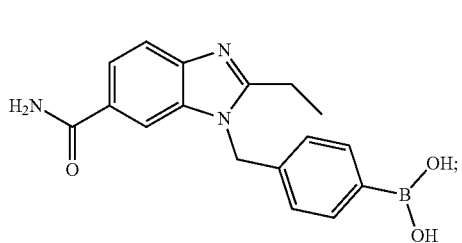 [SMILES: CCc1nc2ccc(C(N)=O)cc2n1Cc1ccc(B(O)O)cc1]

or a pharmaceutically acceptable salt thereof.

9. The compound of claim 2, having the formula

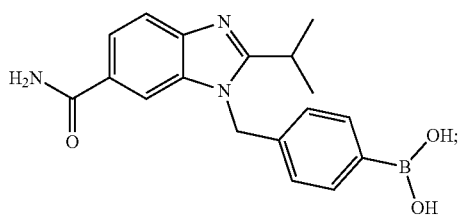 [SMILES: CC(C)c1nc2ccc(C(N)=O)cc2n1Cc1ccc(B(O)O)cc1]

or a pharmaceutically acceptable salt thereof.

10. The compound of claim 2, having the formula

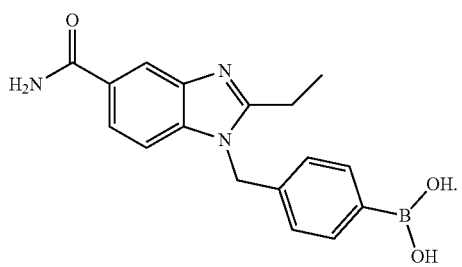

11. The compound of claim 2, having the formula

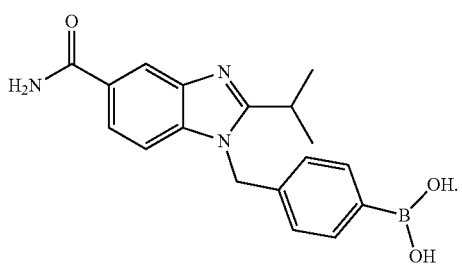 [SMILES: CC(C)c1nc2cc(C(N)=O)ccc2n1Cc1ccc(B(O)O)cc1]

12. The compound of claim 2, having the formula

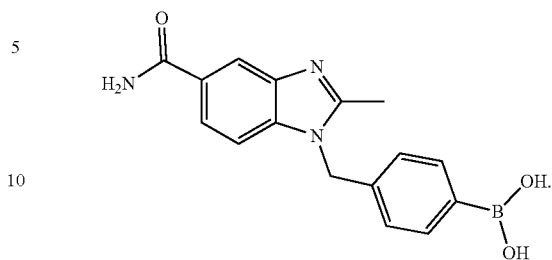

13. The compound of claim 1, having the formula

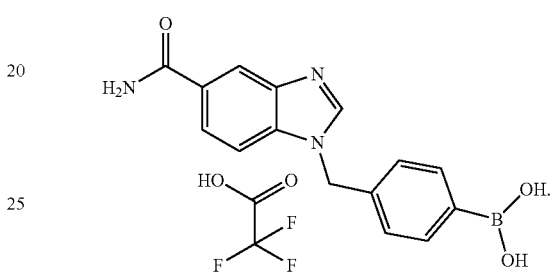

14. The compound of claim 2, having the formula

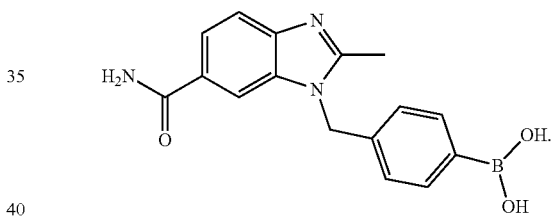

15. The compound of claim 2, having the formula

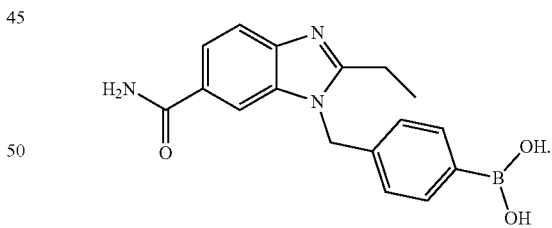

16. The compound of claim 2, having the formula

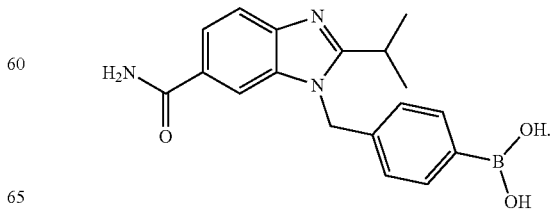

17. The compound of claim 1, having the formula

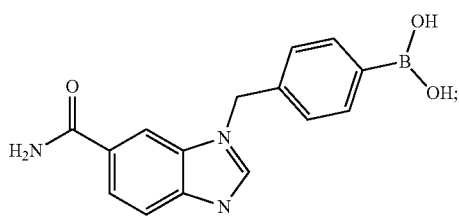

or a pharmaceutically acceptable salt thereof.

18. The compound of claim 1, having the formula

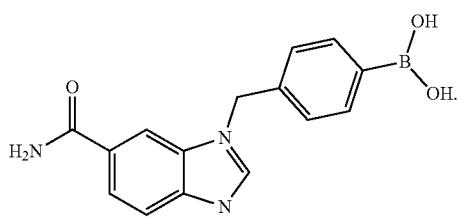

19. The compound of claim 1, having the formula

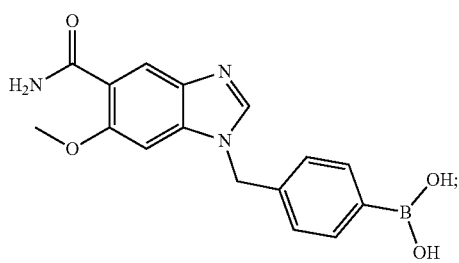 [SMILES: COc1cc2c(cc1C(N)=O)ncn2Cc1ccc(B(O)O)cc1]

or a pharmaceutically acceptable salt thereof.

20. The compound of claim 1, having the formula

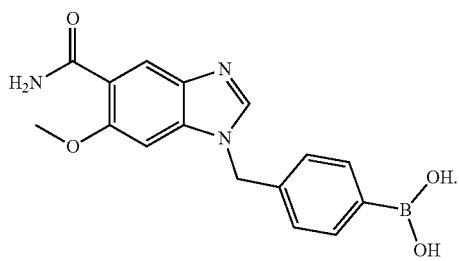 [SMILES: COc1cc2c(cc1C(N)=O)ncn2Cc1ccc(B(O)O)cc1]

21. The compound of claim 1, having the formula

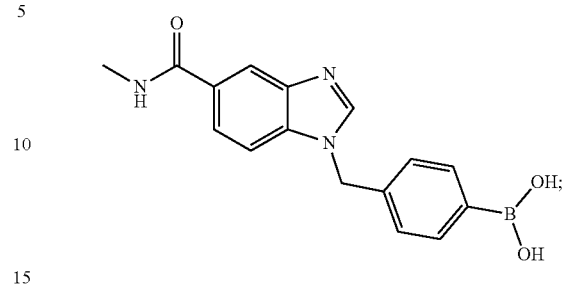

or a pharmaceutically acceptable salt thereof.

22. The compound of claim 1, having the formula

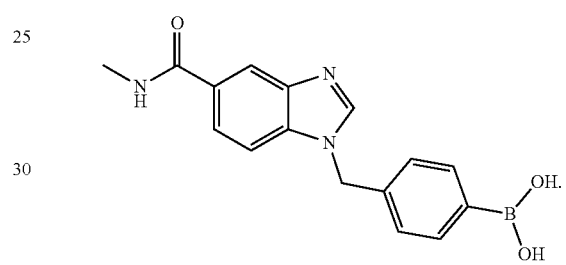

23. The compound of claim 1, having the formula

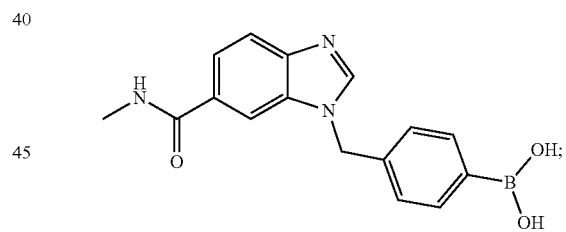

or a pharmaceutically acceptable salt thereof.

24. The compound of claim 1, having the formula

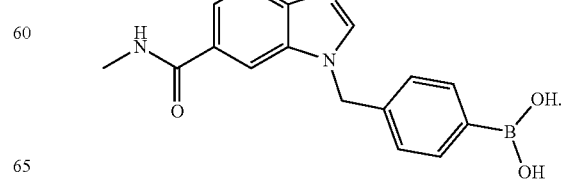

25. The compound of claim 1, having the formula

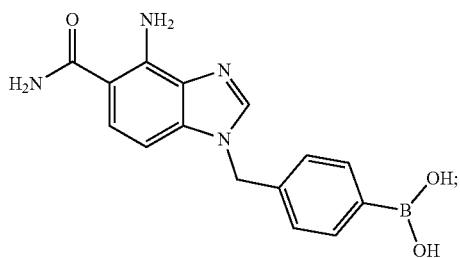 [SMILES: NC(=O)c1ccc2c(ncn2Cc2ccc(B(O)O)cc2)c1N]

or
a pharmaceutically acceptable salt thereof.

26. The compound of claim 1, having the formula

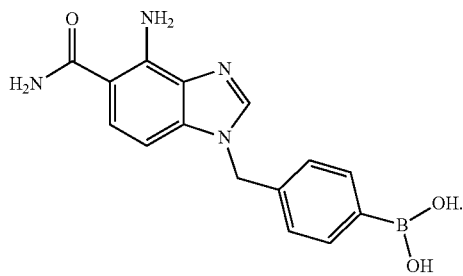 [SMILES: NC(=O)c1ccc2c(ncn2Cc2ccc(B(O)O)cc2)c1N]

27. The compound of claim 1, having the formula

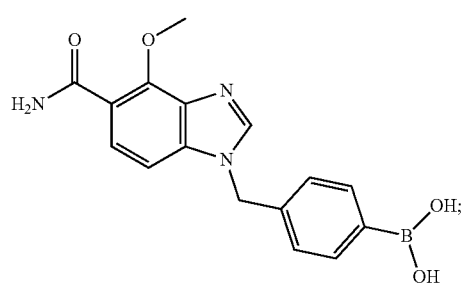

or
a pharmaceutically acceptable salt thereof.

28. The compound of claim 1, having the formula

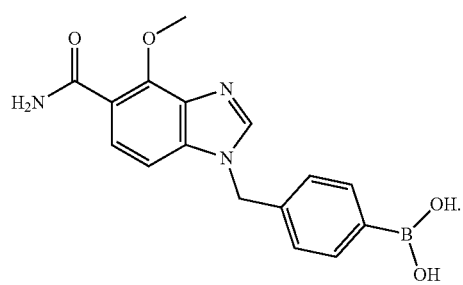

29. The compound of claim 1, having the formula

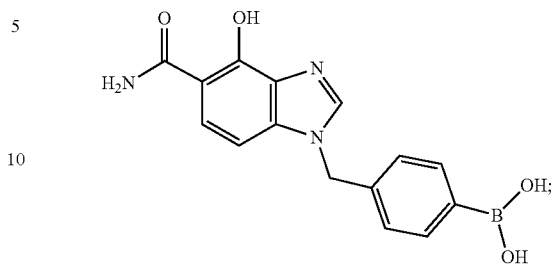

or
a pharmaceutically acceptable salt thereof.

30. The compound of claim 1, having the formula

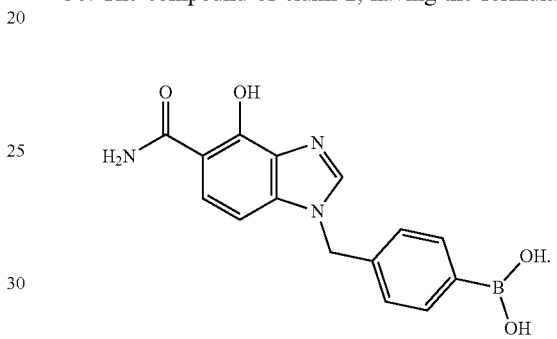

31. The compound of claim 1, having the formula

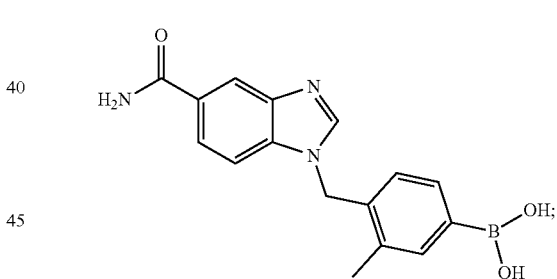

or
a pharmaceutically acceptable salt thereof.

32. The compound of claim 1, having the formula

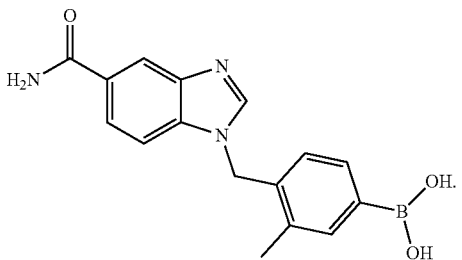 [SMILES: Cc1cc(B(O)O)ccc1Cn1cnc2cc(C(N)=O)ccc21]

33. The compound of claim 1, having the formula

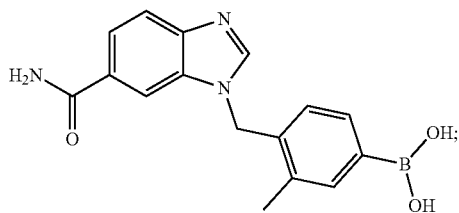

or
a pharmaceutically acceptable salt thereof.
34. The compound of claim 1, having the formula

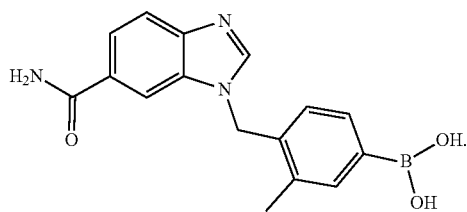 [SMILES: Cc1cc(B(O)O)ccc1Cn1cnc2ccc(C(N)=O)cc21]

35. The compound of claim 1, having the formula

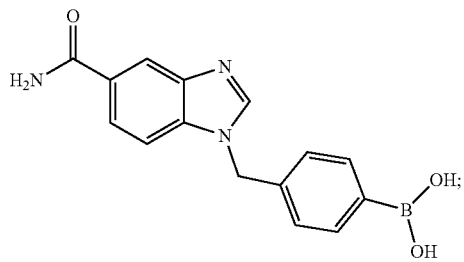 [SMILES: NC(=O)c1ccc2c(c1)ncn2Cc1ccc(B(O)O)cc1]

or
a pharmaceutically acceptable salt thereof.
36. The compound of claim 1, having the formula

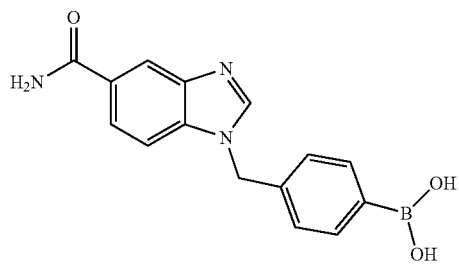 [SMILES: NC(=O)c1ccc2c(c1)ncn2Cc1ccc(B(O)O)cc1]

as a pharmaceutically acceptable salt thereof.

37. The compound of claim 2, having the formula

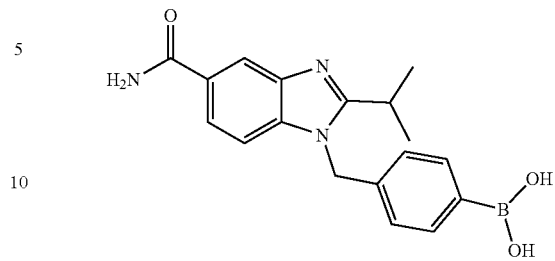

as a pharmaceutically acceptable salt thereof.
38. The compound of claim 2, having the formula

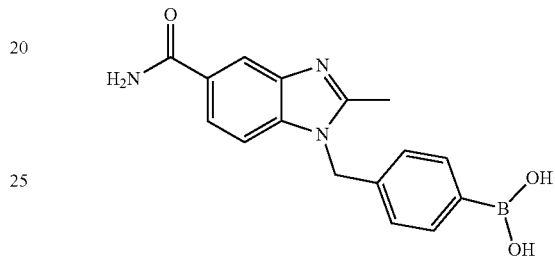

as a pharmaceutically acceptable salt thereof.
39. The compound of claim 2, having the formula

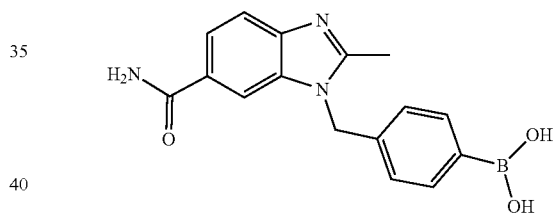

as a pharmaceutically acceptable salt thereof.
40. The compound of claim 2, having the formula

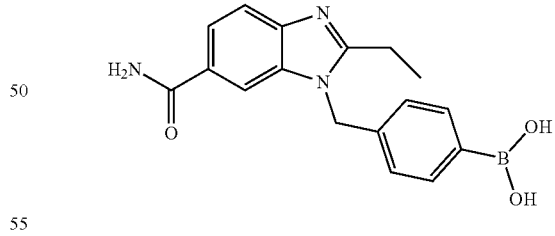

as a pharmaceutically acceptable salt thereof.

* * * * *

UNITED STATES PATENT AND TRADEMARK OFFICE
CERTIFICATE OF CORRECTION

PATENT NO. : 12,029,744 B2  
APPLICATION NO. : 17/264684  
DATED : July 9, 2024  
INVENTOR(S) : Hawley et al.

Page 1 of 2

It is certified that error appears in the above-identified patent and that said Letters Patent is hereby corrected as shown below:

In the Claims

Claim 2, Column 269, Line 15, please delete " 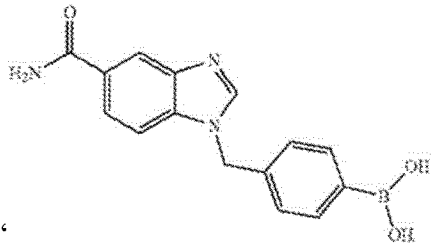 " and insert

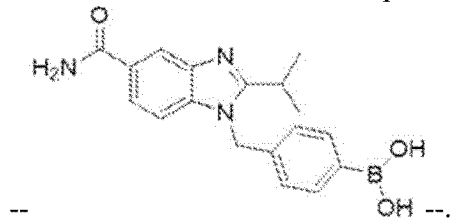

--.

Claim 2, Column 269, Line 25, please delete " 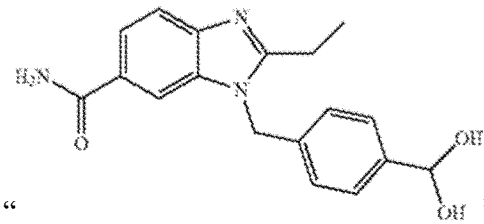 " and insert

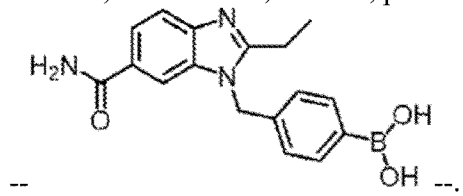

--.

Signed and Sealed this  
Twenty-first Day of January, 2025

Coke Morgan Stewart  
*Acting Director of the United States Patent and Trademark Office*

CERTIFICATE OF CORRECTION (continued)
U.S. Pat. No. 12,029,744 B2

Claim 17, Column 273, Line 5, please delete " 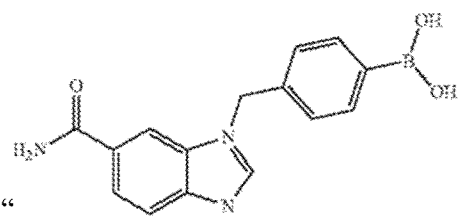 " and insert -- 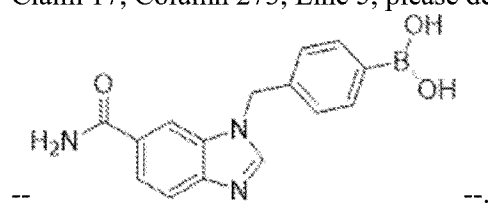 --.

Claim 18, Column 273, Line 25, please delete " 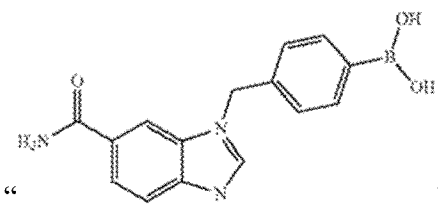 " and insert -- 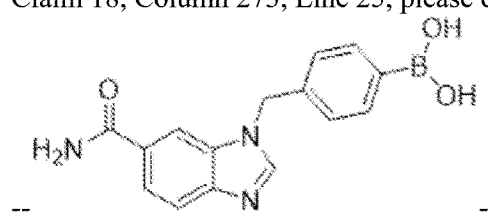 --.